(12) United States Patent
Marumoto et al.

(10) Patent No.: US 9,133,140 B2
(45) Date of Patent: Sep. 15, 2015

(54) CYCLOALKYLAMNE DERIVATIVES

(75) Inventors: Shinji Marumoto, Tokyo (JP); Toyoki Nishimata, Tokyo (JP); Masayuki Ebisawa, Tokyo (JP); Yusuke Asoh, Tokyo (JP); Yasuo Fukushima, Tokyo (JP); Mikio Kato, Tokyo (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 1215 days.

(21) Appl. No.: 13/059,156

(22) PCT Filed: Aug. 20, 2009

(86) PCT No.: PCT/JP2009/064542
§ 371 (c)(1),
(2), (4) Date: Feb. 15, 2011

(87) PCT Pub. No.: WO2010/021351
PCT Pub. Date: Feb. 25, 2010

(65) Prior Publication Data
US 2012/0122941 A1    May 17, 2012
US 2012/0295943 A9    Nov. 22, 2012

(30) Foreign Application Priority Data
Aug. 22, 2008    (JP) ................................ 2008-213843

(51) Int. Cl.
A61K 31/41        (2006.01)
C07D 257/04       (2006.01)
C07C 217/54       (2006.01)
C07C 217/74       (2006.01)
C07C 229/16       (2006.01)
C07C 229/18       (2006.01)
C07C 229/46       (2006.01)
C07C 237/36       (2006.01)
C07C 323/52       (2006.01)

(52) U.S. Cl.
CPC ............ *C07D 257/04* (2013.01); *C07C 217/54* (2013.01); *C07C 217/74* (2013.01); *C07C 229/16* (2013.01); *C07C 229/18* (2013.01); *C07C 229/46* (2013.01); *C07C 237/36* (2013.01); *C07C 323/52* (2013.01); *C07C 2101/04* (2013.01); *C07C 2101/08* (2013.01)

(58) Field of Classification Search
USPC .................. 514/381, 563, 567; 562/450, 457; 548/254
See application file for complete search history.

(56) References Cited

U.S. PATENT DOCUMENTS

2010/0317582 A1* 12/2010 Fensholdt et al. .......... 514/11.9

FOREIGN PATENT DOCUMENTS

| JP | 11-130737 | 5/1999 |
| WO | WO 94/18959 | 9/1994 |
| WO | WO 96/12697 | 5/1996 |
| WO | WO 01/81295 | 11/2001 |
| WO | WO 2005/115975 | 12/2005 |
| WO | WO 2009/065406 | 5/2009 |

OTHER PUBLICATIONS

Nagano, Nobuo. "Pharmacological and clinical properties of calcimimetics: Calcium receptor activators that afford an innovative approach to controlling hyperparathyroidism," Pharmacology & Therapeutics, 109: 339-365 (2006).

* cited by examiner

*Primary Examiner* — Rei-Tsang Shiao
(74) *Attorney, Agent, or Firm* — Dorsey and Whitney LLP

(57) ABSTRACT

Provided is a therapeutic agent for hyperparathyroidism, renal osteodystrophy, hypercalcemia and the like, which has a CaSR activating (agonist) action. A compound represented by the following general formula (1):

[Chemical 1]

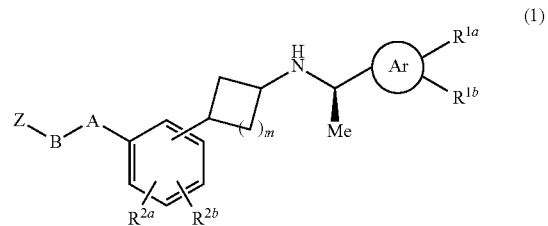

[wherein, Ar which is a partial structure in the general formula (1) represents a phenyl group or a naphthyl group; $R^{1a}$ and $R^{1b}$ are the same or different from each other, and represent a hydrogen atom, a halogeno group, or the like; $R^{2a}$ and $R^{2b}$ are the same or different from each other, and represent a hydrogen atom, a halogeno group, or the like; A represents a single bond, an oxygen atom, or the like; B represents a single bond, a C1-C4 alkanediyl group, or the like; Z represents a carboxyl group or a tetrazolyl group; and m represents an integer of 1 to 3] or a pharmacologically acceptable salt thereof.

40 Claims, 2 Drawing Sheets

CYCLOALKYLAMNE DERIVATIVES

CROSS-REFERENCE TO RELATED APPLICATIONS

This patent application is a National Stage application filed under 35U.S.C. §371 of International Patent Application No. PCT/JP2009/064542, filed Aug. 20, 2009, entitled "Cycloalkylamine Derivative," which claims priority to Japanese Patent Application No. 2008-213843, filed Aug. 22, 2008, the contents of all of which are hereby incorporated by reference in their entirety.

TECHNICAL FIELD

The present invention relates to novel cycloalkylamine derivatives having an excellent calcium sensing receptor (CaSR) activating action.

BACKGROUND ART

Parathyroid hormone (PTH) is a polypeptide hormone consisting of 84-amino acid residues secreted from the parathyroid, and has a function in maintaining homeostasis of calcium concentration in the blood.

Increases in PTH concentration in the blood increase calcium concentration in the blood via an action of enhancing calcium elution from bone to blood, an action of enhancing calcium resorption at the renal tubule, or the like. PTH concentration in the blood and calcium concentration in the blood have a close relationship, and decreases in the calcium concentration in the blood enhance secretion of PTH from the parathyroid, while increases in the calcium concentration in the blood suppress secretion of PTH from the parathyroid. From such feedback system, the calcium concentration in the blood is strictly controlled within a certain range. It is considered that the calcium sensing receptor (CaSR) existing on the cell membrane of the parathyroid is the one that mainly senses changes in calcium concentration in the blood.

CaSR is one of the seven-transmembrane G protein-coupled receptors. It is known that when CaSR of the parathyroid cells is activated by extracellular calcium, it increases the calcium concentration in the cell and decreases the secretion of PTH.

It is known that secondary hyperparathyroidism is often seen in renal failure patients, and PTH secretion is facilitated continuously as renal function decreases. It is considered that in secondary hyperparathyroidism, imbalance between the PTH concentration and the calcium concentration in the blood becomes a cause for arteriosclerosis and myocardial infarction derived from renal osteodystrophy and calcification of the cardiovascular system.

Conventional therapeutic agents for secondary hyperparathyroidism were mainly vitamin D preparations. Although administration of vitamin D preparations suppresses PTH secretion from the parathyroid, it enhances calcium absorption from the intestine, thereby limiting the dosage due to concerns about increases in calcium concentration in the blood. Therefore, administration of vitamin D preparations disadvantageously failed to exhibit a sufficient therapeutic effect.

On the other hand, CaSR activating agents (agonists) have an action mechanism in which the CaSR activating agent exerts its action on the CaSR of the parathyroid by improving the sensitivity of the receptor to calcium in the blood, thereby suppressing PTH secretion from the parathyroid, which provides decreases in the calcium concentration in the blood as a secondary action. Accordingly, it can be expected that PTH concentration in the blood is decreased without causing an increase in calcium concentration in the blood. Therefore, an agent which has a CaSR activating (agonist) action is expected as a therapeutic agent for hyperparathyroidism, renal osteodystrophy, hypercalcemia or the like.

In recent years, cinacalcet which was developed as a CaSR activating agent (agonist) (for example, refer to Patent Document 1) has been used as a novel therapeutic agent for hyperparathyroidism in the clinical field. However, since cinacalcet is disadvantageous in terms of its effectiveness and safety, creation of a CaSR activating agent (agonist) with high potency and high safety is desired (refer to non-Patent Document 1, Patent Document 1 and Patent Document 2). Further, while an arylalkylamine compound having CaSR activating (agonist) action is disclosed (Patent Document 3), it differs from the compound of the present invention in its structure.

PRIOR ART DOCUMENTS

Patent Documents

[Patent Document 1] International Publication No. WO 1994/18959

[Patent Document 2] International Publication No. WO 1996/12697

[Patent Document 3] International Publication No. WO 2005/115975

[Patent Document 4] International Publication No. WO 2009/065406

Non-Patent Document

[non-Patent Document 1] N. Nagano, Pharmacol. Ther., 2006, March, 109 (3), 339-365.

SUMMARY OF THE INVENTION

Problems To Be Solved By The Invention

The CaSR activating agent (agonist) known at present is unsatisfactory in terms of its effectiveness and safety, and therefore a CaSR activating agent (agonist) having excellent effectiveness and safety has been eagerly anticipated.

Means For Solving The Problems

The inventors of the present invention have conducted extensive studies on synthesis in order to obtain a therapeutic agent for secondary hyperparathyroidism, which has an excellent CaSR activating (agonist) action as well as excellent metabolic stability, safety or the like. As a result, a novel cycloalkylamine derivative having the general formula (1), which has an excellent CaSR activating (agonist) action and has excellent qualities such as oral absorbability, metabolic stability, water solubility, safety or the like has been found, thereby leading to completion of the present invention.

The present invention provides a medicament comprising a novel cycloalkylamine derivative represented by the general formula (1) or a pharmacologically acceptable salt thereof, which shows an excellent CaSR activating (agonist) action.

That is, the present invention provides
a compound represented by the following general formula (1):

[Chemical 1]

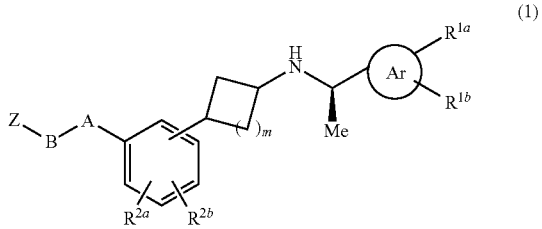

(1)

[wherein,
the partial structure:

[Chemical 2]

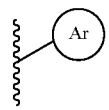

in the general formula (1) represents a phenyl group or a naphthyl group;
$R^{1a}$ and $R^{1b}$ are the same or different from each other, and represent a hydrogen atom, a halogeno group, a C1-C6 alkyl group or a C1-C6 alkoxy group;
$R^{2a}$ and $R^{2b}$ are the same or different from each other, and represent a hydrogen atom, a halogeno group, a C1-C6 alkyl group, a halogeno C1-C6 alkyl group, a hydroxyl group, or a C1-C6 alkoxy group;
A represents a single bond, an oxygen atom, a —$NR^3$— group, a —$NR^3C(=O)$— group, a —$NR^3$—$S(O)_2$— group or a —$S(O)_n$— group (wherein $R^3$ represents a hydrogen atom, a C1-C4 alkyl group or a C1-C4 acyl group, and n represents 0, 1 or 2);
B represents a single bond, a C1-C4 alkanediyl group or a C3-C4 cycloalkanediyl group;
Z represents a carboxy group or a tetrazolyl group (with the proviso that when Z is a carboxy group, B is not a single bond); and
m represents an integer of 1 to 3],
or a pharmacologically acceptable salt thereof;
(2) the compound or pharmacologically acceptable salt thereof according to (1), wherein $R^{1a}$ and $R^{1b}$ are the same or different from each other, and are a hydrogen atom, a halogeno group or a C1-C4 alkyl group;
the compound or pharmacologically acceptable salt thereof according to (1), wherein $R^{1a}$ and $R^{1b}$ are the same or different from each other, and are a hydrogen atom or a halogeno group;
the compound or pharmacologically acceptable salt thereof according to (1), wherein $R^{1a}$ is a halogeno group, and $R^{1b}$ is a hydrogen atom or a halogeno group;
the compound or pharmacologically acceptable salt thereof according to (1), wherein $R^{1a}$ is a halogeno group, and $R^{1b}$ is a hydrogen atom;
the compound or pharmacologically acceptable salt thereof according to (1), wherein $R^{1a}$ is a fluoro group, and $R^{1b}$ is a hydrogen atom;
the compound or pharmacologically acceptable salt thereof according to any one of (1) to (6), wherein the partial structure:

[Chemical 3]

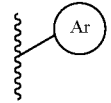

in the general formula (1) is a naphthyl group;
(8) the compound or pharmacologically acceptable salt thereof according to any one of (1) to (6), wherein the partial structure:

[Chemical 4]

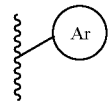

in the general formula (1) is a naphthalen-1-yl group;
(9) the compound or pharmacologically acceptable salt thereof according to (1), wherein the partial structure:

[Chemical 5]

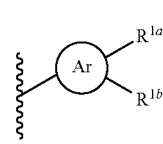

in the general formula (1) is a 4-fluoronaphthalen-1-yl group;
(10) the compound or pharmacologically acceptable salt thereof according to any one of (1) to (9), wherein $R^{2a}$ and $R^{2b}$ are the same or different from each other, and are a hydrogen atom, a halogeno group, a C1-C4 alkyl group, a trifluoromethyl group or a C1-C4 alkoxy group;
(11) the compound or pharmacologically acceptable salt thereof according to any one of (1) to (9), wherein $R^{2a}$ and $R^{2b}$ are the same or different from each other, and are a hydrogen atom, a halogeno group or a C1-C4 alkyl group;
(12) the compound or pharmacologically acceptable salt thereof according to any one of (1) to (11), wherein A is a single bond, an oxygen atom or a —$NR^3C(=O)$— group (wherein $R^3$ represents a hydrogen atom);
(13) the compound or pharmacologically acceptable salt thereof according to any one of (1) to (11), wherein A is a single bond or an oxygen atom;
(14) the compound or pharmacologically acceptable salt thereof according to any one of (1) to (11), wherein A is a —$NR^3$— group or a —$S(O)_n$— group (wherein $R^3$ represents a hydrogen atom, a C1-C4 alkyl group or a C1-C4 acyl group, and n represents 0, 1 or 2);
(15) the compound or pharmacologically acceptable salt thereof according to any one of (1) to (14), wherein B is a single bond or a C1-C4 alkanediyl group;
(16) the compound or pharmacologically acceptable salt thereof according to any one of (1) to (14), wherein B is a single bond, a methylene group or a propane-2,2-diyl group;
(17) the compound or pharmacologically acceptable salt thereof according to any one of (1) to (16), wherein Z is a carboxy group;
(18) the compound or pharmacologically acceptable salt thereof according to any one of (1) to (17), wherein m in the general formula (1) is 2;

(19) a compound represented by the following general formula (1-a-2):

[Chemical 6]

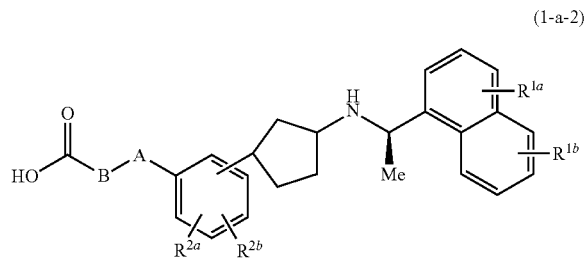

(1-a-2)

[wherein, $R^{1a}$, $R^{1b}$, $R^{2a}$, $R^{2b}$, A and B represent the same as in (1), with the proviso that B is not a single bond], or a pharmacologically acceptable salt thereof;

(20) a compound represented by the following general formula (1-a-2a):

[Chemical 7]

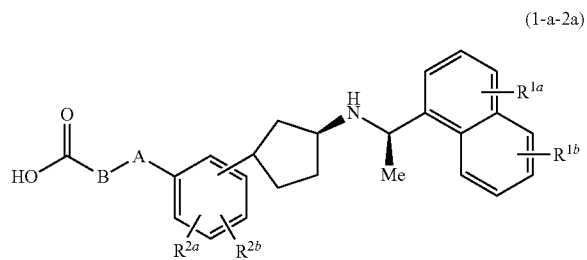

(1-a-2a)

[wherein, $R^{1a}$, $R^{1b}$, $R^{2a}$, $R^{2b}$, A and B represent the same as in (1), with the proviso that B is not a single bond], or a pharmacologically acceptable salt thereof;

(21) the compound or pharmacologically acceptable salt thereof according to (20),
wherein the phenylene group which is a partial structure of the general formula (1-a-2a) is in the m- or p-position;

(22) the compound or pharmacologically acceptable salt thereof according to any one of (19) to (21), wherein $R^{1a}$ and $R^{1b}$ are the same or different from each other, and are a hydrogen atom, a halogeno group or a C1-C4 alkyl group;

(23) the compound or pharmacologically acceptable salt thereof according to any one of (19) to (21), wherein $R^{1a}$ and $R^{1b}$ are the same or different from each other, and are a hydrogen atom or a halogeno group;

(24) the compound or pharmacologically acceptable salt thereof according to any one of (19) to (21), wherein $R^{1a}$ is a halogeno group, and $R^{1b}$ is a hydrogen atom or a halogeno group;

(25) the compound or pharmacologically acceptable salt thereof according to any one of (19) to (21), wherein $R^{1a}$ is a halogeno group, and $R^{1b}$ is a hydrogen atom;

(26) the compound or pharmacologically acceptable salt thereof according to any one of (19) to (21), wherein $R^{1a}$ is a fluoro group, and $R^{1b}$ is a hydrogen atom;

(27) the compound or pharmacologically acceptable salt thereof according to any one of (19) to (21), wherein the partial structure:

[Chemical 8]

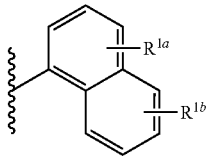

in the general formula (1-a-2) or (1-a-2a) is a 4-fluoronaphthalen-1-yl group;

(28) the compound or pharmacologically acceptable salt thereof according to any one of (19) to (27), wherein $R^{2a}$ and $R^{2b}$ are the same or different from each other, and are a hydrogen atom, a halogeno group, a C1-C4 alkyl group, a trifluoromethyl group or a C1-C4 alkoxy group;

(29) the compound or pharmacologically acceptable salt thereof according to any one of (19) to (27), wherein $R^{2a}$ and $R^{2b}$ are the same or different from each other, and are a hydrogen atom, a halogeno group or a C1-C4 alkyl group;

(30) the compound or pharmacologically acceptable salt thereof according to any one of (19) to (29), wherein A is a single bond, an oxygen atom or a —$NR^3C(=O)$— group (wherein $R^3$ represents a hydrogen atom);

(31) the compound or pharmacologically acceptable salt thereof according to any one of (19) to (29), wherein A is a single bond or an oxygen atom;

(32) the compound or pharmacologically acceptable salt thereof according to any one of (19) to (29), wherein A is a $NR^3$— group or a —$S(O)_n$— group (wherein $R^3$ represents a hydrogen atom, a C1-C4 alkyl group or a C1-C4 acyl group, and n represents 0, 1 or 2);

(33) the compound or pharmacologically acceptable salt thereof according to any one of (19) to (32), wherein B is a C1-C4 alkanediyl group;

(34) the compound or pharmacologically acceptable salt thereof according to any one of (19) to (32), wherein B is a methylene group or a propane-2,2-diyl group;

(35) a compound selected from the group consisting of:
N-[(1R)-1-(naphthalen-1-yl)ethyl]-3-[3-(2H-tetrazol-5-yl)phenyl]cyclopentanamine,
N-[(1R)-1-(naphthalen-1-yl)ethyl]-3-[4-(2H-tetrazol-5-yl)phenyl]cyclopentanamine,
N-{4-[3-{[(1R)-1-(naphthalen-1-yl)ethyl]amino}cyclopentyl]benzoyl}glycine,
{3-[3-{[(1R)-1-(naphthalen-1-yl)ethyl]amino}cyclopentyl]phenyl}acetic acid,
{4-[3-{[(1R)-1-(naphthalen-1-yl)ethyl]amino}cyclopentyl]phenyl}acetic acid,
3-{4-[3-{[(1R)-1-(naphthalen-1-yl)ethyl]amino}cyclopentyl]phenyl}propanoic acid,
{4-[3-{[(1R)-1-(naphthalen-1-yl)ethyl]amino}cyclopentyl]phenoxy}acetic acid,
2-methyl-2-{4-[3-{[(1R)-1-(naphthalen-1-yl)ethyl]amino}cyclopentyl]phenoxy}propanoic acid,
{3-[3-{[(1R)-1-(naphthalen-1-yl)ethyl]amino}cyclopentyl]phenoxy}acetic acid,
2-methyl-2-{3-[3-{[(1R)-1-(naphthalen-1-yl)ethyl]amino}cyclopentyl]phenoxy}propanoic acid,
{2-fluoro-4-[3-{[(1R)-1-(naphthalen-1-yl)ethyl]amino}cyclopentyl]phenoxy}acetic acid,
{4-[3-{[(1R)-1-(4-fluoronaphthalen-1-yl)ethyl]amino}cyclopentyl]phenoxy}acetic acid,
{4-[3-{[(1R)-1-(5-fluoronaphthalen-1-yl)ethyl]amino}cyclopentyl]phenoxy}acetic acid, {4-[3-{[(1R)-1-(3-chlorophenyl)ethyl]amino}cyclopentyl]
phenoxy}acetic acid,
{4-[3-{[(1R)-1-(6-fluoronaphthalen-1-yl)ethyl]
amino}cyclopentyl]phenoxy}acetic acid,
{4-[3-{[(1R)-1-(4,6-difluoronaphthalen-1-yl)ethyl]
amino}cyclopentyl]phenoxy}acetic acid,
{3-[3-{[(1R)-1-(4-fluoronaphthalen-1-yl)ethyl]
amino}cyclopentyl]phenyl}acetic acid,
{4-[3-{[(1R)-1-(4-fluoronaphthalen-1-yl)ethyl]
amino}cyclopentyl]phenyl}acetic acid,
N-[(1R)-1-(4-fluoronaphthalen-1-yl)ethyl]-3-[4-(2H-tetrazol-5-yl)phenyl]cyclopentanamine,
3-{4-[3-{[(1R)-1-(4-fluoronaphthalen-1-yl)ethyl]
amino}cyclopentyl]phenyl}propanoic acid,
2-{4-[3-{[(1R)-1-(4-fluoronaphthalen-1-yl)ethyl]
amino}cyclopentyl]phenoxy}-2-methylpropanoic acid,
{2-methyl-4-[3-{[(1R)-1-(naphthalen-1-yl)ethyl]
amino}cyclopentyl]phenoxy}acetic acid,
N-{4-[3-{[(1R)-1-(naphthalen-1-yl)ethyl]
amino}cyclopentyl]phenyl}glycine,
N-{4-[3-{[(1R)-1-(4-fluoronaphthalen-1-yl)ethyl]
amino}cyclopentyl]phenyl}glycine,
{4-[3-{[(1R)-1-(naphthalen-1-yl)ethyl]amino}cyclopentyl]
phenyl}thio)acetic acid,
{4-[3-{[(1R)-1-(4-fluoronaphthalen-1-yl)ethyl]
amino}cyclopentyl]phenyl}thio)acetic acid,
N-[(1R)-1-(naphthalen-1-yl)ethyl]-[4-(2H-tetrazol-5-yl-methoxy)phenyl]cyclopentanamine, and
N-[(1R)-1-(4-fluoronaphthalen-1-yl)ethyl]-[4-(2H-tetrazol-5-ylmethoxy)phenyl]cyclopentanamine or a pharmacologically acceptable salt thereof;

(36) a compound selected from the group consisting of:
N-{4-[3-{[(1R)-1-(naphthalen-1-yl)ethyl]
amino}cyclopentyl]benzoyl}glycine,
{3-[3-{[(1R)-1-(naphthalen-1-yl)ethyl]amino}cyclopentyl]
phenyl}acetic acid,
{4-[3-{[(1R)-1-(naphthalen-1-yl)ethyl]amino}cyclopentyl]
phenyl}acetic acid,
3-{4-[3-{[(1R)-1-(naphthalen-1-yl)ethyl]
amino}cyclopentyl]phenyl}propanoic acid,
{4-[3-{[(1R)-1-(naphthalen-1-yl)ethyl]amino}cyclopentyl]
phenoxy}acetic acid,
2-methyl-2-{4-[3-{[(1R)-1-(naphthalen-1-yl)ethyl]
amino}cyclopentyl]phenoxy}propanoic acid,
{3-[3-{[(1R)-1-(naphthalen-1-yl)ethyl]amino}cyclopentyl]
phenoxy}acetic acid,
{4-[3-{[(1R)-1-(4-fluoronaphthalen-1-yl)ethyl]amino
}cyclopentyl]phenoxy}acetic acid,
{4-[3-{[(1R)-1-(4,6-difluoronaphthalen-1-yl)ethyl]
amino}cyclopentyl]phenoxy}acetic acid,
{3-[3-{[(1R)-1-(4-fluoronaphthalen-1-yl)ethyl]
amino}cyclopentyl]phenyl}acetic acid,
{4-[3-{[(1R)-1-(4-fluoronaphthalen-1-yl)ethyl]
amino}cyclopentyl]phenyl}acetic acid,
3-{4-[3-{[(1R)-1-(4-fluoronaphthalen-1-yl)ethyl]
amino}cyclopentyl]phenyl}propanoic acid,
2-{4-[3-{[(1R)-1-(4-fluoronaphthalen-1-yl)ethyl]
amino}cyclopentyl]phenoxy}-2-methylpropanoic acid, and
({4-[3-{[(1R)-1-(4-fluoronaphthalen-1-yl)ethyl]
amino}cyclopentyl]phenyl}thio)acetic acid or a pharmacologically acceptable salt thereof;

(37) a compound selected from the group consisting of:
{4-[3-{[(1R)-1-(4-fluoronaphthalen-1-yl)ethyl]
amino}cyclopentyl]phenoxy}acetic acid,
{3-[3-{[(1R)-1-(4-fluoronaphthalen-1-yl)ethyl]
amino}cyclopentyl]phenyl}acetic acid,
{4-[3-{[(1R)-1-(4-fluoronaphthalen-1-yl)ethyl]
amino}cyclopentyl]phenyl}acetic acid,
3-{4-[3-{[(1R)-1-(4-fluoronaphthalen-1-yl)ethyl]
amino}cyclopentyl]phenyl}propanoic acid,
2-{4-[3-{[(1R)-1-(4-fluoronaphthalen-1-yl)ethyl]
amino}cyclopentyl]phenoxy}-2-methylpropanoic acid, and
({4-[3-{[(1R)-1-(4-fluoronaphthalen-1-yl)ethyl]
amino}cyclopentyl]phenyl}thio)acetic acid or a pharmacologically acceptable salt thereof;

(38) a medicament comprising the compound or pharmacologically acceptable salt thereof according to any one of (1) to (37) as an active ingredient;

(39) a calcium-sensing receptor agonist comprising the compound or pharmacologically acceptable salt thereof according to any one of (1) to (37) as an active ingredient;

(40) a calcium-sensing receptor activating agent comprising the compound or pharmacologically acceptable salt thereof according to any one of (1) to (37) as an active ingredient;

(41) a therapeutic agent for hyperparathyroidism comprising the compound or pharmacologically acceptable salt thereof according to any one of (1) to (37) as an active ingredient;

(42) a therapeutic agent for secondary hyperparathyroidism comprising the compound or pharmacologically acceptable salt thereof according to any one of (1) to (37) as an active ingredient;

(43) a therapeutic agent for primary hyperparathyroidism comprising the compound or pharmacologically acceptable salt thereof according to any one of (1) to (37) as an active ingredient;

(44) a therapeutic agent for renal osteodystrophy comprising the compound or pharmacologically acceptable salt thereof according to any one of (1) to (37) as an active ingredient;

(45) a therapeutic agent for hypercalcemia comprising the compound or pharmacologically acceptable salt thereof according to any one of (1) to (37) as an active ingredient;

(46) a pharmaceutical composition comprising the compound or pharmacologically acceptable salt thereof according to any one of (1) to (37), and a pharmacologically acceptable carrier;

(47) a therapeutic method for hyperparathyroidism, secondary hyperparathyroidism, primary hyperparathyroidism, renal osteodystrophy or hypercalcemia, comprising administering a pharmaceutical composition comprising the compound or pharmacologically acceptable salt thereof according to any one of (1) to (37) as an active ingredient.

Effect of the Invention

The novel cycloalkylamine derivatives represented by the general formula (1) of the present invention have an excellent CaSR activating (agonist) action, and show high oral absorbability, plasma concentration, and retention in the blood, thereby exhibiting an excellent pharmacological action. In addition, the compound of the general formula (1) of the present invention is excellent in disposition such as biodistribution, retention in the blood or the like, and its safety towards organs such as the kidney, liver or the like is high.

Accordingly, the novel cycloalkylamine derivatives represented by the general formula (1) of the present invention are useful as a medicament, and are useful as a therapeutic agent especially for hyperparathyroidism, renal osteodystrophy, hypercalcemia or the like.

BEST MODE FOR CARRYING OUT THE INVENTION

Figure 1:
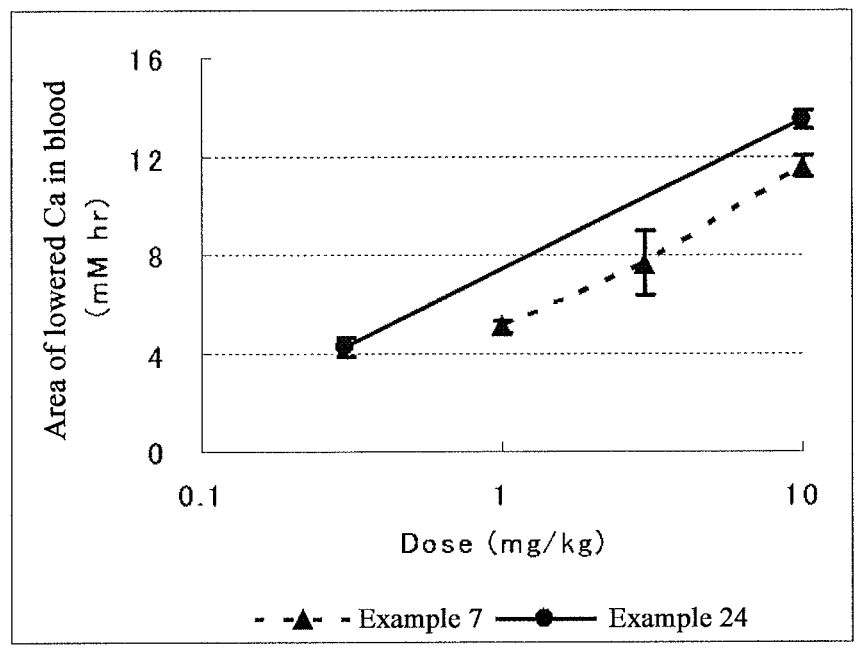
FIG. 1 shows area values of lowered calcium ion concentration in the blood for the compound in Example 7 and the compound in Example 24.

The substituents used herein will be explained hereinafter.

A "halogeno group" means a fluoro group, a chloro group, and a bromo group, preferably a fluoro group and a chloro group.

(2) A "C1-C4 alkyl group" means a linear or branched alkyl group having 1 to 4 carbon atoms, and there may be mentioned, for example a methyl group, an ethyl group, a n-propyl group, an isopropyl group, a n-butyl group, an isobutyl group, a tert-butyl group, or the like. A "C1-C6 alkyl group" means a linear or branched alkyl group having 1 to 6 carbon atoms, and there may be mentioned, for example a n-pentyl group, a n-hexyl group, or the like, in addition to the examples of the aforementioned "C1-C4 alkyl group". As the "C1-C4 alkyl group" and the "C1-C6 alkyl group", a methyl group, an ethyl group, a n-propyl group, an isopropyl group, a n-butyl group and a tert-butyl group are preferred; and a methyl group and an ethyl group are more preferred.

(3) A "C1-C4 alkoxy group" means a C1-C4 alkyloxy group formed from the aforementioned "C1-C4 alkyl group", and represents a linear or branched alkoxy group having 1 to 4 carbon atoms, such as a methoxy group, an ethoxy group, a n-propoxy group, an isopropoxy group, a n-butoxy group, an isobutoxy group, a tert-butoxy group, or the like. A "C1-C6 alkoxy group" means a C1-C6 alkyloxy group formed from the aforementioned "C1-C6 alkyl group", and there may be mentioned, such as a n-pentyloxy group, a n-hexyloxy group, or the like, in addition to the examples of the aforementioned "C1-C4 alkoxy group". As the "C1-C4 alkoxy group" and the "C1-C6 alkoxy group", a methoxy group, an ethoxy group, a n-propoxy group, an isopropoxy group, a n-butoxy group and a tert-butoxy group are preferred; and a methoxy group and an ethoxy group are more preferred.

A "halogeno C1-C6 alkyl group" means a group in which the above-mentioned "C1-C6 alkyl group" is substituted with the same or different 1 to 5 halogeno groups, and there may be mentioned for example, a fluoromethyl group, a difluoromethyl group, a trifluoromethyl group, a chlorodifluoromethyl group, a 2-fluoroethyl group, a 2,2,2-trifluoroethyl group, a pentafluoroethyl group, a 3-fluoropropyl group, a 4-fluorobutyl group, a 5-fluoropentyl group, a 6-fluorohexyl group or the like, preferably a difluoromethyl group and a trifluoromethyl group.

A "C1-C4 acyl group" means, for example, a formyl group, an acetyl group, a propionyl group and a butanoyl group, preferably an acetyl group.

A "C1-C3 alkanediyl group" means a divalent group formed from a linear or branched alkyl group having 1 to 3 carbon atoms, and there may be mentioned for example, a methylene group, an ethylene group, a propane-1,3-diyl group, a propane-1,2-diyl group, a propane-1,1-diyl group, and a propane-2,2-diyl group. A "C1-C4 alkanediyl group" means a divalent group formed from a linear or branched alkyl group having 1 to 4 carbon atoms, and there may be mentioned for example, a butane-1,4-diyl group, a butane-1,3-diyl group, a butane-1,2-diyl group, a butane-1,1-diyl group, a butane-2,2-diyl group, a butane-2,3-diyl group, or the like, in addition to the example of the "C1-C3 alkanediyl group". As the "C1-C3 alkanediyl group" and the "C1-C4 alkanediyl group", a methylene group, an ethylene group and a propane-2,2-diyl group are preferred; and a methylene group and a propane-2,2-diyl group are more preferred.

A "C3-C4 cycloalkanediyl group" means a divalent group formed from a saturated cyclic hydrocarbon group having 3 to 4 carbon atoms, and there may be mentioned for example, a cyclopropane-1,1-diyl group, a cyclopropane-1,2-diyl group, a cyclobutane-1,1-diyl group, a cyclobutane-1,2-diyl group, and a cyclobutane-1,3-diyl group. Regarding the "C3-C4 cycloalkanediyl group", a cyclopropane-1,1-diyl group and a cyclobutane-1,1-diyl group are preferable.

Compounds of the general formula (1) will be explained in detail hereinafter.

[Chemical 9]

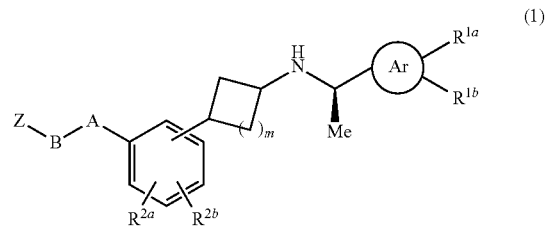

(1)

The partial structure:

[Chemical 10]

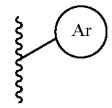

in the general formula (1) represents a phenyl group or a naphthyl group, preferably a naphthyl group; and particularly preferably a naphthalen-1-yl group.

$R^{1a}$ and $R^{1b}$ in the general formula (1) are the same or different from each other, and represent a hydrogen atom, a halogeno group, a C1-C6 alkyl group or a C1-C6 alkoxy group. As $R^{1a}$ and $R^{1b}$, a hydrogen atom, a halogeno group, a methyl group and an ethyl group are preferable; and a hydrogen atom and a halogeno group are more preferable. $R^{1a}$ and $R^{1b}$ are the same or different from each other, and are preferably a hydrogen atom, a halogeno group, or a C1-C4 alkyl group; and $R^{1a}$ and $R^{1b}$ are the same or different from each other, and are more preferably a hydrogen atom or a halogeno group. In addition, preferably $R^{1a}$ is a halogeno group and $R^{1b}$ is a hydrogen atom or a halogeno group, more preferably $R^{1a}$ is a halogeno group and $R^{1b}$ is a hydrogen atom, and further preferably $R^{1a}$ is a fluoro group and $R^{1b}$ is a hydrogen atom.

The partial structure:

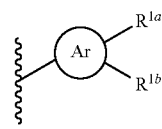

[Chemical 11]

in the general formula (1) is preferably a 4-fluoronaphthalen-1-yl group.

$R^{2a}$ and $R^{2b}$ in the general formula (1) are the same or different from each other, and represent a hydrogen atom, a halogeno group, a C1-C6 alkyl group, a halogeno C1-C6 alkyl group, a hydroxyl group or a C1-C6 alkoxy group. As a preferable group for $R^{2a}$ and $R^{2b}$, there may be mentioned for example, a hydrogen atom, a halogeno group, a C1-C4 alkyl group, a trifluoromethyl group, a C1-C4 alkoxy group, or the like; and a hydrogen atom, a halogeno group and a C1-C4 alkyl group are preferable, and a hydrogen atom and a halogeno group are more preferable.

A in the general formula (1) represents a single bond, an oxygen atom, a —$NR^3$— group, a —$NR^3C(=O)$— group, a —$NR^3$—$S(O)_2$— group or a —$S(O)_n$— group (wherein $R^3$ represents a hydrogen atom, a C1-C4 alkyl group or a C1-C4 acyl group, and n represents 0, 1 or 2).

As A, a single bond, an oxygen atom, a —$NR^3$— group, a —$NR^3C(=O)$— group and a —$S(O)_n$— group (wherein $R^3$ represents a hydrogen atom or a C1-C4 alkyl group, and n represents 0) are preferable; a single bond, an oxygen atom, a —$NR^3$— group, a —$NR^3C(=O)$— group and a —$S(=O)_n$— group (wherein $R^3$ represents a hydrogen atom, and n represents 0) are more preferable, and a single bond, an oxygen atom and a —$NR^3C(=O)$— group (wherein $R^3$ represents a hydrogen atom) are further preferable.

As A, a single bond and an oxygen atom are particularly preferable.

B in the general formula (1) represents a single bond, a C1-C4 alkanediyl group or a C3-C4 cycloalkanediyl group. As B, a single bond and a C1-C4 alkanediyl group are preferable; and a single bond, a methylene group and a propane-2,2-diyl group are more preferable.

Z in the general formula (1) represents a carboxy group or a tetrazolyl group (with the proviso that when Z is a carboxy group, B is not a single bond). As Z, a carboxy group is preferable.

m in the general formula (1) represents an integer of 1 to 3; and m is preferably 2.

As compounds of the general formula (1), compounds represented by the following general formulas (1-a-1), (1-a-2), (1-b-1) and (1-b-2):

[Chemical 12]

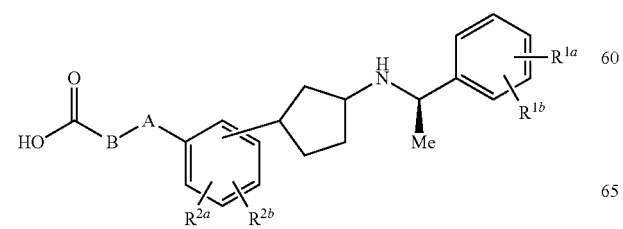

(1-a-1)

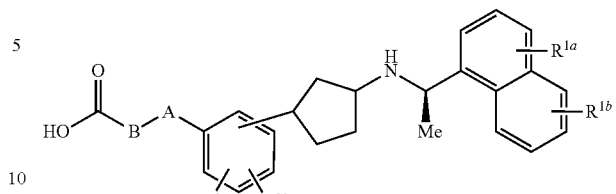

(1-a-2)

(1-b-1)

(1-b-2)

(wherein A, B, $R^{1a}$, $R^{2a}$ and $R^{2b}$ represent the same as above) can be mentioned as preferable compounds.

In addition, as compounds of the general formula (1), compounds represented by the following general formulas (1-a-1a), (1-a-2a), (1-b-1a) and (1-b-2a):

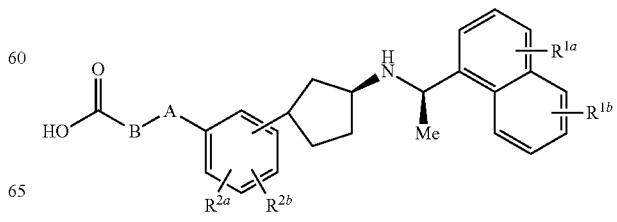

(1-a-1a)

(1-a-2a)

(1-b-1a)

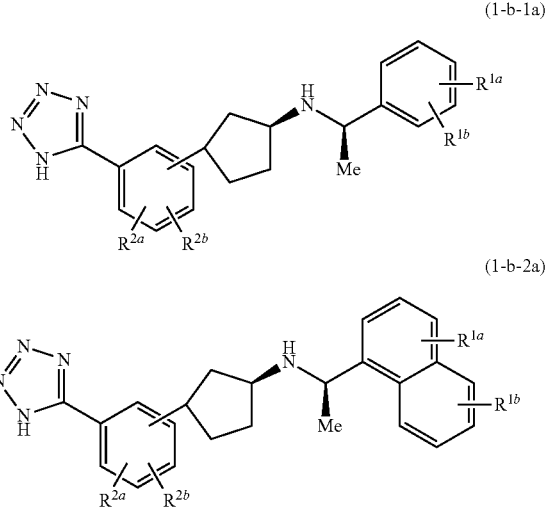

(1-b-2a)

(wherein A, B, $R^{1a}$, $R^{1b}$, $R^{2a}$ and $R^{2b}$ represent the same as above) can be mentioned as preferable compounds.

Further, regarding the phenylene groups at the left side, which are the partial structures of the above-mentioned general formulas (1-a-1a), (1-a-2a), (1-b-1a) and (1-b-2a), the ones represented by the following (m-A), (p-A), (m-B) and (p-B) that are in the m- or p-position:

[Chemical 14]

(m-A)

(p-A)

(m-B)

(p-B)

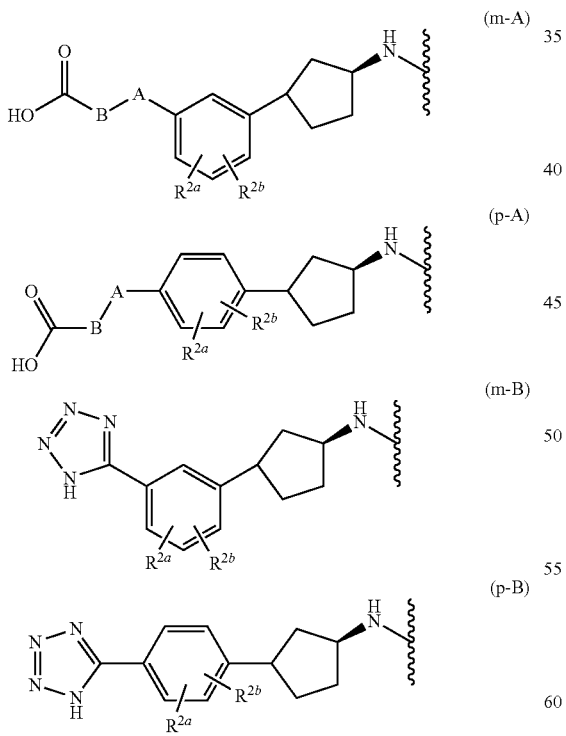

(wherein A, B, $R^{2a}$ and $R^{2b}$ represent the same as above) are preferable;

and the ones represented by the following (m-A-syn), (p-A-syn), (m-B-syn) and (p-B-syn):

[Chemical 15]

(m-A-syn)

(p-A-syn)

(m-B-syn)

(p-B-syn)

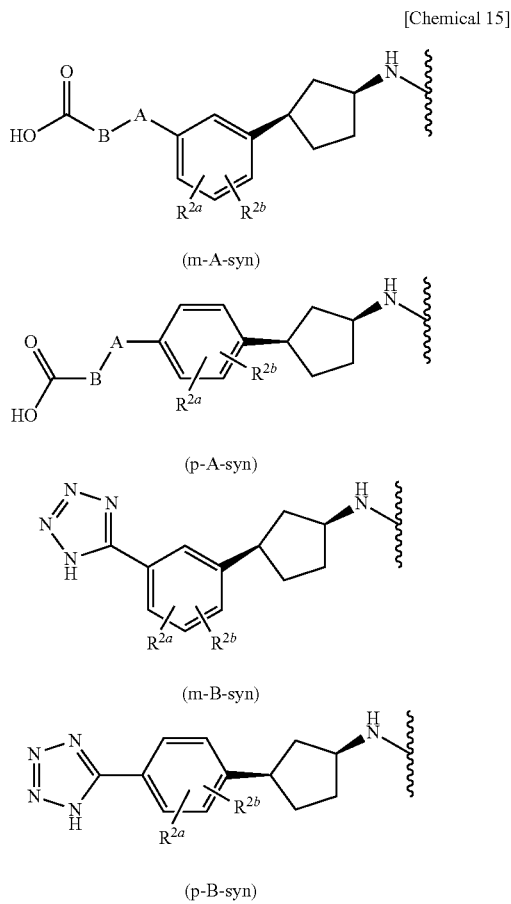

(wherein A, B, $R^{2a}$ and $R^{2b}$ represent the same as above) are more preferable.

Preferable embodiments of A, B, $R^{1a}$, $R^{1b}$, $R^{2a}$ and $R^{2b}$ in the above-mentioned general formulas (1-a-1), (1-a-2), (1-b-1), (1-b-2), (1-a-1a), (1-a-2a), (1-b-1a), (1-b-2a), (m-A), (p-A), (m-B), (p-B), (m-A-syn), (p-A-syn), (m-B-syn) and (p-B-syn) are similar to the preferable embodiments of A, B, $R^{1a}$, $R^{1b}$, $R^{2a}$ and $R^{2b}$ in the general formula (1). The partial structure:

[Chemical 16]

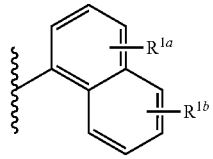

in the general formulas (1-a-2), (1-b-2), (1-a-2a) and (1-b-2a) is preferably a 4-fluoronaphthalen-1-yl group.

In the general formulas (1-a-1), (1-a-2), (1-a-1a), (1-a-2a), (m-A), (p-A), (m-A-syn) and (p-A-syn), B is not a single bond.

Regarding the preferable compounds of the general formula (1), compounds selected from the group consisting of the following:

N-[(1R)-1-(naphthalen-1-yl)ethyl]-3-[3-(2H-tetrazol-5-yl)phenyl]cyclopentanamine, N-[(1R)-1-(naphthalen-1-yl)ethyl]-3-[4-(2H-tetrazol-5-yl)
phenyl]cyclopentanamine,
N-{4-[3-{[(1R)-1-(naphthalen-1-yl)ethyl]
amino}cyclopentyl]benzoyl}glycine,
{3-[3-{[(1R)-1-(naphthalen-1-yl)ethyl]amino}cyclopentyl]
phenyl}acetic acid,
{4-[3-{[(1R)-1-(naphthalen-1-yl)ethyl]amino}cyclopentyl]
phenyl}acetic acid,
3-{4-[3-{[(1R)-1-(naphthalen-1-yl)ethyl]
amino}cyclopentyl]phenyl}propanoic acid,
{4-[3-{[(1R)-1-(naphthalen-1-yl)ethyl]amino}cyclopentyl]
phenoxy}acetic acid,
2-methyl-2-{4-[3-{[(1R)-1-(naphthalen-1-yl)ethyl]
amino}cyclopentyl]phenoxy}propanoic acid,
{3-[3-{[(1R)-1-(naphthalen-1-yl)ethyl]amino}cyclopentyl]
phenoxy}acetic acid,
2-methyl-2-{3-{[(1R)-1-(naphthalen-1-yl)ethyl]
amino}cyclopentyl]phenoxy}propanoic acid,
{2-fluoro-4-[3-{[(1R)-1-(naphthalen-1-yl)ethyl]
amino}cyclopentyl]phenoxy}acetic acid,
{4-[3-{[(1R)-1-(4-fluoronaphthalen-1-yl)ethyl]
amino}cyclopentyl]phenoxy acetic acid,
{4-[3-{[(1R)-1-(5-fluoronaphthalen-1-yl)ethyl]
amino}cyclopentyl]phenoxy}acetic acid,
{4-[3-{[(1R)-1-(3-chlorophenyl)ethyl]amino}cyclopentyl]
phenoxy}acetic acid,
{4-[3-{[(1R)-1-(6-fluoro naphthalen-1-yl)ethyl]
amino}cyclopentyl]phenoxy}acetic acid,
{4-[3-{[(1R)-1-(4,6-difluoronaphthalen-1-yl)ethyl]
amino}cyclopentyl]phenoxy}acetic acid,
{3-[3-{[(1R)-1-(4-fluoronaphthalen-1-yl)ethyl]
amino}cyclopentyl]phenyl}acetic acid,
{4-[3-{[(1R)-1-(4-fluoronaphthalen-1-yl)ethyl]
amino}cyclopentyl]phenyl}acetic acid,
N-[(1R)-1-(4-fluoronaphthalen-1-yl)ethyl]-3-[4-(2H-tetrazol-5-yl)phenyl]cyclopentanamine,
3-{4-[3-{[(1R)-1-(4-fluoronaphthalen-1-yl)ethyl]
amino}cyclopentyl]phenyl}propanoic acid,
2-{4-[3-{[(1R)-1-(4-fluoronaphthalen-1-yl)ethyl]
amino}cyclopentyl]phenoxy}-2-methylpropanoic acid,
{2-methyl-4-[3-{[(1R)-1-(naphthalen-1-yl)ethyl]
amino}cyclopentyl]phenoxy}acetic acid,
N-{4-[3-{[(1R)-1-(naphthalen-1-yl)ethyl]
amino}cyclopentyl]phenyl}glycine,
N-{4-[3-{[(1R)-1-(4-fluoronaphthalen-1-yl)ethyl]
amino}cyclopentyl]phenyl}glycine,
{4-[3-{[(1R)-1-(naphthalen-1-yl)ethyl]amino}cyclopentyl]
phenyl}thio)acetic acid,
{4-[3-{[(1R)-1-(4-fluoronaphthalen-1-yl)ethyl]
amino}cyclopentyl]phenyl}thio)acetic acid,
N-[(1R)-1-(naphthalen-1-yl)ethyl]-3-[4-(2H-tetrazol-5-yl-methoxy)phenyl]cyclopentanamine, and
N-[(1R)-1-(4-fluoronaphthalen-1-yl)ethyl]-3-[4-(2H-tetrazol-5-ylmethoxy)phenyl]cyclopentanamine or a pharmacologically acceptable salt thereof can be mentioned.

In addition, as another embodiment of the above-mentioned preferable compounds of the general formula (1), compounds selected from the following Table 1-1 to Table 1-3 or a pharmacologically acceptable salt thereof can be mentioned; however, the present invention shall not be limited to these compounds.

TABLE 1-1

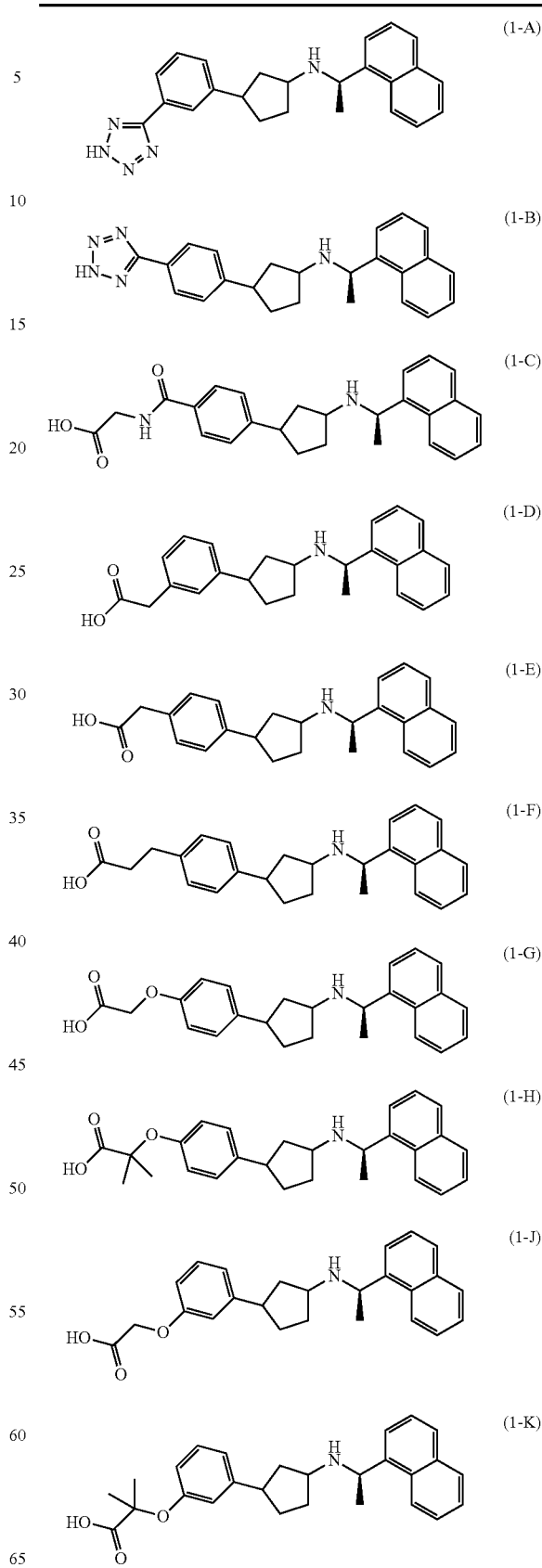

TABLE 1-1-continued

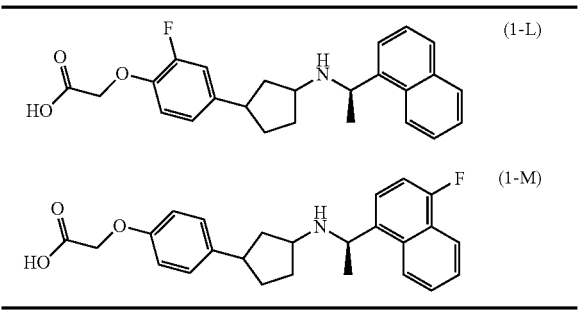

TABLE 1-2

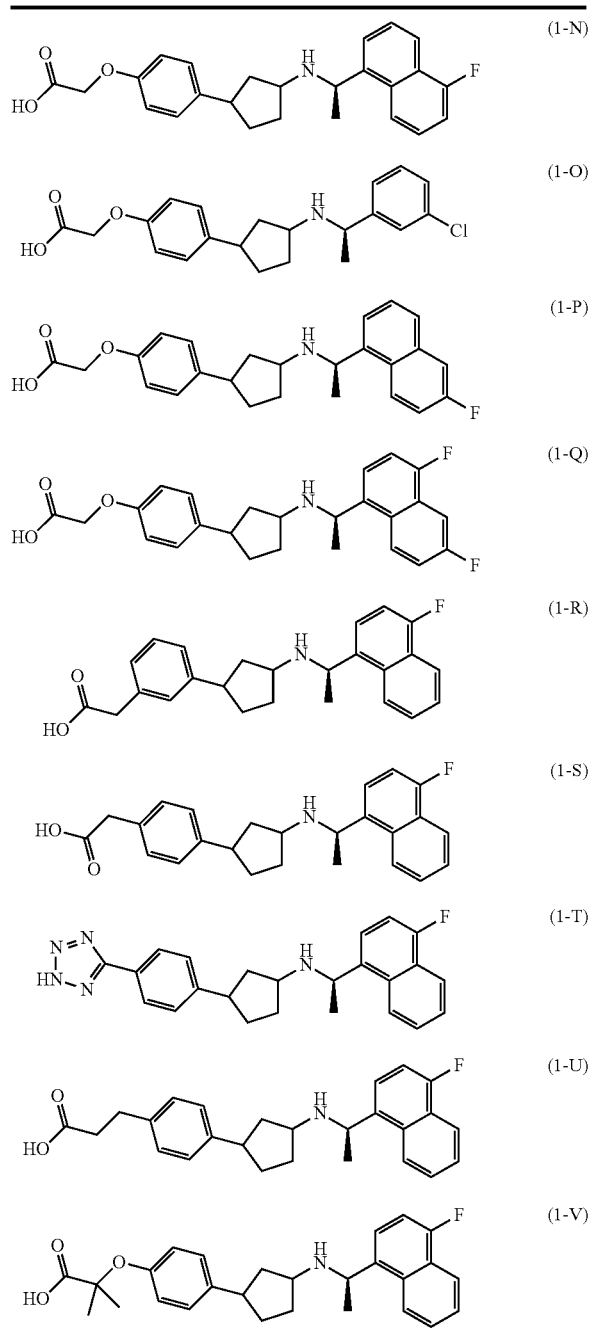

TABLE 1-2-continued

TABLE 1-3

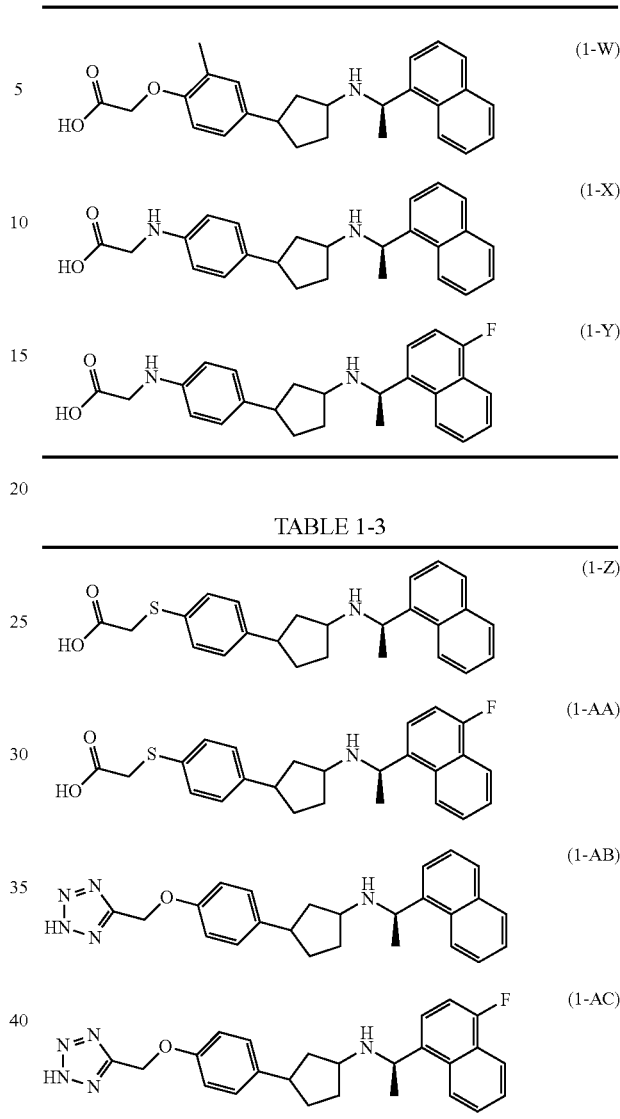

As specific examples of more preferable compounds of the general formula (1), compounds selected from the group consisting of the following:

N-{4-[3-{[(1R)-1-(naphthalen-1-yl)ethyl]amino}cyclopentyl]benzoyl}glycine,

{3-[3-{[(1R)-1-(naphthalen-1-yl)ethyl]amino}cyclopentyl]phenyl}acetic acid,

{4-[3-{[(1R)-1-(naphthalen-1-yl)ethyl]amino}cyclopentyl]phenyl}acetic acid,

3-{4-[3-{[(1R)-1-(naphthalen-1-yl)ethyl]amino}cyclopentyl]phenyl}propanoic acid, {4-[3-{[(1R)-1-(naphthalen-1-yl)ethyl]amino}cyclopentyl]phenoxy}acetic acid, 2-methyl-2-{4-[3-{[(1R)-1-(naphthalen-1-yl)ethyl]amino}cyclopentyl]phenoxy}propanoic acid, {3-[3-{[(1R)-1-(naphthalen-1-yl)ethyl]amino}cyclopentyl]phenoxy}acetic acid, {4-[3-{[(1R)-1-(4-fluoronaphthalen-1-yl)ethyl]amino}cyclopentyl]phenoxy}acetic acid, {4-[3-{[(1R)-1-(4,6-difluoronaphthalen-1-yl)ethyl]amino}cyclopentyl]phenoxy}acetic acid, {3-[3-{[(1R)-1-(4-fluoronaphthalen-1-yl)ethyl]amino}cyclopentyl]phenyl}acetic acid, {4-[3-{[(1R)-1-(4-fluoronaphthalen-1-yl)ethyl]amino}cyclopentyl]phenyl}acetic acid, 3-{4-[3-{[(1R)-1-(4-fluoronaphthalen-1-yl)ethyl]amino}cyclopentyl]phenyl}propanoic acid, 2-{4-[3-{[(1R)-1-(4-fluoronaphthalen-1-yl)ethyl]amino}cyclopentyl]phenoxy}-2-methylpropanoic acid, and ({4-[3-{[(1R)-1-(4-fluoronaphthalen-1-yl)ethyl]amino}cyclopentyl]phenyl}thio)acetic acid or a pharmacologically acceptable salt thereof can be mentioned.

In addition, as another embodiment of the above-mentioned preferable compounds of the general formula (1), compounds selected from the following Table 2 or a pharmacologically acceptable salt thereof can be mentioned; however, the present invention shall not be limited to these compounds.

TABLE 2

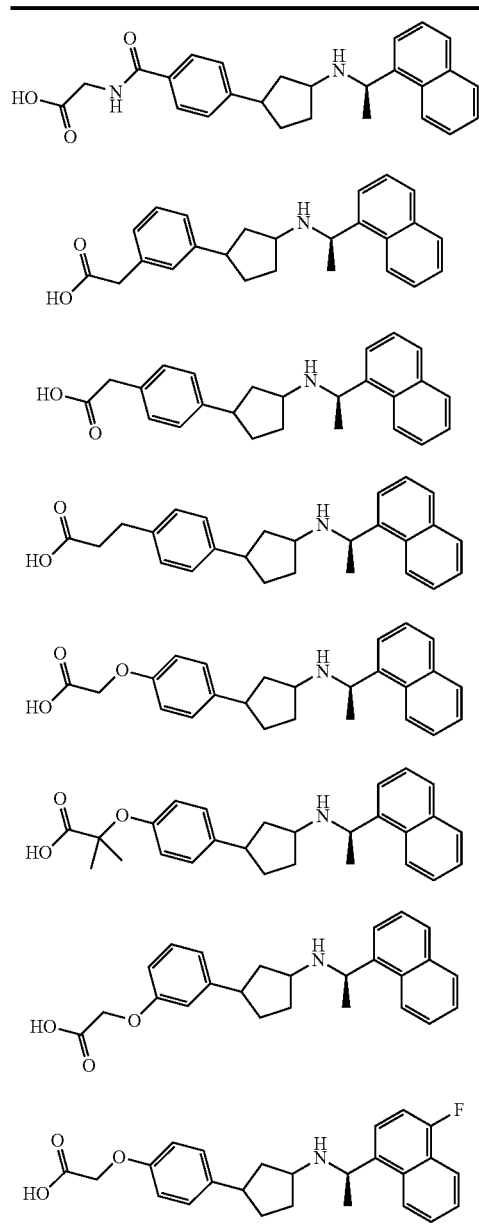

TABLE 2-continued

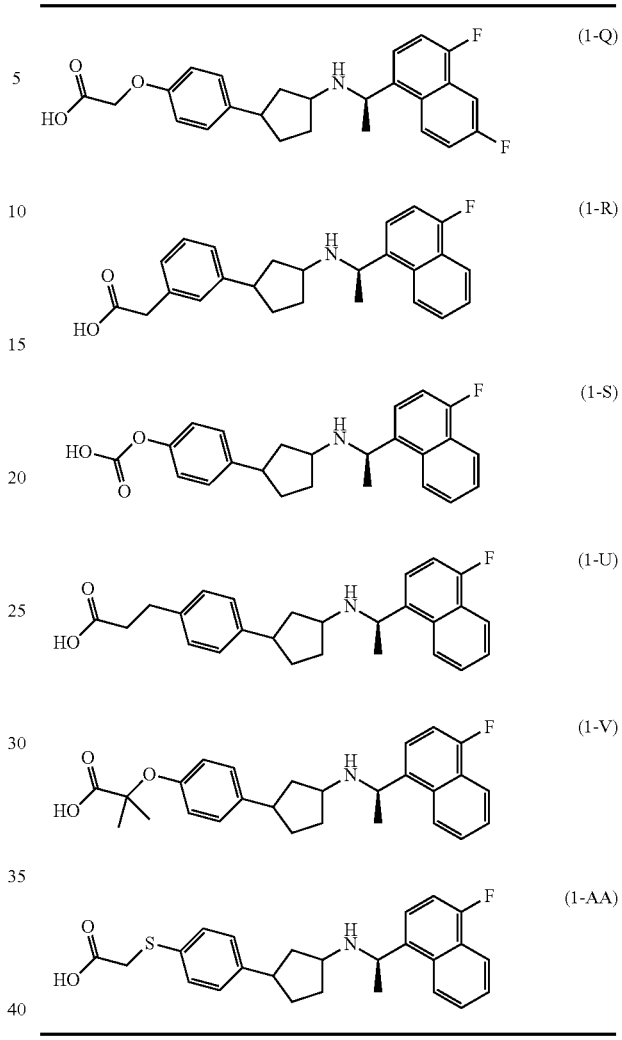

As specific examples of more preferable compounds of the general formula (1), compounds selected from the group consisting of the following:

{4-[3-{[(1R)-1-(4-fluoronaphthalen-1-yl)ethyl]amino}cyclopentyl]phenoxy}acetic acid, {3-[3-{[(1R)-1-(4-fluoronaphthalen-1-yl)ethyl]amino}cyclopentyl]phenyl}acetic acid, {4-[3-{[(1R)-1-(4-fluoronaphthalen-1-yl)ethyl]amino}cyclopentyl]phenyl}acetic acid, 3-{4-[3-{[(1R)-1-(4-fluoronaphthalen-1-yl)ethyl]amino}cyclopentyl]phenyl}propanoic acid, 2-{4-[3-{[(1R)-1-(4-fluoronaphthalen-1-yl)ethyl]amino}cyclopentyl]phenoxy}-2-methylpropanoic acid, and ({4-[3-{[(1R)-1-(4-fluoronaphthalen-1-yl)ethyl]amino}cyclopentyl]phenyl}thio)acetic acid or a pharmacologically acceptable salt thereof can be mentioned.

As specific examples of preferable compounds of the general formula (1), compounds selected from the following Table 3-1 to Table 3-3 or a pharmacologically acceptable salt thereof can be mentioned; however, the present invention shall not be limited to these compounds.

TABLE 3-1
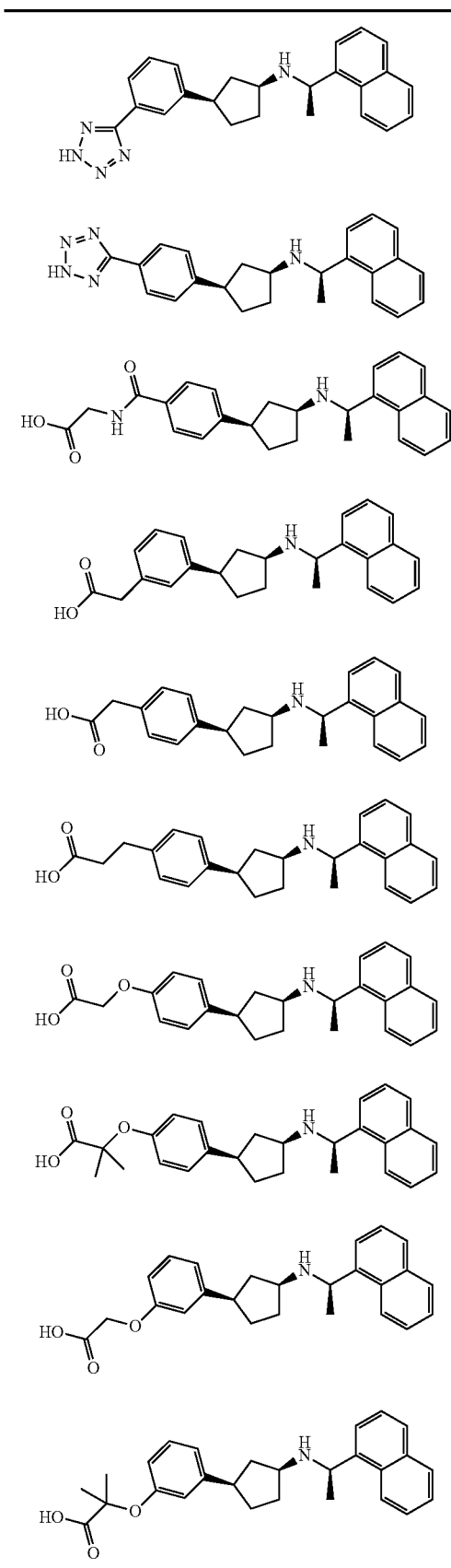
TABLE 3-1-continued
TABLE 3-2
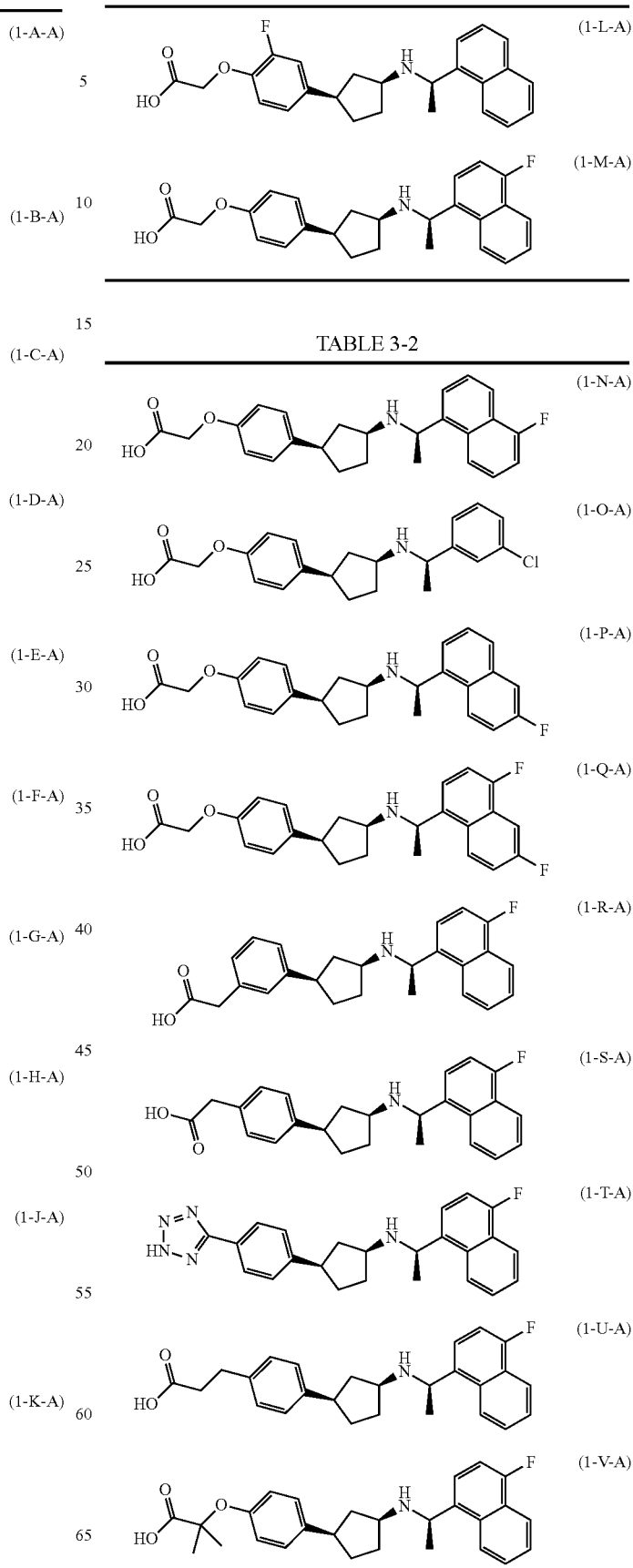

TABLE 3-2-continued (1-W-A)

(1-X-A)

(1-Y-A)

TABLE 3-3

(1-Z-A)

(1-AA-A)

(1-AB-A)

(1-AC-A)

In addition, as specific examples of further preferable compounds of the general formula (1), compounds selected from the following Table 4 or a pharmacologically acceptable salt thereof can be mentioned; however, the present invention shall not be limited to these compounds.

TABLE 4

(1-C-A)

(1-D-A)

TABLE 4-continued (1-E-A)

(1-F-A)

(1-G-A)

(1-H-A)

(1-J-A)

(1-M-A)

(1-Q-A)

(1-R-A)

(1-S-A)

(1-U-A)

(1-V-A)

TABLE 4-continued
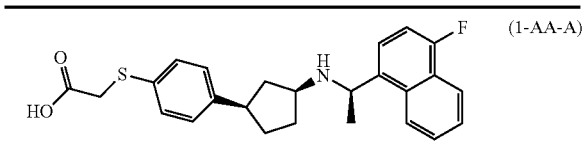
(1-AA-A)
In addition, as examples of compounds of the general formula (1), compounds selected from the following Table 5 or a pharmacologically acceptable salt thereof can be mentioned; however, the present invention shall not be limited to these compounds.
TABLE 5
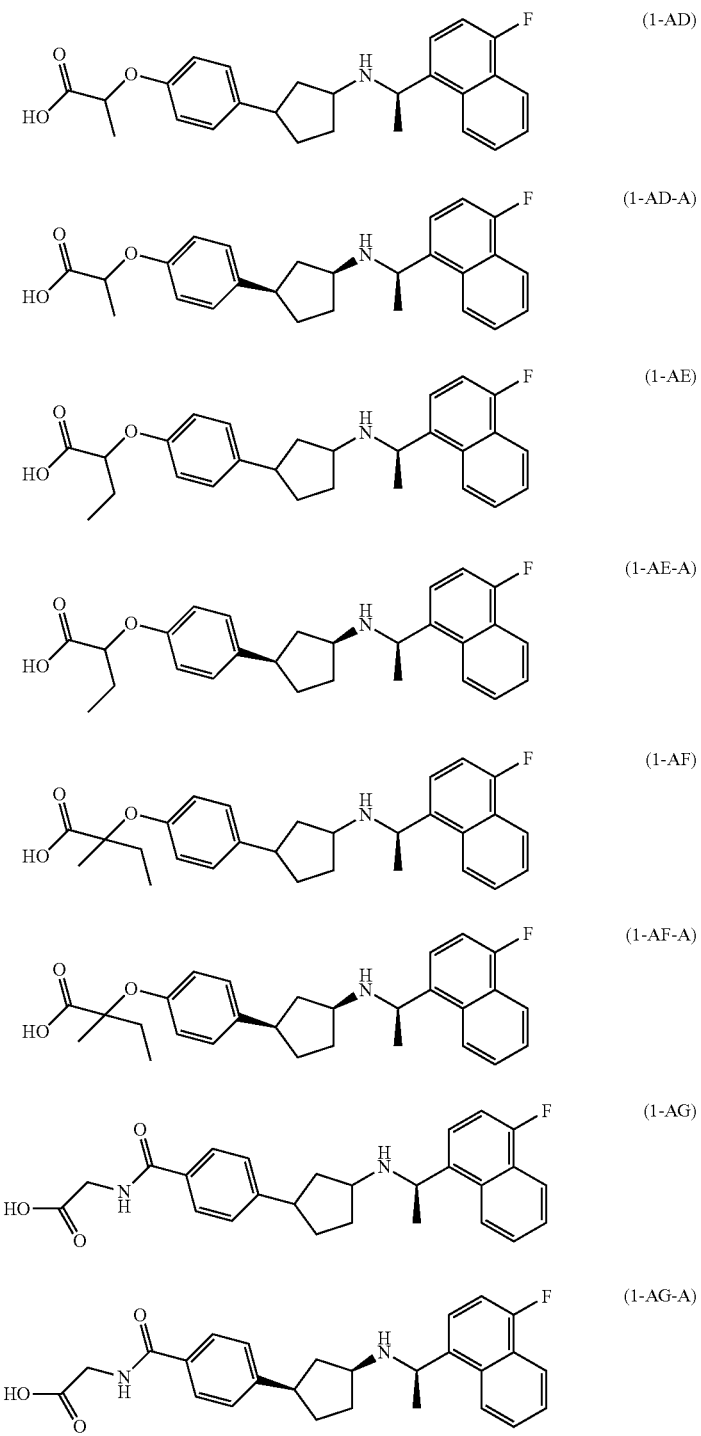

TABLE 5-continued

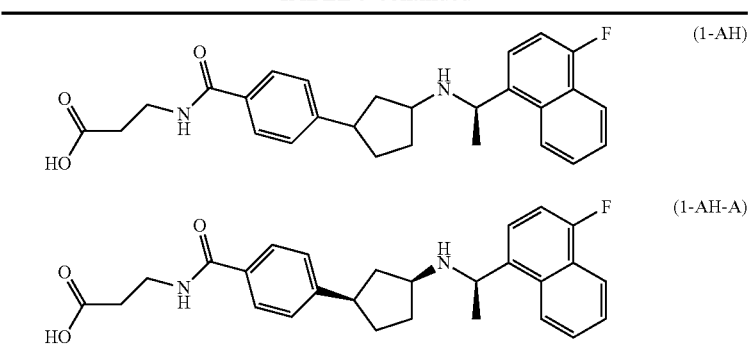

Hereinafter, a method for producing the cycloalkylamine derivatives of the present invention will be explained; however, the present invention shall not be limited to this method.

Cycloalkylamine derivative (1) of the present invention represented by the following general formula (1):

[Chemical 17]

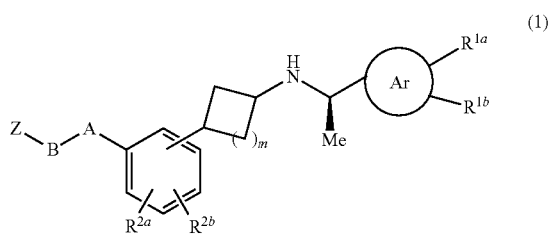

(wherein, Ar, A, B, Z, $R^{1a}$, $R^{1b}$, $R^{2a}$, $R^{2b}$ and m represent the same as described above) can be produced by a method shown in the following [Scheme 1]:

[Scheme 1]

[Chemical 18]

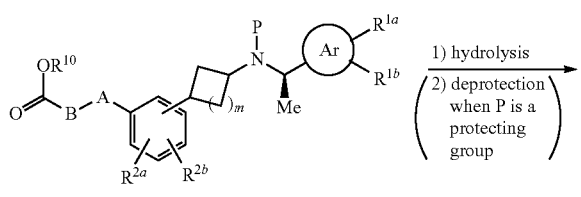

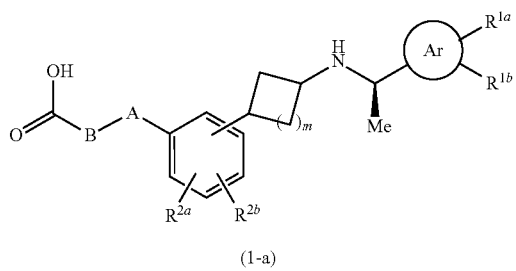

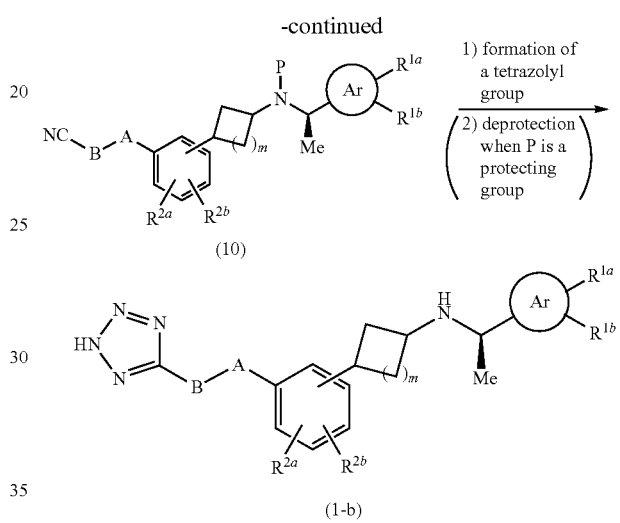

(wherein, P represents a hydrogen atom or a protecting group such as a tert-butoxycarbonyl group; $R^{10}$ represents a C1-C6 alkyl group; Ar, A, B, $R^{1a}$, $R^{1b}$, $R^{2a}$, $R^{2b}$ and m represent the same as above).

Compound (1-a), which is a compound of formula (1) (wherein, B is not a single bond) wherein Z is a carboxy group can be produced by hydrolysis of C1-C6 alkyl esters (7a), (13), (17), (20), (24) or (30), followed by deprotection by acid treatment in the case where P is a tert-butoxycarbonyl group (Boc group). In addition, compound (1-b), which is a compound of formula (1) wherein Z is a tetrazolyl group and A and B are single bonds, can be produced from a cyano compound (10) via formation of a tetrazolyl group, followed by deprotection by acid treatment in the case where P is a Boc group.

Regarding the hydrolysis, alkali hydrolysis is preferable. As a solvent used for the hydrolysis, although there is no particular limitation so long as it is used in a usual hydrolysis reaction, there may be mentioned for example, alcohols such as methanol, ethanol, n-propanol, isopropanol, n-butanol, isobutanol, tert-butanol, isoamyl alcohol, diethylene glycol, glycerin, octanol, cyclohexanol and methyl cellosolve; ethers such as diethyl ether, diisopropyl ether, tetrahydrofuran, 1,4-dioxane, dimethoxyethane, and diethylene glycol dimethyl ether; water; or a solvent mixture of water and the above-mentioned organic solvents. Here, methanol, ethanol, isopropanol, tetrahydrofuran, water; or a solvent mixture of these are preferable.

Regarding the alkali used for the hydrolysis, there may be mentioned for example, alkali metal carbonates such as lithium carbonate, sodium carbonate and potassium carbonate; alkali metal hydroxides such as lithium hydroxide, sodium hydroxide and potassium hydroxide; metal alkoxides such as lithium methoxide, sodium methoxide, sodium ethoxide and potassium tert-butoxide; ammonias such as aqueous ammonia and conc. ammonia-methanol. Here, sodium hydroxide and potassium hydroxide are preferable. Regarding the reaction temperature, the reaction is usually conducted at 0 to 100° C., preferably 0 to 60° C., and more preferably in the range of 20 to 60° C.

With respect to the reaction for the formation of the tetrazolyl group, compound (1-b), which is a tetrazole derivative, can be produced from compound (10), which is a nitrile derivative, in accordance with a known reaction which converts a cyano group into a tetrazolyl group. For example, in an amide solvent such as N,N-dimethylformamide as a solvent, compound (10) may be treated with aluminum azide or ammonium azide in a temperature range such as room temperature to the boiling point of the solvent, preferably in the range of 80 to 120° C., to give compound (1-b) which is in a tetrazole form. The aluminum azide or the ammonium azide used in the above reaction can be easily prepared in accordance with a known method, by treating alkali metal azides such as sodium azide with aluminum chloride or quaternary ammonium salts such as ammonium chloride or pyridine hydrochloric acid salt.

Regarding deprotection of the Boc group, documents described in reviews such as Protective Groups in Organic Synthesis (T. W. Green and P. G. M. Wuts, John Wiley & Sons, Inc., New York, 1991) can be referred to, and as the acid used, hydrochloric acid is preferable.

Compound (7a) in [Scheme 1] can be produced as shown in [Scheme 2]:

[Scheme 2]

[Chemical 19]

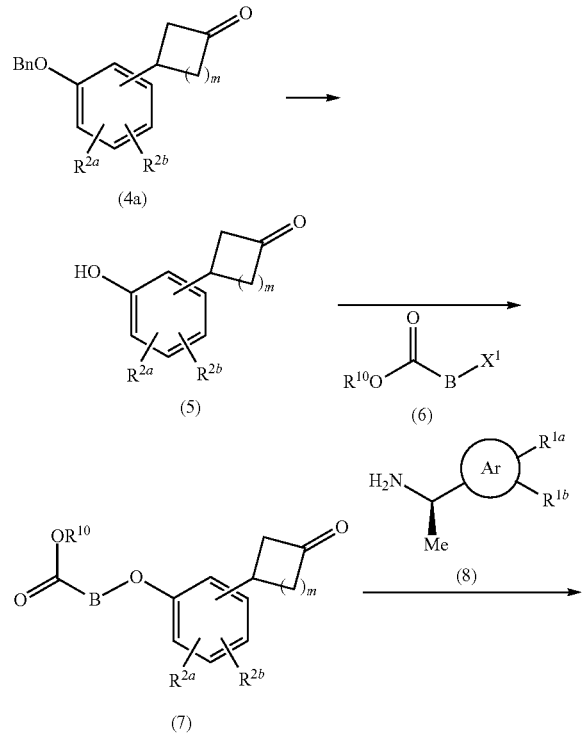

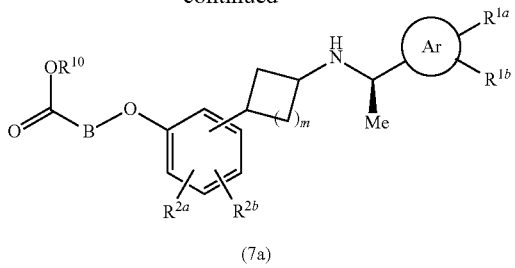

(7a)

(wherein, $X^1$ represents a leaving group such as a halogeno group or a trifluoromethanesulfonyloxy group; Ar, B, $R^{1a}$, $R^{1b}$, $R^{2a}$, $R^{2b}$, $R^{10}$ and m represent the same as above, with the proviso that B is not a single bond). Compound (7a) can be produced by conducting catalytic reduction with compound (4a), which is a benzyl derivative, to produce compound (5) which is a phenol derivative, subjecting compound (5) to alkylation by using compound (6) in the presence of a base to produce compound (7), and then conducting reductive amination reaction by condensing compound (7) with amine compound (8) in the presence of a reducing agent.

As a reference document for conducting catalytic reduction of compound (4a) which is a benzyloxy derivative, thereby achieving elimination of a benzyl group to obtain compound (5) which is a phenol derivative, a document described in reviews such as Protective Groups in Organic Synthesis (T. W. Green and P. G. M. Wuts, John Wiley & Sons, Inc., New York, 1991) can be referred to. Regarding the alkylation reaction, a method which is widely used for alkylation of phenol derivatives can be used, and compound (6) which is used as the alkylating agent in the alkylation reaction is commercially available or can be produced by a known method.

Regarding the reductive amination reaction, there may be mentioned for example, reduction with metal borohydrides such as sodium cyanoborohydride, sodium triacetoxy borohydride, and sodium borohydride; and catalytic hydrogenation in the presence of metal catalysts such as palladium carbon, platinum and Raney nickel. Here, reduction with metal borohydrides is preferable. Regarding the reaction solvent, there is no limitation so long as it does not inhibit the reaction and dissolves the starting material to some extent. There may be mentioned for example, alcohols such as methanol, ethanol and isopropanol; aromatic hydrocarbons such as benzene, toluene and xylene; halogenated hydrocarbons such as dichloromethane, 1,2-dichloroethane, chlorobenzene and dichlorobenzene; and ethers such as diethyl ether, diisopropyl ether, tert-butylmethyl ether and tetrahydrofuran. Here, alcohols and halogenated hydrocarbons are preferable, and methanol, dichloromethane and 1,2-dichloroethane are more preferable. In addition, organic acids such as acetic acid and propionic acid may be added to the reaction solvent. Regarding the reaction temperature, the reaction may be carried out usually in a range of 0 to 50° C., preferably 0 to 30° C. Regarding the reaction time, it is usually 10 minutes to 24 hours.

Further, compound (7a) can also be produced as shown in the following [Scheme 2a]:

[Scheme 2a]

[Chemical 20]

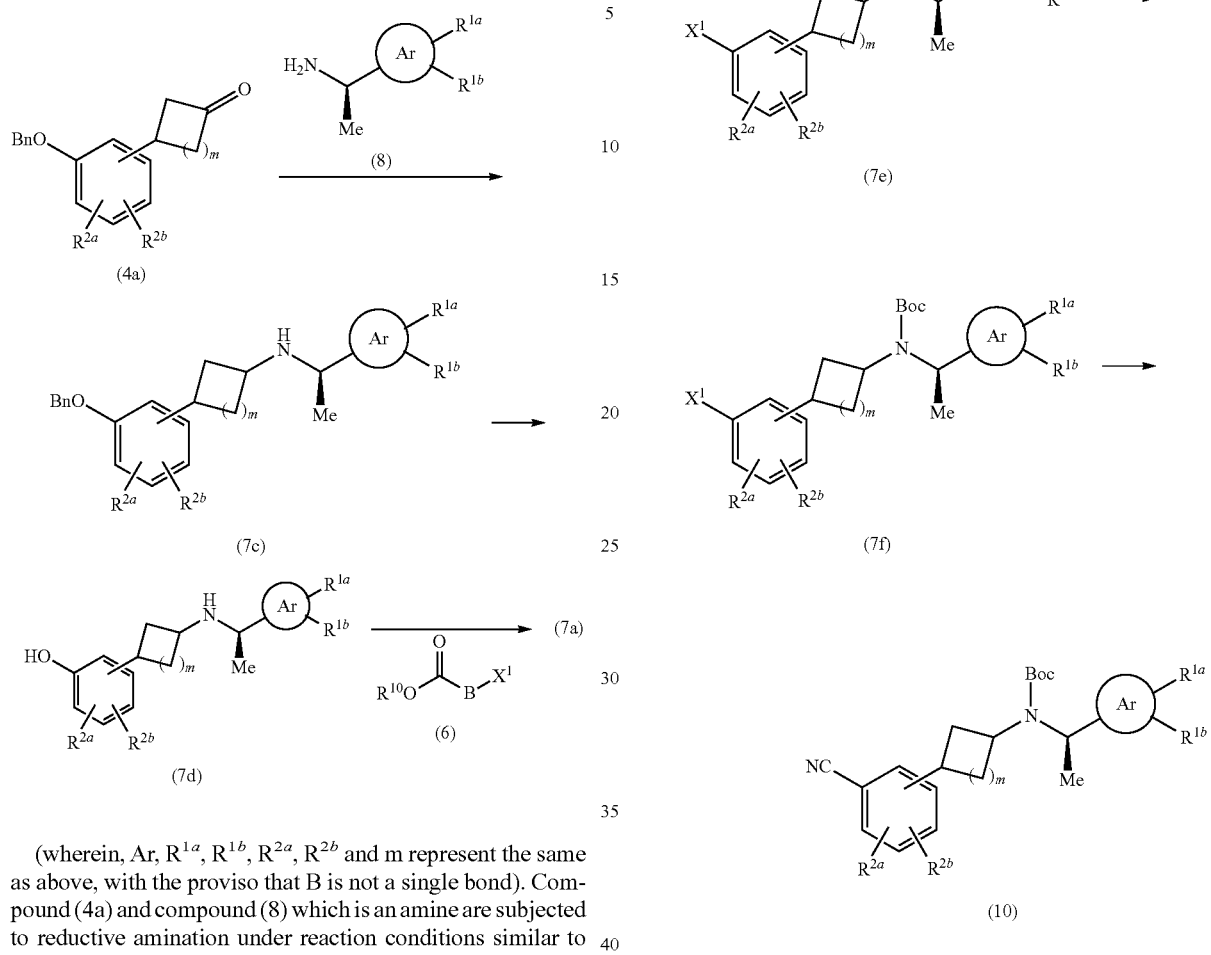

(wherein, Ar, $R^{1a}$, $R^{1b}$, $R^{2a}$, $R^{2b}$ and m represent the same as above, with the proviso that B is not a single bond). Compound (4a) and compound (8) which is an amine are subjected to reductive amination under reaction conditions similar to those used in the production of compound (7a) in [Scheme 2], thereby producing compound (7c). Subsequently, by elimination of the benzyl group of compound (7c) via reductive reaction, compound (7d) which is a phenol derivative is produced, and then compound (7d) can be alkylated under reaction conditions similar to those shown in [Scheme 2], thereby producing compound (7a).

Compound (10) in the above-mentioned [Scheme 1], which is a cyano compound, can be produced as shown in [Scheme 3]:

[Scheme 3]

[Chemical 21]

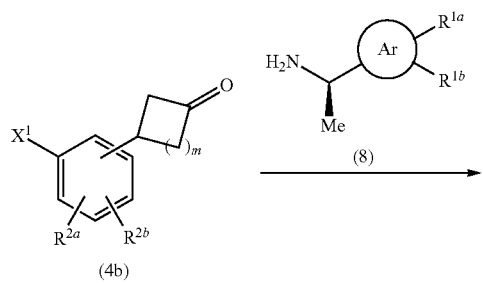

(wherein, Boc represents a tert-butoxycarbonyl group; $X^1$ represents a leaving group such as a halogeno group and a trifluoromethanesulfonyloxy group; and Ar, $R^{1a}$, $R^{1b}$, $R^{2a}$, $R^{2b}$ and m represent the same as described above). Compound (10) can be produced by converting compound (4b) which is a ketone compound and compound (8) which is an amine compound into compound (7e) by way of correspondingly applying the production method of compound (7a) shown in [Scheme 2], followed by introducing Boc group to compound (7e), thereby producing compound (7f), and then subjecting compound (7f) to cyanation.

As a reference document regarding the reaction conditions for introducing Boc group, Protective Groups in Organic Synthesis (T. W. Green and P. G. M. Wuts, John Wiley & Sons, Inc., New York, 1991) can be referred to for example. Preferably, a method which treats with triphosgene-tert-butanol and a method which treats with di(tert-butyl)dicarbonate can be mentioned. As a reference document for cyanation, there can be mentioned for example, methods of T. Desmond et al [Synth. Comm. 1994, 24, 887-890].

Compound (13) in [Scheme 1] can be produced as shown in [Scheme 4]:

[Scheme 4]

[Chemical 22]

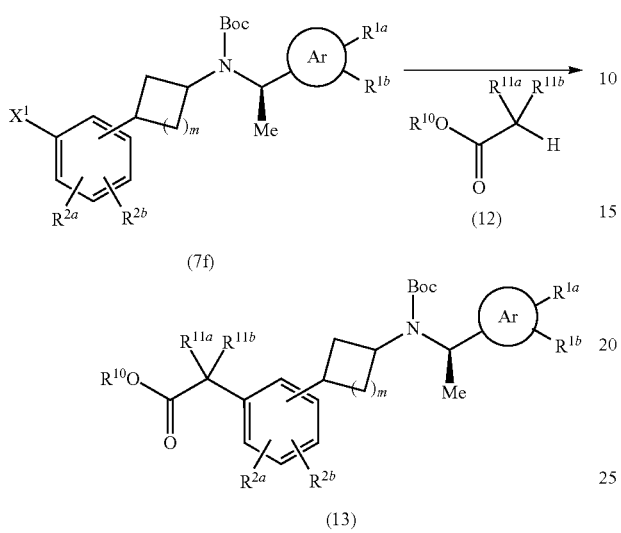

(wherein, Boc represents a tert-butoxycarbonyl group; $R^{11a}$ and $R^{11b}$ are the same or different from each other and represent a hydrogen atom, a methyl group or an ethyl group, or $R^{11a}$ and $R^{11b}$ together with the carbon atom to which they are attached form a cyclopropane ring or a cyclobutane ring; Ar, $R^{1a}$, $R^{1b}$, $R^{2a}$, $R^{2b}$, $R^{10}$, m and $X^1$ represent the same as described above). Compound (13) can be produced by conducting a coupling reaction of compound (7f) and compound (12) in the presence of a metal catalyst. Regarding the coupling reaction of compound (7f) and compound (12) in the presence of a metal catalyst, the method of Hartwig et al. [J. Am. Chem. Soc., 2002, 124, 12557-12565] or the like can be referred to.

Compound (17) in the above-mentioned [Scheme 1] can be produced as shown in 5]:

[Scheme 5]

[Chemical 23]

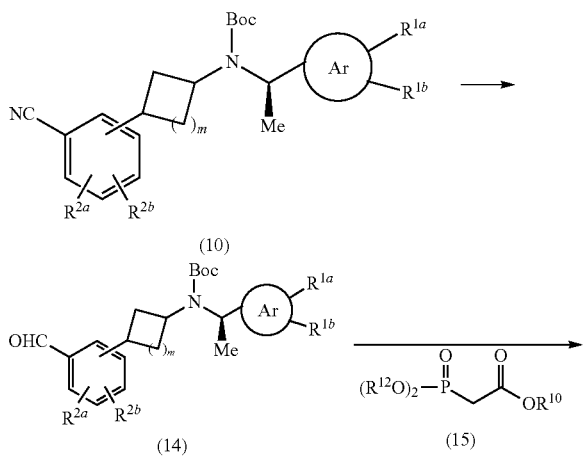

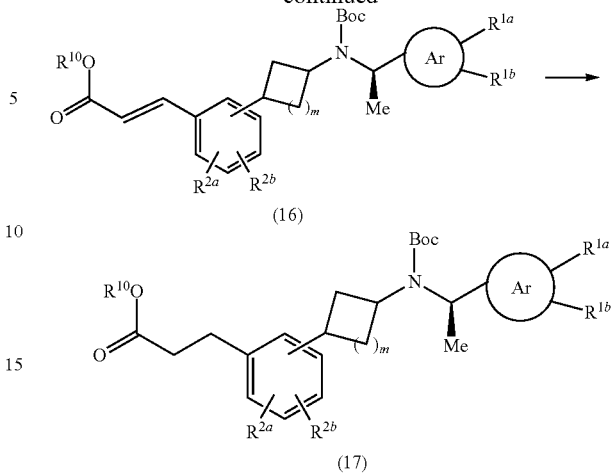

(wherein, Boc represents a tert-butoxycarbonyl group; $R^{12}$ represents a C1-C6 alkyl group; Ar, $R^{1a}$, $R^{1b}$, $R^{2a}$, $R^{2b}$, $R^{10}$ and m represent the same as described above). Compound (17) can be produced by reducing compound (10) which is a cyano compound with a metal hydride to produce compound (14), followed by converting compound (14) into compound (16) which is an α,β-unsaturated ester via Horner-Emmons reaction, and then performing catalytic hydrogenation of compound (16).

Regarding the metal hydride, diisobutyl aluminum hydride is preferable.

Regarding Horner-Emmons reaction, the method of Maryanoff et al. [Chem. Rev. 1989, 89, 863-927] or the like can be mentioned as a reference document, and the reaction involves treating compound (14) which is an aldehyde derivative, with compound (15) which is a phosphoric acid ester derivative, in an inert solvent, in the presence of a base, thereby producing compound (16).

As compound (15) which is a phosphoric acid ester derivative, phosphonoacetic acid triethyl ester is preferable. Regarding the reaction solvent, there is no particular limitation so long as it does not inhibit the reaction and dissolves the starting material to some extent. There may be mentioned for example, aromatic hydrocarbons such as benzene, toluene and xylene; halogenated hydrocarbons such as dichloromethane, 1,2-dichloroethane, chlorobenzene and dichlorobenzene; ethers such as diethyl ether, diisopropyl ether, tert-butylmethyl ether and tetrahydrofuran; nitriles such as acetonitrile and isobutyronitrile; amides such as formamide, N,N-dimethylformamide, N,N-dimethylacetamide and hexamethyl phosphoro triamide; and sulfoxides such as dimethyl sulfoxide and sulfolane. Here, ethers are preferable, and tetrahydrofuran is more preferable.

Regarding the base used in the above-mentioned reaction, there is no particular limitation so long as it is used as a base in usual reactions, and there can be mentioned for example, inorganic bases including alkali metal carbonates such as sodium carbonate, potassium carbonate and lithium carbonate; alkali metal bicarbonates such as sodium bicarbonate, potassium bicarbonate and lithium bicarbonate; alkali metal hydrides such as lithium hydride, sodium hydride and potassium hydride; alkali metal hydroxides such as sodium hydroxide, potassium hydroxide, barium hydroxide and lithium hydroxide; alkali metal fluorides such as sodium fluoride and potassium fluoride; alkali metal alkoxides such as sodium methoxide, sodium ethoxide, potassium methoxide, potassium ethoxide, potassium tert-butoxide and lithium methoxide; organic amines such as N-methylmorpholine, triethylamine, tripropylamine, tributylamine, diisopropylethylamine, dicyclohexylamine, N-methylpiperidine, 4-pyrrolidinopyridine, picoline, 4-(N,N-dimethylamino)pyridine, 2,6-di(tert-butyl)-4-methylpyridine, N,N-dimethylaniline, N,N-diethylaniline, 1,4-diazabicyclo[4.3.0]octane (DABCO), 1,8-diazabicyclo[5.4.0]-7-undecene (DBU) and 1,5-diazabicyclo[4.3.0]-5-nonene (DBN); or organic metal bases such as butyl lithium, lithium diisopropyl amide and lithium bis(trimethylsilyl)amide. Here, alkali metal alkoxides and alkali metal hydrides are preferable, and sodium hydride and potassium hydride are more preferable. The reaction temperature may differ depending on the starting compound, reagent used, and types of solvent; however, it is usually −20 to 100° C., preferably 0 to 60° C., and more preferably 20 to 60° C. The reaction time is usually 10 minutes to 24 hours, and 1 to 24 hours is preferable.

The catalytic hydrogenation reaction which includes producing compound (17) from compound (16) is conducted in an inert solvent, in the presence of a metal catalyst. Regarding the reaction solvent, there is no particular limitation, and it may be alcohols such as methanol, ethanol and isopropanol; ethers such as diethyl ether, diisopropyl ether, tert-butylmethyl ether, tetrahydrofuran and 1,4-dioxane; aromatic hydrocarbons such as benzene, toluene and xylene; aliphatic hydrocarbons such as hexane and cyclohexane; and esters such as ethyl acetate and propyl acetate. Here, alcohols are preferable.

Regarding the metal catalyst, there is no particular limitation so long as it is used in a usual catalytic reduction reaction, and there may be mentioned for example, palladium carbon, palladium black, platinum oxide, platinum black, rhodium-aluminum oxide, triphenylphosphine-rhodium chloride (Wilkinson complex), palladium-barium sulfate and Raney nickel. Here, palladium carbon is preferable.

Regarding the hydrogen pressure, it is usually 1 to 10 atmospheric pressure. Regarding the reaction temperature, the reaction can be carried out at 0 to 50° C., preferably in the range of 0 to 30° C. Regarding the reaction time, it is usually 10 minutes to 24 hours, preferably 1 to 12 hours.

Compound (20) in [Scheme 1] can be produced as shown in [Scheme 6]:

[Scheme 6]

[Chemical 24]

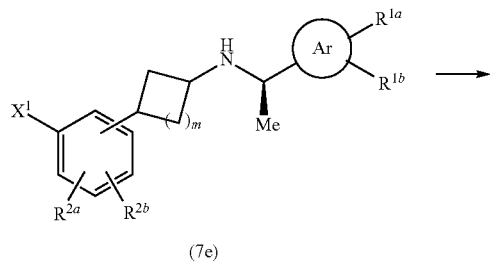

(7e)

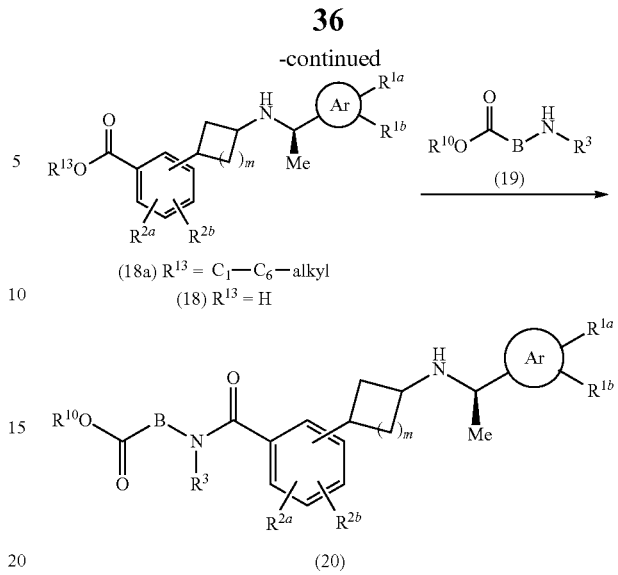

(18a) $R^{13} = C_1\text{—}C_6\text{—alkyl}$
(18) $R^{13} = H$ (20)

(wherein, $R^{13}$ represents a hydrogen atom or a C1-C6 alkyl group; and Ar, B, $R^{1a}$, $R^{1b}$, $R^{2a}$, $R^{2b}$, $R^3$, $R^{10}$, m and $X^1$ represent the same as above, with the proviso that B is not a single bond). Compound (20) can be produced by conducting a carboxylation reaction which treats compound (7e) in the presence of a transition metal catalyst under a carbon monoxide flow to produce compound (18a), followed by alkali hydrolysis of compound (18a) to produce compound (18) which is a carboxylic acid derivative. Subsequently, compound (18) is converted into an acid halide by treatment with a halogenation reagent, followed by condensation with compound (19) which is an amine derivative. Regarding the carboxylation reaction, cited documents described in the reviews of Thompson et al. [Comprehensive Organic Synthesis, Pergamon: Oxford, 1991, Vol. 3, 1015-1043] can be mentioned as reference documents. Compound (18a) can be produced by correspondingly applying the reaction conditions described in these documents. Regarding the alkali hydrolysis to produce compound (18) which is a carboxylic acid derivative from compound (18a), conditions for producing compound (1-a) in [Scheme 1] can be correspondingly applied.

Regarding the halogenation reagent which converts a compound into an acid halide, there may be mentioned for example, oxalyl chloride, thionyl chloride and phosphoryl chloride. Here, oxalyl chloride and thionyl chloride are preferable. Regarding the solvent, there is no particular limitation so long as it is inert with respect to the present reaction, and there may be mentioned for example, halogenated hydrocarbons such as dichloromethane, chloroform, carbon tetrachloride, dichloroethane, chlorobenzene and dichlorobenzene; ethers such as diethyl ether, diisopropyl ether, tetrahydrofuran, 1,4-dioxane, dimethoxyethane and diethylene glycol dimethyl ether. Here, dichloromethane and tetrahydrofuran are preferable. In addition, N,N-dimethylformamide may be added in a catalytic amount in order to accelerate the halogenation reaction.

In the above-mentioned condensation, it is preferable to use a base. As such base, there may be mentioned for example, organic bases such as triethylamine, tributylamine, diisopropylethylamine, N-methylmorpholine, pyridine, 4-(N,N-dimethylamino)pyridine (DMAP), 4-pyrrolidinopyridine, N,N-dimethylaniline, N,N-diethylaniline, 1,5-diazabicyclo[4.3.0]non-5-ene (DBN), 1,4-diazabicyclo[2.2.2]octane (DABCO) and 1,8-diazabicyclo[5.4.0]undec-7-ene (DBU). Here, triethylamine, diisopropylethylamine, pyridine and 4-(N,N-dimethylamino)pyridine are preferable, and triethylamine and pyridine are more preferable. Regarding the reaction temperature for the condensation, the reaction is usually conducted at −20 to 60° C., preferably −20 to 30° C. Regarding the time for the condensation reaction, it is usually in the range of 10 minutes to 24 hours, preferably in the range of 30 minutes to 6 hours.

Compound (24) in [Scheme 1] can be produced as shown in [Scheme 7]:

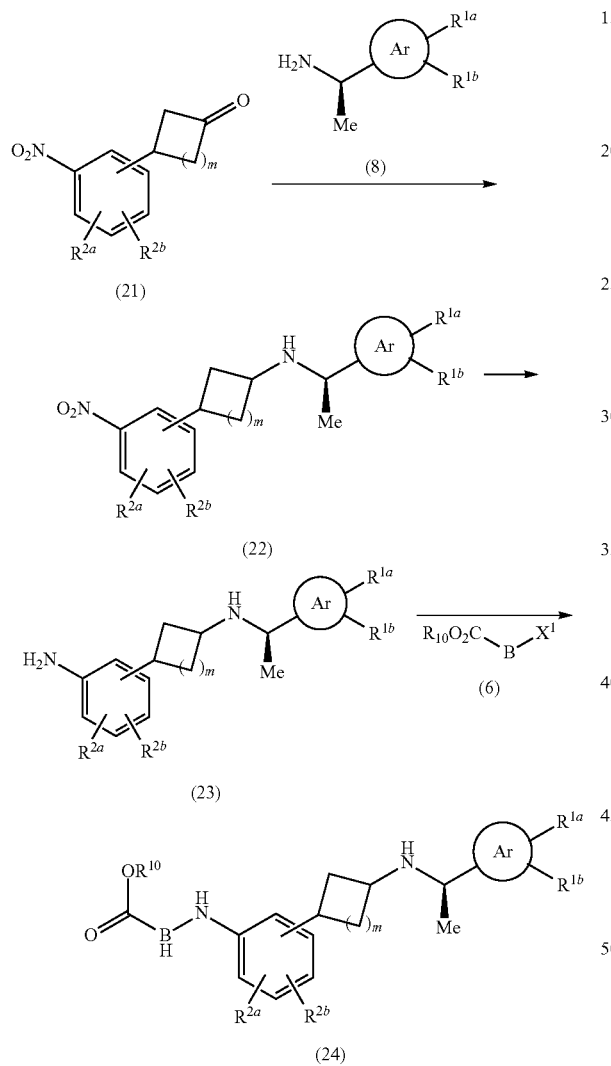

(wherein, Ar, B, $R^{1a}$, $R^{1b}$, $R^{2a}$, $R^{2b}$, $R^{10}$, m and $X^1$ represent the same as above, with the proviso that B is not a single bond). Compound (21) and compound (8) which is an amine are subjected to reductive amination under reaction conditions similar to those used in the production of compound (7a) in [Scheme 2], thereby producing compound (22). Subsequently, via reductive reaction of a nitro group of compound (22), compound (23) which is an aniline derivative is produced, and then compound (23) can be alkylated under reaction conditions similar to those shown in [Scheme 2], thereby producing compound (24).

Compound (30) in [Scheme 1] can be produced as shown in [Scheme 8]:

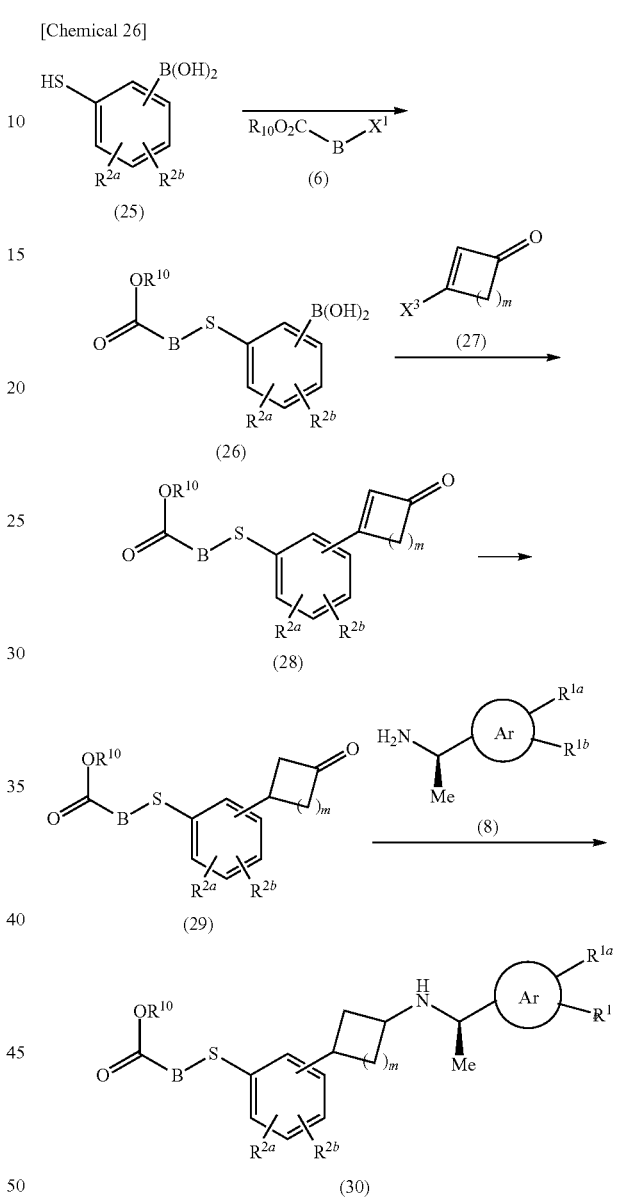

(wherein, Ar, B, $R^{1a}$, $R^{1b}$, $R^{2a}$, $R^{2b}$, $R^{10}$, m and $X^1$ represent the same as above, with the proviso that B is not a single bond). Compound (25) is alkylated under reaction conditions similar to those as shown in [Scheme 2], thereby producing compound (26), which is subjected to Suzuki coupling reaction with compound (27), thereby producing compound (28). Subsequently, via reduction of an enone moiety, a ketone compound (29) is produced, which can be then subjected to reductive amination with compound (8) which is an amine under reaction conditions similar to those used in the production of compound (7a) in [Scheme 2], thereby producing compound (30).

Regarding the Suzuki coupling reaction, [Chem. Rev. 1995, 95, 2457-2483] or the like can be mentioned as a reference document, and the reaction can be carried out in accordance with the above-mentioned document and cited documents in the document.

The reduction reaction for producing compound (29) can be carried out under reaction conditions similar to those used in the production of compound (17) in [Scheme 5]. In addition, the present reaction can be carried out for producing an optically active compound, in accordance with the method described in D. W. C. MacMillan et al. [J. Am. Chem. Soc., 2006, 128, 12662-12663].

Compound (4a) which is a benzyloxy derivative in [Scheme 2] and [Scheme 2a], compound (4b) in which $X^1$ in [Scheme 3] is a halogeno group or a trifluoromethanesulfonyloxy group, and compound (21) which is a nitro derivative in [Scheme 7] can be produced as shown in the following [Scheme 9]:

[Scheme 9]

[Chemical 27]

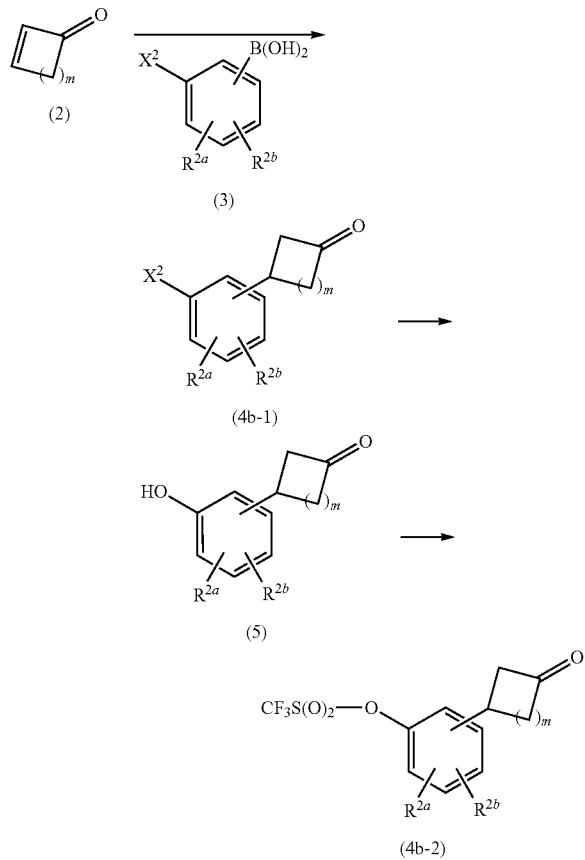

(wherein, $X^2$ represents a halogeno group, a benzyloxy group or a nitro group; $R^{2a}$, $R^{2b}$ and m represent the same as above). Compound (4b-1) can be produced by 1,4-addition reaction of α,β-unsaturated ketone compound (2) with compound (3) which is a phenylboric acid derivative in which $X^2$ is a halogeno group, a benzyloxy group or a nitro group.

Compound (5) which is a phenol derivative can be produced by conducting catalytic reduction of compound (4b-a) in which $X^2$ is a benzyloxy group, as shown in [Scheme 2]. In addition, compound (4b-2) which is a trifluoromethanesulfonyloxy derivative can be produced from compound (5) which is a phenol derivative via introducing a trifluoromethanesulfonyl group. In the 1,4-addition reaction, compound (4b-1) is produced from α,β-unsaturated ketone compound (2) and compound (3) which is a phenylboric acid derivative, in a solvent in the presence of a transition metal catalyst.

Regarding the 1,4-addition reaction of compound (2) and compound (3) in the presence of a metal catalyst, methods of Hayashi et al. [J. Am. Chem. Soc., 2002, 124, 5052-5058] can be referred to.

Regarding the solvent for the reaction, there may be mentioned for example, aromatic hydrocarbons such as benzene, toluene and xylene; halogenated hydrocarbons such as dichloromethane, 1,2-dichloroethane, chlorobenzene and dichlorobenzene; ethers such as diethyl ether, diisopropyl ether, tert-butylmethyl ether and tetrahydrofuran; ketones such as acetone and 2-butanone; nitriles such as acetonitrile and isobutyronitrile; amides such as formamide, N,N-dimethylformamide, N,N-dimethylacetamide and hexamethyl phosphoro triamide; sulfoxides such as dimethyl sulfoxide and sulfolane; and water; or a solvent mixture of water and the above-mentioned organic solvents. Here, 1,4-dioxane, water; or a solvent mixture of these are preferable.

Regarding the transition metal catalyst, there may be mentioned for example, rhodium catalysts such as acetylacetonate bis(ethylene)rhodium(I), [Rh(cod)Cl]$_2$, [Rh(cod)(MeCN)$_2$]BF$_4$ and [Rh(nbd)$_2$]BF$_4$; and palladium catalysts such as palladium acetate, bis benzylidene acetone palladium and tris dibenzylidene acetone palladium. Here, the rhodium catalyst is preferable. In addition, phosphorous compounds such as BINAP or the like may be added to improve reaction yield and efficiency of asymmetric induction. Further, the reaction may be accelerated also by addition of organic bases such as triethylamine, tributylamine and diisopropylethylamine; metal carbonates such as sodium carbonate, potassium carbonate and cesium carbonate. Regarding the reaction temperature, although it may differ depending on the starting compound, transition metal catalyst and type of solvent, the reaction is usually conducted in the range of 0 to 150° C., preferably 20 to 100° C. Regarding the reaction time, although it may differ depending on the reaction temperature, starting compound, reaction reagent or the type of solvent used, it is in the range of 10 minutes to 24 hours, and the reaction is usually completed in 30 minutes to 12 hours.

The compounds and intermediate compounds produced in the above-mentioned [Scheme 1] through [Scheme 9] can be, after the reaction is completed, isolated and purified from the reaction mixture in accordance with an ordinary method. For example, the reaction mixture is appropriately neutralized or is filtered to remove insoluble matter in the case that such insoluble matter exists, and then the reaction solution is extracted with an organic solvent such as ethyl acetate and chloroform which are immiscible with water. Subsequently, after the extracted solution is washed with water or the like, the organic layer containing the desired compound is dried over anhydrous magnesium sulfate, anhydrous sodium sulfate or the like, and then the solvent is distilled off to give the desired compound.

The compound produced in this manner can be separated and purified if necessary, by ordinary methods such as recrystallization, reprecipitation or normal methods commonly used in separation and purification of organic compounds, for example, adsorption column chromatography which uses carriers such as silica gel, alumina, florisil of magnesia-silica gel type; partition column chromatography which uses carriers such as Sephadex LH-20 (manufactured by Pharmacia), Amberlite XAD-11 (manufactured by Rohm and Haas), Diaion HP-20 (manufactured by Mitsubishi Chemicals); ion-exchange chromatography; or normal phase or reverse phase chromatography which uses silica gel or alkylated silica gel. Preferably, separation and purification can be conducted by various kinds of high performance liquid chromatography (HPLC).

In addition, in the case where the desired compound or the intermediate is a mixture of isomers such as stereoisomers, separation and purification can be conducted appropriately by medium pressure preparative chromatography, HPLC, or the like which uses optically active column or the like.

In addition, in the case where compound (1) of the present invention or the intermediate during the production possesses an asymmetric carbon, optical isomers exist. With respect to these optical isomers, each of the optical isomers can be isolated and purified by ordinary methods such as fractional recrystallization (salt resolution) which conducts recrystallization with an appropriate salt or column chromatography. As reference documents regarding the method for resolution of optical isomers from racemates, "Enantiomers, Racemates and Resolution, John Wiley And Sons, Inc." of J. Jacques et al. can be mentioned.

Cycloalkylamine derivatives of the present invention have an excellent CaSR activating (agonist) action, and are also excellent in disposition such as high oral absorbability, retention in blood and metabolic stability. They also have high safety towards organs such as the kidney, liver or the like, thereby being useful as a medicament, especially as a therapeutic agent for hyperparathyroidism, secondary hyperparathyroidism, tertiary hyperparathyroidism, primary hyperparathyroidism, renal osteodystrophy, hypercalcemia or the like. In addition, they are useful as a therapeutic agent for secondary hyperparathyroidism under maintenance dialysis, secondary hyperparathyroidism in chronic renal disease patients under dialysis, secondary hyperparathyroidism in end-stage renal disease patients under maintenance dialysis, hypercalcemia accompanied by a malignant tumor, hypercalcemia in parathyroid cancer patients, or the like.

Since the compound of the present invention represented by the general formula (1) has a basic group such as an amino group or the like, it can form an acid addition salt with a pharmacologically acceptable acid. As for such salts, there may be mentioned for example, hydrohalic acid salts such as hydrofluoride, hydrochloride, hydrobromide and hydroiodide; inorganic acid salts such as nitrate, perchloride, sulfate and phosphate; lower alkanesulfonates such as methanesulfonate, trifluoromethanesulfonate and ethanesulfonate; arylsulfonates such as benzenesulfonate and p-toluenesulfonate; organic acid salts such as acetate, malate, fumarate, succinate, citrate, tartrate, oxalate and maleate; and amino acid salts such as ornithine acid salt, glutamate and aspartate. Here, hydrohalic acid salts and organic acid salts are preferable.

In addition, since the cycloalkylamine derivatives represented by the general formula (1) have an acidic group such as a carboxy group or the like, they can generally form a base addition salt. Regarding the pharmacologically acceptable salts, there may be mentioned for example, alkali metal salts such as sodium salt, potassium salt and lithium salt; alkaline earth metal salts such as calcium salt and magnesium salt; inorganic salts such as ammonium salt; organic amine salts such as dibenzylamine salt, morpholine salt, phenylglycine alkyl ester salt, ethylenediamine salt, N-methylglucamine salt, diethylamine salt, triethylamine salt, cyclohexylamine salt, dicyclohexylamine salt, N,N'-dibenzylethylenediamine salt, diethanolamine salt, N-benzyl-N-(2-phenylethoxy) amine salt, piperazine salt, tetramethylammonium salt and tris(hydroxymethyl)aminomethane salt; and amino acid salts such as arginine salt.

The compound represented by the general formula (1) or a pharmacologically acceptable salt thereof of the present invention may be present in the free form or in a solvated form, and these solvates are also embraced in the scope of the present invention. With respect to such solvates, although there is no particular limitation so long as it is pharmacologically acceptable, in particular, hydrates, ethanolates or the like are preferable. In addition, in the case where there is a nitrogen atom in the compound of the present invention represented by the general formula (1), it may be in an N-oxide form, and these solvates and N-oxides are also included in the scope of the present invention.

With respect to the compound of the present invention represented by the general formula (1) or a pharmacologically acceptable salt thereof and the intermediates in the production of the compound of the present invention, various kinds of isomers may exist depending on the types of substituents and their combinations. Such isomers are, for example, geometrical isomers such as cis-form and trans-form; tautomers such as 1H-tetrazol-5-yl form and 2H-tetrazol-5-yl form; or optical isomers such as d-form and l-form. The compound of the present invention, if not otherwise specified, embraces all of such isomers, stereoisomers, and mixtures of these isomers and stereoisomers in any ratio.

In addition, the compound of the present invention or a pharmacologically acceptable salt thereof may also contain unnatural proportions of atomic isotopes at one or more of atoms constituting such compound. As the atomic isotopes, there may be mentioned for example, deuterium ($^{2}H$), tritium ($^{3}H$), carbon-13 ($^{13}C$), carbon-14 ($^{14}C$), nitrogen-15 ($^{15}N$), chlorine-37 ($^{37}Cl$), iodine-125 ($^{125}I$), or the like. Further, the above-mentioned compound may be radioactively labeled with radioactive isotopes such as tritium ($^{3}H$), iodine-125 ($^{125}I$) or carbon-14 ($^{14}C$). The radioactively labeled compound is useful as a therapeutic or preventive agent, a research reagent, for example an assay reagent, and a diagnostic agent, for example an in vivo diagnostic imaging agent. All the isotope variants of the compounds of the present invention are intended to be embraced in the scope of the present invention, regardless of whether or not they are radioactive.

In addition, the present invention also embraces compounds that are converted into compound (1) which is an active ingredient of the pharmaceutical composition of the present invention, such conversion being realized by reactions with enzymes, gastric acid or the like under physiological conditions within an organism. That is, compounds that are transformed into compound (1) by enzymatic oxidation, reduction, hydrolysis or the like, or "medically acceptable prodrug compounds" that are transformed into compound (1) by hydrolysis or the like with gastric acid or the like, are also embraced in the present invention.

A pharmaceutical composition containing the compound of the present invention represented by the general formula (1) or a pharmacologically acceptable salt thereof can be prepared in accordance with preparation methods for various kinds of preparations that are usually used, by selecting a suitable preparation depending on the administration method.

In the case where a pharmaceutical composition having the compound of the present invention represented by the general formula (1) or a pharmacologically acceptable salt thereof as a main ingredient is administered to mammal (especially human), it can be administered systemically or topically, orally or parenterally. Regarding the form of medicaments for oral administration, there may be mentioned for example, tablets, pills, powders, granules, capsules, pharmaceutical solutions, suspensions, emulsions, syrups and elixirs. Usually, medicaments in these forms have the compound of the present invention represented by the general formula (1) or the pharmacologically acceptable salt thereof as the main ingredient, and are prepared as a pharmaceutical composition combined with diluents, excipients or carriers as pharmaceutically acceptable additives. Preparation of pharmaceutical composition may be conducted in accordance with ordinary methods, by using appropriately selected diluents, excipients or carriers; and in addition to these any suitable pharmaceutically acceptable binders, disintegrants, lubricants, swelling agents, swelling adjuvants, coatings, plasticizers, stabilizers, antiseptics, anti-oxidants, colorants, solubilizing adjuvants, suspending agents, emulsifiers, sweeteners, preservatives, buffers and wetting agents, if necessary.

Regarding the form of medicaments for parenteral administration, there may be mentioned for example, injection, ointment, gel, cream, wet dressing, patch, aerosol, inhalant, spray, eye drop, nasal drop and suppository. Usually, medicaments in these forms have the compound of the present invention represented by the general formula (1) or a pharmacologically acceptable salt thereof as the main ingredient, and are prepared as a pharmaceutical composition combined with diluents, excipients or carriers as a pharmaceutically acceptable additives. Preparation of pharmaceutical compositions may be conducted in accordance with ordinary methods, by using appropriately selected diluents, excipients or carriers; and in addition to these any suitable pharmaceutically acceptable stabilizers, antiseptics, solubilizing adjuvants, moisturizing agents, preservatives, anti-oxidants, aromatizing agents, gelling agents, neutralizers, buffers, isotonic agents, surfactants, colorants, buffer agent, thickening agents, wetting agents, fillers, absorption enhancers, suspending agents and binders.

Regarding a reference document relating to the above-mentioned pharmaceutically acceptable excipients, "Handbook of Pharmaceutical Excipients, 2$^{nd}$ Edition, (1994), Edited by A. Wade and P. J. Weller" can be mentioned for example.

Regarding a reference document relating to the above-mentioned pharmaceutically acceptable carriers or diluents, "Remington's Pharmaceutical Sciences, Mack Publishing Co., (A. R. Gennaro edit. 1985)" can be mentioned for example.

Although the dosage amount of the compound represented by the general formula (1) of the present invention or a pharmacologically acceptable salt thereof varies depending on the symptoms, age, body weight, types and dosage amount of drug administered in combination, or the like, in the case where it is used as a medicament for a human, an equivalent amount of compound (1) for an adult is in the range of 0.001 mg to 1000 mg per dosage, preferably in the range of 0.01 mg to 100 mg, and more preferably in the range of 0.1 mg to 10 mg. In terms of body weight equivalent, compound (1) is in the range of 0.02 µg/kg to 20 mg/kg, preferably in the range of 0.2 µg/kg to 2 mg/kg, and more preferably in the range of 2 µg/kg to 0.2 mg/kg. This daily amount is administered systemically or topically, once per several days or once to several times a day, orally or parenterally. Otherwise, it is continuously administered intravenously within the range of 1 hour to 24 hours a day. Here, the daily amount may exceed the above-mentioned amount if necessary.

EXAMPLES

Hereinafter, the present invention will be specifically explained with reference to Examples and Test Examples; however, the present invention is by no means limited to these.

In the following descriptions of Examples and their steps, the compound names described represent compounds obtained in those Examples and their steps, and the chemical structural formulas described represent the corresponding free foams. For example, in Example 1, the obtained compound is (1S,3R)-N-[(1R)-1-(naphthalen-1-yl)ethyl]-3-[3-(2H-tetrazol-5-yl)phenyl]cyclopentanamine hydrochloride, and the chemical structural formula described represents the chemical structure of (1S,3R)-N-[(1R)-1-(naphthalen-1-yl)ethyl]-3-[3-(2H-tetrazol-5-yl)phenyl]cyclopentanamine.

Here, the symbols "NMR", "IR", "MS" and "HRMS" in the Examples respectively mean "nuclear magnetic resonance spectrum", "infrared absorption spectrum", "mass spectroscopy" and "high resolution mass spectroscopy spectrum". The ratio of solvent for elution described in the section of separation and purification by chromatography refers to volume ratio, unless otherwise noted. "NMR" means $^1$H-NMR unless otherwise noted, the content of the parenthesis shows the solvent for measurement, and TMS (tetramethylsilane) was used as internal standard for all cases.

Example 1

(1S,3R)-N-[(1R)-1-(Naphthalen-1-yl)ethyl]-3-[3-(2H-tetrazol-5-yl)phenyl]cyclopentanamine hydrochloride (Step 1) (3R)-3-(3-Bromophenyl)cyclopentanone

[Chemical 28]

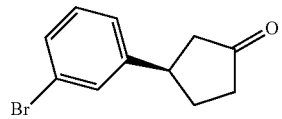

Under a nitrogen stream, 3-bromophenylboric acid (14.2 g, 71 mmol), (R)-2,2'-bis(diphenylphosphino)-1,1'-binaphthyl ((R)-BINAP) (1.06 g, 1.7 mmol), and acetylacetonato bis(ethylene)rhodium(I) (438 mg, 1.7 mmol) were dissolved in a solvent mixture of 1,4-dioxane (150 mL) and water (15 mL), followed by degassing with ultrasonic waves, and then cyclopentenone (2.4 mL, 28 mmol) was added and the mixture was stirred under reflux with heating for 3 hours. The reaction solution was cooled to room temperature, followed by addition of saturated aqueous sodium bicarbonate solution, and then the solvent was distilled off under reduced pressure. The aqueous phase was extracted with ethyl acetate, the organic phase was dried over anhydrous magnesium sulfate, and the solvent was distilled off under reduced pressure. The residue obtained was purified by column chromatography (ethyl acetate/hexane:10/90-20/80) to give the title compound (6.83 g).

$^1$H-NMR (CDCl$_3$) δ: 1.92-2.03 (1H, m), 2.26-2.36 (2H, m), 2.41-2.52 (2H, m), 2.67 (1H, dd, J=18.0, 7.4 Hz), 3.35-3.44 (1H, m), 7.17-7.24 (2H, m), 7.37-7.41 (2H, m); IR (liquid film) υ max 2963, 1742, 1594, 1565, 1477, 1404, 1136, 783, 694 cm$^{-1}$;

MS (EI) m/z: 238 (M)$^+$.

(Step 2) (1S,3R)-3-(3-Bromophenyl)-N-[(1R)-1-(naphthalen-1-yl)ethyl]cyclopentanamine

[Chemical 29]

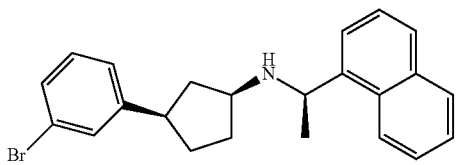

A methanol (150 mL) solution of (R)-naphthylethylamine (4.44 g, 26 mmol) was added to (3R)-3-(3-bromophenyl)cyclopentanone (4.78 g, 20 mmol) obtained in Step 1. After replacing the atmosphere with nitrogen, acetic acid (3 mL) and sodium cyanotrihydroborate (1.51 g, 24 mmol) were added sequentially, and the mixture was stirred overnight at room temperature. A saturated aqueous sodium bicarbonate solution was added to the reaction solution, and the solvent was distilled off under reduced pressure. Subsequently, ethyl acetate and water were added, followed by extraction with ethyl acetate. The extracted solution was dried over anhydrous magnesium sulfate, and the solvent was distilled off under reduced pressure. The obtained residue was purified by column chromatography (ethyl acetate/hexane: 25/75-50/50) to give the title compound (2.83 g, 36%).

$^1$H-NMR (CDCl$_3$) δ: 1.40-1.80 (3H, m), 1.51 (3H, d, J=6.6 Hz), 1.92-2.03 (2H, m), 2.24-2.32 (1H, m), 2.83-2.93 (1H, m), 3.14-3.22 (1H, m), 4.75 (1H, q, J=6.6 Hz), 7.11-7.14 (2H, m), 7.27-7.31 (1H, m), 7.36 (1H, s), 7.46-7.54 (3H, m), 7.65 (1H, d, J=7.0 Hz), 7.76 (1H, d, J=8.2 Hz), 7.88 (1H, d, J=7.8 Hz), 8.21 (1H, d, J=8.2 Hz);

IR (ATR) υ max 2951, 2861, 1593, 1564, 1475, 1133, 1072, 775, 693 cm$^{-1}$;

MS (FAB) m/z: 394 (M+H)$^+$

(Step 3) [(1S,3R)-3-(3-Bromophenyl)cyclopentyl][(1R)-1-(naphthalen-1-yl)ethyl]carbamic acid tert-butyl ester

[Chemical 30]

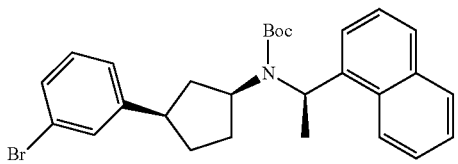

Under a nitrogen stream, (1S,3R)-3-(3-bromophenyl)-N-[(1R)-1-(naphthalen-1-yl)ethyl]cyclopentanamine (2.53 g, 6.4 mmol) was dissolved in methylene chloride (40 mL). After addition of triethylamine (3.6 mL, 26 mmol), a methylene chloride solution of triphosgene (1.26 g, 4.2 mmol) was slowly added dropwise under ice-cooling conditions, and the mixture was stirred for 1 hour at room temperature. Water was added to the reaction solution, followed by extraction with methylene chloride. The extracted solution was dried over anhydrous magnesium sulfate, and then the solvent was distilled off under reduced pressure. Tert-butanol (40 mL) and diisopropylethylamine (2 mL) were added to the obtained residue, and the mixture was heated under reflux for 6 hours. The reaction mixture was left to stand for cooling, and the solvent was distilled off under reduced pressure. Then, the residue was purified by column chromatography (ethyl acetate/hexane:5/95-15/85) to give the title compound (3.08 g, 97%).

$^1$H-NMR (CDCl$_3$) δ: 0.49 (1H, br s), 1.39 (1H, br s), 1.50-1.64 (2H, m), 1.61 (9H, s), 1.65 (3H, d, J=6.6 Hz), 1.89-1.97 (1H, m), 2.35 (1H, br s), 2.62-2.73 (1H, m), 3.25-3.35 (1H, m), 6.18 (1H, br s), 7.08-7.14 (2H, m), 7.26-7.30 (1H, m), 7.32 (1H, s), 7.46-7.55 (4H, m), 7.82 (1H, d, J=7.8 Hz), 7.85-7.88 (1H, m), 8.11-8.15 (1H, m);

IR (KBr) υ max 2969, 1676, 1447, 1365, 1325, 1153, 1024, 785 cm$^{-1}$;

MS (FAB) m/z: 494 (M+H)$^+$.

(Step 4) [(1S,3R)-3-(3-Cyanophenyl)cyclopentyl][(1R)-1-(naphthalen-1-yl)ethyl]carbamic acid tert-butyl ester

[Chemical 31]

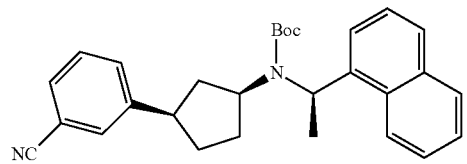

Under a nitrogen stream, (1S,3R)-3-(3-bromophenyl)cyclopentyl][(1R)-1-(naphthalen-1-yl)ethyl]carbamic acid tert-butyl ester (1.50 g, 3.0 mmol) and zinc cyanide (427 mg, 3.6 mmol) were suspended in N,N-dimethylformamide (15 mL), followed by addition of tetrakis triphenylphosphine palladium (350 mg, 0.30 mmol), and the mixture was stirred for 2 hours at 100° C. The reaction solution was cooled to room temperature, and water was added to the solution. After insoluble matter was filtered off, the solvent of the filtrate was distilled off under reduced pressure. Water and ethyl acetate were added to the residue, followed by extraction with ethyl acetate. The extracted solution was washed with water and saturated brine, and was then dried over anhydrous magnesium sulfate. Then, the solvent was distilled off under reduced pressure. The obtained residue was purified by column chromatography (ethyl acetate/hexane:5/95-15/85) to give the title compound (1.17 g, 87%).

$^1$H-NMR (CDCl$_3$) δ: 0.51 (1H, br s), 1.55-1.67 (3H, m), 1.61 (9H, s), 1.65 (3H, d, J=6.6 Hz), 1.92-1.99 (1H, m), 2.37 (1H, br s), 2.68-2.78 (1H, m), 3.28-3.37 (1H, m), 6.17 (1H, br s), 7.35 (1H, t, J=7.8 Hz), 7.40-7.55 (7H, m), 7.83 (1H, d, J=8.2 Hz), 7.85-7.89 (1H, m), 8.10-8.14 (1H, m);

IR (thin film) υ max 2975, 2228, 1677, 1450, 1366, 1326, 1156, 780, 757 cm$^{-1}$;

MS (FAB) m/z: 441 (M+H)$^+$.

(Step 5) [(1R)-1-(Naphthalen-1-yl)ethyl]{(1S,3R)-3-[3-(2H-tetrazol-5-yl)phenyl]cyclopentyl}carbamic acid tert-butyl ester

[Chemical 32]

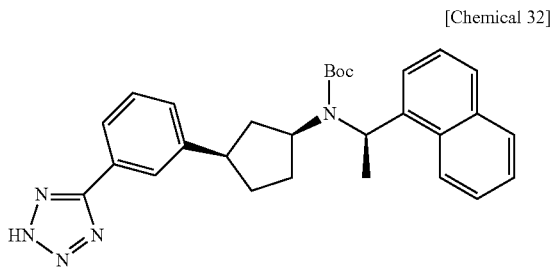 [SMILES: C[C@H](c1cccc2ccccc12)N(C(=O)OC(C)(C)C)[C@H]1CC[C@@H](c2cccc(-c3nn[nH]n3)c2)C1]

[(1S,3R)-3-(3-Cyanophenyl)cyclopentyl][(1R)-1-(naphthalen-1-yl)ethyl]carbamic acid tert-butyl ester (450 mg, 1.0 mmol), ammonium chloride (1.09 g, 20 mmol) and sodium azide (0.99 g, 15 mmol) were suspended in N,N-dimethylformamide (10 mL), and the mixture was stirred at 100° C. for 8 hours. The reaction solution was cooled to room temperature, and was then acidified with 1N aqueous hydrochloric acid. The aqueous phase was extracted with ethyl acetate, the extracted solution was dried over anhydrous magnesium sulfate, and the solvent was distilled off under reduced pressure. The obtained residue was purified by column chromatography (ethyl acetate/hexane:30/70-100/0, and 10/90 methanol-methylene chloride) to give the title compound (393 mg, 80%).

$^1$H-NMR (CDCl$_3$) δ: 0.43-0.54 (1H, m), 1.53-1.74 (15H, m), 2.05 (br s), 2.47 (1H, br s), 2.85 (1H, br s), 3.30-3.40 (1H, m), 6.10 (1H, br s), 7.26-7.40 (2H, m), 7.48-7.57 (5H, m), 7.84 (1H, d, J=8.2 Hz), 7.87-7.90 (1H, m), 7.92-7.97 (1H, m), 8.09-8.13 (1H, m);

IR (KBr) υ max 2976, 1674, 1652, 1452, 1367, 1327, 1155, 1028, 779 cm$^{-1}$;

MS (FAB) m/z: 484 (M+H)$^+$.

(Step 6) (1S,3R)-N-[(1R)-1-(Naphthalen-1-yl)ethyl]-3-[3-(2H-tetrazol-5-yl)phenyl]cyclopentanamine hydrochloride

[Chemical 33]

[(1R)-1-(Naphthalen-1-yl)ethyl]{(1S,3R)-3-[3-(2H-tetrazol-5-yl)phenyl]cyclopentyl}carbamic acid tert-butyl ester (390 mg, 0.81 mmol) was dissolved in ethyl acetate (5 mL), followed by addition of an ethyl acetate solution of 4N hydrochloric acid (5 mL), and the mixture was stirred overnight at room temperature. Hexane was added to the reaction solution, and the precipitated solid was collected by filtration to give the title compound (306 mg, 90%).

$^1$H-NMR (CD$_3$OD) δ: 1.76-1.85 (1H, m), 1.85 (3H, d, J=6.7 Hz), 1.89-2.01 (1H, m), 2.07-2.25 (3H, m), 2.56-2.63 (1H, m), 3.13-3.23 (1H, m), 3.67-3.76 (1H, m), 5.47 (1H, q, J=6.7 Hz), 7.47-7.55 (2H, m), 7.58-7.70 (3H, m), 7.77 (1H, d, J=7.4 Hz), 7.82-7.85 (1H, m), 7.97-8.02 (3H, m), 8.24 (1H, d, J=8.6 Hz);

IR (KBr) υ max 3394, 2964, 2802, 1796, 1653, 1583, 1450, 1381, 1067, 1000, 803, 777, 698 cm$^{-1}$;

MS (FAB) m/z: 384 (M+H)$^+$.

Example 2

(1R,3R)-N-[(1R)-1-(Naphthalen-1-yl)ethyl]-3-[3-(2H-tetrazol-5-yl)phenyl]cyclohexanamine hydrochloride (Step 1) (3R)-3-(3-Bromophenyl)cyclohexanone

[Chemical 34]

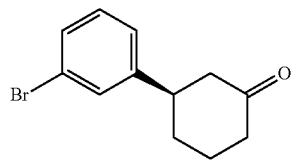

Cyclohexenone (0.98 mL, 10 mmol) was used and treated in a similar manner to (Step 1) of (Example 1) to give the title compound (1.52 g, 60%).

$^1$H-NMR (CDCl$_3$) δ: 1.71-1.89 (2H, m), 2.05-2.11 (1H, m), 2.13-2.19 (1H, m), 2.33-2.42 (1H, m), 2.44-2.53 (2H, m), 2.55-2.62 (1H, m), 2.98 (1H, tt, J=11.7, 3.9 Hz), 7.14 (1H, d, J=8.0 Hz), 7.20 (1H, t, J=8.0 Hz), 7.36-7.39 (2H, m);

IR (liquid film) υ max 2938, 1712, 1593, 1476, 1427, 1224, 781, 694 cm$^{-1}$;

MS (EI) m/z: 252 (M)$^+$.

(Step 2) (1R,3R)-3-(3-Bromophenyl)-N-[(1R)-1-(naphthalen-1-yl)ethyl]cyclohexanamine

[Chemical 35]

(3R)-3-(3-Bromophenyl)cyclohexanone (1.50 g, 5.9 mmol) was used and treated in a similar manner to (Step 2) of (Example 1) to give the title compound (1.08 g, 45%).

$^1$H-NMR (CDCl$_3$) δ: 1.35-1.59 (4H, m), 1.51 (3H, d, J=6.6 Hz), 1.63-1.95 (4H, m), 2.94-3.02 (2H, m), 4.73 (1H, q, J=6.6 Hz), 7.10-7.15 (2H, m), 7.28-7.31 (1H, m), 7.36 (1H, s), 7.44-7.51 (3H, m), 7.66 (1H, d, J=7.4 Hz), 7.74 (1H, d, J=7.8 Hz), 7.87 (1H, d, J=7.0 Hz), 8.21 (1H, d, J=7.8 Hz);

IR (liquid film) υ max 2925, 1594, 1565, 1475, 1449, 1132, 798, 778, 693 cm$^{-1}$;

MS (FAB) m/z: 408 (M+H)$^+$.

(Step 3) [(1R,3R)-3-(3-Bromophenyl)cyclohexyl][(1R)-1-(naphthalen-1-yl)ethyl]carbamic acid tert-butyl ester

[Chemical 36]

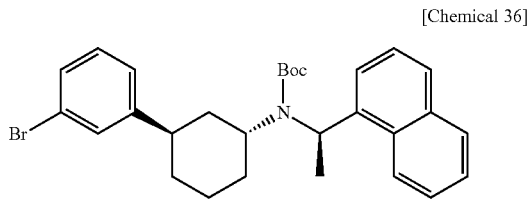 [SMILES: C[C@H](c1cccc2ccccc12)N(C(=O)OC(C)(C)C)[C@@H]1CCC[C@@H](c2cccc(Br)c2)C1]

(1R,3R)-3-(3-Bromophenyl)-N-[(1R)-1-(naphthalen-1-yl)ethyl]cyclohexanamine (1.00 g, 2.4 mmol) was used and treated in a similar manner to (Step 3) of (Example 1) to give the title compound (928 mg, 74%).

$^1$H-NMR (CDCl$_3$) δ: 0.70-0.76 (1H, m), 1.54-1.65 (16H, m), 1.87-1.94 (1H, m), 2.22 (2H, s), 2.73 (1H, br s), 2.81 (1H, tt, J=12.3, 3.8 Hz), 5.67 (1H, d, J=7.4 Hz), 6.15 (1H, br s), 6.80 (1H, t, J=8.0 Hz), 6.95 (1H, s), 7.16 (1H, d, J=8.0 Hz), 7.28-7.34 (2H, m), 7.47-7.54 (2H, m), 7.82 (1H, dd, J=7.4, 2.0 Hz), 7.87 (1H, dd, J=6.8, 2.5 Hz), 8.13-8.16 (1H, m);

IR (liquid film) υ max 2972, 2931, 1674, 1475, 1453, 1436, 1419, 1366, 1304, 1157, 779 cm$^{-1}$;

MS (FAB) m/z: 508 (M+H)$^+$.

(Step 4) [(1R,3R)-3-(3-Cyanophenyl)cyclohexyl][(1R)-1-(naphthalen-1-yl)ethyl]carbamic acid tert-butyl ester

[Chemical 37]

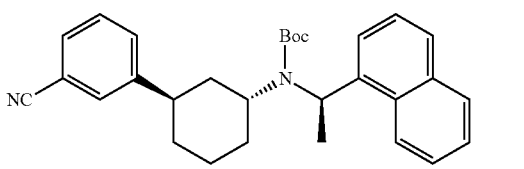

[(1R,3R)-3-(3-Bromophenyl)cyclohexyl][(1R)-1-(naphthalen-1-yl)ethyl]carbamic acid tert-butyl ester (300 mg, 0.59 mmol) was used and treated in a similar manner to (Step 4) of (Example 1) to give the title compound (207 mg, 77%).

$^1$H-NMR (CDCl$_3$) δ: 0.70-0.76 (1H, m), 1.24-1.35 (1H, m), 1.51-1.68 (15H, m), 1.88-1.96 (1H, m), 2.16-2.55 (2H, m), 2.66-2.78 (2H, m), 6.14 (1H, br s), 6.20 (1H, d, J=7.8 Hz), 6.89 (1H, s), 7.06 (1H, t, J=7.8 Hz), 7.24-7.29 (2H, m), 7.33 (1H, d, J=7.8 Hz), 7.49-7.55 (2H, m), 7.82-7.85 (1H, m), 7.90-7.93 (1H, m), 8.10-8.15 (1H, m);

IR (KBr) υ max 2971, 2932, 2228, 1673, 1437, 1367, 1305, 1164, 780 cm$^{-1}$;

MS (FAB) m/z: 455 (M+H)$^+$.

(Step 5) [(1R)-1-(Naphthalen-1-yl)ethyl]{(1R,3R)-3-[3-(2H-tetrazol-5-yl)phenyl]cyclohexyl}carbamic acid tert-butyl ester

[Chemical 38]

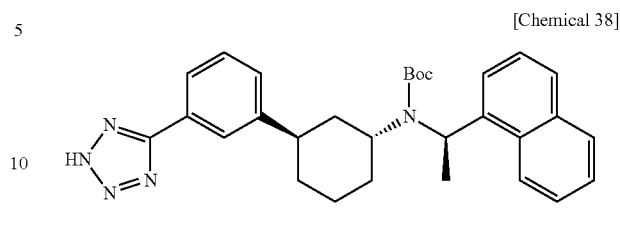

[(1R,3R)-3-(3-Cyanophenyl)cyclohexyl][(1R)-1-(naphthalen-1-yl)ethyl]carbamic acid tert-butyl ester (203 mg, 0.45 mmol) was used and treated in a similar manner to (Step 5) of (Example 1) to give the title compound (189 mg, 85%).

IR (KBr) υ max 3439, 2971, 2930, 1671, 1652, 1440, 1367, 1306, 1253, 1158, 782 cm$^{-1}$.

(Step 6) (1R,3R)-N-[(1R)-1-(Naphthalen-1-yl)ethyl]-3-[3-(2H-tetrazol-5-yl)phenyl]cyclohexanamine hydrochloride

[Chemical 39]

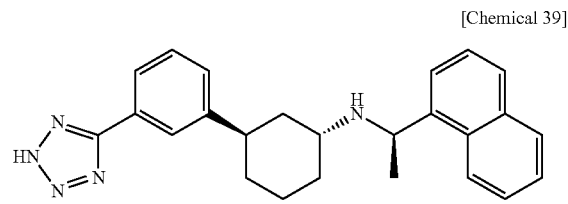 [SMILES: C[C@@H](N[C@@H]1CCC[C@@H](c2cccc(-c3nn[nH]n3)c2)C1)c1cccc2ccccc12]

[(1R)-1-(Naphthalen-1-yl)ethyl]{(1R,3R)-3-[3-(2H-tetrazol-5-yl)phenyl]cyclohexyl}carbamic acid tert-butyl ester (183 mg, 0.37 mmol) was used and treated in a similar manner to (Step 6) of (Example 1) to give the title compound (132 mg, 83%).

$^1$H-NMR (CD$_3$OD) δ: 1.60-1.69 (1H, m), 1.74-2.00 (5H, m), 1.82 (3H, d, J=6.6 Hz), 2.05-2.13 (1H, m), 2.18-2.25 (1H, m), 3.20-3.28 (2H, m), 5.58 (1H, q, J=6.6 Hz), 7.04 (1H, d, J=7.8 Hz), 7.20 (1H, t, J=7.8 Hz), 7.51-7.61 (3H, m), 7.70 (1H, d, J=7.8 Hz), 7.74 (1H, d, J=7.4 Hz), 7.82 (1H, s), 7.94 (2H, d, J=8.2 Hz), 8.21 (1H, d, J=8.6 Hz);

IR (KBr) υ max 3392, 2944, 1654, 1582, 1454, 1385, 1067, 1004, 804, 779, 706 cm$^{-1}$;

MS (FAB) m/z: 398 (M+H)$^+$.

Example 3

(1S,3R)-N-[(1R)-1-(Naphthalen-1-yl)ethyl]-3-[4-(2H-tetrazol-5-yl)phenyl]cyclopentanamine hydrochloride (Step 1) (3R)-3-(4-Bromophenyl)cyclopentanone

[Chemical 40]

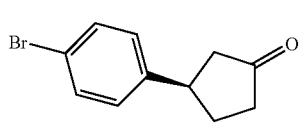

Under nitrogen stream, 4-bromophenylboric acid (15.7 g, 78 mmol), (R)-BINAP 1.17 g (1.9 mmol), and acetylacetonato bis(ethylene)rhodium(I) (486 mg, 1.9 mmol) were dissolved in a solvent mixture of 1,4-dioxane (150 mL) and water (15 mL), followed by degassing with ultrasonic waves. Subsequently, cyclopentenone (2.6 mL, 31 mmol) was added and the mixture was stirred under reflux with heating for 3 hours. The reaction solution was cooled to room temperature, followed by addition of saturated aqueous sodium bicarbonate solution, and then the solvent was distilled off under reduced pressure. The aqueous phase was extracted with ethyl acetate. The extracted solution was dried over anhydrous magnesium sulfate, and the solvent was distilled off under reduced pressure. The residue obtained was purified by column chromatography (ethyl acetate/hexane:20/80-30/70) to give the title compound (6.94 g, 91%).

$^1$H-NMR (CDCl$_3$) δ: 1.90-2.00 (1H, m), 2.25-2.35 (2H, m), 2.40-2.51 (2H, m), 2.66 (1H, dd, J=17.8, 7.6 Hz), 3.33-3.43 (1H, m), 7.13 (2H, d, J=8.2 Hz), 7.46 (2H, d, J=8.2 Hz);

IR (KBr) υ max 2969, 2903, 1738, 1492, 1402, 1133, 1009, 822 cm$^{-1}$;

MS (EI) m/z: 238 (M)$^+$.

(Step 2) (1S,3R)-3-(4-Bromophenyl)-N-[(1R)-1-(naphthalen-1-yl)ethyl]cyclopentanamine

[Chemical 41]

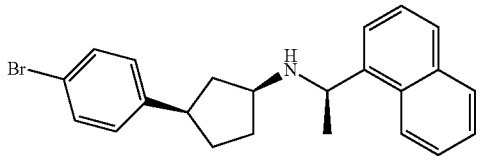

A methanol (150 mL) solution of (1S,3R)-N-[(1R)-1-(naphthalen-1-yl)ethyl]-3-[4-(2H-tetrazol-5-yl)phenyl]cyclopentanamine (6.45 g, 38 mmol) was added. After replacing the atmosphere with nitrogen, acetic acid (3 mL) and sodium cyanotrihydroborate (2.19 g, 35 mmol) were added sequentially, and the mixture was stirred overnight at room temperature. A saturated aqueous sodium bicarbonate solution was added, and the solvent was distilled off under reduced pressure. Subsequently, ethyl acetate and water were added to the residue, followed by extraction with ethyl acetate. The extracted solution was dried over anhydrous magnesium sulfate, and the solvent was distilled off under reduced pressure. The obtained residue was purified by column chromatography (ethyl acetate/hexane:20/80-70/30) to give the title compound (4.96 g, 43%).

$^1$H-NMR (CDCl$_3$) δ: 1.40-1.47 (1H, m), 1.51 (3H, d, J=6.7 Hz), 1.62-1.77 (2H, m), 1.93-2.02 (2H, m), 2.23-2.30 (1H, m), 2.83-2.90 (1H, m), 3.15-3.21 (1H, m), 4.75 (1H, q, J=6.7 Hz), 7.08 (2H, d, J=8.0 Hz), 7.37 (2H, d, J=8.0 Hz), 7.46-7.54 (3H, m), 7.64 (1H, d, J=7.3 Hz), 7.76 (1H, d, J=8.3 Hz), 7.88 (1H, d, J=7.8 Hz), 8.20 (1H, d, J=7.8 Hz);

IR (thin film) υ max 2953, 2862, 1489, 1134, 1073, 1009, 799, 778 cm$^{-1}$;

MS (FAB) m/z: 394 (M+14)$^+$.

(Step 3) [(1S,3R)-3-(4-Bromophenyl)cyclopentyl][(1R)-1-(naphthalen-1-yl)ethyl]carbamic acid tert-butyl ester

[Chemical 42]

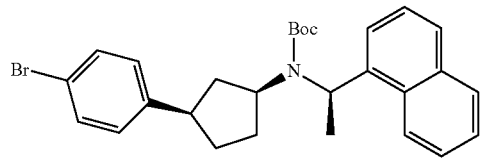

(1S,3R)-3-(4-Bromophenyl)-N-[(1R)-1-(naphthalen-1-yl)ethyl]cyclopentanamine (1.52 g, 3.9 mmol) was used and treated in a similar manner to (Step 3) of (Example 1) to give the title compound (1.96 g).

$^1$H-NMR (CDCl$_3$) δ: 0.50 (1H, br s), 1.52-1.60 (3H, m), 1.59 (9H, s), 1.64 (3H, d, J=7.0 Hz), 1.88-1.94 (1H, m), 2.35 (1H, br s), 2.61-2.70 (1H, m), 3.26-3.35 (1H, m), 6.15 (1H, br s), 7.04 (2H, d, J=7.8 Hz), 7.36 (2H, d, J=8.6 Hz), 7.44-7.55 (4H, m), 7.81 (1H, d, J=8.2 Hz), 7.83-7.88 (1H, m), 8.10-8.14 (1H, m);

IR (thin film) υ max 2974, 1676, 1489, 1448, 1365, 1326, 1156, 1027, 1010, 779 cm$^{-1}$;

MS (FAB) m/z: 494 (M+H)$^+$.

(Step 4) [(1S,3R)-3-(4-Cyanophenyl)cyclopentyl][(1R)-1-(naphthalen-1-yl)ethyl]carbamic acid tert-butyl ester

[Chemical 43]

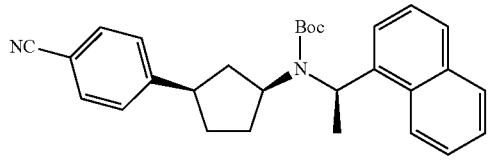

[(1S,3R)-3-(4-Bromophenyl)cyclopentyl][(1R)-1-(naphthalen-1-yl)ethyl]carbamic acid tert-butyl ester (1.96 g, 3.9 mmol) was used and treated in a similar manner to (Step 4) of (Example 1) to give the title compound (1.35 g, 74%).

$^1$H-NMR (CDCl$_3$) δ: 0.52 (1H, br s), 1.57-1.62 (3H, m), 1.60 (9H, s), 1.65 (3H, d, J=7.0 Hz), 1.92-1.98 (1H, m), 2.39 (1H, s), 2.70-2.80 (1H, m), 3.32 (1H, tt, J=10.8, 5.0 Hz), 6.17 (1H, br s), 7.28 (2H, br s), 7.46-7.56 (6H, m), 7.82 (1H, d, J=8.2 Hz), 7.85-7.88 (1H, m), 8.09-8.14 (1H, m);

IR (KBr) υ max 2972, 2226, 1677, 1607, 1449, 1366, 1326, 1301, 1155, 1107, 1027, 780 cm$^{-1}$;

MS (FAB) m/z: 441 (M+H)$^+$.

53

(Step 5) [(1R)-1-(Naphthalen-1-yl)ethyl]{(1S,3R)-3-[4-(2H-tetrazol-5-yl)phenyl]cyclopentyl}carbamic acid tert-butyl ester

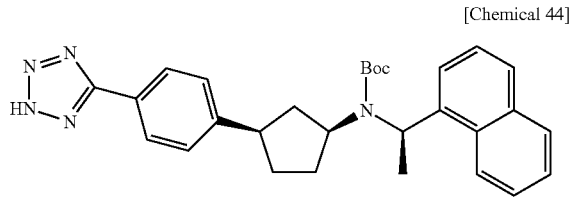 [SMILES: C[C@H](c1cccc2ccccc12)N(C(=O)OC(C)(C)C)[C@H]1CC[C@@H](c2ccc(-c3nn[nH]n3)cc2)C1]

[Chemical 44]

[(1S,3R)-3-(4-Cyanophenyl)cyclopentyl][(1R)-1-(naphthalen-1-yl)ethyl]carbamic acid tert-butyl ester (425 mg, 0.96 mmol) was used and treated in a similar manner to (Step 5) of (Example 1) to give the title compound (360 mg, 77%).

$^1$H-NMR (DMSO-D$_6$) δ: 0.42 (1H, br s), 1.26 (1H, br s), 1.53-1.59 (2H, m), 1.54 (9H, s), 1.61 (3H, d, J=6.8 Hz), 1.98-2.04 (1H, m), 2.29 (1H, br s), 2.85 (1H, br s), 3.35-3.46 (1H, m), 6.03 (1H, br s), 7.38-7.42 (2H, m), 7.51-7.59 (3H, m), 7.66 (1H, d, J=6.8 Hz), 7.90-7.99 (4H, m), 8.03-8.09 (1H, m);

IR (KBr) υ max 3431, 3092, 3049, 2975, 2936, 1639, 1451, 1370, 1332, 1155, 841, 786 cm$^{-1}$;

MS (FAB) m/z: 484 (M+H)$^+$.

(Step 6) (1S,3R)-N-[(1R)-1-(Naphthalen-1-yl)ethyl]-3-[4-(2H-tetrazol-5-yl)phenyl]cyclopentanamine hydrochloride

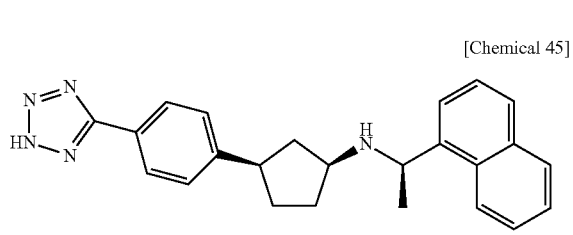 [SMILES: C[C@@H](N[C@H]1CC[C@@H](c2ccc(-c3nn[nH]n3)cc2)C1)c1cccc2ccccc12]

[Chemical 45]

[(1R)-1-(Naphthalen-1-yl)ethyl]{(1S,3R)-3-[4-(2H-tetrazol-5-yl)phenyl]cyclopentyl carbamic acid tert-butyl ester (355 mg, 0.73 mmol) was used and treated in a similar manner to (Step 6) of (Example 1) to give the title compound (320 mg).

$^1$H-NMR (DMSO-D$_6$) δ: 1.73 (3H, d, J=6.3 Hz), 1.79-1.89 (2H, m), 1.92-2.05 (2H, m), 2.15 (1H, brs), 2.49-2.56 (1H, m), 3.09 (1H, br s), 3.58 (1H, br s), 5.35 (1H, br s), 7.48 (2H, d, J=8.3 Hz), 7.59-7.68 (3H, m), 7.95-8.05 (5H, m), 8.32 (1H, d, J=8.8 Hz), 9.34 (1H, br s), 9.84 (1H, brs);

IR (KBr) υ max 3405, 2961, 1736, 1619, 1496, 1440, 1245, 1072, 998, 847, 804, 780, 551 cm$^{-1}$;

MS (FAB) m/z: 384 (M+H)$^+$.

54

Example 4

(3S)-N-[(1R)-1-(Naphthalen-1-yl)ethyl]-3-[4-(2H-tetrazol-5-yl)phenyl]cyclopentanamine hydrochloride (Step 1) (3S)-3-(4-Bromophenyl)cyclopentanone

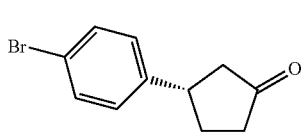

[Chemical 46]

4-Bromophenylboric acid (3.61 g, 18 mmol), cyclopentenone (0.50 mL, 6.0 mmol) and (S)-BINAP (224 mg, 0.36 mmol) were used and treated in a similar manner to (Step 1) of (Example 1) to give the title compound (1.31 g, 90%).

$^1$H-NMR (CDCl$_3$) δ: 1.90-2.00 (1H, m), 2.25-2.35 (2H, m), 2.40-2.51 (2H, m), 2.66 (1H, dd, J=17.8, 7.6 Hz), 3.33-3.43 (1H, m), 7.13 (2H, d, J=8.2 Hz), 7.46 (H, d, J=8.2 Hz);

IR (KBr) υ max 2969, 2903, 1738, 1492, 1402, 1133, 1009, 822 cm$^{-1}$;

MS (EI) m/z: 238 (M)$^+$.

(Step 2) (3S)-3-(4-Bromophenyl)-N-[(1R)-1-(naphthalen-1-yl)ethyl]cyclopentanamine

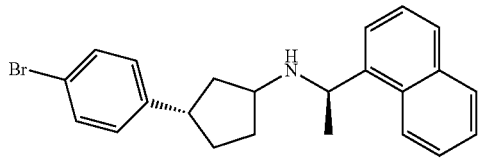

[Chemical 47]

(3S)-3-(4-Bromophenyl)cyclopentanone (1.00 g, 4.1 mmol) was used and treated in a similar manner to (Step 2) of (Example 1) to give the title compound (a mixture of diastereomers) (1.60 g, 97%).

$^1$H-NMR (CDCl$_3$) δ: 1.41-2.16 (5.5H, m), 1.50 and 1.50 (3H, d, J=6.6 Hz), 2.29-2.36 (0.5H, m), 2.81-2.91 (0.5H, m), 3.15-3.23 (1H, m), 3.28-3.35 (0.5H, m), 4.69-4.76 (1H, m), 7.01 and 7.09 (2H, d, J=8.6 Hz), 7.35 and 7.38 (2H, d, J=8.6 Hz), 7.45-7.54 (3H, m), 7.64 (1H, d, J=7.4 Hz), 7.76 (1H, d, J=7.8 Hz), 7.87-7.90 (1H, m), 8.17-8.23 (1H, m);

IR (thin film) υ max 2954, 2863, 1595, 1489, 1444, 1173, 1135, 1074, 1010, 820, 800, 779, 526 cm$^{-1}$;

MS (FAB) m/z: 394 (M+H)$^+$.

(Step 3) [(3S)-3-(4-Bromophenyl)cyclopentyl][(1R)-1-(naphthalen-1-yl)ethyl]carbamic acid tert-butyl ester

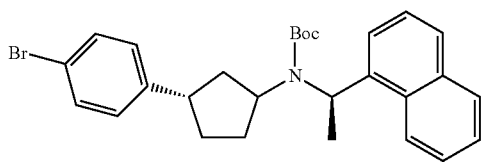

[Chemical 48]

(3S)-3-(4-Bromophenyl)-N-[(1R)-1-(naphthalen-1-yl)ethyl]cyclopentanamine (1.20 g, 3.0 mmol) was used and treated in a similar manner to (Step 3) of (Example 1) to give the title compound (a mixture of diastereomers) (1.36 g, 91%).

¹H-NMR (CDCl₃) δ: 0.31 and 0.43 (1H, br s), 1.56-1.96 (16H, m), 2.31-2.46 (1H, m), 3.17-3.42 (2H, m), 6.15 (1H, br s), 6.85 and 6.99 (2H, d, J=8.2 Hz), 7.25 and 7.35 (2H, d, J=8.2 Hz), 7.43-7.53 (4H, m), 7.78-7.87 (2H, m), 8.11-8.15 (1H, m);

IR (thin film) υ max 2974, 1676, 1489, 1445, 1365, 1325, 1154, 1105, 1027, 1010, 779 cm⁻¹;

MS (FAB) m/z: 494 (M+H)⁺.

(Step 4) [(3S)-3-(4-Cyanophenyl)cyclopentyl][(1R)-1-(naphthalen-1-yl)ethyl]carbamic acid tert-butyl ester

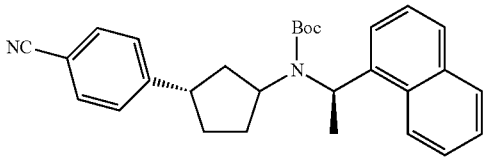

[Chemical 49]

[(3S)-3-(4-Bromophenyl)cyclopentyl][(1R)-1-(naphthalen-1-yl)ethyl]carbamic acid tert-butyl ester (600 mg, 1.2 mmol) was used and treated in a similar manner to (Step 4) of (Example 1) to give the title compound (a mixture of diastereomers) (292 mg, 55%).

¹H-NMR (CDCl₃) δ: 0.33 and 0.47 (1H, br s), 1.51-2.56 (18H, m), 3.32-3.44 (1H, m), 6.16 (1H, br s), 7.07 and 7.21 (2H, d, J=8.2 Hz), 7.40-7.54 (6H, m), 7.78-7.88 (2H, m), 8.10-8.15 (1H, m);

IR (KBr) υ max 2974, 2226, 1678, 1607, 1446, 1366, 1326, 1154, 1106, 1027, 780, 561 cm⁻¹;

MS (FAB) m/z: 441 (M+H)⁺.

(Step 5) [(1R)-1-(Naphthalen-1-yl)ethyl]{(3S)-3-[4-(2H-tetrazol-5-yl)phenyl]cyclopentyl}carbamic acid tert-butyl ester

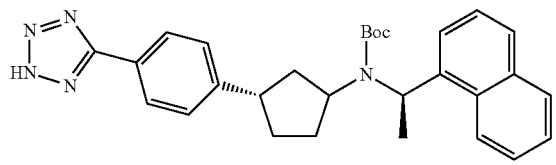

[Chemical 50]

[(3S)-3-(4-Cyanophenyl)cyclopentyl][(1R)-1-(naphthalen-1-yl)ethyl]carbamic acid tert-butyl ester (170 mg, 0.39 mmol) was used and treated in a similar manner to (Step 5) of (Example 1) to give the title compound (a mixture of diastereomers) (59 mg, 32%).

¹H-NMR (CDCl₃) δ: 0.33 and 0.49 (1H, br s), 1.12 (0.5H, br s), 1.54-2.54 (17.5H, m), 3.36-3.45 (1H, m), 6.15 (1H, br s), 7.06 and 7.21 (2H, d, J=8.3 Hz), 7.42-7.55 (4H, m), 7.78-7.88 (3.5H, m), 7.94-8.04 (0.5H, br s), 8.10-8.13 (1H, m);

MS (FAB) m/z: 484 (M+H)⁺.

(Step 6) (3S)-N-[(1R)-1-(Naphthalen-1-yl)ethyl]-3-[4-(2H-tetrazol-5-yl)phenyl]cyclopentanamine hydrochloride

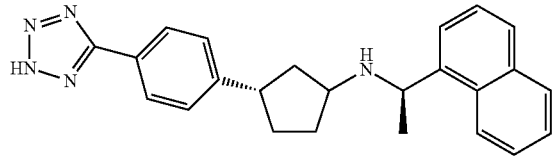

[Chemical 51]

[(1R)-1-(Naphthalen-1-yl)ethyl]{(3S)-3-[4-(2H-tetrazol-5-yl)phenyl]cyclopentyl}carbamic acid tert-butyl ester (59 mg, 0.12 mmol) was used and treated in a similar manner to (Step 6) of (Example 1) to give the title compound (a mixture of diastereomers) (51 mg, 92%).

¹H-NMR (CD₃OD) δ: 1.65-1.74 (1H, m), 1.84 and 1.85 (3H, d, J=6.3 Hz), 1.89-1.99 (2H, m), 2.09-2.49 (3H, m), 3.09-3.18 (1H, m), 3.66-3.80 (1H, m), 5.43-5.49 (1H, m), 7.41 and 7.48 (2H, d, J=8.3 Hz), 7.59-7.70 (3H, m), 7.76-7.79 (1H, m), 7.93 and 7.96 (2H, d, J=8.3 Hz), 7.99-8.03 (2H, m), 8.23-8.27 (1H, m);

IR (KBr) υ max 3379, 2962, 1739, 1618, 1511, 1496, 1440, 1384, 1066, 998, 846, 803, 779 cm⁻¹;

MS (FAB) m/z: 384 (M+H)⁺.

Example 5

N-{4-[(1R,3S)-3-{[(1R)-1-(Naphthalen-1-yl)ethyl]amino}cyclopentyl]benzoyl glycine hydrochloride (Step 1) 4-[(1R,3S)-3-{[(1R)-1-(Naphthalen-1-yl)ethyl]amino}cyclopentyl]benzoic acid ethyl ester

[Chemical 52]

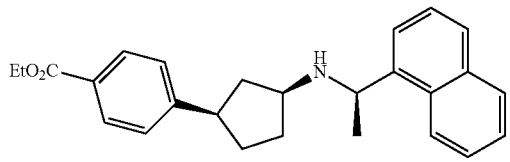

Under a nitrogen stream, (1S,3R)-3-(4-bromophenyl)-N-[(1R)-1-(naphthalen-1-yl)ethyl]cyclopentanamine (199 mg, 0.50 mmol) obtained in (Step 3) of (Example 3) was dissolved in N,N-dimethylformamide (2 mL) and ethanol (2 mL), followed by addition of diisopropylethylamine (0.44 mL, 2.5 mmol) and [1,1'-bis(diphenylphosphino)ferrocene]dichloropalladium (II) dichloromethane complex (165 mg, 0.20 mmol). After the solution mixture was degassed with ultrasonic waves, the mixture was stirred overnight at 70° C. under carbon monoxide stream. The reaction solution was cooled to room temperature, followed by addition of water, and then the solvent was distilled off under reduced pressure. The aqueous phase was extracted with ethyl acetate, the organic phase was dried over anhydrous magnesium sulfate, and the solvent was distilled off under reduced pressure. The obtained residue was purified by column chromatography (NH silica; ethyl acetate/hexane:2/98-10/90) to give the title compound (166 mg, 85%).

$^1$H-NMR (CDCl$_3$) δ: 1.37 (3H, t, J=7.3 Hz), 1.45-1.51 (1H, m), 1.51 (3H, d, J=6.6 Hz), 1.64-1.82 (2H, m), 1.95-2.05 (2H, m), 2.26-2.32 (1H, m), 2.93-3.00 (1H, m), 3.17-3.24 (1H, m), 4.35 (2H, q, J=7.3 Hz), 4.75 (1H, q, J=6.6 Hz), 7.26 (2H, d, J=8.3 Hz), 7.46-7.53 (3H, m), 7.65 (1H, d, J=7.3 Hz), 7.75 (1H, d, J=8.3 Hz), 7.88 (1H, d, J=7.8 Hz), 7.93 (2H, d, J=8.3 Hz), 8.21 (1H, d, J=8.3 Hz);

IR (liquid film) υ max 2956, 1714, 1609, 1366, 1276, 1178, 1102, 1021, 800, 778 cm$^{-1}$;

MS (FAB) m/z: 388 (M+H)$^+$.

(Step 2) 4-[(1R,3S)-3-[(1R)-1-(Naphthalen-1-yl)ethyl]amino}cyclopentyl]benzoic acid hydrochloride

[Chemical 53]

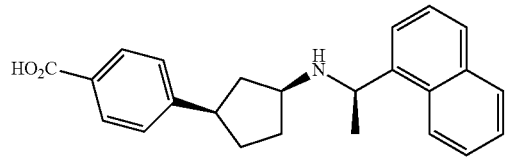

4-[(1R,3S)-3-{[(1R)-1-(Naphthalen-1-yl)ethyl]amino}cyclopentyl]benzoic acid ethyl ester (166 mg, 0.45 mmol) was dissolved in ethanol (2 mL) and tetrahydrofuran (2 mL), followed by addition of 2N aqueous potassium hydroxide solution, and the mixture was stirred overnight at room temperature. 1N hydrochloric acid was added dropwise to the reaction mixture to make the reaction solution acidic, and then the solvent was distilled off under reduced pressure. The solid matter obtained was collected by filtration, and washed with water and ethyl acetate, to give the title compound (144 mg, 85%).

$^1$H-NMR (CD$_3$OD) δ: 1.71-1.94 (2H, m), 1.84 (3H, d, J=6.6 Hz), 2.04-2.23 (3H, m), 2.51-2.59 (1H, m), 3.09-3.19 (1H, m), 3.65-3.74 (1H, m), 5.45 (1H, q, J=6.6 Hz), 7.35 (2H, d, J=8.2 Hz), 7.59-7.70 (3H, m), 7.74-7.80 (1H, m), 7.95 (2H, d, J=8.2 Hz), 8.01 (2H, d, J=8.2 Hz), 8.23 (1H, d, J=8.2 Hz);

IR (KBr) υ max 2957, 2817, 1721, 1610, 1583, 1385, 1217, 1174, 1107, 806, 780 cm$^{-1}$;

MS (FAB) m/z: 360 (M+H)$^+$.

(Step 3) N-{4-[(1R,3S)-3-{[(1R)-1-(Naphthalen-1-yl)ethyl]amino}cyclopentyl]benzoyl}glycine ethyl ester

[Chemical 54]

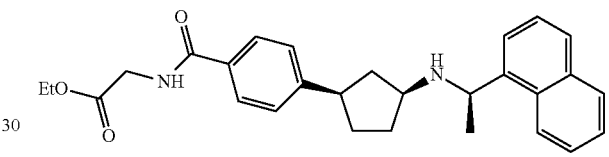

Under a nitrogen stream, 4-[(1R,3S)-3-{[(1R)-1-(naphthalen-1-yl)ethyl]amino}cyclopentyl]benzoic acid hydrochloride (130 mg, 0.33 mmol) was dissolved in methylene chloride (2 mL), followed by dropwise addition of oxalyl chloride (35 μL, 0.39 mmol). After the dropwise addition was completed, one drop of N,N-dimethylformamide was added, and the mixture was stirred for 2 hours at room temperature. The reaction solvent was distilled off under reduced pressure to give a crude product of the acid chloride. Under a nitrogen stream, glycine ethyl ester hydrochloride (55 mg, 0.39 mmol) was dissolved in methylene chloride (2 mL), followed by addition of triethylamine (0.18 mL, 1.3 mmol). A methylene chloride solution of the acid chloride was added dropwise to the mixture, and the mixture was stirred for 1 hour at room temperature. Saturated sodium bicarbonate was added to the reaction solution, and the mixture was then extracted with methylene chloride. After the extracted solution was dried over anhydrous magnesium sulfate, the solvent was distilled off under reduced pressure. The obtained residue was purified by column chromatography (NH silica; ethyl acetate/hexane: 30/70-60/40) to give the title compound (141 mg, 97%).

$^1$H-NMR (CDCl$_3$) δ: 1.31 (3H, t, J=7.0 Hz), 1.45-1.53 (1H, m), 1.51 (3H, d, J=6.4 Hz), 1.64-1.83 (2H, m), 1.94-2.06 (2H, m), 2.27-2.34 (1H, m), 2.92-3.01 (1H, m), 3.16-3.24 (1H, m), 4.23 (2H, d, J=4.7 Hz), 4.26 (2H, q, J=7.0 Hz), 4.76 (1H, q, J=6.4 Hz), 6.60 (1H, t, J=4.7 Hz), 7.28 (2H, d, J=8.2 Hz), 7.46-7.54 (3H, m), 7.65 (1H, d, J=7.0 Hz), 7.72 (2H, d, J=8.2 Hz), 7.76 (1H, d, J=8.2 Hz), 7.89 (1H, dd, J=7.6, 1.8 Hz), 8.21 (1H, d, J=8.6 Hz);

IR (thin film) υ max 3329, 2956, 1749, 1648, 1540, 1503, 1375, 1202, 1025, 780 cm$^{-1}$;

MS (FAB) m/z: 445 (M+H)$^+$.

(Step 4) N-{4-[(1R,3S)-3-{[(1R)-1-(Naphthalen-1-yl)ethyl]amino}cyclopentyl]benzoyl}glycine hydrochloride

[Chemical 55]

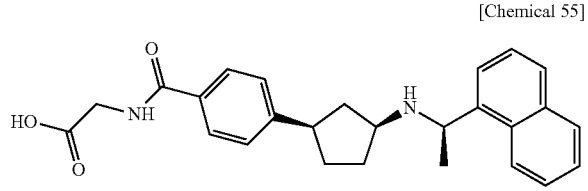 [SMILES: C[C@@H](N[C@H]1CC[C@@H](c2ccc(C(=O)NCC(=O)O)cc2)C1)c1cccc2ccccc12]

N-{4-[(1R,3S)-3-{[(1R)-1-(Naphthalen-1-yl)ethyl]amino}cyclopentyl]benzoyl}glycine ethyl ester (139 mg, 0.31 mmol) was dissolved in ethanol (2 mL), followed by addition of 1N aqueous sodium hydroxide (2 mL), and the mixture was stirred for 4 hours at room temperature. 1N hydrochloric acid was added dropwise to the reaction mixture to make the reaction solution acidic, and the solvent was distilled off under reduced pressure. Diisopropyl ether and water were added to the reaction mixture, followed by ultrasonic wave treatment, and then the solid generated was collected by filtration to give the title compound (52 mg, 37%).

$^1$H-NMR (CD$_3$OD) δ: 1.71-1.90 (2H, m), 1.83 (3H, d, J=6.6 Hz), 2.03-2.18 (3H, m), 2.47-2.53 (1H, m), 3.04-3.13 (1H, m), 3.60-3.68 (1H, m), 3.98 (2H, s), 5.45 (1H, q, J=6.6 Hz), 7.32 (2H, d, J=8.2 Hz), 7.57-7.69 (3H, m), 7.75-7.80 (3H, m), 7.99 (2H, d, J=8.2 Hz), 8.23 (1H, d, J=8.6 Hz);

IR (KBr) υ max 3380, 2934, 1611, 1568, 1546, 1501, 1387, 1297, 780 cm$^{-1}$;

MS (FAB) m/z: 417 (M+H)$^+$.

Example 6

N-Methyl-N-{4-[(1R,3S)-3-{[(1R)-1-(naphthalen-1-yl)ethyl]amino}cyclopentyl]benzoyl}glycine hydrochloride (Step 1) N-Methyl-N-{4-[(1R,3S)-3-{[(1R)-1-(naphthalen-1-yl)ethyl]amino}cyclopentyl]benzoyl}glycine methyl ester

[Chemical 56]

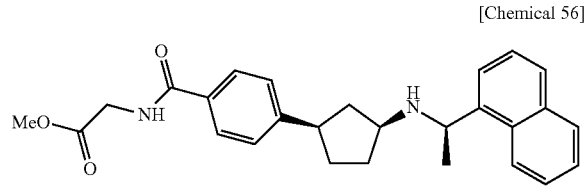 [SMILES: COC(=O)CNC(=O)c1ccc([C@@H]2CC[C@H](N[C@H](C)c3cccc4ccccc34)C2)cc1]

4-[(1R,3S)-3-{[(1R)-1-(Naphthalen-1-yl)ethyl]amino}cyclopentyl]benzoic acid hydrochloride (140 mg, 0.35 mmol) obtained in (Step 2) of (Example 5) and N-methylglycine methyl ester hydrochloride (59 mg, 0.42 mmol) were used and treated in a similar manner to (Step 3) of (Example 5) to give the title compound (120 mg, 76%).

$^1$H-NMR (CDCl$_3$) δ: 1.40-1.51 (1H, m), 1.49 (3H, d, J=6.6 Hz), 1.61-1.81 (2H, m), 1.92-2.02 (2H, m), 2.23-2.31 (1H, m), 2.87-2.970 (1H, m), 3.04 and 3.08 (3H, s), 3.14-3.22 (1H, m), 3.74 and 3.76 (3H, s), 4.00 and 4.26 (2H, s), 4.74 (1H, q, J=6.6 Hz), 7.18-7.39 (4H, m), 7.44-7.53 (3H, m), 7.64 (1H, d, J=7.0 Hz), 7.74 (1H, d, J=8.2 Hz), 7.87 (1H, dd, J=7.8, 1.6 Hz), 8.19 (1H, d, J=8.6 Hz);

IR (thin film) υ max 2953, 1749, 1639, 1482, 1446, 1394, 1210, 1174, 1076, 845, 802, 781 cm$^{-1}$;

MS (FAB) m/z: 445 (M+H)$^+$.

(Step 2) N-Methyl-N-{4-[(1R,3S)-3-{[(1R)-1-(naphthalen-1-yl)ethyl]amino}cyclopentyl]benzoyl}glycine hydrochloride

[Chemical 57]

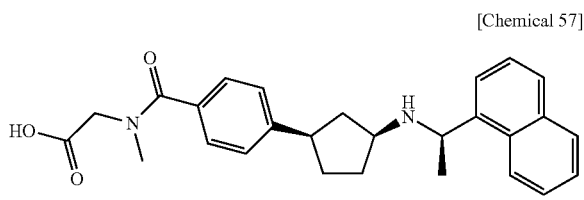 [SMILES: C[C@@H](N[C@H]1CC[C@@H](c2ccc(C(=O)N(C)CC(=O)O)cc2)C1)c1cccc2ccccc12]

N-Methyl-N-{4-[(1R,3S)-3-{[(1R)-1-(naphthalen-1-yl)ethyl]amino}cyclopentyl]benzoyl}glycine methyl ester (118 mg, 0.27 mmol) was used and treated in a similar manner to (Step 4) of (Example 5) to give the title compound (56 mg, 45%).

$^1$H-NMR (CD$_3$OD) δ: 1.66-1.90 (2H, m), 1.82 and 1.83 (3H, d, J=6.6 Hz), 1.99-2.21 (3H, m), 2.46-2.56 (1H, m), 3.00 and 3.09 (3H, s), 3.03-3.15 (1H, m), 3.60-3.71 (1H, m), 3.80 and 4.17 (2H, s), 5.41-5.48 (1H, m), 7.27 and 7.32 (2H, d, J=8.2 Hz), 7.38 and 7.43 (2H, d, J=8.2 Hz), 7.58-7.69 (3H, m), 7.74-7.77 (1H, m), 8.00 (2H, d, J=8.2 Hz), 8.21-8.25 (1H, m);

IR (KBr) υ max 3413, 2971, 1729, 1610, 1482, 1450, 1386, 1077, 804, 780 cm$^{-1}$;

MS (FAB) m/z: 431 (M+H)$^+$.

Example 7

{3-[(1R,3S)-3-{[(1R)-1-(Naphthalen-1-yl)ethyl]amino}cyclopentyl]phenyl}acetic acid hydrochloride (Step 1) {3-[(1R,3S)-3-{(tert-Butoxycarbonyl)[(1R)-1-(naphthalen-1-yl)ethyl]amino}cyclopentyl]phenyl}acetic acid isopropyl ester

[Chemical 58]

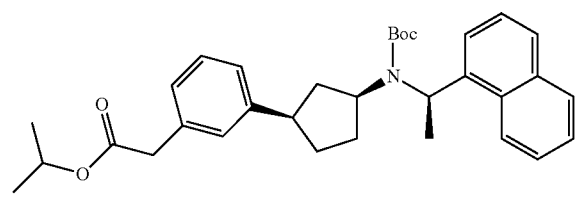

Under a nitrogen stream, lithium hexamethyldisilazide (1.0M hexane solution) (7.6 mL, 7.6 mmol) was added dropwise to bis(dibenzylideneacetone)palladium (35 mg, 0.06 mmol) and 1,3-bis(2,6-diisopropylphenyl)-4,5-dihydroimidazolium tetrahydroborate (29 mg, 0.06 mmol), and then [(1S,3R)-3-(3-bromophenyl)cyclopentyl][(1R)-1-(naphthalen-1-yl)ethyl]carbamic acid tert-butyl ester (50 mg, 1.5 mmol) obtained in (Step 3) of (Example 1), isopropyl acetate (0.36 mL, 3.0 mmol), and toluene (10 mL) were sequentially added to the mixture. The mixture was stirred for 1 hour at room temperature. Water was added to the reaction solution, and the mixture was then extracted with ether. The extracted solution was dried over anhydrous magnesium sulfate, and then the solvent was distilled off under reduced pressure. The obtained residue was purified by column chromatography (ethyl acetate/hexane:5/95-15/85) to give the title compound (596 mg, 76%).

$^1$H-NMR (CDCl$_3$) δ: 0.49 (1H, br s), 1.21 (6H, d, J=6.3 Hz), 1.58-1.67 (3H, m), 1.60 (9H, s), 1.65 (3H, d, J=7.0 Hz), 1.89-1.96 (1H, m), 2.36 (1H, br s), 2.63-2.74 (1H, m), 3.30 (1H, tt, J=10.9, 5.0 Hz), 3.52 (2H, s), 4.99 (1H, sep, J=6.3 Hz), 6.17 (1H, br s), 7.05-7.11 (3H, m), 7.18-7.23 (1H, m), 7.45-7.56 (4H, m), 7.80-7.88 (2H, m), 8.11-8.16 (1H, m);

IR (ATR) υ max 2976, 1729, 1672, 1446, 1364, 1324, 1302, 1252, 1152, 1105, 778 cm$^{-1}$;

MS (FAB) m/z: 516 (M+H)$^+$.

(Step 2) {3-[(1R,3S)-3-{[(tert-Butoxycarbonyl) [(1R)-1-(naphthalen-1-yl)ethyl]amino}cyclopentyl] phenyl}acetic acid

[Chemical 59]

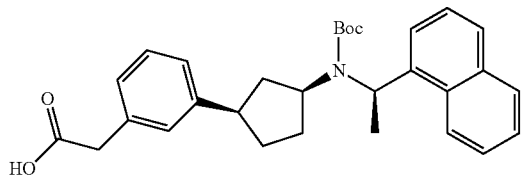

{3-[(1R,3S)-3-{(tert-Butoxycarbonyl)[(1R)-1-(naphthalen-1-yl)ethyl]amino}cyclopentyl]phenyl}acetic acid isopropyl ester (590 mg, 1.1 mmol) was dissolved in isopropanol (5 mL) and tetrahydrofuran (5 mL), followed by addition of 4N aqueous potassium hydroxide solution, and the mixture was stirred overnight at room temperature. 1N hydrochloric acid was added dropwise to the reaction mixture to make the reaction solution acidic, and the solvent was distilled off under reduced pressure. The reaction mixture was extracted with ethyl acetate, the extracted solution was dried over anhydrous magnesium sulfate, and then the solvent was distilled off under reduced pressure. The obtained residue was purified by column chromatography (ethyl acetate/hexane:30/70-50/50) to give the title compound (419 mg, 77%).

$^1$H-NMR (CDCl$_3$) δ: 0.49 (1H, br s), 1.56-1.66 (3H, m), 1.59 (9H, s), 1.64 (3H, d, J=7.0 Hz), 1.88-1.95 (1H, m), 2.35 (1H, br s), 2.63-2.74 (1H, m), 3.30 (1H, tt, J=10.8, 5.0 Hz), 3.59 (2H, s), 6.17 (1H, br s), 7.06-7.13 (3H, m), 7.22 (1H, t, J=7.8 Hz), 7.46-7.56 (4H, m), 7.82 (1H, d, J=8.2 Hz), 7.84-7.88 (1H, m), 8.11-8.15 (1H, m);

IR (KBr) υ max 2974, 1735, 1711, 1675, 1451, 1366, 1326, 1155, 1028, 780 cm$^{-1}$;

MS (FAB) m/z: 474 (M+H)$^+$.

(Step 3) {3-[(1R,3S)-3-{[(1R)-1-(Naphthalen-1-yl) ethyl]amino}cyclopentyl]phenyl}acetic acid hydrochloride

[Chemical 60]

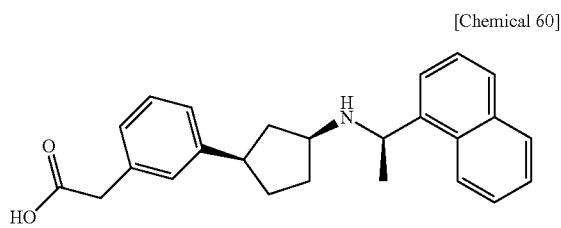 [SMILES: C[C@@H](N[C@H]1CC[C@@H](c2cccc(CC(=O)O)c2)C1)c1cccc2ccccc12]

{3-[(1R,3S)-3-{(tert-Butoxycarbonyl)[(1R)-1-(naphthalen-1-yl)ethyl]amino}cyclopentyl]phenyl}acetic acid (417 mg, 0.88 mmol) was dissolved in 1,4-dioxane (6 mL), followed by addition of a 1,4-dioxane solution of 4N hydrochloric acid (2 mL), and the mixture was stirred for 2 days at room temperature. The reaction solvent was distilled off under reduced pressure, followed by addition of water and methylene chloride. Then, the mixture was neutralized with a 1N aqueous sodium hydroxide solution, and was then extracted with methylene chloride. After the extracted solution was dried over anhydrous magnesium sulfate, the solvent was distilled off under reduced pressure. The obtained residue was dissolved in methylene chloride (6 mL), followed by addition of an ethyl acetate solution of 1N hydrochloric acid (2 mL), and then the solvent was distilled off under reduced pressure. Hexane was added to the residue, followed by ultrasonic wave treatment, and then the solid matter generated was collected by filtration to give the title compound (324 mg, 90%).

$^1$H-NMR (CD$_3$OD) δ: 1.70-1.92 (2H, m), 1.83 (3H, d, J=6.6 Hz), 2.00-2.21 (3H, m), 2.47-2.55 (1H, m), 2.99-3.09 (1H, m), 3.56 (2H, s), 3.61-3.70 (1H, m), 5.44 (1H, q, J=6.6 Hz), 7.11-7.17 (3H, m), 7.24 (1H, t, J=7.6 Hz), 7.58-7.69 (3H, m), 7.77 (1H, d, J=7.0 Hz), 8.00 (2H, d, J=8.2 Hz), 8.23 (1H, d, J=8.6 Hz);

IR (KBr) υ max 3418, 2957, 1725, 1586, 1446, 1383, 1247, 1173, 804, 780 cm$^{-1}$;

MS (FAB) m/z: 374 (M+H)$^+$.

Example 8

{4-[(1R,3S)-3-{[(1R)-1-(Naphthalen-1-yl)ethyl] amino}cyclopentyl]phenyl}acetic acid hydrochloride (Step 1) {4-[(1R,3S)-3-{(tert-Butoxycarbonyl)[(1R)-1-(naphthalen-1-yl)ethyl]amino}cyclopentyl] phenyl}acetic acid isopropyl ester

[Chemical 61]

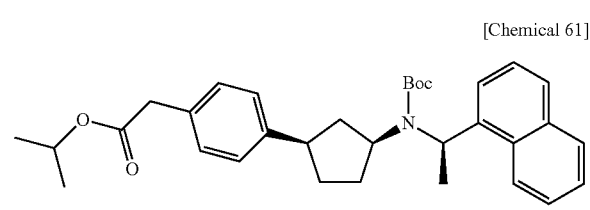 [SMILES: CC(C)OC(=O)Cc1ccc([C@@H]2CC[C@H](N(C(=O)OC(C)(C)C)[C@H](C)c3cccc4ccccc34)C2)cc1]

(1S,3R)-3-(4-Bromophenyl)cyclopentyl]][[(1R)-1-(naphthalen-1-yl)ethyl]carbamic acid tert-butyl ester (1.00 g, 2.0 mmol) obtained in (Step 3) of (Example 3) was used and treated in a similar manner to (Step 1) of (Example 7) to give the title compound (617 mg, 59%).

¹H-NMR (CDCl₃) δ: 0.48 (1H, br s), 1.22 (6H, d, J=6.3 Hz), 1.58-1.67 (3H, m), 1.60 (9H, s), 1.65 (3H, d, J=6.6 Hz), 1.88-1.94 (1H, m), 2.36 (1H, br s), 2.63-2.73 (1H, m), 3.30 (1H, tt, J=10.9, 4.9 Hz), 3.52 (2H, s), 4.99 (1H, sep, J=6.3 Hz), 6.17 (1H, br s), 7.11-7.19 (4H, m), 7.45-7.56 (4H, m), 7.78-7.89 (2H, m), 8.10-8.17 (1H, m);

IR (ATR) υ max 2976, 1729, 1672, 1446, 1364, 1324, 1294, 1253, 1153, 1104, 1026, 804, 778 cm⁻¹;

MS (FAB) m/z: 516 (M+H)⁺.

(Step 2) {4-[(1R,3S)-3-{(tert-Butoxycarbonyl)[(1R)-1-(naphthalen-1-yl)ethyl]amino}cyclopentyl]phenyl}acetic acid

[Chemical 62]

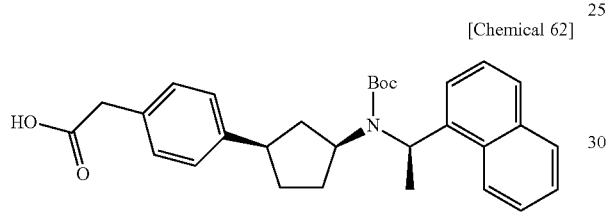

{4-[(1R,3S)-3-{(tert-Butoxycarbonyl)[(1R)-1-(naphthalen-1-yl)ethyl]amino}cyclopentyl]phenyl}acetic acid isopropyl ester (610 mg, 1.2 mmol) was used and treated in a similar manner to (Step 2) of (Example 7) to give the title compound (495 mg, 88%).

¹H-NMR (CDCl₃) δ: 0.48 (1H, s), 1.51-1.60 (3H, m), 1.59 (9H, s), 1.64 (3H, d, J=7.0 Hz), 1.86-1.93 (1H, m), 2.35 (1H, s), 2.62-2.73 (1H, m), 3.30 (1H, tt, J=10.8, 5.0 Hz), 3.59 (2H, s), 6.17 (1H, s), 7.11-7.19 (4H, m), 7.45-7.55 (4H, m), 7.81 (1H, d, J=8.2 Hz), 7.83-7.88 (1H, m), 8.10-8.15 (1H, m);

IR (KBr) υ max 2975, 1737, 1710, 1675, 1452, 1366, 1327, 1302, 1238, 1156, 805, 779 cm⁻¹;

MS (FAB) m/z: 474 (M+H)⁺.

(Step 3) {4-(1R,3S)-3-{[(1R)-1-(Naphthalen-1-yl)ethyl]amino}cyclopentyl]phenyl}acetic acid hydrochloride

[Chemical 63]

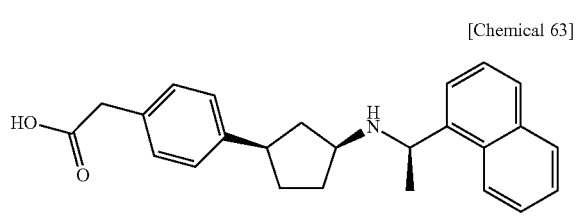 [SMILES: C[C@@H](N[C@H]1CC[C@@H](c2ccc(CC(=O)O)cc2)C1)c1cccc2ccccc12]

{4-[(1R,3S)-3-{[(tert-Butoxycarbonyl)[(1R)-1-(naphthalen-1-yl)ethyl]amino}cyclopentyl]phenyl}acetic acid (489 mg, 1.0 mmol) was used and treated in a similar manner to (Step 3) of (Example 7) to give the title compound (381 mg, 90%).

¹H-NMR (CD₃OD) δ: 1.73 (1H, td, J=12.1, 10.2 Hz), 1.80-1.91 (1H, m), 1.83 (3H, d, J=6.7 Hz), 2.00-2.21 (3H, m), 2.46-2.52 (1H, m), 2.98-3.07 (1H, m), 3.55 (2H, s), 3.61-3.69 (1H, m), 5.44 (1H, q, J=6.7 Hz), 7.20 (4H, s), 7.58-7.70 (3H, m), 7.77 (1H, d, J=6.6 Hz), 8.00 (2H, d, J=8.2 Hz), 8.22 (1H, d, J=8.6 Hz);

IR (KBr) υ max 3420, 2956, 2684, 1712, 1580, 1517, 1404, 1383, 1235, 806, 779 cm⁻¹;

MS (FAB) m/z: 374 (M+H)⁺.

Example 9

3-{4-(1R,3S)-3-{[(1R)-1-(Naphthalen-1-yl)ethyl]amino}cyclopentyl]phenyl}propanoic acid hydrochloride (Step 1) [(1S,3R)-3-(4-Formylphenyl)cyclopentyl][(1R)-1-(naphthalen-1-yl)ethyl]carbamic acid tert-butyl ester

[Chemical 64]

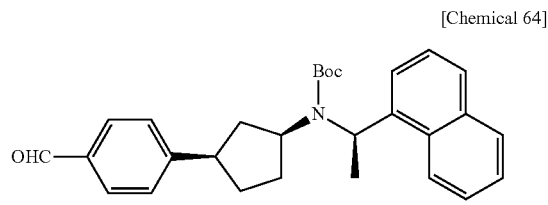 [SMILES: C[C@H](c1cccc2ccccc12)N(C(=O)OC(C)(C)C)[C@H]1CC[C@@H](c2ccc(C=O)cc2)C1]

Under a nitrogen stream, [(1S,3R)-3-(4-cyanophenyl)cyclopentyl][(1R)-1-(naphthalen-1-yl)ethyl]carbamic acid tert-butyl ester (441 mg, 1.0 mmol) obtained in (Step 4) of (Example 3) was dissolved in methylene chloride (5 mL). The mixture was cooled to −78° C., followed by dropwise addition of diisobutylaluminum hydride (1.0M toluene solution) (1.2 mL, 1.2 mmol). After dropwise addition was completed, the temperature of the reaction mixture was raised to room temperature, and then the mixture was stirred for 1 hour. Sodium hydrogensulfate decahydrate was added to the reaction mixture, and the mixture was further stirred for 30 minutes. The reaction solution was filtered to remove insoluble matter, and the filtrate was distilled off under reduced pressure. The residue obtained was purified by column chromatography (ethyl acetate/hexane:10/90-15/85) to give the title compound (416 mg, 94%).

¹H-NMR (CDCl₃) δ: 0.52 (1H, br s), 1.58-1.63 (3H, m), 1.61 (9H, s), 1.66 (3H, d, J=6.6 Hz), 1.93-2.00 (1H, m), 2.41 (1H, br s), 2.74-2.84 (1H, m), 3.29-3.38 (1H, m), 6.19 (1H, br s), 7.34 (2H, d, J=7.2 Hz), 7.47-7.53 (2H, m), 7.54 (2H, d, J=7.2 Hz), 7.78 (2H, d, J=8.2 Hz), 7.83 (1H, d, J=8.2 Hz), 7.85-7.89 (1H, m), 8.11-8.14 (1H, m), 9.95 (1H, s);

IR (KBr) υ max 2974, 1677, 1605, 1448, 1366, 1326, 1169, 1155, 780 cm⁻¹;

MS (FAB) m/z: 444 (M+H)⁺.

(Step 2) (2E)-3-{4-[(1R,3S)-3-{(tert-Butoxycarbonyl)[(1R)-1-(naphthalen-1-yl)ethyl]amino}cyclopentyl]phenyl}acrylic acid ethyl ester

[Chemical 65]

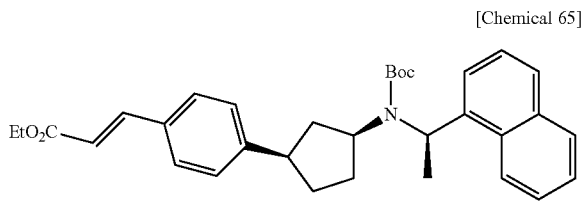 [SMILES: CCOC(=O)/C=C/c1ccc([C@@H]2CC[C@H](N(C(=O)OC(C)(C)C)[C@H](C)c3cccc4ccccc34)C2)cc1]

Under a nitrogen stream, sodium hydride (60% in mineral-oil dispersion) (44 mg, 1.1 mmol) was suspended in tetrahydrofuran (5 mL), followed by addition of ethyl diethylphosphonoacetate (0.24 mL, 1.2 mmol), and the mixture was stirred for 10 minutes at room temperature. A tetrahydrofuran solution of [(1S,3R)-3-(4-formylphenyl)cyclopentyl][(1R)-1-(naphthalen-1-yl)ethyl]carbamic acid tert-butyl ester (407 mg, 0.92 mmol) was added to the mixture, and the mixture was stirred further for 1 hour at room temperature. A saturated aqueous ammonium chloride solution was added to the reaction solution, and the solution was extracted with ethyl acetate. The extracted solution was dried over anhydrous magnesium sulfate, and then the solvent was distilled off under reduced pressure. The residue obtained was purified by column chromatography (ethyl acetate/hexane: 10/90-15/85) to give the title compound (475 mg).

¹H-NMR (CDCl₃) δ: 0.51 (1H, br s), 1.33 (3H, t, J=7.1 Hz), 1.56-1.63 (3H, m), 1.60 (9H, s), 1.65 (3H, d, J=7.0 Hz), 1.90-1.96 (1H, m), 2.39 (1H, br s), 2.67-2.77 (1H, m), 3.27-3.36 (1H, m), 4.25 (2H, q, J=7.1 Hz), 6.18 (1H, br s), 6.38 (1H, d, J=16.0 Hz), 7.19 (2H, d, J=8.2 Hz), 7.42 (2H, d, J=8.2 Hz), 7.46-7.52 (3H, m), 7.54 (1H, d, J=6.6 Hz), 7.64 (1H, d, J=16.0 Hz), 7.82 (1H, d, J=8.2 Hz), 7.84-7.88 (1H, m); 8.11-8.15 (1H, m);

IR (KBr) ν max 2976, 1713, 1676, 1635, 1448, 1366, 1325, 1309, 1157, 1106, 1028, 982, 779 cm⁻¹;

MS (FAB) m/z: 514 (M+H)⁺.

(Step 3) 3-{4-[(1R,3S)-3-{[(tert-Butoxycarbonyl)[(1R)-1-(naphthalen-1-yl)ethyl]amino}cyclopentyl]phenyl}propanoic acid ethyl ester

[Chemical 66]

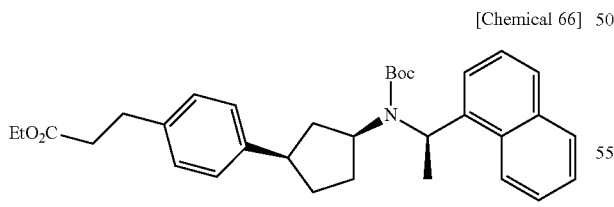

Under a nitrogen stream, (2E)-3-{4-[(1R,3S)-3-{(tert-butoxycarbonyl)[(1R)-1-(naphthalen-1-yl)ethyl]amino}cyclopentyl]phenyl}acrylic acid ethyl ester (470 mg, 0.91 mmol) was dissolved in ethanol (5 mL). After adding 10% palladium/carbon (40 mg) to the mixture, the atmosphere was replaced with hydrogen, and then the mixture was stirred for 6 hours at room temperature. The catalyst was filtered off, and the solvent of the filtrate was distilled off under reduced pressure. The residue obtained was purified by column chromatography (ethyl acetate/hexane:5/95-15/85) to give the title compound (420 mg, 89%).

¹H-NMR (CDCl₃) δ: 0.48 (1H, br s), 1.22 (3H, t, J=7.1 Hz), 1.51-1.62 (3H, m), 1.60 (9H, s), 1.64 (3H, d, J=6.6 Hz), 1.86-1.93 (1H, m), 2.36 (1H, br s), 2.58 (2H, t, J=7.8 Hz), 2.61-2.71 (1H, m), 2.89 (2H, t, J=7.8 Hz), 3.25-3.35 (1H, m), 4.11 (2H, q, J=7.1 Hz), 6.17 (1H, br s), 7.10 (4H, s), 7.45-7.55 (4H, m), 7.81 (1H, d, J=8.2 Hz), 7.83-7.88 (1H, m), 8.11-8.15 (1H, m);

IR (thin film) ν max 2976, 1735, 1676, 1513, 1448, 1366, 1326, 1302, 1156, 1107, 1028, 805, 780 cm⁻¹;

MS (FAB) m/z: 516 (M+H)⁺.

(Step 4) 3-{4-[(1R,3S)-3-{(tert-Butoxycarbony)[(1R)-1-(naphthalen-1-yl)ethyl]amino}cyclopentyl]phenyl}propanoic acid

[Chemical 67]

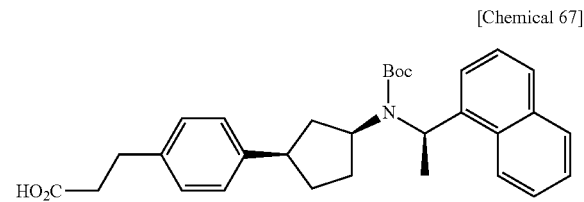 [SMILES: C[C@H](c1cccc2ccccc12)N(C(=O)OC(C)(C)C)[C@H]1CC[C@@H](c2ccc(CCC(=O)O)cc2)C1]

3-{4-[(1R,3S)-3-{[(tert-Butoxycarbonyl)[(1R)-1-(naphthalen-1-yl)ethyl]amino}cyclopentyl]phenyl}propanoic acid ethyl ester (200 mg, 0.39 mmol) was used and treated in a similar manner to (Step 4) of (Example 5) to give the title compound (188 mg, 100%).

¹H-NMR (CDCl₃) δ: 0.48 (1H, br s), 1.51-1.62 (3H, m), 1.60 (9H, s), 1.64 (3H, d, J=6.6 Hz), 1.87-1.93 (1H, m), 2.35 (1H, br s), 2.62-2.72 (1H, m), 2.65 (2H, t, J=7.8 Hz), 2.90 (2H, t, J=7.8 Hz), 3.25-3.35 (1H, m), 6.17 (1H, br s), 7.10 (4H, s), 7.46-7.51 (3H, m), 7.54 (1H, d, J=7.4 Hz), 7.81 (1H, d, J=7.8 Hz), 7.84-7.87 (1H, m), 8.11-8.15 (1H, m);

IR (KBr) ν max 2975, 1738, 1710, 1675, 1513, 1451, 1366, 1326, 1303, 1240, 1156, 1106, 1028, 805, 779 cm⁻¹;

MS (FAB) m/z: 488 (M+H)⁺.

(Step 5) 3-{4-[(1R,3S)-3-{[(1R)-1-(Naphthalen-1-yl)ethyl]amino}cyclopentyl]phenyl}propanoic acid hydrochloride

[Chemical 68]

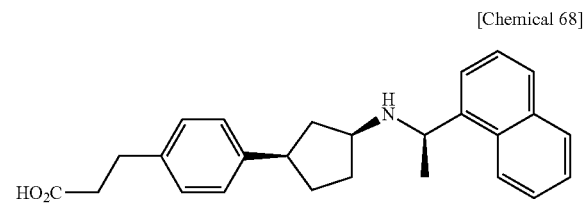 [SMILES: C[C@@H](N[C@H]1CC[C@@H](c2ccc(CCC(=O)O)cc2)C1)c1cccc2ccccc12]

3-{4-[(1R,3S)-3-{(tert-Butoxycarbonyl)[(1R)-1-(naphthalen-1-yl)ethyl]amino}cyclopentyl]phenyl}propanoic acid (182 mg, 0.37 mmol) was used and treated in a similar manner to (Step 3) of (Example 7) to give the title compound (159 mg, 100%).

¹H-NMR (CD₃OD) δ: 1.68-1.75 (1H, m), 1.82-1.89 (1H, m), 1.83 (3H, d, J=6.4 Hz), 2.00-2.20 (3H, m), 2.45-2.51 (1H, m), 2.56 (2H, t, J=7.6 Hz), 2.86 (2H, t, J=7.6 Hz), 2.97-3.05

(1H, m), 3.61-3.69 (1H, m), 5.43 (1H, q, J=6.4 Hz), 7.15 (4H, s), 7.58-7.69 (3H, m), 7.76 (1H, d, J=7.3 Hz), 8.00 (2H, d, J=8.3 Hz)

8.22 (1H, d, J=8.8 Hz);

IR (KBr) υ max 2956, 2830, 1735, 1696, 1581, 1516, 1442, 1384, 1234, 1144, 805, 779 cm$^{-1}$;

MS (FAB) m/z: 388 (M+H)$^+$.

Example 10

{4-[(1R,3S)-3-{[(1R)-1-(Naphthalen-1-yl)ethyl]amino}cyclopentyl]phenoxy}acetic acid hydrochloride (Step 1)
(3R)-3-[4-(Benzyloxy)phenyl]cyclopentanone

[Chemical 69]

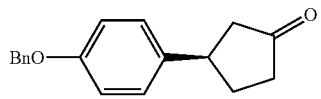

4-Benzyloxyphenylboric acid (15.1 g, 66 mmol) and cyclopentenone (2.5 mL, 30 mmol) were used and treated in a similar manner to (Step 1) of (Example 3) to give the title compound (5.09 g, 64%).

$^1$H-NMR (CDCl$_3$) δ: 1.89-2.00 (1H, m), 2.23-2.35 (2H, m), 2.38-2.50 (2H, m), 2.65 (1H, dd, J=18.4, 7.4 Hz), 3.32-3.43 (1H, m), 5.06 (2H, s), 6.96 (2H, d, J=8.6 Hz), 7.18 (2H, d, J=8.6 Hz), 7.31-7.45 (5H, m);

IR (KBr) υ max 2889, 1735, 1612, 1514, 1454, 1380, 1253, 1134, 1044, 831, 740 cm$^{-1}$;

MS (EI) m/z: 266 (M)$^+$.

(Step 2) (1S,3R)-3-[4-(Benzyloxy)phenyl]-N-[(1R)-1-(naphthalen-1-yl)ethyl]cyclopentanamine

[Chemical 70]

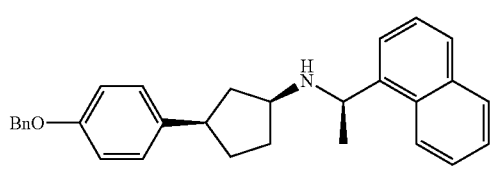

(3R)-3-[4-(Benzyloxy)phenyl]cyclopentanone (894 mg, 5.2 mmol) was used and treated in a similar manner to (Step 2) of (Example 1) to give the title compound (746 mg, 44%).

$^1$H-NMR (CDCl$_3$) δ: 1.41-1.49 (1H, m), 1.50 (3H, d, J=6.5 Hz), 1.61-1.78 (2H, m), 1.92-2.01 (2H, m), 2.23-2.30 (1H, m), 2.82-2.91 (1H, m), 3.15-3.20 (1H, m), 4.75 (1H, q, J=6.5 Hz), 5.03 (2H, s), 6.89 (2H, d, J=8.5 Hz), 7.13 (2H, d, J=8.5 Hz), 7.31 (1H, t, J=7.1 Hz), 7.38 (2H, t, J=7.6 Hz), 7.42 (2H, d, J=7.3 Hz), 7.46-7.53 (3H, m), 7.65 (1H, d, J=6.8 Hz), 7.75 (1H, d, J=7.8 Hz), 7.88 (1H, d, J=7.8 Hz), 8.20 (1H, d, J=8.3 Hz);

IR (thin film) υ max 2951, 2862, 1609, 1511, 1453, 1239, 1176, 1025, 800, 779, 736, 696 cm$^{-1}$;

MS (EI) m/z: 421 (M)$^{+\cdot}$.

(Step 3) 4-[(1R,3S)-3-{[(1R)-1-(Naphthalen-1-yl)ethyl]amino}cyclopentyl]phenol

[Chemical 71]

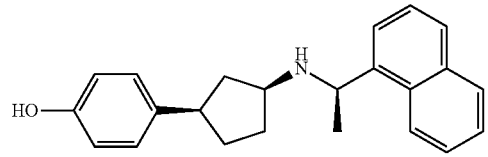

Under a nitrogen stream, (1S,3R)-3-[4-(benzyloxy)phenyl]-N-[(1R)-1-(naphthalen-1-yl)ethyl]cyclopentanamine (740 mg, 1.8 mmol) was dissolved in methanol (10 mL). After adding 10% palladium/carbon (70 mg) to the mixture, the atmosphere was replaced with hydrogen, and then the mixture was stirred for 16 hours at room temperature. The catalyst was filtered off, and the solvent of the filtrate was distilled off under reduced pressure. The residue obtained was purified by column chromatography (methanol/methylene chloride: 0/100-10/90) to give the title compound (427 mg, 73%).

$^1$H-NMR (CDCl$_3$) δ: 1.47-1.60 (1H, m), 1.57 (3H, d, J=6.6 Hz), 1.68-1.80 (2H, m), 1.86-1.99 (2H, m), 2.22-2.32 (1H, m), 2.76-2.87 (1H, m), 3.12-3.22 (1H, m), 4.82 (1H, q, J=6.6 Hz), 6.72 (2H, d, J=8.6 Hz), 7.03 (2H, d, J=8.6 Hz), 7.47-7.56 (3H, m), 7.72 (1H, br d), 7.77 (1H, d, J=8.2 Hz), 7.87-7.91 (1H, m), 8.16 (1H, d, J=8.2 Hz);

IR (KBr) υ max 3283, 2953, 1612, 1595, 1515, 1447, 1370, 1246, 1172, 830, 800, 779 cm$^{-1}$;

MS (FAB) m/z: 332 (M+H)$^+$.

(Step 4) {4-[(1R,3S)-3-{[(1R)-1-(Naphthalen-1-yl)ethyl]amino}cyclopentyl]phenoxy}acetic acid ethyl ester

[Chemical 72]

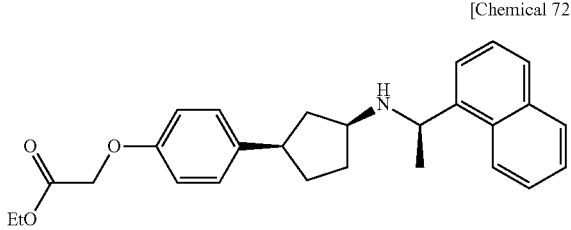

Under a nitrogen stream, N,N-dimethylformamide (5 mL) and ethyl bromoacetate (0.13 mL, 1.2 mmol) were added to 4-[(1R,3S)-3-{[(1R)-1-(naphthalen-1-yl)ethyl]amino}cyclopentyl]phenol (331 mg, 1.0 mmol) and potassium carbonate (207 mg, 1.5 mmol), and the mixture was stirred overnight at room temperature. Water was added to the reaction solution, followed by extraction with ethyl acetate. After the extracted solution was dried over anhydrous magnesium sulfate, the solvent was distilled off under reduced pressure. The residue obtained was purified by column chromatography (NH silica; ethyl acetate/hexane: 5/95-8/92) to give the title compound (298 mg, 71%).

¹H-NMR (CDCl₃) δ: 1.29 (3H, t, J=7.1 Hz), 1.39-1.50 (1H, m), 1.51 (3H, d, J=6.6 Hz), 1.62-1.78 (2H, m), 1.91-2.01 (2H, m), 2.22-2.30 (1H, m), 2.81-2.92 (1H, m), 3.13-3.21 (1H, m), 4.27 (2H, q, J=7.1 Hz), 4.58 (2H, s), 4.75 (1H, q, J=6.6 Hz), 6.82 (2H, d, J=8.6 Hz), 7.12 (2H, d, J=8.6 Hz), 7.46-7.54 (3H, m), 7.65 (1H, d, J=7.4 Hz), 7.75 (1H, d, J=8.2 Hz), 7.86-7.90 (1H, m), 8.20 (1H, d, J=8.2 Hz);

IR (ATR) υ max 2942, 2861, 1756, 1733, 1676, 1510, 1192, 1179, 1083, 800, 778 cm⁻¹;

MS (FAB) m/z: 418 (M+H)⁺.

(Step 5) {4-[(1R,3S)-3-{[(1R)-1-(Naphthalen-1-yl)ethyl]amino}cyclopentyl]phenoxy}acetic acid hydrochloride

[Chemical 73]

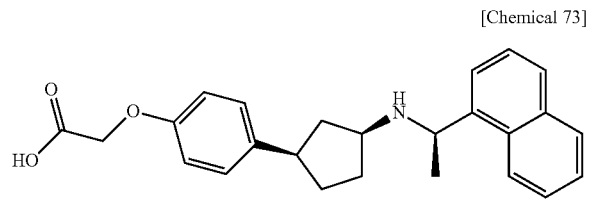 [SMILES: C[C@@H](N[C@H]1CC[C@@H](c2ccc(OCC(=O)O)cc2)C1)c1cccc2ccccc12]

{4-[(1R,3S)-3-{[(1R)-1-(Naphthalen-1-yl)ethyl]amino}cyclopentyl]phenoxy}acetic acid ethyl ester (720 mg, 1.7 mmol) was dissolved in ethanol (5 mL), followed by addition of 1N aqueous sodium hydroxide solution (5 mL), and the mixture was stirred for 1 hour at room temperature. 1N hydrochloric acid was added dropwise to the reaction mixture to make the reaction solution acidic, and then the solvent was distilled off under reduced pressure. The aqueous phase was extracted with methylene chloride, the extracted solution was dried over anhydrous magnesium sulfate, and then the solvent was distilled off under reduced pressure. The residue obtained was dissolved in methylene chloride (6 mL), followed by addition of an ethyl acetate solution of 1N hydrochloric acid (2 mL), and then the solvent was distilled off under reduced pressure. Ethyl acetate and hexane were added to the residue, followed by treatment with ultrasonic waves, and then the solid matter generated was collected by filtration to give the title compound (237 mg, 87%).

¹H-NMR (CD₃OD) δ: 1.63-1.73 (1H, m), 1.79-1.87 (1H, m), 1.82 (3H, d, J=6.6 Hz), 1.98-2.20 (3H, m), 2.43-2.50 (1H, m), 2.94-3.04 (1H, m), 3.60-3.69 (1H, m), 4.61 (2H, s), 5.43 (1H, q, J=6.6 Hz), 6.86 (2H, d, J=8.6 Hz), 7.16 (2H, d, J=8.6 Hz), 7.58-7.69 (3H, m), 7.75 (1H, d, J=7.0 Hz), 8.00 (2H, d, J=8.6 Hz), 8.22 (1H, d, J=8.6 Hz);

IR (KBr) υ max 3411, 2966, 1734, 1609, 1512, 1402, 1223, 1179, 1066, 829, 803, 779 cm⁻¹;

MS (FAB) m/z: 390 (M+H)⁺.

Example 11

2-Methyl-2-{4-[(1R,3S)-3-{[(1R)-1-(naphthalen-1-yl)ethyl]amino}cyclopentyl]phenoxy}propanoic acid hydrochloride (Step 1) 2-Methyl-2-{4-[(1R,3S)-3-{[(1R)-1-(naphthalen-1-yl)ethyl]amino}cyclopentyl]phenoxy}propanoic acid ethyl ester

[Chemical 74]

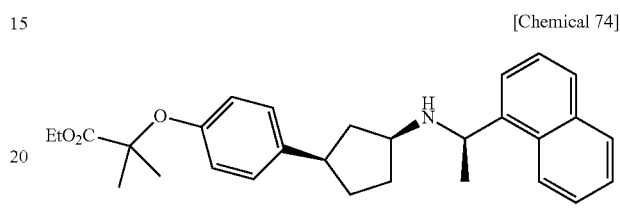

Under a nitrogen stream, N,N-dimethylformamide (3 mL) was added to 4-[(1R,3S)-3-{[(1R)-1-(naphthalen-1-yl)ethyl]amino}cyclopentyl]phenol (180 mg, 0.49 mmol) obtained in (Step 3) of (Example 10) and potassium carbonate (135 mg, 0.98 mmol). 2-Bromo-2-methylpropionic acid ethyl ester (86 μL, 0.59 mmol) was further added, and the mixture was stirred for 2 days at 100° C. After the reaction solution was cooled to room temperature, water was added and the mixture was extracted with ethyl acetate. The extracted solution was dried over anhydrous magnesium sulfate, and then the solvent was distilled off under reduced pressure. The residue obtained was purified by column chromatography (NH silica; ethyl acetate/hexane:2/98-10/90) to give the title compound (131 mg, 60%).

¹H-NMR (CDCl₃) δ: 1.25 (3H, t, J=7.1 Hz), 1.43 (1H, td, J=11.8, 9.5 Hz), 1.50 (3H, d, J=6.6 Hz), 1.57 (6H, s), 1.59-1.77 (2H, m), 1.91-2.01 (2H, m), 2.23-2.30 (1H, m), 2.80-2.90 (1H, m), 3.13-3.21 (1H, m), 4.23 (2H, q, J=7.1 Hz), 4.75 (1H, q, J=6.6 Hz), 6.74 (2H, d, J=8.6 Hz), 7.06 (2H, d, J=8.6 Hz), 7.46-7.54 (3H, m), 7.65 (1H, d, J=7.4 Hz), 7.75 (1H, d, J=8.2 Hz), 7.88 (1H, d, J=7.8 Hz), 8.20 (1H, d, J=8.2 Hz);

IR (thin film) υ max 2944, 2864, 1732, 1509, 1283, 1234, 1176, 1138, 1023, 800, 779 cm⁻¹;

MS (FAB) m/z: 446 (M+H)⁺.

(Step 2) 2-Methyl-2-{4-[(1R,3S)-3-{[(1R)-1-(naphthalen-1-yl)ethyl]amino}cyclopentyl]phenoxy}propanoic acid hydrochloride

[Chemical 75]

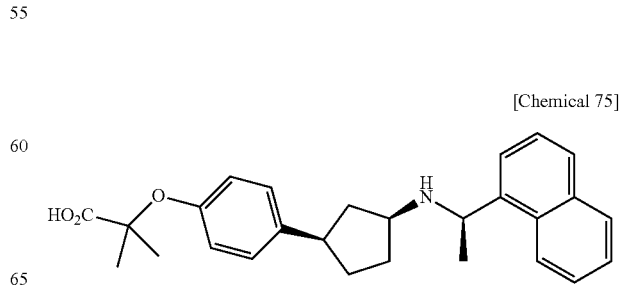

2-Methyl-2-{4-[(1R,3S)-3-{[(1R)-1-(naphthalen-1-yl) ethyl]amino}cyclopentyl]phenoxy}propanoic acid ethyl ester (130 mg, 0.29 mmol) was dissolved in ethanol (2 mL) and tetrahydrofuran (2 mL), followed by addition of 2N aqueous potassium hydroxide solution, and the mixture was stirred overnight at room temperature. 1N hydrochloric acid was added dropwise to the reaction mixture to make the reaction solution acidic, and the solvent was distilled off under reduced pressure. The aqueous phase was extracted with ethyl acetate, the extracted solution was dried over anhydrous magnesium sulfate, and then the solvent was distilled off under reduced pressure. The residue obtained was dissolved in ethyl acetate (3 mL), followed by addition of an ethyl acetate solution of 1N hydrochloric acid (1 mL), and the solvent was distilled off under reduced pressure. Ethyl acetate and hexane were added to the residue, followed by treatment with ultrasonic waves, and then the solid matter generated was collected by filtration to give the title compound (102 mg, 77%).

$^1$H-NMR (CD$_3$OD) δ: 1.52 (6H, s), 1.62-1.72 (1H, m), 1.78-1.87 (1H, m), 1.82 (3H, d, J=6.7 Hz), 1.97-2.19 (3H, m), 2.44-2.52 (1H, m), 2.95-3.05 (1H, m), 3.61-3.70 (1H, m), 5.43 (1H, q, J=6.7 Hz), 6.83 (2H, d, J=8.8 Hz), 7.12 (2H, d, J=8.8 Hz), 7.58-7.69 (3H, m), 7.74 (1H, d, J=7.0 Hz), 8.00 (2H, d, J=8.2 Hz)

, 8.21 (1H, d, J=8.6 Hz);

IR (KBr) υ max 3419, 2941, 1732, 1584, 1510, 1466, 1385, 1237, 1148, 803, 780 cm$^{-1}$;

MS (FAB) m/z: 418 (M+H)$^+$.

Example 12

{3-[(1R,3S)-3-{[(1R)-1-(Naphthalen-1-yl)ethyl] amino}cyclopentyl]phenoxy}acetic acid hydrochloride (Step 1)
(3R)-3-[4-(Benzyloxy)phenyl]cyclopentanone

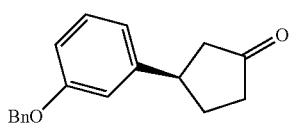

[Chemical 76]

3-Benzyloxyphenylboric acid (15.0 g, 66 mmol) and cyclopentenone (2.5 mL, 30 mmol) were used and treated in a similar manner to (Step 1) of (Example 3) to give the title compound (8.35 g).

$^1$H-NMR (CDCl$_3$) δ: 1.92-2.05 (1H, m), 2.24-2.37 (2H, m), 2.39-2.50 (2H, m), 2.66 (1H, dd, J=18.2, 7.6 Hz), 3.35-3.44 (1H, m), 5.07 (2H, s), 6.85-6.89 (3H, m), 7.24-7.29 (1H, m), 7.31-7.46 (5H, m);

IR (ATR) υ max 2960, 2880, 1737, 1580, 1489, 1445, 1255, 1148, 1025, 736, 693 cm$^{-1}$;

MS (EI) m/z: 266 (M)$^+$.

(Step 2) (1S,3R)-3-[3-(Benzyloxy)phenyl]-N-[(1R)-1-(naphthalen-1-yl)ethyl]cyclopentanamine

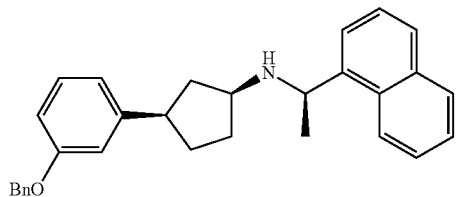

[Chemical 77]

(3R)-3-[4-(Benzyloxy)phenyl]cyclopentanone (1.71 g, 10.0 mmol) was used and treated in a similar manner to (Step 2) of (Example 1) to give the title compound (984 mg, 30%).

$^1$H-NMR (CDCl$_3$) δ: 1.42-1.53 (1H, m), 1.51 (3H, d, J=6.6 Hz), 1.60-1.82 (2H, m), 1.92-2.03 (2H, m), 2.25-2.32 (1H, m), 2.85-2.95 (1H, m), 3.14-3.22 (1H, m), 4.75 (1H, q, J=6.6 Hz), 5.02 (2H, s), 6.78 (1H, dd, J=7.8, 2.3 Hz), 6.82 (1H, d, J=7.8 Hz), 6.85-6.87 (1H, m), 7.18 (1H, t, J=7.8 Hz), 7.29-7.54 (8H, m), 7.65 (1H, d, J=6.6 Hz), 7.75 (1H, d, J=8.2 Hz), 7.86-7.89 (1H, m), 8.21 (1H, d, J=8.2 Hz);

IR (ATR) υ max 2949, 2861, 1580, 1486, 1444, 1257, 1155, 1026, 776, 734, 694 cm$^{-1}$;

MS (FAB) m/z: 422 (M+H)$^+$.

(Step 3) 3-[(1R,3S)-3-{[(1R)-1-(Naphthalen-1-yl) ethyl]amino}cyclopentyl]phenol

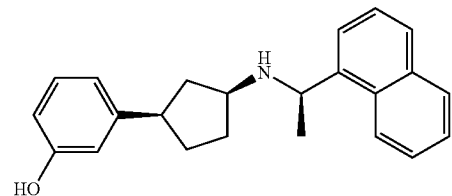

[Chemical 78]

(1S,3R)-3-[3-(Benzyloxy)phenyl]-N-[(1R)-1-(naphthalen-1-yl)ethyl]cyclopentanamine (971 mg, 2.3 mmol) was used and treated in a similar manner to (Step 3) of (Example 10) to give 530 mg (69%) of the title compound.

$^1$H-NMR (CDCl$_3$) δ: 1.46-1.55 (1H, m), 1.54 (3H, d, J=6.6 Hz), 1.65-1.81 (2H, m), 1.90-2.01 (2H, m), 2.23-2.31 (1H, m), 2.82-2.91 (1H, m), 3.14-3.22 (1H, m), 4.78 (1H, q, J=6.6 Hz), 6.63 (1H, dd, J=7.8, 2.5 Hz), 6.68 (1H, s), 6.75 (1H, d, J=7.8 Hz), 7.11 (1H, t, J=7.8 Hz), 7.46-7.55 (3H, m), 7.66 (1H, d, J=7.0 Hz), 7.76 (1H, d, J=8.2 Hz), 7.89 (1H, d, J=7.8 Hz), 8.19 (1H, d, J=8.2 Hz);

IR (KBr) υ max 3277, 3047, 2953, 2866, 1597, 1585, 1453, 1268, 1157, 861, 779, 699 cm$^{-1}$;

MS (FAB) m/z: 332 (M+H)$^+$.

(Step 4) {3-[(1R,3S)-3-{[(1R)-1-(Naphthalen-1-yl)ethyl]amino}cyclopentyl]phenoxy}acetic acid ethyl ester

[Chemical 79]

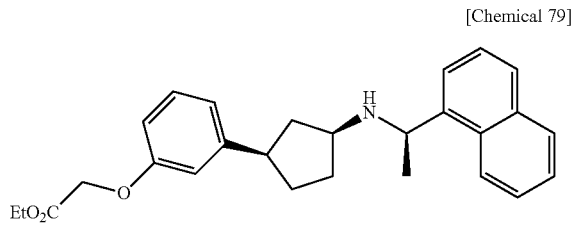 [SMILES: CCOC(=O)COc1cccc([C@@H]2CC[C@H](N[C@H](C)c3cccc4ccccc34)C2)c1]

3-[(1R,3S)-3-{[(1R)-1-(Naphthalen-1-yl)ethyl]amino}cyclopentyl]phenol (149 mg, 0.45 mmol) was used and treated in a similar manner to (Step 4) of (Example 10) to give the title compound (41 mg, 22%).

$^1$H-NMR (CDCl$_3$) δ: 1.29 (3H, t, J=7.0 Hz), 1.42-1.52 (1H, m), 1.51 (3H, d, J=6.6 Hz), 1.60-1.81 (2H, m), 1.92-2.03 (2H, m), 2.24-2.31 (1H, m), 2.84-2.94 (1H, m), 3.13-3.21 (1H, m), 4.27 (2H, q, J=7.0 Hz), 4.59 (2H, s), 4.75 (1H, q, J=6.6 Hz), 6.69 (1H, dd, J=7.6, 2.3 Hz), 6.81 (1H, s), 6.85 (1H, d, J=7.6 Hz), 7.18 (1H, t, J=7.6 Hz), 7.46-7.54 (3H, m), 7.65 (1H, d, J=7.0 Hz), 7.75 (1H, d, J=8.2 Hz), 7.88 (1H, d, J=8.2 Hz), 8.21 (1H, d, J=8.2 Hz).

(Step 5) {3-[(1R,3S)-3-{[(1R)-1-(Naphthalen-1-yl)ethyl]amino}cyclopentyl]phenoxy}acetic acid hydrochloride

[Chemical 80]

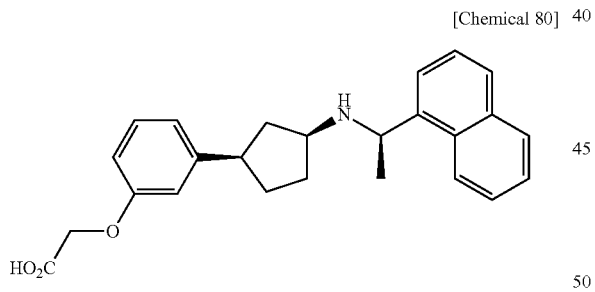

{3-[(1R,3S)-3-{[(1R)-1-(Naphthalen-1-yl)ethyl]amino}cyclopentyl]phenoxy}acetic acid ethyl ester (40 mg, 0.10 mmol) was used and treated in a similar manner to (Step 5) of (Example 10) to give the title compound (31 mg, 76%).

$^1$H-NMR (CD$_3$OD) δ: 1.71 (1H, td, J=12.1, 10.2 Hz), 1.81-1.90 (1H, m), 1.83 (3H, d, J=6.6 Hz), 1.98-2.20 (3H, m), 2.46-2.53 (1H, m), 2.99-3.09 (1H, m), 3.61-3.70 (1H, m), 4.61 (2H, s), 5.44 (1H, q, J=6.6 Hz), 6.76 (1H, dd, J=8.0, 2.1 Hz), 6.83 (1H, d, J=2.1 Hz), 6.85 (1H, d, J=8.0 Hz), 7.20 (1H, t, J=8.0 Hz), 7.59-7.70 (3H, m), 7.75 (1H, d, J=7.4 Hz), 8.00 (2H, d, J=8.2 Hz), 8.22 (1H, d, J=8.6 Hz);

IR (KBr) υ max 3410, 2956, 2820, 1736, 1585, 1442, 1244, 1161, 1075, 804, 780, 698 cm$^{-1}$;

MS (FAB) m/z: 390 (M+H)$^+$.

Example 13

2-Methyl-2-{3-[(1R,3S)-3-{[(1R)-1-(naphthalen-1-yl)ethyl]amino}cyclopentyl]phenoxy}propanoic acid hydrochloride (Step 1) 2-Methyl-2-{3-[(1R,3S)-3-{[(1R)-1-(naphthalen-1-yl)ethyl]amino}cyclopentyl]phenoxy}propanoic acid ethyl ester

[Chemical 81]

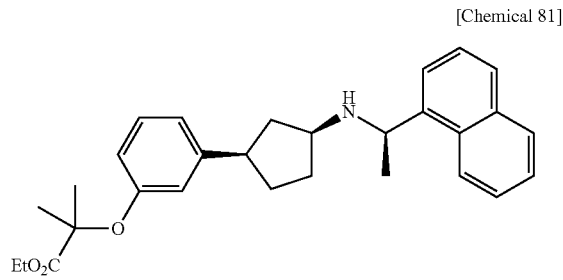 [SMILES: CCOC(=O)C(C)(C)Oc1cccc([C@@H]2CC[C@H](N[C@H](C)c3cccc4ccccc34)C2)c1]

3-[(1R,3S)-3-{[(1R)-1-(Naphthalen-1-yl)ethyl]amino}cyclopentyl]phenol (193 mg, 0.58 mmol) obtained in (Step 3) of (Example 12) was used and treated in a similar manner to (Step 1) of (Example 11) to give the title compound (100 mg, 44%).

$^1$H-NMR (CDCl$_3$) δ: 1.23 (3H, t, J=7.0 Hz), 1.39-1.48 (1H, m), 1.50 (3H, d, J=6.6 Hz), 1.58 (6H, s), 1.61-1.78 (2H, m), 1.91-2.00 (2H, m), 2.23-2.30 (1H, m), 3.12-3.21 (1H, m), 4.03-4.17 (1H, m), 4.22 (2H, q, J=7.0 Hz), 4.75 (1H, q, J=6.6 Hz), 6.61 (1H, d, J=7.7 Hz), 6.73 (1H, s), 6.83 (1H, d, J=7.7 Hz), 7.11 (1H, t, J=7.7 Hz), 7.46-7.54 (3H, m), 7.66 (1H, d, J=7.0 Hz), 7.75 (1H, d, J=8.2 Hz), 7.88 (1H, d, J=7.8 Hz), 8.21 (1H, d, J=8.2 Hz).

(Step 2) 2-Methyl-2-{3-[(1R,3S)-3-{[(1R)-1-(naphthalen-1-yl)ethyl]amino}cyclopentyl]phenoxy}propanoic acid hydrochloride

[Chemical 82]

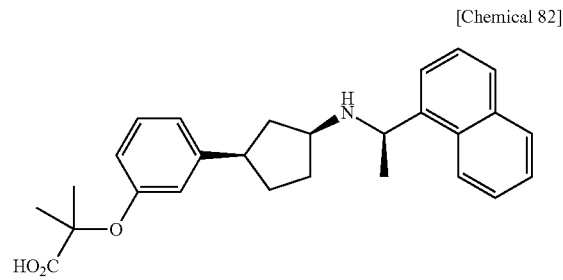 [SMILES: C[C@@H](N[C@H]1CC[C@@H](c2cccc(OC(C)(C)C(=O)O)c2)C1)c1cccc2ccccc12]

2-Methyl-2-{3-[(1R,3S)-3-{[(1R)-1-(naphthalen-1-yl)ethyl]amino}cyclopentyl]phenoxy}propanoic acid ethyl ester (100 mg, 0.22 mmol) was used and treated in a similar manner to (Step 2) of (Example 11) to give the title compound (52 mg, 51%).

$^1$H-NMR (CD$_3$OD) δ: 1.54 (6H, s), 1.69 (1H, td, J=12.1, 10.2 Hz), 1.79-1.88 (1H, m), 1.82 (3H, d, J=6.8 Hz), 1.97-2.19 (3H, m), 2.46-2.53 (1H, m), 2.96-3.06 (1H, m), 3.61-3.70 (1H, m), 5.43 (1H, q, J=6.8 Hz), 6.72 (1H, dd, J=7.8, 2.0 Hz), 6.79 (1H, t, J=2.0 Hz), 6.87 (1H, d, J=7.8 Hz), 7.16 (1H, t, J=7.8H z), 7.58-7.70 (3H, m), 7.74 (1H, dd, J=7.2, 1.0 Hz), 8.00 (2H, d, J=7.8 Hz), 8.22 (1H, d, J=8.6 Hz);

IR (KBr) υ max 3419, 2958, 1735, 1602, 1583, 1487, 1467, 1444, 1252, 1149, 803, 780 cm$^{-1}$;

MS (FAB) m/z: 418 (M+H)$^+$.

Example 14

{2-Fluoro-4-[(1R,3S)-3-{[(1R)-1-(naphthalen-1-yl)ethyl]amino}cyclopentyl]phenoxy}acetic acid hydrochloride (Step 1) 1-(Benzyloxy)-4-bromo-2-fluorobenzene

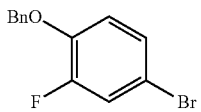

[Chemical 83]

Under a nitrogen stream, 4-bromo-2-fluorophenol (14.9 g, 78 mmol) and potassium carbonate (13.0 g, 94 mmol) were dissolved in N,N-dimethylformamide (100 mL), followed by addition of benzyl bromide (10.2 mL, 86 mmol), and the mixture was stirred overnight at room temperature. Water was added to the reaction solution, and the solvent was concentrated under reduced pressure. The aqueous phase was extracted with ethyl acetate. The extracted solution was dried over anhydrous magnesium sulfate, and then the solvent was distilled off under reduced pressure. The residue obtained was purified by column chromatography (ethyl acetate/hexane:0/100-5/95) to give the title compound (21.9 g, 100%).

$^1$H-NMR (CDCl$_3$) δ: 5.12 (2H, s), 6.86 (1H, t, J=8.6 Hz), 7.13-7.16 (1H, m), 7.25 (1H, dd, J=8.6, 2.3 Hz), 7.31-7.44 (5H, m);

IR (KBr) υ max 2937, 1582, 1498, 1388, 1302, 1266, 1201, 1131, 1008, 865, 805, 754, 700 cm$^{-1}$;

MS (EI) m/z: 280 (M)$^+$.

(Step 2) [4-(Benzyloxy)-3-fluorophenyl]boronic acid

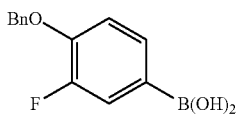

[Chemical 84]

Under nitrogen stream, 1-(benzyloxy)-4-bromo-2-fluorobenzene (12.0 g, 43 mmol) was dissolved in tetrahydrofuran, followed by addition of triisopropyl borate (11.8 mL, 51 mmol), and then the mixture was cooled to −78° C. Butyl lithium (1.55M hexane solution) (30 mL, 47 mmol) was slowly added dropwise, and the mixture was stirred for 1 hour at −78° C. A 1N aqueous hydrochloric acid solution (100 mL) was added to the reaction mixture, and the mixture was stirred for 1 hour at room temperature. The solvent was distilled off under reduced pressure. The aqueous phase was extracted with ethyl acetate, the extracted solution was dried over anhydrous magnesium sulfate, and then the solvent was distilled off under reduced pressure. The residue obtained was suspended in hexane, and was then collected by filtration to give the title compound (9.27 g, 88%).

MS (EI)m/z: 246 (M)$^+$.

(Step 3) (3R)-3-[4-(Benzyloxy)-3-fluorophenyl]cyclopentanone

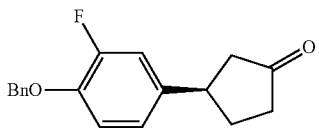

[Chemical 85]

[4-(Benzyloxy)-3-fluorophenyl]boronic acid (5.00 g, 20 mmol) and cyclopentenone (0.85 mL, 10 mmol) were used and treated in a similar manner to (Step 1) of (Example 3) to give the title compound (1.95 g, 68%).

$^1$H-NMR (CDCl$_3$) δ: 1.88-1.97 (1H, m), 2.23-2.33 (2H, m), 2.38-2.48 (2H, m), 2.64 (1H, dd, J=18.3, 7.1 Hz), 3.35 (1H, tt, J=10.7, 5.0 Hz), 5.14 (2H, s), 6.90 (1H, dd, J=8.4, 2.2 Hz), 6.96 (1H, t, J=8.4 Hz), 7.00 (1H, dd, J=12.2, 2.2 Hz), 7.31-7.35 (1H, m), 7.37-7.41 (2H, m), 7.43-7.45 (2H, m);

IR (KBr) υ max 2909, 1731, 1519, 1462, 1387, 1279, 1215, 1119, 1024, 870, 813, 739 cm$^{-1}$;

MS (EI) m/z: 284 (M)$^+$.

(Step 4) (1S,3R)-3-[4-(Benzyloxy)-3-fluorophenyl]-N-[(1R)-1-(naphthalen-1-yl)ethyl]cyclopentanamine

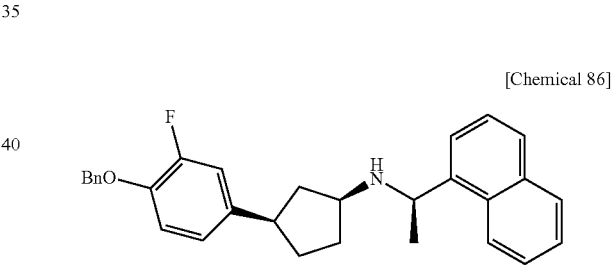

[Chemical 86]

(3R)-3-[4-(Benzyloxy)-3-fluorophenyl]cyclopentanone (1.90 g, 6.7 mmol) and (R)-naphthylethylamine (1.49 g, 8.7 mmol) were used and treated in a similar manner to (Step 2) of (Example 1) to give the title compound (1.33 g, 45%).

$^1$H-NMR (CDCl$_3$) δ: 1.41 (1H, td, J=12.0, 9.4 Hz), 1.50 (3H, d, J=6.8 Hz), 1.61-1.74 (2H, m), 1.91-1.99 (2H, m), 2.22-2.28 (1H, m), 2.80-2.88 (1H, m), 3.13-3.20 (1H, m), 4.74 (1H, q, J=6.8 Hz), 5.10 (2H, s), 6.84 (1H, dd, J=8.5, 2.1 Hz), 6.88 (1H, t, J=8.5 Hz), 6.96 (1H, dd, J=12.5, 2.1 Hz), 7.30-7.33 (1H, m)

7.37 (2H, t, J=7.3 Hz), 7.43 (2H, d, J=7.3 Hz), 7.46-7.53 (3H, m), 7.64 (1H, d, J=7.3 Hz), 7.75 (1H, d, J=8.3 Hz), 7.88 (1H, d, J=7.8 Hz), 8.20 (1H, d, J=8.3 Hz);

IR (ATR) υ max 2946, 2861, 1513, 1273, 1217, 1120, 1007, 799, 777, 734, 694 cm$^{-1}$;

MS (FAB) m/z: 440 (M+H)$^+$.

(Step 5) 2-Fluoro-4-[(1R,3S)-3-{[(1R)-1-(naphthalen-1-yl)ethyl]amino}cyclopentyl]phenol

[Chemical 87]

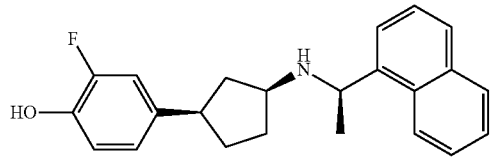

(1S,3R)-3-[4-(Benzyloxy)-3-fluorophenyl]-N-[(1R)-1-(naphthalen-1-yl)ethyl]cyclopentanamine (1.25 g, 2.8 mmol) was used and treated in a similar manner to (Step 3) of (Example 10) to give the title compound (895 mg, 90%).

$^1$H-NMR (CDCl$_3$) δ: 1.35-1.44 (1H, m), 1.52 (3H, d, J=6.6 Hz), 1.63-1.74 (2H, m), 1.88-1.99 (2H, m), 2.21-2.28 (1H, m), 2.77-2.87 (1H, m), 3.11-3.19 (1H, m), 4.77 (1H, q, J=6.6 Hz), 6.82 (1H, dd, J=8.3, 2.0 Hz), 6.87 (1H, t, J=8.3 Hz), 6.90 (1H, dd, J=11.7, 2.0 Hz), 7.47-7.55 (3H, m), 7.64 (1H, d, J=7.0 Hz), 7.76 (1H, d, J=7.8 Hz), 7.87-7.90 (1H, m), 8.19 (1H, d, J=8.2 Hz);

IR (KBr) υ max 2955, 2868, 1596, 1519, 1443, 1291, 1112, 864, 800, 779 cm$^{-1}$;

MS (FAB) m/z: 350 (M+H)$^+$.

(Step 6) {2-Fluoro-4-[(1R,3S)-3-{[(1R)-1-(naphthalen-1-yl)ethyl]amino}cyclopentyl]phenoxy}acetic acid ethyl ester

[Chemical 88]

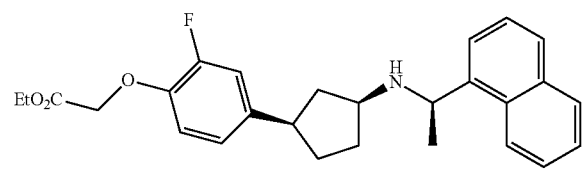

2-Fluoro-4-[(1R,3S)-3-{[(1R)-1-(naphthalen-1-yl)ethyl]amino}cyclopentyl]phenol (200 mg, 0.57 mmol) was used and treated in a similar manner to (Step 4) of (Example 10) to give the title compound (226 mg, 91%).

$^1$H-NMR (CDCl$_3$) δ: 1.29 (3H, t, J=7.0 Hz), 1.40 (1H, td, J=11.6, 9.6 Hz), 1.50 (3H, d, J=6.6 Hz), 1.60-1.75 (2H, m), 1.91-2.00 (2H, m), 2.22-2.28 (1H, m), 2.80-2.88 (1H, m), 3.12-3.20 (1H, m), 4.26 (2H, q, J=7.0 Hz), 4.64 (2H, s), 4.74 (1H, q, J=6.6 Hz), 6.82 (1H, t, J=8.3 Hz), 6.86 (1H, dd, J=8.3, 1.8 Hz), 6.96 (1H, dd, J=12.7, 1.8 Hz), 7.46-7.54 (3H, m), 7.64 (1H, d, J=7.0 Hz), 7.76 (1H, d, J=8.2 Hz), 7.86-7.90 (1H, m), 8.20 (1H, d, J=8.2 Hz);

IR (ATR) υ max 2953, 1756, 1515, 1441, 1281, 1194, 1126, 1069, 800, 778 cm$^{-1}$;

MS (FAB) m/z: 436 (M+H)$^+$.

(Step 7) {2-Fluoro-4-[(1R,3S)-3-{[(1R)-1-(naphthalen-1-yl)ethyl]amino}cyclopentyl]phenoxy}acetic acid hydrochloride

[Chemical 89]

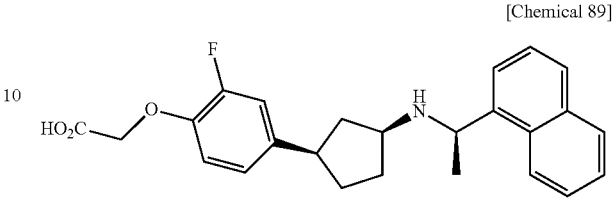

{2-Fluoro-4-[(1R,3S)-3-{[(1R)-1-(naphthalen-1-yl)ethyl]amino}cyclopentyl]phenoxy}acetic acid ethyl ester (214 mg, 0.49 mmol) was used and treated in a similar manner to (Step 5) of (Example 10) to give the title compound (191 mg, 88%).

$^1$H-NMR (CD$_3$OD) δ: 1.60-1.70 (1H, m), 1.76-1.85 (1H, m), 1.82 (3H, d, J=6.6 Hz), 1.97-2.21 (3H, m), 2.45-2.54 (1H, m), 2.95-3.07 (1H, m), 3.60-3.70 (1H, m), 4.68 (2H, s), 5.43 (1H, q, J=6.6 Hz), 6.93-7.05 (3H, m), 7.58-7.70 (3H, m), 7.74 (1H, d, J=7.0 Hz), 7.98-8.03 (2H, m), 8.22 (1H, d, J=8.6 Hz);

IR (KBr) υ max 3404, 2957, 2821, 1738, 1586, 1518, 1436, 1281, 1211, 1129, 1068, 804, 780 cm$^{-1}$;

MS (FAB) m/z: 408 (M+H)$^+$.

Example 15

2-{2-Fluoro-4-[(1R,3S)-3-{[(1R)-1-(naphthalen-1-yl)ethyl]amino}cyclopentyl]phenoxy}-2-methylpropanoic acid hydrochloride (Step 1) 2-{2-Fluoro-4-[(1R,3S)-3-{[(1R)-1-(naphthalen-1-yl)ethyl]amino}cyclopentyl]phenoxy}-2-methylpropanoic acid ethyl ester

[Chemical 90]

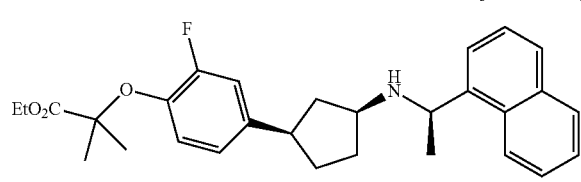

2-Fluoro-4-[(1R,3S)-3-{[(1R)-1-(naphthalen-1-yl)ethyl]amino}cyclopentyl]phenol (250 mg, 0.72 mmol) obtained in (Step 5) of (Example 14) was used and treated in a similar manner to (Step 1) of (Example 11) to give the title compound (272 mg, 82%).

$^1$H-NMR (CDCl$_3$) δ: 1.28 (3H, t, J=7.2 Hz), 1.36-1.45 (1H, m), 1.50 (3H, d, J=6.6 Hz), 1.55 (6H, s), 1.58-1.76 (2H, m), 1.90-2.05 (2H, m), 2.22-2.29 (1H, m), 2.80-2.87 (1H, m), 3.12-3.21 (1H, m), 4.24 (2H, q, J=7.2 Hz), 4.74 (1H, q, J=6.6 Hz), 6.81 (1H, dd, J=8.4, 2.1 Hz), 6.86 (1H, t, J=8.4 Hz), 6.92 (1H, dd, J=12.3, 2.1 Hz), 7.46-7.54 (3H, m), 7.65 (1H, d, J=7.4 Hz), 7.76 (1H, d, J=8.2 Hz), 7.88 (1H, d, J=7.8 Hz), 8.21 (1H, d, J=8.2 Hz);

IR (ATR) υ max 2943, 1732, 1687, 1506, 1280, 1174, 1134, 1022, 800, 778 cm$^{-1}$;

MS (FAB) m/z: 464 (M+H)$^+$.

(Step 2) 2-{2-Fluoro-4-[(1R,3S)-3-{[(1R)-1-(naphthalen-1-yl)ethyl]amino}cyclopentyl]phenoxy}-2-methylpropanoic acid hydrochloride

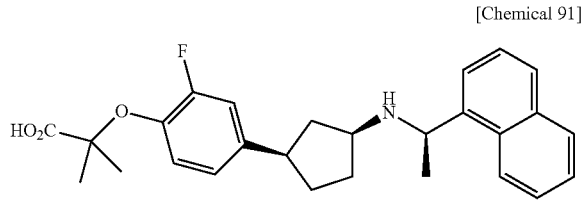 [SMILES: C[C@@H](N[C@H]1CC[C@@H](c2ccc(OC(C)(C)C(=O)O)c(F)c2)C1)c1cccc2ccccc12]

[Chemical 91]

2-{2-Fluoro-4-[(1R,3S)-3-{[(1R)-1-(naphthalen-1-yl)ethyl]amino}cyclopentyl]phenoxy}-2-methylpropanoic acid ethyl ester (259 mg, 0.56 mmol) was used and treated in a similar manner to (Step 2) of (Example 11) to give the title compound (213 mg, 81%).

$^1$H-NMR (CD$_3$OD) δ: 1.51 (6H, s), 1.67 (1H, q, J=11.4 Hz), 1.76-1.88 (1H, m), 1.83 (3H, d, J=6.8 Hz), 1.98-2.21 (3H, m), 2.45-2.54 (1H, m), 2.96-3.06 (1H, m), 3.61-3.69 (1H, m), 5.43 (1H, q, J=6.3 Hz), 6.93 (1H, d, J=8.3 Hz), 6.98-7.05 (2H, m), 7.57-7.70 (3H, m), 7.76 (1H, d, J=7.3 Hz), 8.00 (2H, d, J=8.3 Hz)

8.22 (1H, d, J=8.8 Hz);

IR (KBr) υ max 3398, 2955, 1735, 1583, 1511, 1279, 1145, 803, 780 cm$^{-1}$;

MS (FAB) m/z: 436 (M+H)$^+$.

Example 16

{4-[(1R)-3-{[(1R)-1-(4-Fluoronaphthalen-1-yl)ethyl]amino}cyclopentyl]phenoxy}acetic acid (Step 1) (R)-3-(4-Hydroxyphenyl)cyclopentanone

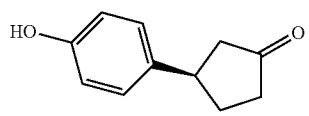

[Chemical 92]

(3R)-3-[4-(Benzyloxy)phenyl]cyclopentanone (4.00 g, 15 mmol) obtained in (Step 1) of (Example 10) was used and treated in a similar manner to (Step 3) of (Example 10) to give the title compound (2.61 g, 98%).

$^1$H-NMR (CDCl$_3$) δ: 1.89-2.00 (1H, m), 2.25-2.35 (2H, m), 2.38-2.51 (2H, m), 2.65 (1H, dd, J=18.0, 7.0 Hz), 3.32-3.41 (1H, m), 6.82 (2H, d, J=8.6 Hz), 7.13 (2H, d, J=8.6 Hz).

(Step 2) {4-[(1R)-3-Oxocyclopentyl]phenoxy}acetic acid methyl ester

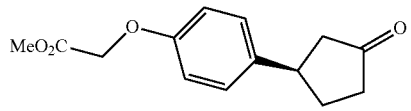

[Chemical 93]

(R)-3-(4-Hydroxyphenyl)cyclopentanone (0.82 g, 4.6 mmol) and methyl bromoacetate (0.9 mL, 10 mmol) were used and treated in a similar manner to (Step 4) of (Example 10) to give the title compound (1.15 g, 100%).

$^1$H-NMR (CDCl$_3$) δ: 1.94 (1H, m), 2.26-2.33 (2H, m), 2.39-2.48 (2H, m), 2.65 (1H, dd, J=7.3, 18.1 Hz), 3.34-3.41 (1H, m), 3.81 (3H, s), 4.64 (2H, s), 6.89 (2H, d, J=8.8 Hz), 7.18 (2H, d, J=8.8 Hz).

(Step 3) N-[(1R)-1-(4-Fluoronaphthalen-1-yl)ethyl]-2-methylpropane-2-sulfinamide

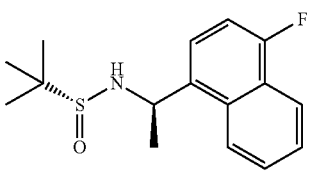

[Chemical 94]

Titanium tetraisopropoxide (3.0 mL, 10 mmol) was added to a tetrahydrofuran (20 mL) solution of 4'-fluoro-1'-acetonaphthone 0.94 mL (6.0 mmol) and (R)-(+)-tert-butyl sulfinamide (610 mg, 5.0 mmol), and the mixture was heated under reflux for one full day. The reaction mixture was cooled to −78° C., followed by addition of sodium borohydride (0.76 g, 20 mmol), and then the temperature of the mixture was gradually raised to room temperature. Methanol (5 mL) and then water (20 mL) were added to the mixture under ice-cooling conditions, and the solid matter generated was filtered. The oil obtained was extracted with methylene chloride (20 mL), the organic phase was dried over sodium sulfate, and then the solvent was distilled off under reduced pressure. The crude product was purified by silica gel column chromatography (ethyl acetate/hexane:67/33) to give the title compound (527 mg, 45%).

$^1$H-NMR (CDCl$_3$) δ: 1.23 (9H, s), 1.68 (3H, d, J=6.8 Hz), 3.54 (1H, br s), 5.29-5.33 (1H, m), 7.13 (1H, dd, J=10.3, 7.8 Hz), 7.52-7.64 (3H, m), 8.16 (1H, d, J=7.3 Hz), 8.24 (1H, d, J=8.3 Hz).

(Step 4) (1R)-1-(4-Fluoronaphthalen-1-yl)ethanamine hydrochloride

[Chemical 95]

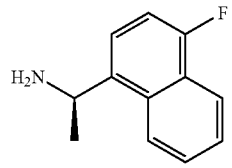

A 1,4-dioxane solution of 4N hydrochloric acid (5 mL) was added to N-[(1R)-1-(4-fluoronaphthalen-1-yl)ethyl]-2-methylpropane-2-sulfinamide (527 mg, 2.2 mmol), and the mixture was stirred for 30 minutes at room temperature. The precipitate generated was filtered, washed with ether, and was then dried under reduced pressure to give the title compound (358 mg, 70%).

$^1$H-NMR (CDCl$_3$-CD$_3$OD) δ: 1.81 (3H, d, J=6.8 Hz), 5.25 (1H, q, J=6.8 Hz), 7.23 (1H, dd, J=10.0, 8.1 Hz), 7.62-7.71 (3H, m), 8.06 (1H, d, J=8.3 Hz), 8.20 (1H, d, J=7.8 Hz).

(Step 5) {4-[(1R)-3-{[(1R)-1-(4-Fluoronaphthalen-1-yl)ethyl]amino}cyclopentyl]phenoxy}acetic acid methyl ester

[Chemical 96]

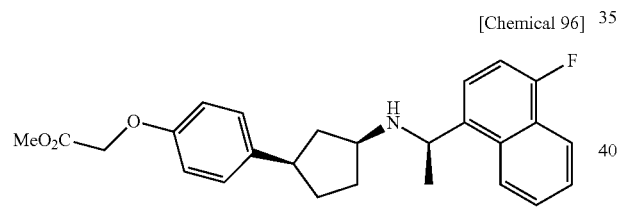

Sodium triacetoxy borohydride (64 mg, 0.3 mmol) was added to a methylene chloride solution (2 mL) of methyl {4-[(1R)-3-oxocyclopentyl]phenoxy}acetate (50 mg, 0.2 mmol) obtained in (Step 2) of (Example 16) and (1R)-1-(4-fluoronaphthalen-1-yl)ethanamine hydrochloride (45 mg, 0.2 mmol) obtained in (Step 4) of (Example 16). The mixture was stirred for one full day at room temperature. Saturated sodium bicarbonate (2 mL) was added to the reaction mixture. The organic phase was extracted with methylene chloride, dried over sodium sulfate, and the solvent was distilled off under reduced pressure. The crude product was purified by NH-silica gel column chromatography (ethyl acetate/hexane:33/67) to give the title compound (a mixture of diastereomers) (72 mg, 85%).

$^1$H-NMR (CDCl$_3$) δ: 1.38-2.10 (6H, m), 1.48 (3H, d, J=6.6 Hz), 2.22-2.28 (0.5H, m), 2.81-2.90 (0.5H, m), 3.12-3.28 (1H, m), 3.80 (3H, s), 4.60 (2H, br s), 4.62-4.71 (1H, m), 6.76-6.83 (2H, m), 7.07-7.18 (3H, m), 7.52-7.61 (3H, m), 8.14-8.23 (2H, m).

(Step 6) {4-[(1R)-3-{[(1R)-1-(4-Fluoronaphthalen-1-yl)ethyl]amino}cyclopentyl]phenoxy}acetic acid

[Chemical 97]

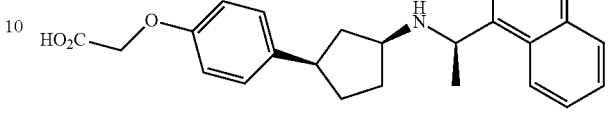

A solution of methyl {4-[(1R)-3-{[(1R)-1-(4-fluoronaphthalen-1-yl)ethyl]amino}cyclopentyl]phenoxy}acetate (72 mg, 0.17 mmol) and potassium hydroxide (56 mg, 1.0 mmol) in methanol (2 mL) and water (0.5 mL) was heated under reflux for 2 hours. 2N hydrochloric acid was added to the reaction solution to make the pH 7, and the solution was purified by high performance liquid chromatography (water: acetonitrile) to give the title compound (a mixture of diastereomers) (36 mg, 52%).

$^1$H-NMR (CD$_3$OD) δ: 1.44-2.41 (6H, m), 1.80 (3H, d, J=6.6 Hz), 2.82-2.96 (0.5H, m), 3.09-3.21 (0.5H, m), 3.47-3.65 (1H, m), 4.37 (2H, s), 5.34-5.41 (1H, m), 6.76-6.83 (2H, m), 6.92-7.10 (2H, m), 7.33-7.37 (1H, m), 7.66-7.78 (3H, m), 8.19-8.27 (2H, m).

Example 17

{4-[(1R,3S)-3-{[(1R)-1-(4-Fluoronaphthalen-1-yl)ethyl]amino}cyclopentyl]phenoxy}acetic acid (Step 1) (1S,3R)-3-[4-(Benzyloxy)phenyl]-N-[(1R)-1-(4-fluoronaphthalen-1-yl)ethyl]cyclopentanamine

[Chemical 98]

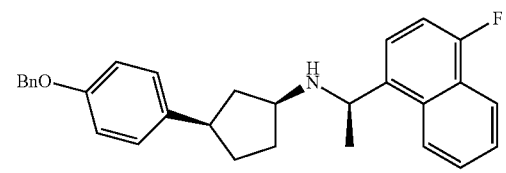

Sodium triacetoxy borohydride 2.44 g (12 mmol) was added to a methylene chloride (50 mL) solution of (3R)-3-[4-(benzyloxy)phenyl]cyclopentanone (2.60 g, 9.7 mmol) obtained in (Step 1) of (Example 10) and (1R)-1-(4-fluoronaphthalen-1-yl)ethanamine hydrochloride (2.00 g, 8.9 mmol) obtained in (Step 4) of (Example 16), and the mixture was stirred for 3 hours at room temperature. A saturated aqueous sodium bicarbonate solution was added to the reaction solution, and the aqueous phase was extracted with methylene chloride. The extracted solution was dried over anhydrous magnesium sulfate, and the solvent was distilled off under reduced pressure. The residue obtained was purified by column chromatography (ethyl acetate/hexane:20/80-40/60) to give the title compound (1.62 g, 42%).

$^1$H-NMR (CDCl$_3$) δ: 1.38-1.46 (1H, m), 1.48 (3H, d, J=6.6 Hz), 1.61-1.78 (2H, m), 1.91-2.02 (2H, m), 2.22-2.29 (1H, m), 2.82-2.92 (1H, m), 3.12-3.20 (1H, m), 4.69 (1H, q, J=6.6

Hz), 5.03 (2H, S), 6.89 (2H, d, J=8.6 Hz), 7.11-7.17 (3H, m), 7.29-7.44 (5H, m), 7.52-7.61 (3H, m), 8.13-8.17 (1H, m), 8.19-8.24 (1H, m);

IR (ATR) υ max 2945, 2862, 1510, 1235, 1223, 1019, 826, 760, 734, 695 cm$^{-1}$; MS (FAB) m/z: 440 (M+H)$^+$.

(Step 2) 4-[(1R,3S)-3-{[(1R)-1-(4-Fluoronaphthalen-1-yl)ethyl]amino}cyclopentyl]phenol

[Chemical 99]

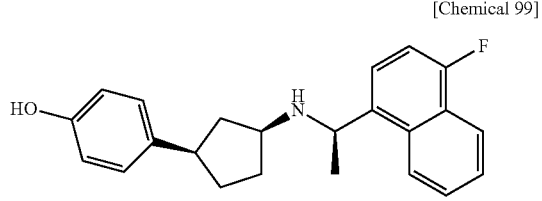 [SMILES: C[C@@H](N[C@H]1CC[C@@H](c2ccc(O)cc2)C1)c1ccc(F)c2ccccc12]

(1S,3R)-3-[4-(Benzyloxy)phenyl]-N-[(1R)-1-(4-fluoronaphthalen-1-yl)ethyl]cyclopentanamine (1.61 g, 3.7 mmol) was used and treated in a similar manner to (Step 3) of (Example 10) to give the title compound 1.02 g (80%).

$^1$H-NMR (CDCl$_3$) δ: 1.42 (1H, td, J=11.8, 9.6 Hz), 1.49 (3H, d, J=6.6 Hz), 1.61-1.76 (2H, m), 1.92-2.00 (2H, m), 2.22-2.28 (1H, m), 2.82-2.89 (1H, m), 3.13-3.19 (1H, m), 4.69 (1H, q, J=6.6 Hz), 6.73 (2H, d, J=8.8 Hz), 7.06 (2H, d, J=8.8 Hz), 7.14 (1H, dd, J=10.3, 8.3 Hz), 7.53-7.59 (3H, m), 8.14-8.17 (1H, m), 8.19-8.22 (1H, m);

IR (KBr) υ max 2945, 2866, 1605, 1516, 1471, 1395, 1251, 832, 760, 709, 543 cm$^{-1}$;

MS (FAB) m/z: 350 (M+H)$^+$.

(Step 3) {4-[(1R,3S)-3-{[(1R)-1-(4-Fluoronaphthalen-1-yl)ethyl]amino}cyclopentyl]phenoxy}acetic acid ethyl ester

[Chemical 100]

4-[(1R,3S)-3-{[(1R)-1-(4-Fluoronaphthalen-1-yl)ethyl]amino}cyclopentyl]phenol (700 mg, 2.0 mmol) was used and treated in a similar manner to (Step 4) of (Example 10) to give the title compound (852 mg, 98%).

$^1$H-NMR (CDCl$_3$) δ: 1.29 (3H, t, J=7.2 Hz), 1.42 (1H, td, J=11.8, 9.4 Hz), 1.48 (3H, d, J=6.7 Hz), 1.59-1.76 (2H, m), 1.92-2.01 (2H, m), 2.22-2.28 (1H, m), 2.83-2.91 (1H, m), 3.13-3.19 (1H, m), 4.26 (2H, q, J=7.2 Hz), 4.58 (2H, s), 4.68 (1H, q, J=6.7 Hz), 6.82 (2H, d, J=8.8 Hz), 7.10-7.16 (3H, m), 7.52-7.60 (3H, m), 8.14-8.16 (1H, m), 8.20-8.23 (1H, m);

IR (ATR) υ max 2952, 2864, 1757, 1734, 1510, 1192, 1179, 1082, 827, 760 cm$^{-1}$;

MS (FAB) m/z: 436 (M+H)$^+$.

(Step 4) {4-[(1R,3S)-3-{[(1R)-1-(4-Fluoronaphthalen-1-yl)ethyl]amino}cyclopentyl]phenoxy}acetic acid

[Chemical 101]

{4-[(1R,3S)-3-{[(1R)-1-(4-Fluoronaphthalen-1-yl)ethyl]amino}cyclopentyl]phenoxy}acetic acid ethyl ester (800 mg, 1.8 mmol) was dissolved in ethanol (5 mL), followed by addition of 1N aqueous sodium hydroxide solution (5 mL), and the mixture was stirred for 30 minutes at room temperature. 1N hydrochloric acid was added dropwise to the reaction mixture to make the reaction solution acidic, and the solvent was distilled off under reduced pressure. The aqueous phase was extracted with chloroform, the extracted solution was dried over anhydrous magnesium sulfate, and then the solvent was distilled off under reduced pressure to give the title compound (742 mg, 99%).

$^1$H-NMR (CD$_3$OD) δ: 1.65-1.75 (2H, m), 1.80 (3H, d, J=6.7 Hz), 1.90-2.05 (3H, m), 2.33-2.41 (1H, m), 2.82-2.96 (1H, m), 3.47-3.55 (1H, m), 4.37 (2H, s), 5.37 (1H, q, J=6.7 Hz), 6.81 (2H, d, J=8.8 Hz), 7.06 (2H, d, J=8.8 Hz), 7.34 (1H, dd, J=10.3, 8.3 Hz), 7.69 (1H, t, J=7.6 Hz), 7.73-7.78 (2H, m), 8.21 (1H, d, J=8.3 Hz), 8.25 (1H, d, J=8.8 Hz);

IR (KBr) υ max 3404, 2952, 2872, 1633, 1605, 1583, 1512, 1402, 1262, 1225, 1051, 830, 762 cm$^{-1}$;

MS (FAB) m/z: 408 (M+H).

Example 18

{4-[(1R)-3-{[(1R)-1-(5-Fluoronaphthalen-1-yl)ethyl]amino}cyclopentyl]phenoxy}acetic acid (Step 1) N-[(1R)-1-(5-Fluoronaphthalen-1-yl)ethyl]-2-methylpropane-2-sulfinamide

[Chemical 102]

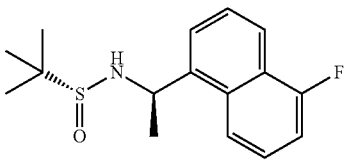

5-Fluoroacetonaphthone (2.26 g, 12 mmol) was used and treated in a similar manner to (Step 3) of (Example 16) to give the title compound as an oil (1.25 g, 53%).

$^1$H-NMR (CDCl$_3$) δ: 1.24 (9H, s), 1.69 (3H, d, J=6.6 Hz), 3.58 (1H, br s), 5.35 (1H, br q, J=5.9 Hz), 7.18 (1H, m), 7.45-7.51 (1H, m), 7.54 (1H, t, J=7.6 Hz), 7.67 (1H, d, J=7.0 Hz), 8.00 (1H, d, J=8.6 Hz), 8.10 (1H, d, J=8.6 Hz).

(Step 2) (1R)-1-(5-Fluoronaphthalen-1-yl)ethanamine hydrochloride

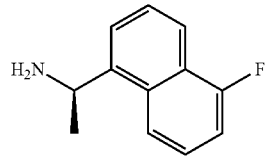

[Chemical 103]

N-[(1R)-1-(5-Fluoronaphthalen-1-yl)ethyl]-2-methylpropane-2-sulfinamide (1.25 g, 6.4 mmol) was used and treated in a similar manner to (Step 4) of (Example 16) to give the title compound (0.81 g, 68%).

¹H-NMR (CDCl₃-CD₃OD) δ: 1.83 (3H, d, J=6.8 Hz), 5.26 (1H, q, J=6.8 Hz), 7.24 (1H, dd, J=10.3, 7.8 Hz), 7.53-7.58 (1H, m), 7.63 (1H, t, J=7.8 Hz), 7.78 (1H, d, J=7.3 Hz), 7.82 (1H, d, J=8.3 Hz), 8.18 (1H, d, J=8.3 Hz).

(Step 3) {4-[(1R)-3-{[(1R)-1-(5-Fluoronaphthalen-1-yl)ethyl]amino}cyclopentyl]phenoxy}acetic acid methyl ester

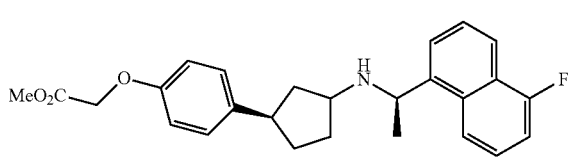

[Chemical 104]

(1R)-1-(5-Fluoronaphthalen-1-yl)ethanamine hydrochloride (45 mg, 0.2 mmol) was used and treated in a similar manner to (Step 5) of (Example 16) to give the title compound (a mixture of diastereomers) (71 mg, 84%).

¹H-NMR (CDCl₃) δ: 1.40-2.10 (9H, m), 2.22-2.27 (0.5H, m), 2.82-2.91 (0.5H, m), 3.13-3.26 (1H, m), 3.80 (3H, br s), 4.60 (2H, br s), 4.63-4.72 (0.5H, m), 4.95 (0.5H, q, J=6.8 Hz), 6.81 (2H, m), 7.08-7.18 (3H, m), 7.40-7.48 (1H, m), 7.54-7.58 (1H, m), 7.73 (1H, t, J=7.3 Hz), 7.92 (0.5H, d, J=8.3 Hz), 7.99 (0.5H, dd, J=8.8, 5.9 Hz), 8.05 (1H, d, J=8.3 Hz).

(Step 4) {4-[(1R)-3-{[(1R)-1-(5-Fluoronaphthalen-1-yl)ethyl]amino}cyclopentyl]phenoxy}acetic acid

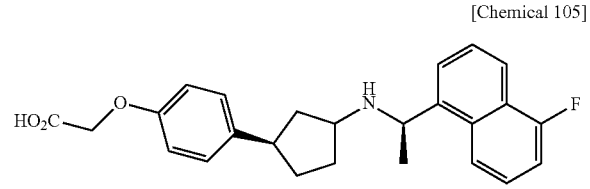 [SMILES: C[C@@H](NC1CC[C@@H](c2ccc(OCC(=O)O)cc2)C1)c1cccc2c(F)cccc12]

[Chemical 105]

{4-[(1R)-3-{[(1R)-1-(5-Fluoronaphthalen-1-yl)ethyl]amino}cyclopentyl]phenoxy}acetic acid methyl ester (71 mg, 0.17 mmol) was used and treated in a similar manner to (Step 6) of (Example 16) to give the title compound (a mixture of diastereomers) (41 mg, 60%).

¹H-NMR (CD₃OD) δ: 1.46-2.41 (6H, m), 1.80 (3H, d, J=6.6 Hz), 2.85-2.96 (0.5H, m), 3.14-3.21 (0.5H, m), 3.47-3.64 (1H, m), 4.35 (2H, s), 5.36-5.43 (1H, m), 6.78 (1H, d, J=8.6 Hz), 6.81 (1H, d, J=8.6 Hz), 6.97 (1H, d, J=8.6 Hz), 7.06 (1H, d, J=8.6 Hz), 7.29-7.35 (1H, m), 7.57-7.66 (1H, m), 7.72 (1H, t, J=7.8 Hz), 7.85 (1H, d, J=7.4 Hz), 8.03 (1H, br t, J=9.6 Hz), 8.22 (1H, d, J=8.2 Hz).

Example 19

{4-[(1R)-3-{[(1R)-1-(3-Methylphenyl)ethylamino]cyclopentyl}phenoxy}acetic acid (Step 1) 2-Methyl-N-[(1R)-1-(3-methylphenyl)ethyl]propane-2-sulfinamide

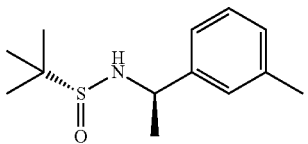

[Chemical 106]

3'-Methylacetophenone (804 mg, 6 mmol) was used and treated in a similar manner to (Step 3) of (Example 16) to give the title compound as an oil (732 mg, 62%).

¹H-NMR (CDCl₃) δ: 1.24 (9H, s), 1.50 (3H, d, J=6.5 Hz), 2.36 (3H, s), 3.38 (1H, br s), 4.51 (1H, m), 7.10 (1H, d, J=7.4 Hz), 7.13-7.17 (2H, m), 7.23 (1H, d, J=7.8 Hz).

(Step 2) (1R)-1-(3-Methylphenyl)ethanamine hydrochloride

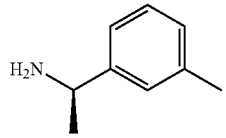

[Chemical 107]

2-Methyl-N-[(1R)-1-(3-methylphenyl)ethyl]propane-2-sulfinamide (732 mg, 3.1 mmol) was used and treated in a similar manner to (Step 4) of (Example 16) to give the title compound (485 mg, 90%).

¹H-NMR (CDCl₃) δ: 1.66 (3H, d, J=6.8 Hz), 2.32 (3H, s), 4.33 (1H, br t, J=5.9 Hz), 7.13 (1H, d, J=7.3 Hz), 7.24 (1H, t, J=7.3 Hz), 7.26-7.29 (2H, m), 8.71 (3H, br s).

(Step 3) {4-[(1R)-3-{[(1R)-1-(3-Methylphenyl)ethyl]amino}cyclopentyl]phenoxy}acetic acid methyl ester

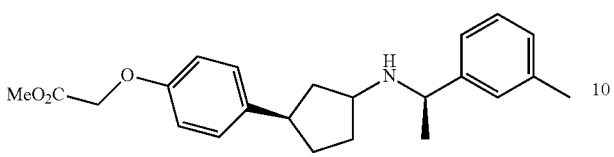

(1R)-1-(3-Methylphenyl)ethanamine hydrochloride (35 mg, 0.2 mmol) was used and treated in a similar manner to (Step 5) of (Example 16) to give the title compound (a mixture of diastereomers) (66 mg, 90%).

¹H-NMR (CDCl₃) δ: 1.38-2.10 (9H, m), 2.22-2.28 (0.5H, m), 2.36 (3H, s), 2.81-2.91 (0.5H, m), 3.02-3.12 (1H, m), 3.80 (3.5H, m), 4.08 (0.5H, q, J=6.6 Hz), 4.61 (2H, s), 6.82 d, J=8.6 Hz), 7.05-7.17 (5H, m), 7.22 (1H, t, J=7.4 Hz).

(Step 4) {4-[(1R)-3-{[(1R)-1-(3-Methylphenyl)ethyl]amino}cyclopentyl]phenoxy}acetic acid

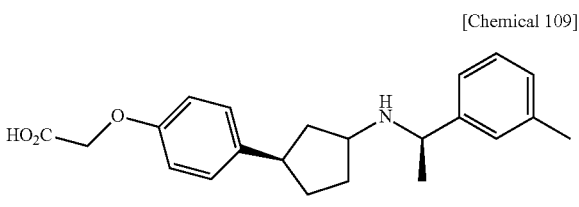 [SMILES: Cc1cccc([C@@H](C)NC2CC[C@@H](c3ccc(OCC(=O)O)cc3)C2)c1]

{4-[(1R)-3-{[(1R)-1-(3-Methylphenyl)ethyl]amino}cyclopentyl]phenoxy}acetic acid methyl ester (66 mg, 0.18 mmol) was used and treated in a similar manner to (Step 6) of (Example 16) to give the title compound (a mixture of diastereomers) (40 mg, 63%).

¹H-NMR (CD₃OD) δ: 1.51-2.33 (6H, m), 1.66 (3H, d, J=6.8 Hz), 2.39 (3H, s), 2.88-2.99 (0.5H, m), 3.12-3.23 (0.5H, m), 3.33-3.55 (1H, m), 4.33 (2H, s), 4.34-4.40 (1H, m), 6.79-6.84 (2H, m), 6.99-7.11 (2H, m), 7.24-7.37 (4H, m).

Example 20

{4-[(1R)-3-{[(1R)-1-(3-Chlorophenyl)ethyl]amino}cyclopentyl]phenoxy}acetic acid (Step 1) 2-Methyl-N-[(1R)-1-(3-chlorophenyl)ethyl]propane-2-sulfinamide

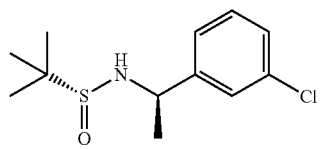

3'-Chloroacetophenone (928 mg, 6 mmol) was used and treated in a similar manner to (Step 3) of (Example 16) to give the title compound (870 mg, 67%).

¹H-NMR (CDCl₃) δ: 1.24 (9H, s), 1.50 (3H, d, J=6.6 Hz), 3.39 (1H, br s), 4.49-4.55 (1H, m), 7.22-7.29 (3H, m), 7.33 (1H, br s).

(Step 2) (1R)-1-(3-Chlorophenyl)ethanamine hydrochloride

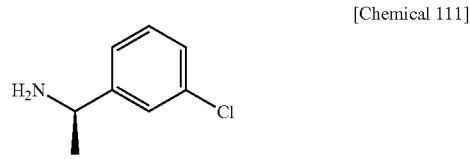

2-Methyl-N-[(1R)-1-(3-chlorophenyl)ethyl]propane-2-sulfinamide (870 mg, 3.3 mmol) was used and treated in a similar manner to (Step 4) of (Example 16) to give the title compound (297 mg, 45%).

¹H-NMR (CDCl₃) δ: 1.67 (3H, d, J=7.0 Hz), 4.36 (1H, br t, J=5.9 Hz), 7.30-7.33 (2H, m), 7.39-7.41 (1H, m), 7.50 (1H, s), 8.77 (3H, br s).

(Step 3) {4-[(1R)-3-{[(1R)-1-(3-Chlorophenyl)ethyl]amino}cyclopentyl]phenoxy}acetic acid methyl ester

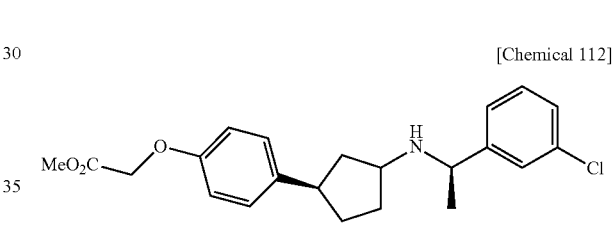

(1R)-1-(3-Chlorophenyl)ethanamine hydrochloride (39 mg, 0.2 mmol) was used and treated in a similar manner to (Step 5) of Example 16 to give the title compound (a mixture of diastereomers) (42 mg, 54%).

¹H-NMR (CDCl₃) δ: 1.50-2.20 (6H, m), 1.34 (3H, d, J=6.6 Hz), 2.83-2.92 (0.5H, m), 2.98-3.06 (0.5H, m), 3.08-3.22 (1H, m), 3.81 (4H, brs), 4.61 (2H, s), 6.82 (2H, d, J=8.6 Hz), 7.12 (2H, t, J=8.2 Hz), 7.17-7.35 (4H, m).

(Step 4) {4-[(1R)-3-{[(1R)-1-(3-Chlorophenyl)ethyl]amino}cyclopentyl]phenoxy}acetic acid

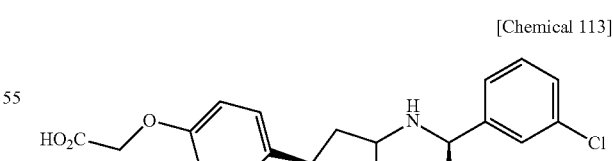

{4-[(1R)-3-{[(1R)-1-(3-Chlorophenyl)ethyl]amino}cyclopentyl]phenoxy}acetic acid methyl ester (42 mg, 0.11 mmol) was used and treated in a similar manner to (Step 6) of (Example 16) to give the title compound (a mixture of diastereomers) (24 mg, 60%).

¹H-NMR (CD₃OD) δ: 1.48-2.36 (6H, m), 1.67 (3H, d, J=6.6 Hz), 2.90-3.00 (0.5H, m), 3.12-3.24 (0.5H, m), 3.40-

3.59 (1H, m), 4.35 (2H, s), 4.40-4.47 (1H, m), 6.80-6.84 (2H, m), 7.02-7.09 (2H, m), 7.42-7.50 (3H, m), 7.57 (1H, br s).

Example 21

{4-[(1R)-3-{[(1R)-1-(6-Fluoronaphthalen-1-yl)ethyl]amino}cyclopentyl]phenoxy}acetic acid (Step 1) N-[(1R)-1-(6-Fluoronaphthalen-1-yl)ethyl]-2-methylpropane-2-sulfinamide

[Chemical 114]

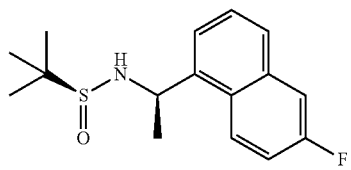

(S)-(+)-tert-Butyl sulfinamide (1.45 g, 12 mmol) and titanium isopropoxide (12 ml, 40 mmol) were added to a dichloroethane (5 ml) solution of 6-fluoroacetonaphthone (1.99 g, 10.5 mmol) described in Intermediate 5 in Published Patent EP291172A1, and the mixture was heated under reflux for 4 hours. After the mixture was cooled to room temperature, water (20 ml) was added. The reaction mixture was extracted with methylene chloride (20 ml), the organic phase was washed with saturated brine and dried over anhydrous sodium sulphate, and then the solvent was distilled off under reduced pressure. The crude product was purified by silica gel column chromatography (hexane/ethyl acetate) to give imine (1.39 g, 43%). Imine obtained was dissolved in tetrahydrofuran (20 ml), followed by dropwise addition of a tetrahydrofuran solution (5 ml, 5 mmol) of 1N L-selectride at −78° C., and the temperature of the mixture was gradually raised to room temperature over 1.5 hours. Methanol (10 ml) and water (50 ml) were added to the reaction mixture to collect the solid matter by filtration, and the mother liquor obtained was extracted with methylene chloride (50 ml). The organic phase was washed with saturated brine and dried over anhydrous sodium sulfate, and the solvent was distilled off under reduced pressure. The crude product was purified by silica gel column chromatography (hexane/ethyl acetate) to give the title compound (1.08 g, 82%).

$^1$H-NMR (CDCl$_3$) δ: 1.21 (9H, s), 1.74 (3H, d, J=6.8 Hz), 3.40 (1H, d, J=4.4 Hz), 5.32 (1H, dq, J=4.4, 6.8 Hz), 7.30 (1H, m), 7.43-7.45 (2H, m), 7.54 (1H, d, J=6.8 Hz), 7.73 (1H, d, J=7.8 Hz), 8.17 (1H, dd, J=5.4, 9.3 Hz).

(Step 2) (1R)-1-(6-Fluoronaphthalen-1-yl)ethanamine hydrochloride

[Chemical 115]

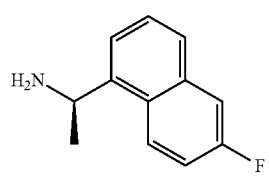

N-[(1R)-1-(6-Fluoronaphthalen-1-yl)ethyl]-2-methylpropane-2-sulfinamide (920 mg, 3.1 mmol) was used and treated in a similar manner to (Step 4) of (Example 16) to give the title compound (666 mg, 95%).

$^1$H-NMR (CDCl$_3$-CD$_3$OD) δ: 1.82 (3H, d, J=6.6 Hz), 5.27 (1H, m), 7.37 (1H, m), 7.51 (1H, m), 7.54 (1H, t, J=7.4 Hz), 7.76 (1H, d, J=7.0 Hz), 7.79 (1H, d, J=8.2 Hz), 8.02 (1H, m).

(Step 3) {4-[(1R)-3-{[(1R)-1-(6-Fluoronaphthalen-1-yl)ethyl]amino}cyclopentyl]phenoxy}acetic acid methyl ester

[Chemical 116]

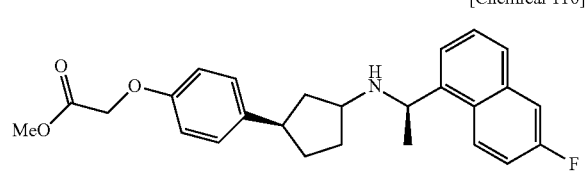

(1R)-1-(6-Fluoronaphthalen-1-yl)ethanamine hydrochloride (90 mg, 0.4 mmol) was used and treated in a similar manner to (Step 5) of Example 16 to give the title compound (a mixture of diastereomers) (74 mg, 88%).

$^1$H-NMR (CDCl$_3$) δ: 1.40-2.25 (6H, m), 1.49 (3H, d, J=6.6 Hz), 2.88 (0.5H, m), 3.10-3.27 (1.5H, m), 3.80 (3H, br s), 4.60 (2H, br d, J=3.1 Hz), 4.65 (1H, m), 6.79-6.82 (2H, m), 7.08-7.13 (2H, m), 7.25-7.30 (1H, m), 7.46-7.52 (2H, m), 7.59 (1H, d, J=7.0 Hz), 7.69 (1H, d, J=8.2 Hz), 8.23-8.27 (1H, m).

(Step 4) {4-[(1R)-3-{[(1R)-1-(6-Fluoronaphthalen-1-yl)ethyl]amino}cyclopentyl]phenoxy}acetic acid

[Chemical 117]

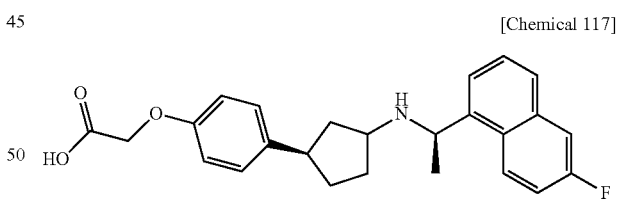

{4-[(1R)-3-{[(1R)-1-(6-Fluoronaphthalen-1-yl)ethyl]amino}cyclopentyl]phenoxy}acetic acid methyl ester (74 mg, 0.17 mmol) was used and treated in a similar manner to (Step 6) of (Example 16) to give the title compound (a mixture of diastereomers) (56 mg, 78%).

$^1$H-NMR (CD$_3$OD) δ: 1.50-2.40 (6H, m), 1.79 (3H, br d, J=6.6 Hz), 2.91 (0.5H, m), 3.18 (0.5H, m), 3.50-3.65 (1H, m), 4.35 (2H, br s), 5.38 (1H, m), 6.77-6.83 (2H, m), 6.96 (1H, br d, J=8.0 Hz), 7.05 (1H, br d, J=8.0 Hz), 7.47 (1H, m), 7.63-7.70 (2H, m), 7.73 (1H, br d, J=7.0 Hz), 7.96 (1H, d, J=8.0 Hz), 8.27 (1H, m).

Example 22

{4-[(1R)-3-{[(1R)-1-(4-Methylnaphthalen-1-yl)ethyl]amino}cyclopentyl]phenoxy}acetic acid (Step 1) 2-Methyl-N-[(1R)-1-(4-methylnaphthalen-1-yl)ethyl]propane-2-sulfinamide

[Chemical 118]

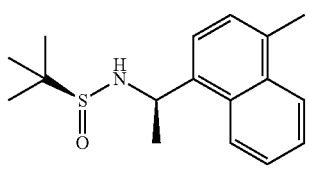

1-(4-Methylnaphthalen-1-yl)ethanone (5.0 mg, 27 mmol) was used and treated in a similar manner to (Step 1) of (Example 21) to give the title compound (2.51 g, 32%).
$^1$H-NMR (CDCl$_3$) δ: 1.20 (9H, s), 1.74 (3H, d, J=6.8 Hz), 2.69 (3H, s), 3.38 (1H, d, J=4.9 Hz), 5.35 (1H, m), 7.31 (1H, d, J=7.3 Hz), 7.47 (1H, d, J=7.3 Hz), 7.53 (2H, m), 8.04 (1H, m), 8.18 (1H, m).

(Step 2) (1R)-1-(4-Methylnaphthalen-1-yl)ethanamine hydrochloride

[Chemical 119]

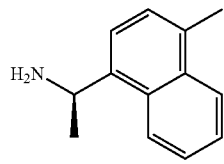

2-Methyl-N-[(1R)-1-(4-methylnaphthalen-1-yl)ethyl]propane-2-sulfinamide (2.51 g, 8.6 mmol) was used and treated in a similar manner to (Step 4) of (Example 16) to give the title compound (1.84 g, 96%).
$^1$H-NMR (CDCl$_3$) δ: 1.82 (3H, d, J=6.8 Hz), 2.69 (3H, s), 5.31 (1H, m), 7.28 (1H, d, J=7.8 Hz), 7.57 (2H, m), 7.73 (1H, d, J=7.8 Hz), 7.95 (1H, m), 8.06 (1H, m), 9.07 (3H, brs).

(Step 3) {4-[(1R)-3-{[(1R)-1-(4-Methylnaphthalen-1-yl)ethyl]amino}cyclopentyl]phenoxy}acetic acid methyl ester

[Chemical 120]

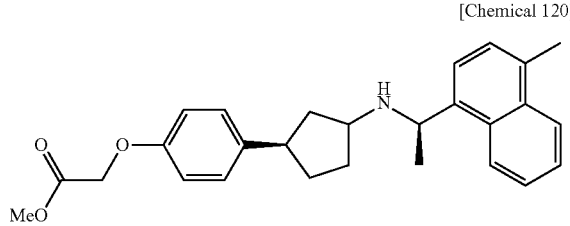

(1R)-1-(4-Methylnaphthalen-1-yl)ethanamine hydrochloride (66 mg, 0.3 mmol) was used and treated in a similar manner to (Step 5) of Example 16 to give the title compound (a mixture of diastereomers) (72 mg, 86%).
$^1$H-NMR (CDCl$_3$) δ: 1.40-1.75 (4H, m), 1.49 (3H, d, J=6.6 Hz), 1.90-2.30 (2H, m), 2.67 (3H, s), 2.85 (0.5H, m), 3.15-3.30 (1.5H, m), 3.80 (3H, br s), 4.60 (2H, br s), 4.71 (1H, m), 6.80 (1H, br t, J=9.0 Hz), 7.08 (1H, d, J=9.0 Hz), 7.13 (1H, d, J=9.0 Hz), 7.34 (1H, d, J=7.0 Hz), 7.53 (3H, m), 8.05 (1H, m), 8.22 (1H, m).

(Step 4) {4-[(1R)-3-{[(1R)-1-(4-Methylnaphthalen-1-yl)ethyl]amino}cyclopentyl]phenoxy}acetic acid

[Chemical 121]

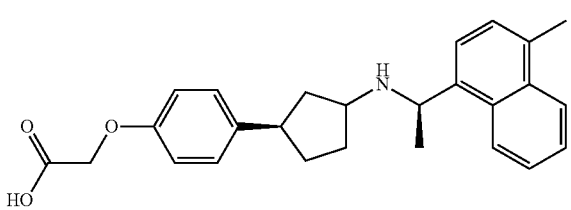

{4-[(1R)-3-{[(1R)-1-(4-Methylnaphthalen-1-yl)ethyl]amino}cyclopentyl]phenoxy}acetic acid methyl ester (76 mg, 0.17 mmol) was used and treated in a similar manner to (Step 6) of (Example 16) to give the title compound (a mixture of diastereomers) (39 mg, 56%).
$^1$H-NMR (CD$_3$OD) δ: 1.40-2.40 (6H, m), 1.80 (3H, d, J=6.3 Hz), 2.69 (3H, s), 2.85 (0.5H, m), 3.18 (0.5H, m), 3.55 (1H, m), 4.38 (2H, brs), 5.38 (1H, m), 6.75-6.85 (2H, m), 6.90 (1H, m), 7.05 (1H, m), 7.48 (1H, d, J=7.4 Hz), 7.63 (3H, m), 8.12-8.22 (2H, m).
MS (FAB) m/z: 404 (M+H)$^+$.

Example 23

{4-[(1R,3S)-3-{[(1R)-1-(4,6-Difluoronaphthalen-1-yl)ethyl]amino}cyclopentyl]phenoxy}acetic acid (Step 1) 1-(4,6-Difluoronaphthalen-1-yl)ethanone

[Chemical 122]

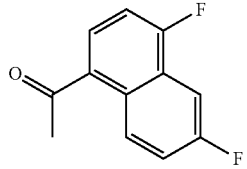

Aluminium chloride (2.53 g, 19 mmol) was suspended in methylene chloride (10 ml), followed by dropwise addition of a solution mixture of 1,7-difluoroacetonaphthone (2.01 g, 12 mmol) synthesized according to the method of W. Adcock et al. [J. Am. Chem. Soc. 1976, 98, 1701-1711] and acetyl chloride (0.94 ml, 13.2 mmol) at room temperature, and the mixture was stirred for 3 hours. Ice was added to stop the reaction, and the reaction mixture was extracted with methylene chloride (20 ml). The organic phase was washed with saturated brine and dried over anhydrous sodium sulfate, and then the solvent was distilled off under reduced pressure. The crude product was purified by silica gel column chromatography (hexane/ethyl acetate) to give the title compound (1.13 g, 46%).

$^1$H-NMR (CDCl$_3$) δ: 2.73 (3H, s), 7.20 (1H, brt, J=9.0 Hz), 7.43 (1H, m), 7.74 (1H, dd, J=2.7, 9.5 Hz), 7.96 (1H, dd, J=5.5, 8.2 Hz), 8.97 (1H, ddd, J=1.9, 5.5, 9.5 Hz).

(Step 2) N-[(1R)-1-(4,6-Difluoronaphthalen-1-yl)ethyl]-2-methylpropane-2-sulfinamide

[Chemical 123]

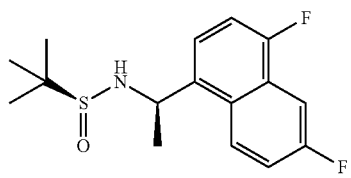

1-(4,6-Difluoronaphthalen-1-yl)ethanone (1.13 g, 5.5 mmol) was used and treated in a similar manner to (Step 1) of (Example 21) to give the title compound (0.95 g, 55%).

$^1$H-NMR (CDCl$_3$) δ: 1.19 (9H, s), 1.72 (3H, d, J=6.6 Hz), 3.39 (1H, d, J=4.3 Hz), 5.26 (1H, m), 7.15 (1H, dd, J=8.1, 10.2 Hz), 7.34 (1H, m), 7.47 (1H, dd, J=5.3, 8.1 Hz), 7.73 (1H, dd, J=2.5, 9.6 Hz), 8.19 (1H, ddd, J=1.8, 5.3, 9.4 Hz).

(Step 3) (1R)-1-(4,6-Difluoronaphthalen-1-yl)ethanamine hydrochloride

[Chemical 124]

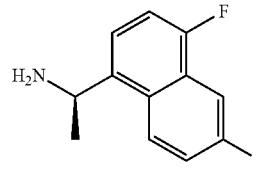

N-[(1R)-1-(4,6-Difluoronaphthalen-1-yl)ethyl]-2-methylpropane-2-sulfinamide (0.95 g, 3.0 mmol) was used and treated in a similar manner to (Step 4) of (Example 16) to give the title compound (704 mg, 95%).

$^1$H-NMR (CDCl$_3$-CD$_3$OD) δ: 1.80 (3H, d, J=6.6 Hz), 5.22 (1H, m), 7.26 (1H, t, J=9.0 Hz), 7.46 (1H, brt, J=8.8 Hz), 7.66 (1H, m), 7.78 (1H, d, J=9.4 Hz), 8.10 (1H, m).

(Step 4) (1S,3R)-3-[4-(Benzyloxy)phenyl]-N-[(1R)-1-(4,6-difluoronaphthalen-1-yl)ethyl]cyclopentanamine

[Chemical 125]

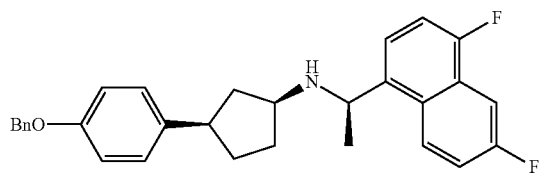

(3R)-3-[4-(Benzyloxy)phenyl]cyclopentanone (756 mg, 2.8 mmol) obtained in (Step 1) of (Example 10) and (1R)-1-(4,6-difluoronaphthalen-1-yl)ethanamine hydrochloride (631 mg, 2.6 mmol) were used and treated in a similar manner to (Step 1) of (Example 17) to give the title compound (602 mg, 51%).

$^1$H-NMR (CDCl$_3$) δ: 1.40-1.50 (1H, m), 1.47 (3H, d, J=6.8 Hz), 1.63 (1H, m), 1.72 (1H, m), 1.92-2.01 (2H, m), 2.23 (1H, m), 2.87 (1H, m), 3.14 (1H, m), 4.62 (1H, q, J=6.5 Hz), 5.03 (2H, s), 6.88 (2H, d, J=8.8 Hz), 7.11 (2H, d, J=8.8 Hz), 7.16 (1H, dd, J=8.3, 10.3 Hz), 7.32 (2H, m), 7.37 (2H, t, J=7.3 Hz), 7.42 (2H, d, J=6.8 Hz), 7.53 (1H, brt, J=6.8 Hz), 7.73 (1H, dd, J=2.9, 9.8 Hz), 8.28 (1H, dd, J=5.4, 8.3 Hz).

(Step 5) 4-[(1R,3S)-3-{[(1R)-1-(4,6-Difluoronaphthalen-1-yl)ethyl]amino}cyclopentyl]phenol

[Chemical 126]

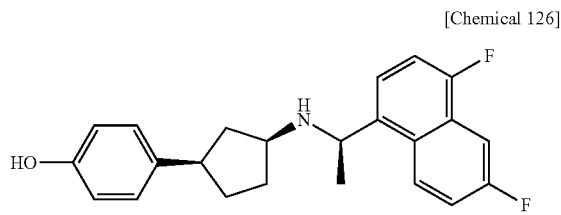 [SMILES: C[C@@H](N[C@H]1CC[C@@H](c2ccc(O)cc2)C1)c1ccc(F)c2cc(F)ccc12]

(1S,3R)-3-[4-(Benzyloxy)phenyl]-N-[(1R)-1-(4,6-difluoronaphthalen-1-yl)ethyl]cyclopentanamine (600 mg, 1.3 mmol) was used and treated in a similar manner to (Step 3) of (Example 10) to give the title compound (432 mg, 90%).

$^1$H-NMR (CDCl$_3$) δ: 1.38-1.48 (1H, m), 1.48 (3H, d, J=6.4 Hz), 1.60-1.80 (2H, m), 1.92-2.02 (2H, m), 2.22 (1H, m), 2.85 (1H, m), 3.14 (1H, m), 4.63 (1H, q, J=6.4 Hz), 6.73 (2H, d, J=8.8 Hz), 7.05 (2H, d, J=8.8 Hz), 7.17 (1H, dd, J=8.3, 9.8 Hz), 7.32 (1H, m), 7.53 (1H, br t, J=6.6 Hz), 7.73 (1H, dd, J=2.9, 9.8 Hz), 8.27 (1H, dd, J=5.1, 9.0 Hz).

(Step 6) {4-[(1R,3S)-3-{[(1R)-1-(4,6-Difluoronaphthalen-1-yl)ethyl]amino}cyclopentyl]phenoxy}acetic acid methyl ester

[Chemical 127]

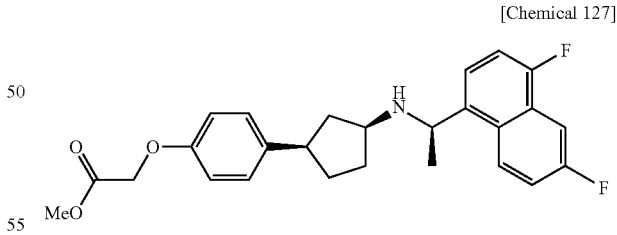

4-[(1R,3S)-3-{[(1R)-1-(4,6-Difluoronaphthalen-1-yl)ethyl]amino}cyclopentyl]phenol (425 mg, 1.2 mmol) was used and treated in a similar manner to (Step 4) of (Example 10) to give the title compound (407 mg, 80%).

$^1$H-NMR (CDCl$_3$) δ: 1.37-1.47 (1H, m), 1.47 (3H, d, J=6.8 Hz), 1.58-1.76 (2H, m), 1.92-2.02 (2H, m), 2.22(1H, m), 2.86(1H, m), 3.14(1H, m), 3.80 (3H, s), 4.60 (2H, s), 4.58-4.62(1H, m), 6.81 (2H, d, J=8.8 Hz), 7.12 (2H, d, J=8.8 Hz), 7.16(1H, brt, J=9.0 Hz), 7.32(1H, td, J=8.8, 2.6 Hz), 7.53(1H, brt, J=6.6 Hz), 7.73(1H, dd, J=9.8, 2.4 Hz), 8.29(1H, m).

(Step 7) {4-[(1R,3S)-3-{[(1R)-1-(4,6-Difluoronaphthalen-1-yl)ethyl]amino}cyclopentyl]phenoxy}acetic acid

[Chemical 128]

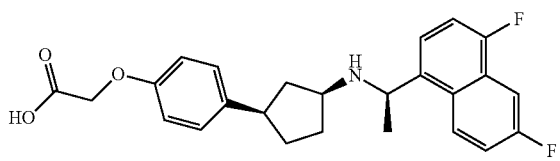

{4-[(1R,3S)-3-{[(1R)-1-(4,6-Difluoronaphthalen-1-yl)ethyl]amino}cyclopentyl]phenoxy}acetic acid methyl ester (402 mg, 0.91 mmol) was used and treated in a similar manner to (Step 4) of (Example 17) to give the title compound (391 mg, 100%).

$^1$H-NMR (DMSO-$d_6$) δ: 1.40-1.50(1H, m), 1.45 (3H, d, J=6.3 Hz), 1.55-1.85 (4H, m), 2.11(1H, m), 2.79(1H, m), 3.06(1H, m), 4.49 (2H, s), 4.79(1H, q, J=6.3 Hz), 6.78 (2H, d, J=8.6 Hz), 7.08 (2H, d, J=8.6 Hz), 7.43(1H, br t, J=9.2 Hz), 7.57(1H, br t, J=8.8 Hz), 7.72-7.79 (2H, m), 8.51 (1H, m);

MS (FAB) m/z: 425 (M+H)$^+$.

Example 24

{3-[(1R,3S)-3-{[(1R)-1-(4-Fluoronaphthalen-1-yl)ethyl]amino}cyclopentyl]phenyl}acetic acid hydrochloride (Step 1) (1S,3R)-3-(3-Bromophenyl)-N-[(1R)-1-(4-fluoronaphthalen-1-yl)ethyl]cyclopentanamine

[Chemical 129]

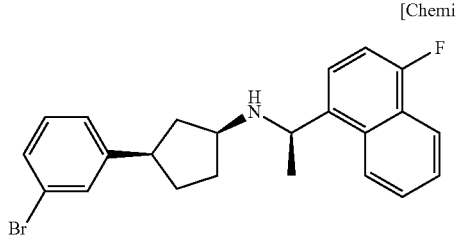

(3R)-3-(3-Bromophenyl)cyclopentanone (1.50 g, 6.3 mmol) obtained in (Step 1) of (Example 1) and (1R)-1-(4-fluoronaphthalen-1-yl)ethanamine hydrochloride (1.56 g, 6.9 mmol) obtained in (Step 4) of (Example 16) were used and treated in a similar manner to (Step 1) of (Example 17) to give the title compound (713 mg, 28%).

$^1$H-NMR (CDCl$_3$) δ: 1.38-1.46 (1H, m), 1.49 (3H, d, J=6.7 Hz), 1.59-1.82 (2H, m), 1.91-2.04 (2H, m), 2.22-2.31(1H, m), 2.81-2.96(1H, m), 3.10-3.21(1H, m), 4.68(1H, q, J=6.7 Hz), 7.09-7.18 (3H, m), 7.27-7.32(1H, m), 7.36 (1H, s), 7.52-7.63 (3H, m), 8.13-8.26 (2H, m).

(Step 2) [(1S,3R)-3-(3-Bromophenyl)cyclopentyl][(1R)-1-(4-fluoronaphthalen-1-yl)ethyl]carbamic acid tert-butyl ester

[Chemical 130]

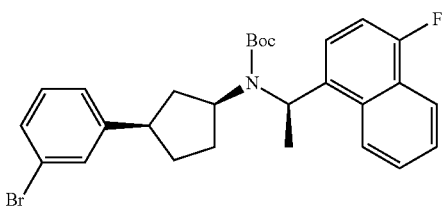

(1S,3R)-3-(3-Bromophenyl)-N-[(1R)-1-(4-fluoronaphthalen-1-yl)ethyl]cyclopentanamine (713 mg, 1.7 mmol) was used and treated in a similar manner to (Step 3) of (Example 1) to give the title compound (822 mg, 93%).

$^1$H-NMR (CDCl$_3$) δ: 0.54(1H, br s), 1.57-1.65(15H, m), 1.89-1.96(1H, m), 2.34(1H, br s), 2.62-2.73(1H, m), 3.14-3.25(1H, m), 6.14(1H, br s), 7.06-7.16 (3H, m), 7.27-7.30 (1H, m), 7.32(1H, s), 7.42-7.48(1H, m), 7.54-7.59 (2H, m), 8.11-8.17 (2H, m).

(Step 3) {3-[(1R,3S)-3-(tert-Butoxycarbonyl)[(1R)-1-(4-fluoronaphthalen-1-yl)ethyl]amino}cyclopentyl]phenyl}acetic acid isopropyl ester

[Chemical 131]

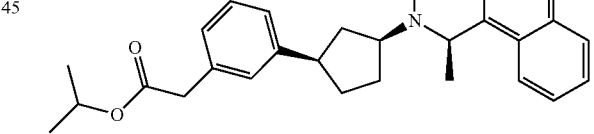

[(1S,3R)-3-(3-Bromophenyl)cyclopentyl][(1R)-1-(4-fluoronaphthalen-1-yl)ethyl]carbamic acid tert-butyl ester (822 mg, 1.6 mmol) was used and treated in a similar manner to (Step 1) of (Example 7) to give the title compound (494 mg, 58%).

$^1$H-NMR (CDCl$_3$) δ: 0.54 (1H, br s), 1.21 (6H, d, J=6.3 Hz), 1.57-1.69 (15H, m), 1.87-1.97 (1H, m), 2.28-2.46 (1H, m), 2.64-2.76 (1H, m), 3.23-3.34 (1H, m), 3.53 (2H, s), 4.96-5.03 (1H, m), 6.13 (1H, br s), 7.05-7.25 (5H, m), 7.43-7.49 (1H, m), 7.53-7.62 (2H, m), 8.11-8.20 (2H, m).

(Step 4) {3-[(1R,3S)-3-{[(tert-Butoxycarbonyl)[(1R)-1-(4-fluoronaphthalen-1-yl)ethyl]amino}cyclopentyl]phenyl}acetic acid

[Chemical 132]

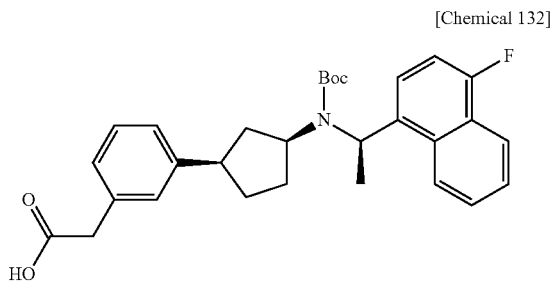 [SMILES: C[C@H](c1ccc(F)c2ccccc12)N(C(=O)OC(C)(C)C)[C@H]1CC[C@@H](c2cccc(CC(=O)O)c2)C1]

{3-[(1R,3S)-3-{(tert-Butoxycarbonyl)[(1R)-1-(4-fluoronaphthalen-1-yl)ethyl]amino}cyclopentyl]phenyl}acetic acid isopropyl ester (494 mg, 0.93 mmol) was used and treated in a similar manner to (Step 2) of (Example 7) to give the title compound (471 mg).

$^1$H-NMR (CDCl$_3$) δ: 0.45-0.63 (1H, m), 1.54-1.67 (15H, m), 1.86-1.97 (1H, m), 2.37 (1H, br s), 2.64-2.77(1H, m), 3.22-3.34 (1H, m), 3.60 (2H, s), 6.14 (1H, br s), 7.06-7.26 (5H, m), 7.43-7.48 (1H, m), 7.53-7.60 (2H, m), 8.09-8.18 (2H, m).

(Step 5) {3-[(1R,3S)-3-{[(1R)-1-(4-Fluoronaphthalen-1-yl)ethyl]amino}cyclopentyl]phenyl}acetic acid hydrochloride

[Chemical 133]

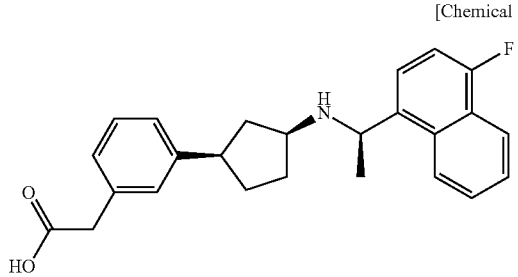

{3-[(1R,3S)-3-{[(tert-butoxycarbonyl)[(1R)-1-(4-fluoronaphthalen-1-yl)ethyl]amino}cyclopentyl]phenyl}acetic acid (471 mg) was used and treated in a similar manner to (Step 3) of (Example 7) to give the title compound (319 mg, 2 steps 81%).

$^1$H-NMR (CD$_3$OD) δ: 1.68-1.79(1H, m), 1.83 (3H, d, J=6.8 Hz), 1.86-1.94(1H, m), 1.98-2.25 (3H, m), 2.49-2.60 (1H, m), 3.01-3.12 (1H, m), 3.57 (2H, s), 3.63-3.74 (1H, m), 5.41 (1H, q, J=6.8 Hz), 7.11-7.28 (4H, m), 7.34-7.42 (1H, m), 7.68-7.82 (3H, m), 8.20-8.32 (2H, m);

HRMS (ESI$^+$) calcd for C25H$_{27}$FNO$_2$ [M+14]$^+$. required m/z: 392.2026. found 392.2019.

Example 25

{4-[(1R,3S)-3-{[(1R)-1-(4-Fluoronaphthalen-1-yl)ethyl]amino}cyclopentyl]phenyl}acetic acid hydrochloride (Step 1) (1S,3R)-3-(4-Bromophenyl)-N-[(1R)-1-(4-fluoronaphthalen-1-yl)ethyl]cyclopentanamine

[Chemical 134]

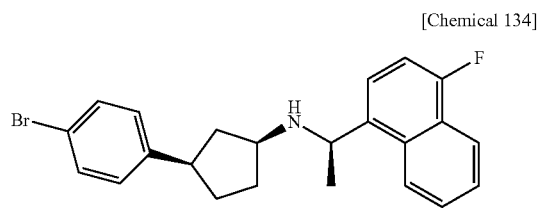 [SMILES: C[C@@H](N[C@H]1CC[C@@H](c2ccc(Br)cc2)C1)c1ccc(F)c2ccccc12]

(3R)-3-(4-Bromophenyl)cyclopentanone (4.78 g, 20 mmol) obtained in (Step 1) of (Example 3) and (1R)-1-(4-fluoronaphthalen-1-yl)ethanamine hydrochloride (4.51 g, 20 mmol) obtained in (Step 4) of (Example 16) were used and treated in a similar manner to (Step 1) of (Example 17) to give the title compound (3.82 g, 46%).

$^1$H-NMR (CDCl$_3$) δ: 1.37-1.48 (1H, m), 1.48 (3H, d, J=6.5 Hz), 1.60-1.78 (2H, m), 1.91-2.02 (2H, m), 2.22-2.30 (1H, m), 2.82-2.92 (1H, m), 3.12-3.21 (1H, m), 4.68 (1H, q, J=6.5 Hz), 7.07 (2H, d, J=8.2 Hz), 7.14 (1H, t, J=8.8 Hz), 7.37 (2H, d, J=8.2 Hz), 7.52-7.60 (3H, m), 8.13-8.18 (1H, m), 8.21 (1H, d, J=7.8 Hz);

IR (ATR) υ max 2952, 1742, 1602, 1489, 1393, 1258, 1220, 1146, 1073, 1046, 1009, 820, 759 cm$^{-1}$;

MS (EI) m/z: 411 M$^+$.

(Step 2) [(1S,3R)-3-(4-Bromophenyecyclopentyl][(1R)-1-(4-fluoronaphthalen-1-yl)ethyl]carbamic acid tert-butyl ester

[Chemical 135]

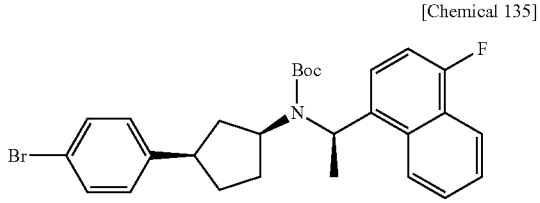 [SMILES: C[C@H](c1ccc(F)c2ccccc12)N(C(=O)OC(C)(C)C)[C@H]1CC[C@@H](c2ccc(Br)cc2)C1]

(1S,3R)-3-(4-Bromophenyl)-N-[(1R)-1-(4-fluoronaphthalen-1-yl)ethyl]cyclopentanamine (3.80 g, 9.2 mmol) was used and treated in a similar manner to (Step 3) of (Example 1) to give the title compound (3.89 g, 82%).

$^1$H-NMR (CDCl$_3$) δ: 0.48-0.60 (1H, m), 1.57-1.64 (3H, m), 1.59 (9H, s), 1.63 (3H, d, J=6.6 Hz), 1.87-1.94 (1H, m), 2.33 (1H, br s), 2.62-2.72 (1H, m), 3.20-3.32 (1H, m), 6.12 (1H, br s), 7.05 (2H, d, J=8.0 Hz), 7.13 (1H, dd, J=10.0, 8.0 Hz), 7.37 (2H, d, J=8.0 Hz), 7.44 (1H, dd, J=8.0, 5.3 Hz), 7.54-7.58 (2H, m), 8.11-8.16 (2H, m);

IR (ATR) υ max 2973, 1674, 1447, 1364, 1320, 1151, 1029, 1010, 829, 762 cm$^{-1}$;

MS (FAB) m/z: 512 (M+H)$^+$.

(Step 3) {4-[(1R,3S)-3-{[(tert-Butoxycarbonyl)[(1R)-1-(4-fluoronaphthalen-1-yl)ethyl]amino}cyclopentyl]phenyl}acetic acid isopropyl ester

[Chemical 136]

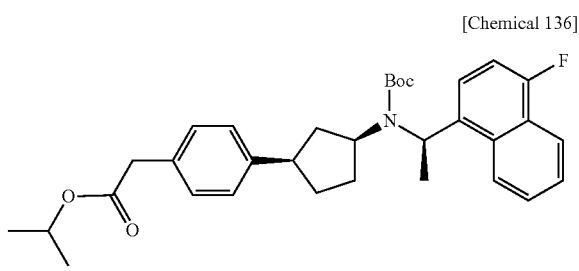 [SMILES: CC(C)OC(=O)Cc1ccc([C@@H]2CC[C@H](N(C(=O)OC(C)(C)C)[C@H](C)c3ccc(F)c4ccccc34)C2)cc1]

[(1S,3R)-3-(4-Bromophenyl)cyclopentyl][(1R)-1-(4-fluoronaphthalen-1-yl)ethyl]carbamic acid tert-butyl ester (3.89 g, 7.6 mmol) was used and treated in a similar manner to (Step 1) of (Example 7) to give the title compound (2.78 g, 69%).

$^1$H-NMR (CDCl$_3$) δ: 0.48-0.59 (1H, m), 1.22 (6H, d, J=6.3 Hz), 1.57-1.64 (2H, m), 1.59 (9H, s), 1.63 (3H, d, J=6.6 Hz), 1.87-1.93 (1H, m), 2.35 (1H, br s), 2.64-2.74 (1H, m), 3.28 (1H, tt, J=10.9, 6.8 Hz), 3.52 (2H, s), 4.99 (1H, q, J=6.3 Hz), 6.12 (1H, br s), 7.11-7.19 (5H, m), 7.45 (1H, dd, J=7.8, 5.5 Hz), 7.53-7.58 (2H, m), 8.11-8.17 (2H, m);

IR (ATR) υ max 2976, 1730, 1673, 1447, 1365, 1320, 1151, 1105, 1029, 962, 831, 763 cm$^{-1}$;

MS (FAB) m/z: 534 (M+H)$^+$.

(Step 4) {4-[(1R,3S)-3-{(tert-butoxycarbonyl)[(1R)-1-(4-fluoronaphthalen-1-yl)ethyl]amino}cyclopentyl]phenyl}acetic acid

[Chemical 137]

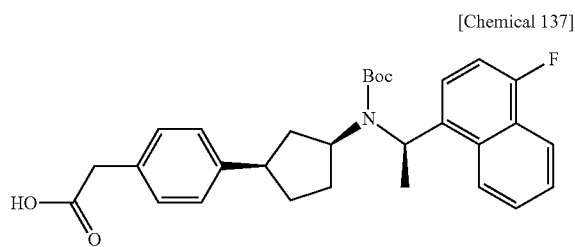 [SMILES: C[C@H](c1ccc(F)c2ccccc12)N(C(=O)OC(C)(C)C)[C@H]1CC[C@@H](c2ccc(CC(=O)O)cc2)C1]

{4-[(1R,3S)-3-{[(tert-butoxycarbonyl)[(1R)-1-(4-fluoronaphthalen-1-yl)ethyl]amino}cyclopentyl]phenyl}acetic acid isopropoyl ester (2.78 g, 5.2 mmol) was used and treated in a similar manner to (Step 2) of (Example 7) to give the title compound (2.34 g, 92%).

$^1$H-NMR (CDCl$_3$) δ: 0.47-0.58 (1H, m), 1.55-1.63 (2H, m), 1.59 (9H, s), 1.62 (3H, d, J=6.6 Hz), 1.86-1.93 (1H, m), 2.36 (1H, br s), 2.64-2.74 (1H, m), 3.28 (1H, tt, J=10.9, 6.8 Hz), 3.60 (2H, s), 6.12 (1H, brs), 7.11-7.19 (5H, m), 7.45 (1H, dd, J=8.0, 5.3 Hz), 7.53-7.58 (2H, m), 8.11-8.16 (2H, m);

IR (KBr) υ max 2976, 1711, 1676, 1515, 1452, 1367, 1322, 1155, 1038, 832, 765 cm$^{-1}$;

MS (FAB) m/z: 492 (M+H)$^+$.

(Step 5) {4-[(1R,3S)-3-{[(1R)-1-(4-Fluoronaphthalen-1-yl)ethyl]amino}cyclopentyl]phenyl}acetic acid hydrochloride

[Chemical 138]

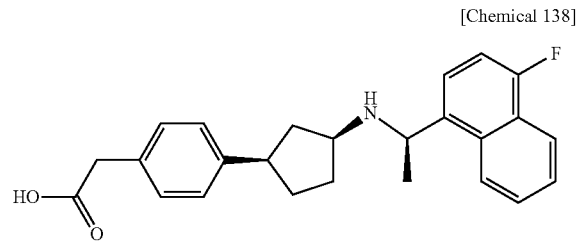 [SMILES: C[C@@H](N[C@H]1CC[C@@H](c2ccc(CC(=O)O)cc2)C1)c1ccc(F)c2ccccc12]

{4-[(1R,3S)-3-{[(tert-Butoxycarbonyl)[(1R)-1-(4-fluoronaphthalen-1-yl)ethyl]amino}cyclopentyl]phenyl}acetic acid (2.34 g, 4.8 mmol) was used and treated in a similar manner to (Step 3) of (Example 7) to give the title compound (1.91 g, 94%).

$^1$H-NMR (CD$_3$OD) δ: 1.71 (1H, td, J=12.0, 9.9 Hz), 1.82 (3H, d, J=6.6 Hz), 1.85-1.91 (1H, m), 1.98-2.20 (3H, m), 2.49-2.56 (1H, m), 3.01-3.11 (1H, m), 3.56 (2H, s), 3.63-3.72 (1H, m), 5.40 (1H, q, J=6.6 Hz), 7.21 (4H, s), 7.37 (1H, dd, J=10.2, 8.2 Hz), 7.68-7.79 (3H, m), 8.23 (1H, d, J=8.2 Hz), 8.27 (1H, d, J=8.6 Hz);

IR (KBr) υ max 3419, 2958, 2742, 1733, 1581, 1517, 1394, 1263, 1225, 1164, 848, 770 cm$^{-1}$;

MS (FAB) m/z: 392 (M+H)$^+$.

Example 26

(1S,3R)-N-[(1R)-1-(4-Fluoronaphthalen-1-yl)ethyl]-3-[4-(2H-tetrazol-5-yl)phenyl]cyclopentanamine hydrochloride (Step 1) [(1S,3R)-3-(4-Cyanophenyl)cyclopentyl][(1R)-1-(4-fluoronaphthalen-1-yl)ethyl]carbamic acid tert-butyl ester

[Chemical 139]

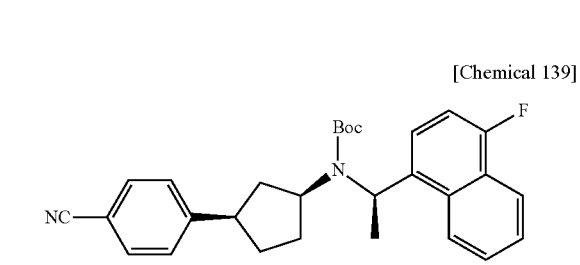 [SMILES: C[C@H](c1ccc(F)c2ccccc12)N(C(=O)OC(C)(C)C)[C@H]1CC[C@@H](c2ccc(C#N)cc2)C1]

[(1S,3R)-3-(4-Bromophenyl)cyclopentyl][(1R)-1-(4-fluoronaphthalen-1-yl)ethyl]carbamic acid tert-butyl ester (5.02 g, 9.8 mmol) obtained in (Step 2) of (Example 25) was used and treated in a similar manner to (Step 4) of (Example 1) to give the title compound (3.21 g, 71%).

$^1$H-NMR (CDCl$_3$) δ: 0.50-0.62 (1H, m), 1.58-1.67 (3H, m), 1.60 (9H, s), 1.63 (3H, d, J=6.6 Hz), 1.91-1.98 (1H, m), 2.39 (1H, br s), 2.72-2.82 (1H, m), 3.30 (1H, tt, J=10.9, 7.0 Hz), 6.10 (1H, br s), 7.14 (1H, dd, J=10.2, 7.8 Hz), 7.25-7.31 (2H, m), 7.45 (1H, dd, J=7.8, 5.1 Hz), 7.52-7.59 (4H, m), 8.10-8.17 (2H, m);

IR (ATR) υ max 2974, 2226, 1738, 1673, 1446, 1365, 1321, 1151, 1029, 830, 763, 559 cm$^{-1}$;

MS (FAB) m/z: 459 (M+H)$^+$.

101

(Step 2) [(1R)-1-(4-Fluoronaphthalen-1-yl)ethyl]{(1S,3R)-3-[4-(2H-tetrazol-5-yl)phenyl]cyclopentyl}carbamic acid tert-butyl ester

[Chemical 140]

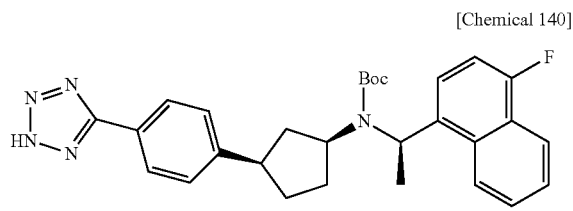 [SMILES: C[C@H](c1ccc(F)c2ccccc12)N(C(=O)OC(C)(C)C)[C@H]1CC[C@@H](c2ccc(-c3nn[nH]n3)cc2)C1]

[(1S,3R)-3-(4-Cyanophenyl)cyclopentyl][(1R)-1-(4-fluoronaphthalen-1-yl)ethyl]carbamic acid tert-butyl ester (732 mg, 1.6 mmol) was used and treated in a similar manner to (Step 5) of (Example 1) to give the title compound (641 mg, 80%).

$^1$H-NMR (DMSO-D$_6$) δ: 0.42-0.54 (1H, m), 1.22-1.32 (1H, m), 1.50-1.65 (2H, m), 1.53 (9H, s), 1.60 (3H, d, J=6.7 Hz), 1.97-2.05 (1H, m), 2.23-2.34 (1H, m), 2.81-2.91 (1H, m), 3.33-3.44 (1H, m), 5.99 (1H, br s), 7.36-7.40 (1H, m), 7.39 (2H, d, J=8.2 Hz), 7.62-7.68 (3H, m), 7.94 (2H, d, J=8.2 Hz), 8.10-8.13 (2H, m);

IR (KBr) υ max 3436, 3096, 2974, 1677, 1647, 1467, 1452, 1368, 1325, 1155, 1039, 843, 764 cm$^{-1}$;

MS (FAB) m/z: 502 (M+H)$^+$.

(Step 3) (1S,3R)-N-[(1R)-1-(4-Fluoronaphthalen-1-yl)ethyl]-3-[4-(2H-tetrazol-5-yl)phenyl]cyclopentanamine hydrochloride

[Chemical 141]

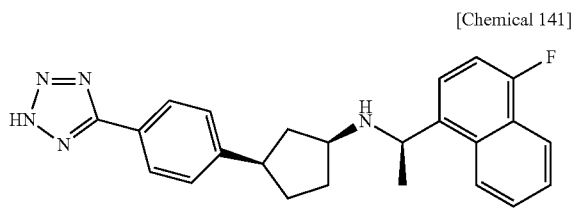 [SMILES: C[C@@H](N[C@H]1CC[C@@H](c2ccc(-c3nn[nH]n3)cc2)C1)c1ccc(F)c2ccccc12]

[(1R)-1-(4-Fluoronaphthalen-1-yl)ethyl]{(1S,3R)-3-[4-(2H-tetrazol-5-yl)phenyl]cyclopentyl}carbamic acid tert-butyl ester (135 mg, 0.27 mmol) was used and treated in a similar manner to (Step 6) of (Example 1) to give the title compound (116 mg, 98%).

$^1$H-NMR (DMSO-D$_6$) δ: 1.73 (3H, d, J=6.6 Hz), 1.80-2.06 (4H, m), 2.10-2.18 (1H, m), 2.48-2.55 (1H, m), 3.04-3.13 (1H, m), 3.57 (1H, brs), 5.33 (1H, br s), 7.48 (2H, d, J=8.2 Hz), 7.53 (1H, dd, J=10.4, 8.4 Hz), 7.71-7.79 (2H, m), 7.98-8.01 (1H, m), 8.01 (2H, d, J=8.2 Hz), 8.15-8.18 (1H, m), 8.40 (1H, d, J=7.8 Hz), 9.39 (1H, br s), 9.91 (1H, br s);

IR (KBr) υ max 3395, 2971, 2825, 1619, 1605, 1584, 1496, 1438, 1399, 1263, 1225, 1152, 1050, 998, 841, 763 cm$^{-1}$;

MS (FAB) m/z: 402 (M+H)$^+$.

102

(Example 27)

3-{4-[(1R,3S)-3-{[(1R)-1-(4-Fluoronaphthalen-1-yl)ethyl]amino}cyclopentyl]phenyl}propanoic acid hydrochloride (Step 1) [(1R)-1-(4-Fluoronaphthalen-1-yl)ethyl][(1S,3R)-3-(4-formylphenyl)cyclopentyl]carbamic acid tert-butyl ester

[Chemical 142]

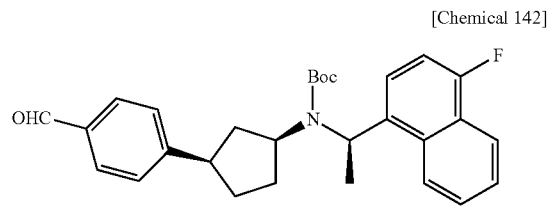 [SMILES: C[C@H](c1ccc(F)c2ccccc12)N(C(=O)OC(C)(C)C)[C@H]1CC[C@@H](c2ccc(C=O)cc2)C1]

[(1S,3R)-3-(4-Cyanophenyl)cyclopentyl][(1R)-1-(4-fluoronaphthalen-1-yl)ethyl]carbamic acid tert-butyl ester (2.31 g, 5.0 mmol) obtained in (Step 1) of (Example 26) was used and treated in a similar manner to (Step 1) of (Example 9) to give the title compound (2.12 g, 91%).

$^1$H-NMR (CDCl$_3$) δ: 0.51-0.63 (1H, m), 1.36-1.67 (3H, m), 1.60 (9H, s), 1.64 (3H, d, J=7.0 Hz), 1.93-2.00 (1H, m), 2.42 (1H, br s), 2.75-2.85 (1H, m), 3.31 (1H, tt, J=10.9, 7.0 Hz), 6.12 (1H, br s), 7.14 (1H, dd, J=10.2, 7.8 Hz), 7.34 (2H, d, J=8.0 Hz), 7.45 (1H, dd, J=7.8, 5.5 Hz), 7.55-7.59 (2H, m), 7.78 (2H, d, J=8.0 Hz), 8.12-8.16 (2H, m), 9.95 (1H, s);

IR (KBr) υ max 2975, 1677, 1605, 1448, 1366, 1322, 1155, 829, 765 cm$^{-1}$;

MS (FAB) m/z: 462 (M+H)$^+$.

(Step 2) (2E)-3-{4-[(1R,3S)-3-{[(tert-Butoxycarbonyl)[(1R)-1-(4-fluoronaphthalen-1-yl)ethyl]amino}cyclopentyl]phenyl}acrylic acid ethyl ester

[Chemical 143]

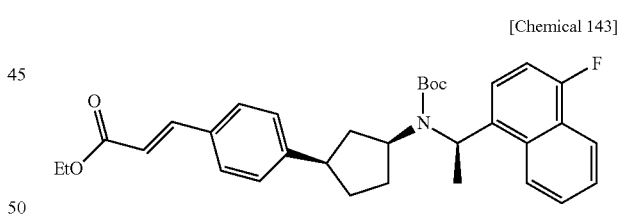

[(1R)-1-(4-Fluoronaphthalen-1-yl)ethyl][(1S,3R)-3-(4-formylphenyl)cyclopentyl]carbamic acid tert-butyl ester (2.10 g, 4.5 mmol) was used and treated in a similar manner to (Step 2) of (Example 9) to give the title compound (2.25 g, 93%).

$^1$H-NMR (CDCl$_3$) δ: 0.49-0.61 (1H, m), 1.33 (3H, t, J=7.2 Hz), 1.53-1.68 (3H, m), 1.60 (9H, s), 1.63 (3H, d, J=6.6 Hz), 1.89-1.96 (1H, m), 2.38 (1H, br s), 2.68-2.78 (1H, m), 3.29 (1H, tt, J=10.9, 6.6 Hz), 4.25 (2H, q, J=7.2 Hz), 6.12 (1H, br s), 6.38 (1H, d, J=16.0 Hz), 7.14 (1H, dd, J=10.2, 7.8 Hz), 7.20 (2H, d, J=8.2 Hz), 7.42 (2H, d, J=8.2 Hz), 7.45 (1H, dd, J=7.8, 5.1 Hz), 7.54-7.59 (2H, m), 7.64 (1H, d, J=16.0 Hz), 8.12-8.16 (2H, m);

IR (KBr) υ max 2977, 1713, 1676, 1635, 1366, 1322, 1158, 1038, 829, 764 cm$^{-1}$;

MS (FAB) m/z: 532 (M+H)$^+$.

(Step 3) 3-{4-[(1R,3S)-3-{(tert-Butoxycarbonyl)[(1R)-1-(4-fluoronaphthalen-1-yl)ethyl]amino}cyclopentyl]phenyl}propanoic acid ethyl ester

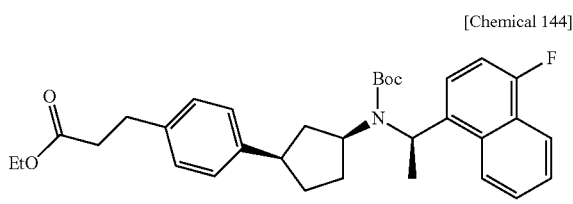 [SMILES: CCOC(=O)CCc1ccc([C@@H]2CC[C@H](N(C(=O)OC(C)(C)C)[C@H](C)c3ccc(F)c4ccccc34)C2)cc1]

[Chemical 144]

(2E)-3-{4-[(1R,3S)-3-{[(tert-Butoxycarbonyl)[(1R)-1-(4-fluoronaphthalen-1-yl)ethyl]amino}cyclopentyl]phenyl}acrylic acid ethyl ester (2.21 g, 4.2 mmol) was used and treated in a similar manner to (Step 3) of (Example 9) to give the title compound (2.18 g, 98%).

$^1$H-NMR (CDCl$_3$) δ: 0.47-0.59 (1H, m), 1.22 (3H, t, J=7.1 Hz), 1.54-1.64 (3H, m), 1.60 (9H, s), 1.62 (3H, d, J=6.6 Hz), 1.86-1.93 (1H, m), 2.36 (1H, br s), 2.58 (2H, t, J=7.8 Hz), 2.63-2.73 (1H, m), 2.89 (2H, t, J=7.8 Hz), 3.27 (1H, tt, J=10.9, 7.0 Hz), 4.12 (2H, q, J=7.1 Hz), 6.12 (1H, br s), 7.10 (4H, s), 7.13 (1H, dd, J=10.2, 8.2 Hz), 7.45 (1H, dd, J=7.8, 5.1 Hz), 7.54-7.58 (2H, m), 8.11-8.16 (2H, m);

IR (ATR) υ max 2975, 1733, 1672, 1445, 1365, 1320, 1150, 1029, 829, 762 cm$^{-1}$;

MS (FAB) m/z: 534 (M+H)$^+$.

(Step 4) 3-{4-[(1R,3S)-3-{(tert-Butoxycarbonyl)[(1R)-1-(4-fluoronaphthalen-1-yl)ethyl]amino}cyclopentyl]phenyl}propanoic acid

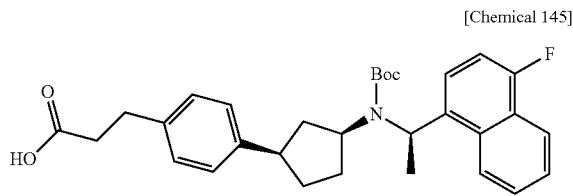 [SMILES: C[C@H](c1ccc(F)c2ccccc12)N(C(=O)OC(C)(C)C)[C@H]1CC[C@@H](c2ccc(CCC(=O)O)cc2)C1]

[Chemical 145]

3-{4-[(1R,3S)-3-{(tert-Butoxycarbonyl)[(1R)-1-(4-fluoronaphthalen-1-yl)ethyl]amino}cyclopentyl]phenyl}propanoic acid ethyl ester (2.17 g, 4.1 mmol) was used and treated in a similar manner to (Step 4) of (Example 5) to give the title compound (2.02 g, 98%).

$^1$H-NMR (CDCl$_3$) δ: 0.47-0.59 (1H, m), 1.54-1.65 (3H, m), 1.60 (9H, s), 1.62 (3H, d, J=7.0 Hz), 1.86-1.93 (1H, m), 2.34 (1H, br s), 2.62-2.73 (1H, m), 2.65 (2H, t, J=7.8 Hz), 2.91 (2H, t, J=7.8 Hz), 3.28 (1H, tt, J=10.9, 7.0 Hz), 6.12 (1H, br s), 7.10 (4H, s), 7.13 (1H, dd, J=10.2, 7.8 Hz), 7.45 (1H, dd, J=7.6, 5.3 Hz), 7.53-7.58 (2H, m), 8.11-8.15 (2H, m);

IR (KBr) υ max 2976, 1737, 1711, 1675, 1515, 1451, 1366, 1322, 1154, 1038, 831, 764 cm$^{-1}$;

MS (FAB) m/z: 506 (M+H)$^+$.

(Step 5) 3-{4-[(1R,3S)-3-{[(1R)-1-(4-Fluoronaphthalen-1-yl)ethyl]amino}cyclopentyl]phenyl}propanoic acid hydrochloride

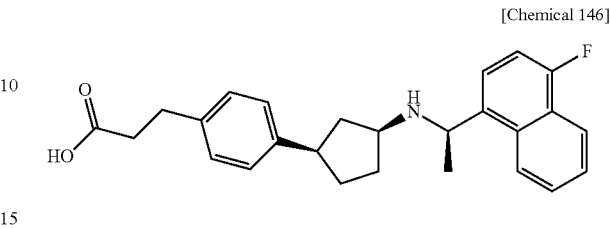

[Chemical 146]

3-{4-[(1R,3S)-3-{(tert-Butoxycarbonyl)[(1R)-1-(4-fluoronaphthalen-1-yl)ethyl]amino}cyclopentyl]phenyl}propanoic acid (1.30 g, 2.6 mmol) was used and treated in a similar manner to (Step 3) of (Example 7) to give the title compound (1.03 g, 90%).

$^1$H-NMR (CD$_3$OD) δ: 1.71 (1H, td, J=12.2, 10.3 Hz), 1.80-1.89 (1H, m), 1.83 (3H, d, J=6.8 Hz), 1.99-2.10 (2H, m), 2.11-2.20 (1H, m), 2.47-2.53 (1H, m), 2.56 (2H, t, J=7.6 Hz), 2.87 (2H, t, J=7.6 Hz), 2.99-3.07 (1H, m), 3.66 (1H, tt, J=9.3, 6.8 Hz), 5.40 (1H, q, J=6.8 Hz), 7.15 (4H, s), 7.37 (1H, dd, J=10.3, 8.3 Hz), 7.71 (1H, t, J=7.3 Hz), 7.74-7.78 (2H, m), 8.22 (1H, d, J=8.3 Hz), 8.27 (1H, d, J=8.8 Hz);

IR (KBr) υ max 3456, 2963, 2826, 1732, 1585, 1517, 1398, 1225, 1150, 1049, 845, 829, 765 cm$^{-1}$;

MS (FAB) m/z: 406 (M+H)$^+$.

Example 28

{4-[(1S,3S)-3-{[(1R)-1-(4-Fluoronaphthalen-1-yl)ethyl]amino}cyclopentyl]phenoxy}acetic acid (Step 1)
(3S)-3-[4-(Benzyloxy)phenyl]cyclopentanone

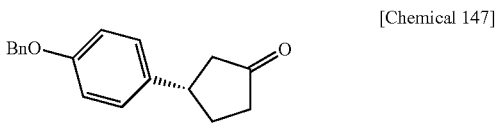 [SMILES: O=C1CC[C@H](c2ccc(OCc3ccccc3)cc2)C1]

[Chemical 147]

4-Benzyloxyphenylboric acid (3.42 g, 15 mmol), cyclopentenone (1.1 mL, 13 mmol) and (S)-BINAP were used as ligands and treated in a similar manner to (Step 1) of (Example 3) to give the title compound (3.16 g, 95%).

$^1$H-NMR (CDCl$_3$) δ: 1.89-2.00 (1H, m), 2.23-2.35 (2H, m), 2.38-2.50 (2H, m), 2.65 (1H, dd, J=18.4, 7.4 Hz), 3.32-3.43 (1H, m), 5.06 (2H, s), 6.96 (2H, d, J=8.6 Hz), 7.18 (2H, d, J=8.6 Hz), 7.31-7.45 (5H, m);

IR (KBr) υ max 2889, 1735, 1612, 1514, 1454, 1380, 1253, 1134, 1044, 831, 740 cm$^{-1}$;

MS (EI) m/z: 266 (M)$^+$.

(Step 2) (3S)-3-[4-(Benzyloxy)phenyl]-N-[(1R)-1-(4-fluoronaphthalen-1-yl)ethyl]cyclopentanamine

[Chemical 148]

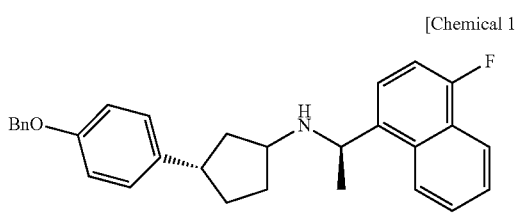

(3S)-3-[4-(Benzyloxy)phenyl]cyclopentanone (2.66 g, 10 mmol) and (1R)-1-(4-fluoronaphthalen-1-yl)ethanamine hydrochloride (2.26 g, 10 mmol) obtained in (Step 4) of (Example 16) were used and treated in a similar manner to (Step 1) of (Example 17) to give the title compound (a mixture of diastereomers) (4.25 g, 97%).

$^1$H-NMR (CDCl$_3$) δ: 1.40-2.00 (5H, m), 1.47 (3/2H, d, J=6.6 Hz), 1.48 (3/2H, d, J=6.6 Hz), 2.05-2.15 (0.5H, m), 2.27-2.34 (0.5H, m), 2.81-2.91 (0.5H, m), 3.12-3.23 (1H, m), 3.26-3.33 (0.5H, m), 4.63-4.71 (1H, m), 5.02 and 5.03 (2H, s), 6.87 (2/2H, d, J=8.6 Hz), 6.89 (2/211, d, J=8.6 Hz), 7.07 (2/2H, d, J=8.2 Hz), 7.11-7.18 (1H, m), 7.14 (2/2H, d, J=8.6 Hz), 7.29-7.44 (5H, m), 7.51-7.61 (3H, m), 8.13-8.17 (1H, m), 8.18-8.24 (1H, m).

(Step 3) 4-[(1S,3S)-3-{[(1R)-1-(4-Fluoronaphthalen-1-yl)ethyl]amino}cyclopentyl]phenol

[Chemical 149]

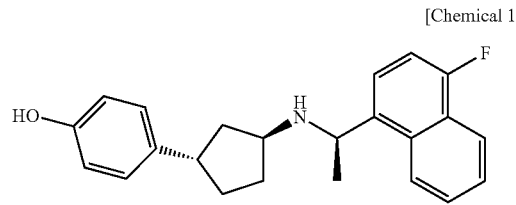

(3S)-3-[4-(Benzyloxy)phenyl]-N-[(1R)-1-(4-fluoronaphthalen-1-yl)ethyl]cyclopentanamine (879 mg, 2.0 mmol) was used and treated in a similar manner to (Step 3) of (Example 10) to give a mixture of diastereomers of the title compound (637 mg, 91%). The product obtained was purified using CHIRALPAK AD-H to give the title compound.

$^1$H-NMR (CDCl$_3$) δ: 1.42-1.58 (2H, m), 1.49 (3H, d, J=6.4 Hz), 1.73-1.81 (1H, m), 1.84-1.92 (1H, m), 2.05-2.14 (2H, m), 3.14-3.23 (1H, m), 3.26-3.33 (1H, m), 4.67 (1H, q, J=6.4 Hz), 6.71 (2H, d, J=8.4 Hz), 7.01 (2H, d, J=8.4 Hz), 7.14 (1H, dd, J=10.2, 7.8 Hz), 7.52-7.60 (3H, m), 8.14-8.17 (1H, m), 8.20-8.23 (1H, m);

IR (KBr) υ max 3252, 2956, 1605, 1514, 1463, 1447, 1397, 1259, 1222, 833, 763 cm$^{-1}$;

MS (EI) m/z: 349 M$^+$.

(Step 4){14-[(1S,3S)-3-{[(1R)-1-(4-Fluoronaphthalen-1-yl)ethyl]amino}cyclopentyl]phenoxy}acetic acid ethyl ester

[Chemical 150]

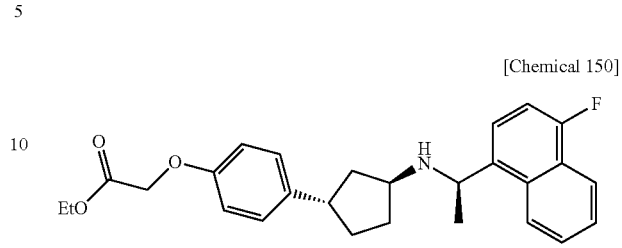

4-[(1S,3S)-3-{[(1R)-1-(4-Fluoronaphthalen-1-yl)ethyl]amino}cyclopentyl]phenol (500 mg, 1.4 mmol) was used and treated in a similar manner to (Step 4) of (Example 10) to give the title compound (609 mg, 98%).

$^1$H-NMR (CDCl$_3$) δ: 1.29 (3H, t, J=7.2 Hz), 1.47-1.54 (2H, m), 1.48 (3H, d, J=6.5 Hz), 1.74-1.80 (1H, m), 1.84-1.90 (1H, m), 2.06-2.14 (2H, m), 3.16-3.23 (1H, m), 3.27-3.32 (1H, m), 4.26 (2H, q, J=7.2 Hz), 4.57 (2H, s), 4.66 (1H, q, J=6.5 Hz), 6.79 (2H, d, J=8.6 Hz), 7.06 (2H, d, J=8.6 Hz), 7.14 (1H, dd, J=10.3, 7.8 Hz), 7.52-7.60 (3H, m), 8.14-8.16 (1H, m), 8.22 (1H, d, J=8.3 Hz);

IR (ATR) υ max 2945, 1757, 1603, 1510, 1193, 1179, 1083, 827, 760 cm$^{-1}$;

MS (FAB) m/z: 436 (M+H)$^+$.

(Step 5) {4-[(1S,3S)-3-{[(1R)-1-(4-Fluoronaphthalen-1-yl)ethyl]amino}cyclopentyl]phenoxy}acetic acid

[Chemical 151]

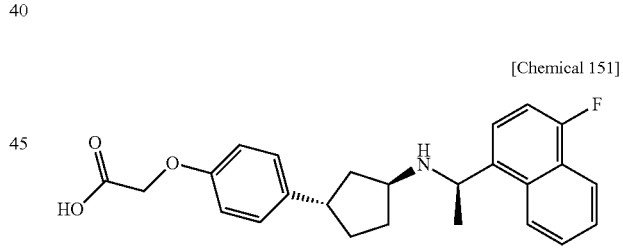

{4-[(1S,3S)-3-{[(1R)-1-(4-Fluoronaphthalen-1-yl)ethyl]amino}cyclopentyl]phenoxy}acetic acid ethyl ester (600 mg, 1.4 mmol) was used and treated in a similar manner to (Step 4) of (Example 17) to give the title compound (562 g, 100%).

$^1$H-NMR (CD$_3$OD) δ: 1.46-1.54 (1H, m), 1.79 (3H, d, J=6.5 Hz), 1.86-1.94 (2H, m), 2.01-2.14 (3H, m), 3.10-3.18 (1H, m), 3.54-3.61 (1H, m), 4.40 (2H, s), 5.38 (1H, q, J=6.5 Hz), 6.79 (2H, d, J=8.3 Hz), 6.97 (2H, d, J=8.3 Hz), 7.34 (1H, dd, J=10.3, 8.3 Hz), 7.69 (1H, t, J=7.6 Hz), 7.73-7.79 (2H, m), 8.20 (1H, d, J=7.8 Hz), 8.27 (1H, d, J=8.3 Hz);

IR (ATR) υ max 3413, 2956, 2819, 1735, 1605, 1585, 1513, 1401, 1224, 1051, 832, 763 cm$^{-1}$;

MS (FAB) m/z: 408 (M+H)$^+$.

Example 29

3-{4-[(1S,3S)-3-[(1R)-1-(4-Naphthalen-1-yl)ethyl]amino}cyclopentyl]phenyl}propanoic acid hydrochloride (Step 1) 3-{4-[(1S)-3-Oxocyclopentyl]phenyl}propanoic acid ethyl ester

[Chemical 152]

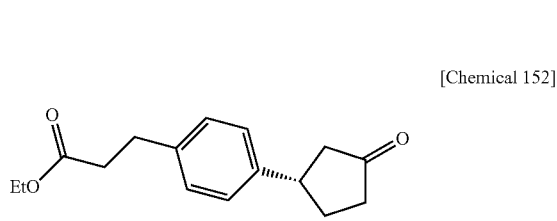 [SMILES: CCOC(=O)CCc1ccc([C@H]2CCC(=O)C2)cc1]

Under an argon stream, [4-(3-ethoxy-3-oxopropyl)phenyl]boric acid (2.33 g, 15 mmol) and Rh[(S)-BINAP(nbd)]BF$_4$ (226 mg, 0.25 mmol) was dissolved in a solvent mixture of 1,4-dioxane (30 mL) and water (5 mL), followed by degassing with ultrasonic waves. Then, triethylamine (2.1 mL, 13 mmol) and cyclopentenone (1.1 mL, 13 mmol) were sequentially added, and the mixture was stirred overnight at room temperature. A saturated aqueous sodium bicarbonate solution was added to the reaction solution, and the solvent was distilled off under reduced pressure. The aqueous phase was extracted with ethyl acetate, the organic phase was dried over anhydrous magnesium sulfate, and the solvent was distilled off under reduced pressure. The residue obtained was purified by column chromatography (ethyl acetate/hexane: 15/85-25/75) to give the title compound (2.76 g, 85%).

$^1$H-NMR (CDCl$_3$) δ: 1.24 (3H, t, J=7.2 Hz), 1.91-2.02 (1H, m), 2.24-2.36 (2H, m), 2.39-2.50 (2H, m), 2.61-2.71 (1H, m), 2.62 (3H, t, J=7.8 Hz), 2.94 (2H, t, J=7.8 Hz), 3.34-3.44 (1H, m), 4.13 (2H, q, J=7.2 Hz), 7.18 (4H, s);

IR (ATR) υ max 2978, 1730, 1516, 1372, 1150, 1039, 1019, 824, 547 cm$^{-1}$;

MS (FAB) m/z: 261 (M+H)$^+$.

(Step 2) 3-{4-[(1S,3S)-3-{[(1R)-1-(Naphthalen-1-yl)ethyl]amino}cyclopentyl]phenyl}propanoic acid ethyl ester

[Chemical 153]

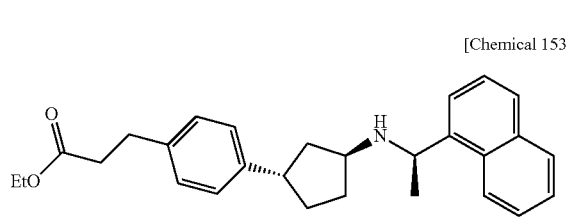 [SMILES: CCOC(=O)CCc1ccc([C@H]2CC[C@H](N[C@H](C)c3cccc4ccccc34)C2)cc1]

3-{4-[(1S)-3-Oxocyclopentyl]phenyl}propanoic acid ethyl ester (2.66 g, 10 mmol) was used and treated in a similar manner to (Step 2) of (Example 1) to give a mixture of diastereomers of the title compound (3.83 g, 90%). The product obtained was purified using CHIRALPAK AD-H to give the title compound.

$^1$H-NMR (CDCl$_3$) δ: 1.23 (3H, t, J=7.1 Hz) 1.48-1.60 (2H, m) 1.51 (3H, d, J=6.7Hz) 1.76-1.95 (2H, m) 2.05-2.17 (2H, m) 2.58 (2H, t, J=7.8 Hz) 2.89 (2H, t, J=7.8 Hz) 3.17-3.36 (2H, m) 4.12 (2H, q, J=7.1 Hz) 4.73 (1H, q, J=6.7 Hz) 7.08 (4H, s) 7.45-7.54 (3H, m) 7.63-7.67 (1H, m) 7.75 (1H, d, J=8.2 Hz) 7.86-7.90 (1H, m) 8.22 (1H, d, J=8.2 Hz).

(Step 3) 3-{4-[(1S,3S)-3-{[(1R)-1-(Naphthalen-1-yl)ethyl]amino}cyclopentyl]phenyl}propanoic acid hydrochloride

[Chemical 154]

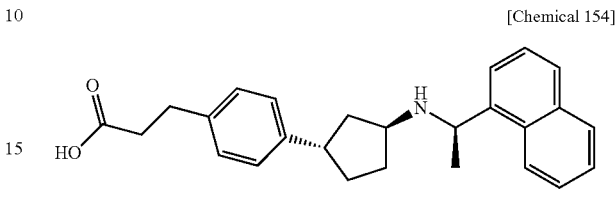

3-{4-[(1S,3S)-3-{[(1R)-1-(Naphthalen-1-yl)ethyl]amino}cyclopentyl]phenyl}propanoic acid ethyl ester (1.28 g, 3.1 mmol) was used and treated in a similar manner to (Step 5) of (Example 10) to give the title compound (1.28 g, 98%).

$^1$H-NMR (CDCl$_3$) δ: 1.28-1.39 (1H, m) 1.93-2.32 (7H, m) 2.49-2.63 (2H, m) 2.72-2.86 (3H, m) 3.39 (1H, br s) 3.52-3.63 (1H, m) 5.31 (1H, br s) 6.88 (4H, s) 7.53-7.70 (3H, m) 7.88-7.96 (2H, m) 8.02 (1H, d, J=8.8 Hz) 8.36 (1H, d, J=7.3 Hz) 10.10 (1H, br s) 10.56 (1H, br s);

HRMS (ESI$^+$) calcd for C26H30NO2 [M+H]$^+$. required m/z: 388.2277. found 388.2280.

Example 30

3-{4-[(1S,3S)-3-{[(1R)-1-(4-Fluoronaphthalen-1-yl)ethyl]amino}cyclopentyl]phenyl}propanoic acid hydrochloride (Step 1) 3-{4-[(1S,3S)-3-{[(1R)-1-(4-Fluoronaphthalen-1-yl)ethyl]amino}cyclopentyl]phenyl}propanoic acid ethyl ester

[Chemical 155]

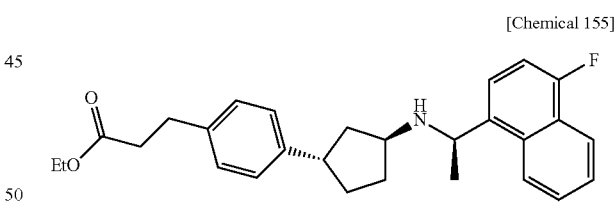

3-{4-[(1S)-3-Oxocyclopentyl]phenyl}propanoic acid ethyl ester (1.00 g, 3.8 mmol) obtained in (Step 1) of (Example 29) and (1R)-1-(4-fluoronaphthalen-1-yl)ethanamine hydrochloride (1.04 g, 4.6 mmol) obtained in (Step 4) of (Example 16) were used and treated in a similar manner to (Step 1) of (Example 17) to give a mixture of diastereomers of the title compound (1.11 g, 66%). The product obtained was purified using CHIRALPAK AD-H to give the title compound.

$^1$H-NMR (CDCl$_3$) δ: 1.22 (3H, t, J=7.2 Hz), 1.46-1.57 (2H, m), 1.49 (3H, d, J=6.6 Hz), 1.76-1.93 (2H, m), 2.06-2.16 (2H, m), 2.58 (2H, t, J=7.8 Hz), 2.89 (2H, t, J=7.8 Hz), 3.17-3.26 (1H, m), 3.26-3.34 (1H, m), 4.11 (2H, q, J=7.2 Hz), 4.66 (1H, q, J=6.6 Hz), 7.07 (4H, s), 7.14 (1H, dd, J=10.2, 7.8 Hz), 7.52-7.61 (3H, m), 8.14-8.17 (1H, m), 8.22 (1H, d, J=7.8 Hz);

IR (ATR) υ max 2952, 1730, 1603, 1513, 1444, 1391, 1370, 1258, 1147, 1045, 828, 759 cm$^{-1}$;

MS (FAB) m/z: 434 (M+H)$^+$.

(Step 2) 3-{4-[(1S,3S)-3-{[(1R)-1-(4-Fluoronaphthalen-1-yl)ethyl]amino}cyclopentyl]phenyl}propanoic acid hydrochloride

[Chemical 156]

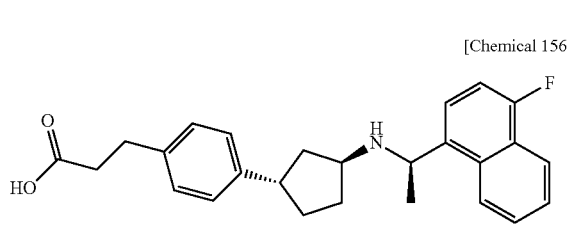 [SMILES: CCOC(=O)CCc1ccc([C@H]2CC[C@H](N[C@H](C)c3ccc(F)c4ccccc34)C2)cc1]

3-{4-[(1S,3S)-3-{[(1R)-1-(4-Fluoronaphthalen-1-yl)ethyl]amino}cyclopentyl]phenyl}propanoic acid ethyl ester (150 mg, 0.35 mmol) was used and treated in a similar manner to (Step 5) of (Example 10) to give the title compound (153 mg, 97%).

$^1$H-NMR (CD$_3$OD) δ: 1.59-1.68 (1H, m), 1.82 (3H, d, J=6.8 Hz), 1.84-1.93 (1H, m), 2.04 (1H, dt, J=14.2, 9.3 Hz), 2.11-2.19 (2H, m), 2.21-2.28 (1H, m), 2.55 (2H, t, J=7.7 Hz), 2.85 (2H, t, J=7.7 Hz), 3.24-3.30 (1H, m), 3.68-3.74 (1H, m), 5.40 (1H, q, J=6.8 Hz), 7.09 (2H, d, J=8.3 Hz), 7.13 (2H, d, J=8.3 Hz), 7.37 (1H, dd, J=10.0, 8.1 Hz), 7.71 (1H, t, J=7.3 Hz), 7.74-7.79 (2H, m), 8.22 (1H, d, J=8.3 Hz), 8.29 (1H, d, J=8.8 Hz);

IR (KBr) υ max 3407, 2957, 2807, 1711, 1585, 1517, 1441, 1400, 1263, 1224, 1151, 1050, 836, 764 cm$^{-1}$;

MS (FAB) m/z: 406 (M+H)$^+$.

Example 31) 2-{4-[(1R,3S)-3-{[(1R)-1-(4-Fluoronaphthalen-1-yl)ethyl]amino}cyclopentyl]phenoxy}-2-methylpropanoic acid hydrochloride (Step 1) 2-{4-[(1R,3S)-3-{[(1R)-1-(4-Fluoronaphthalen-1-yl)ethyl]amino}cyclopentyl]phenoxy}-2-methylpropanoic acid ethyl ester

[Chemical 157]

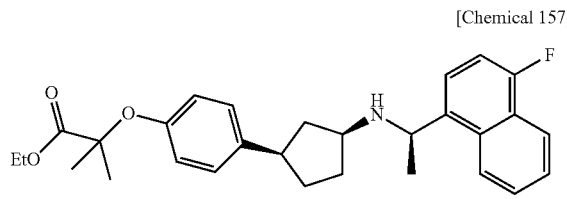

4-[(1R,3S)-3 {[(1R)-1-(4-Fluoronaphthalen-1-yl)ethyl]amino}cyclopentyl]phenol (3.49 g, 10 mmol) obtained in (Step 2) of (Example 17) was used and treated in a similar manner to (Step 1) of (Example 11) to give the title compound (3.75 g, 81%).

$^1$H-NMR (CDCl$_3$) δ: 1.25 (3H, t, J=7.1 Hz), 1.36-1.46 (1H, m), 1.48 (3H, d, J=6.6 Hz), 1.56 (6H, s), 1.58-1.77 (2H, m), 1.90-2.01 (2H, m), 2.21-2.29 (1H, m), 2.81-2.90 (1H, m), 3.11-3.19 (1H, m), 4.23 (2H, q, J=7.1 Hz), 4.68 (1H, q, J=6.6 Hz), 6.74 (2H, d, J=8.6 Hz), 7.05 (2H, d, J=8.6 Hz), 7.14 (1H, dd, J=10.2, 8.2 Hz), 7.52-7.61 (3H, m), 8.14-8.17 (1H, m), 8.21 (1H, d, J=8.2 Hz);

IR (ATR) υ max 2942, 1730, 1603, 1508, 1228, 1173, 1134, 830, 760 cm$^{-1}$;

MS (FAB) m/z: 464 (M+H)$^+$.

(Step 2) 2-{4-[(1R,3S)-3-{[(1R)-1-(4-Fluoronaphthalen-1-yl)ethyl]amino}cyclopentyl]phenoxy}-2-methylpropanoic acid hydrochloride

[Chemical 158]

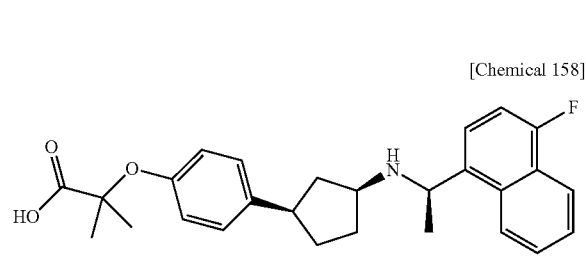 [SMILES: C[C@@H](N[C@H]1CC[C@@H](c2ccc(OC(C)(C)C(=O)O)cc2)C1)c1ccc(F)c2ccccc12]

2-{4-[(1R,3S)-3-{[(1R)-1-(4-Fluoronaphthalen-1-yl)ethyl]amino}cyclopentyl]phenoxy}-2-methylpropanoic acid ethyl ester (3.70 g, 8.0 mmol) was used and treated in a similar manner to (Step 2) of (Example 11) to give the title compound (3.68 g, 98%).

$^1$H-NMR (DMSO-D$_6$) δ: 1.48 (6H, s), 1.70-1.78 (2H, m), 1.71 (3H, d, J=6.3 Hz), 1.87-1.95 (2H, m), 2.05-2.12 (1H, m), 2.39-2.45 (1H, m), 2.87-2.94 (1H, m), 3.51 (1H, br s), 5.30 (1H, br s), 6.76 (2H, d, J=8.8 Hz), 7.12 (2H, d, J=8.8 Hz), 7.52 (1H, dd, J=10.0, 8.5 Hz), 7.71-7.77 (2H, m), 7.97-8.01 (1H, m), 8.16 (1H, d, J=7.8 Hz), 8.39 (1H, d, J=8.3 Hz), 9.34 (1H, br s), 9.88 (1H, br s), 12.97 (1H, br s);

IR (KBr) υ max 3396, 2957, 2821, 1732, 1605, 1584, 1511, 1227, 1151, 835, 764 cm$^{-1}$;

MS (FAB) m/z: 436 (M+H)$^+$.

Example 32

{2-Methyl-4-[(1R,3S)-3-{[(1R)-1-(naphthalen-1-yl)ethyl]amino}cyclopentyl]phenoxy}acetic acid hydrochloride (Step 1) (3R)-3-[4-(Benzyloxy)-3-methylphenyl]cyclopentanone

[Chemical 159]

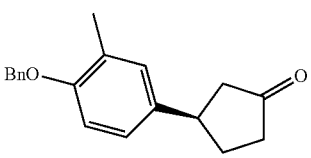

[4-(Benzyloxy)-3-methylphenyl]boric acid (2.42 g, 10 mmol) was used and treated in a similar manner to (Step 1) of (Example 29) to give the title compound (1.16 g, 41%).

$^1$H-NMR (CDCl$_3$) δ: 1.89-2.00 (2H, m), 2.24-2.34 (4H, m), 2.36-2.50 (2H, m), 2.64 (1H, m), 3.33 (1H, m), 5.16 (2H, s), 6.84 (1H, d, J=8.7 Hz), 7.01 (1H, m), 7.05 (1H, m), 7.32 (1H, m), 7.37-7.41 (2H, m), 7.44-7.45 (2H, m).

(Step 2) (1S,3R)-3-[4-(Benzyloxy)-3-methylphenyl]-N-[(1R)-1-(naphthalen-1-yl)ethyl]cyclopentanamine

[Chemical 160]

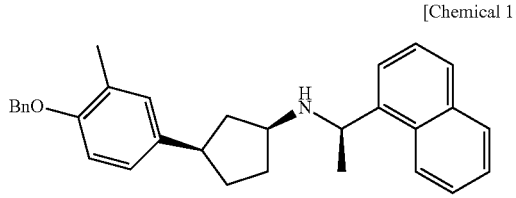

(3R)-3-[4-(Benzyloxy)-3-methylphenyl]cyclopentanone (1.16 g, 4.1 mmol) was used and treated in a similar manner to (Step 2) of (Example 1) to give the title compound (839 mg, 47%).

$^1$H-NMR (CDCl$_3$) δ: 1.46 (1H, m), 1.51 (3H, d, J=6.8 Hz), 1.62-1.78 (2H, m), 1.95-1.97 (2H, m), 2.25 (3H, s), 2.26 (1H, m), 2.84 (1H, m), 3.18 (1H, m), 4.85 (1H, q, J=6.8 Hz), 5.05 (2H, s), 6.79 (1H, d, J=8.3 Hz), 6.97 (1H, m), 7.02 (1H, m), 7.31 (1H, m), 7.36-7.39 (2H, m), 7.43-7.44 (2H, m), 7.46-7.54 (3H, m), 7.65 (1H, d, J=7.8 Hz), 7.75 (1H, d, J=7.8 Hz), 7.87 (1H, m), 8.20 (1H, d, J=8.3 Hz).

(Step 3) 2-Methyl-4-[(1R,3S)-3-{[(1R)-1-(naphthalen-1-yl)ethyl]amino}cyclopentyl]phenol

[Chemical 161]

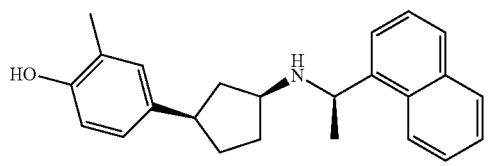

(1S,3R)-3-[4-(Benzyloxy)-3-methylphenyl]-N-[(1R)-1-(naphthalen-1-yl)ethyl]cyclopentanamine (835 mg, 1.9 mmol) was used and treated in a similar manner to (Step 3) of (Example 10) to give the title compound (511 mg, 77%).

$^1$H-NMR (CDCl$_3$) δ: 1.32-1.48 (2H, m), 1.52 (3H, d, J=6.3 Hz), 1.68-1.78 (2H, m), 1.91-1.95 (2H, m), 2.20 (3H, s), 2.25 (1H, m), 2.82 (1H, m), 3.09-3.20 (2H, m), 4.77 (1H, q, J=6.3 Hz), 6.66 (1H, d, J=7.8 Hz), 6.87 (1H, m), 6.95 (1H, s), 7.46-7.53 (3H, m), 7.63 (1H, d, J=7.3 Hz), 7.75 (1H, d, J=7.8 Hz), 7.87 (1H, m), 8.19 (1H, d, J=8.3 Hz).

(Step 4) {2-Methyl-4-[(1R,3S)-3-{[(1R)-1-(naphthalen-1-yl)ethyl]amino}cyclopentyl]phenoxy}acetic acid ethyl ester

[Chemical 162]

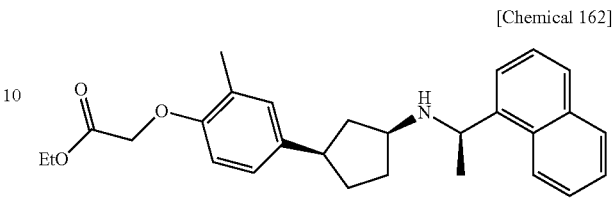

2-Methyl-4-[(1R,3S)-3-{[(1R)-1-(naphthalen-1-yl)ethyl]amino}cyclopentyl]phenol (511 mg, 1.5 mmol) was used and treated in a similar manner to (Step 4) of (Example 10) to give the title compound (520 mg, 81%).

$^1$H-NMR (CDCl$_3$) δ: 1.28 (3H, t, J=7.1 Hz), 1.43 (1H, m), 1.50 (3H, d, J=6.8 Hz), 1.61-1.78 (2H, m), 1.91-1.98 (2H, m), 2.24 (1H, m), 2.25 (3H, s), 2.82 (1H, m), 3.16 (1H, m), 4.24 (2H, q, J=7.1 Hz), 4.59 (2H, s), 4.74 (1H, q, J=7.1 Hz), 6.60 (1H, d, J=8.3 Hz), 6.94 (1H, m), 6.99 (1H, s), 7.45-7.52 (3H, m), 7.64 (1H, d, J=7.3 Hz), 7.74 (1H, d, J=8.3 Hz), 7.87 (1H, d, J=7.8 Hz), 8.19 (1H, d, J=8.3 Hz).

(Step 5) {2-Methyl-4-[(1R,3S)-3-{[(1R)-1-(naphthalen-1-yl)ethyl]amino}cyclopentyl]phenoxy}acetic acid hydrochloride

[Chemical 163]

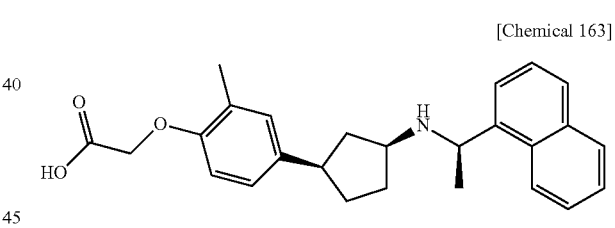

{2-Methyl-4-[(1R,3S)-3-{[(1R)-1-(naphthalen-1-yl)ethyl]amino}cyclopentyl]phenoxy}acetic acid ethyl ester (520 mg, 1.2 mmol) was used and treated in a similar manner to (Step 4) of (Example 5) to give the title compound (513 mg, 97%).

$^1$H-NMR (DMSO-D$_6$) δ: 1.70 (3H, t, J=6.3 Hz), 1.71-1.78 (2H, m), 1.90-1.93 (2H, m), 2.05 (1H, m), 2.16 (3H, s), 2.38 (1H, m), 2.86 (1H, m), 3.50 (1H, t, J=6.8 Hz), 4.62 (2H, s), 5.29 (1H, m), 6.73 (1H, d, J=8.3 Hz), 6.96-6.97 (1H, m), 7.00 (1H, s), 7.60-7.64 (3H, m), 7.96-8.01 (3H, m), 8.30 (1H, d, J=8.8 Hz).

Anal. Calcd. For C$_{26}$H$_{29}$NO$_3$.HCl.0.7H$_2$O Found C, 69.03. H, 6.92. N, 3.18. Cl, 7.86.

IR (KBr) υ max 3395, 2951, 2819, 1737, 1586, 1504, 1441, 1214, 1138, 1072, 804, 780 cm$^{-1}$;

MS (FAB) m/z: 404 (M+H)$^+$.

Example 33

N-{4-[(1R,3S)-3-{[(1R)-1-(Naphthalen-1-yl)ethyl]amino}cyclopentyl]phenyl}glycine 0.4 hydrochloride (Step 1) (3R)-3-(4-Nitrophenyl)cyclopentanone

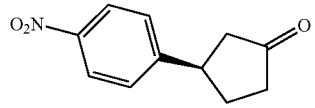

[Chemical 164]

4-Nitrophenylboric acid (5.00 g, 30 mmol) was used and treated in a similar manner to (Step 1) of (Example 29) to give the title compound (0.94 g, 23%).

$^1$H-NMR (CDCl$_3$) δ: 2.05 (1H, m), 2.40 (2H, m), 2.54 (2H, m), 2.74 (1H, m), 3.57 (1H, m), 7.45 (2H, d, J=9.0 Hz), 8.24 (2H, d, J=9.0 Hz).

(Step 2) (1S,3R)-N-[(1R)-1-(Naphthalen-1-yl)ethyl]-3-(4-nitrophenyl)cyclopentanamine

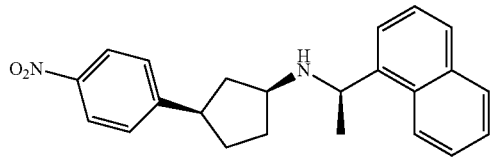

[Chemical 165]

(3R)-3-(4-Nitrophenyl)cyclopentanone (1.46 g, 7.1 mmol) was used and treated in a similar manner to (Step 2) of (Example 1) to give the title compound (1.00 g, 39%).

$^1$H-NMR (CDCl$_3$) δ: 1.47 (1H, m), 1.52 (3H, d, J=6.8 Hz), 1.66-1.86 (2H, m), 1.95-2.10 (2H, m), 1.92 (1H, m), 3.02 (1H, m), 3.22 (1H, m), 4.75 (1H, m), 7.35 (2H, d, J=8.8 Hz), 7.47-7.55 (3H, m), 7.64 (1H, d, J=6.8 Hz), 7.76 (1H, d, J=8.3 Hz), 7.89 (1H, m), 8.12 (2H, d, J=8.8 Hz), 8.21 (1H, d, J=8.3 Hz).

(Step 3) 4-[(1R,3S)-3-{[(1R)-1-(Naphthalen-1-yl)ethyl]amino}cyclopentyl]aniline

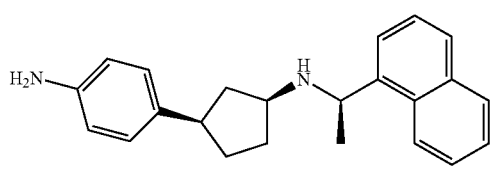

[Chemical 166]

(1S,3R)-N-[(1R)-1-(Naphthalen-1-yl)ethyl]-3-(4-nitrophenyl)cyclopentanamine 0.99 g (2.71 mmol) was dissolved in 2 mL of ethyl acetate, followed by addition of 0.20 g of 10% palladium-carbon catalyst, and the mixture was subjected to catalytic hydrogen reduction for 1.5 hours at room temperature. The reaction solution was filtered, and the filtrate was concentrated to give the title compound (0.89 g, 97%).

$^1$H-NMR (CDCl$_3$) δ: 1.39-1.45 (2H, m), 1.50 (3H, d, J=6.3 Hz), 1.62-1.76 (2H, m), 1.91-1.98 (2H, m), 2.25 (1H, m), 2.81 (1H, m), 3.15 (1H, m), 3.54 (2H, s), 4.75 (1H, q, J=6.3 Hz), 6.62 (2H, d, J=8.5 Hz), 7.00 (2H, d, J=8.5 Hz), 7.45-7.54 (3H, m), 7.65 (1H, d, J=7.0 Hz), 7.75 (1H, d, J=8.2 Hz), 7.88 (1H, m), 8.20 (1H, d, J=8.2 Hz).

(Step 4) N-{4-[(1R,3S)-3-{[(1R)-1-(Naphthalen-1-yl)ethyl]amino}cyclopentyl]phenyl}glycine ethyl ester

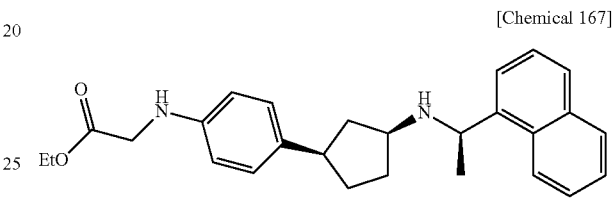

[Chemical 167]

4-[(1R,3S)-3-{[(1R)-1-(Naphthalen-1-yl)ethyl]amino}cyclopentyl]aniline (400 mg, 1.2 mmol) was used and treated in a similar manner to (Step 4) of (Example 10) to give the title compound (237 mg, 49%).

$^1$H-NMR (CDCl$_3$) δ: 1.29 (3H, t, J=7.0 Hz), 1.38-1.47 (2H, m), 1.50 (3H, d, J=6.6 Hz), 1.62-1.74 (2H, m), 1.91-1.99 (2H, m), 2.26 (1H, m), 2.80 (1H, m), 3.16 (1H, m), 3.87 (2H, d, J=6.6 Hz), 4.14 (1H, m), 4.24 (2H, q, J=7.0 Hz), 4.77 (1H, m), 6.54 (2H, d, J=8.2 Hz), 7.05 (2H, d, J=8.2 Hz), 7.47-7.51 (3H, m), 7.65 (1H, d, J=7.0 Hz), 7.75 (1H, d, J=8.2 Hz), 7.88 (1H, d, J=7.8 Hz), 8.20 (1H, d, J=8.2 Hz).

(Step 5) N-{4-[(1R,3S)-3-{[(1R)-1-(Naphthalen-1-yl)ethyl]amino}cyclopentyl]phenyl}glycine 0.4 hydrochloride

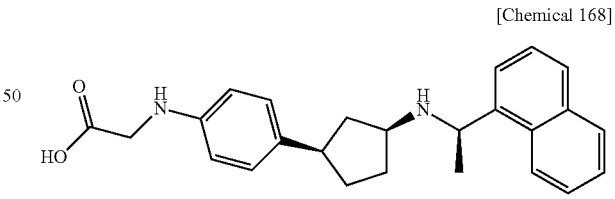

[Chemical 168]

N-{4-[(1R,3S)-3-{[(1R)-1-(Naphthalen-1-yl)ethyl]amino}cyclopentyl]phenyl}glycine ethyl ester (237 mg, 0.59 mmol) was used and treated in a similar manner to (Step 4) of (Example 5) to give the title compound (134 mg, 56%).

$^1$H-NMR (DMSO-D$_6$) δ: 1.39 (1H, m), 1.45 (3H, t, J=6.3 Hz), 1.62 (1H, m), 1.71-1.82 (3H, m), 2.12 (1H, m), 2.70 (1H, m), 3.09 (1H, m), 3.67 (2H, s), 4.82 (1H, m), 6.44 (2H, d, J=8.6 Hz), 6.92 (2H, d, J=8.6 Hz), 7.51-7.56 (3H, m), 7.77 (1H, d, J=7.4 Hz), 7.83 (1H, d, J=8.2 Hz), 7.94 (1H, d, J=7.0 Hz), 8.29 (1H, d, J=8.2 Hz);

Anal. Calcd. For C25H28N2O2.0.4HCl.0.25H2O Found C, 73.55. H, 7.45. N, 6.92. Cl, 3.59

IR (KBr) υ max 3393, 2955, 2868, 1615, 1521, 1388, 1301, 1248, 803, 779 cm⁻¹;

MS (FAB) m/z: 389 (M+H)⁺.

Example 34

N-{4-[(1R,3S)-3-{[(1R)-1-(Naphthalen-1-yl)ethyl]amino}cyclopentyl]phenyl}-β-alanine 0.5 hydrochloride (Step 1) N-{4-[(1R,3S)-3-{[(1R)-1-(Naphthalen-1-yl)ethyl]amino}cyclopentyl]phenyl}-β-alanine methyl ester

[Chemical 169]

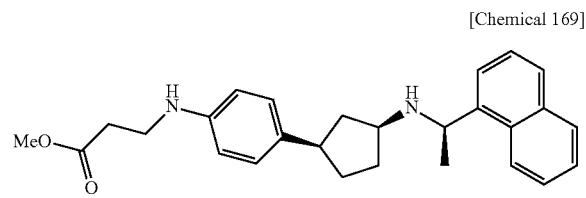 [SMILES: COC(=O)CCNc1ccc([C@@H]2CC[C@H](N[C@H](C)c3cccc4ccccc34)C2)cc1]

4-[(1R,3S)-3-{[(1R)-1-(Naphthalen-1-yl)ethyl]amino}cyclopentyl]aniline 80 mg (1.45 mmol) obtained in (Step 3) in (Example 33) was dissolved in 8 mL of acetic acid, followed by addition of methyl acrylate 0.16 mL (150 mg, 1.74 mmol), and the mixture was stirred for 6 hours at 70° C., followed by stirring for 3 days at room temperature. A saturated aqueous sodium bicarbonate solution was added to the reaction solution to neutralize the solution, and the neutralized solution was extracted with ethyl acetate, washed with saturated brine, and dried over anhydrous magnesium sulfate. The solvent was concentrated and the crude product obtained was purified by silica gel column chromatography (Biotage, solvent for elution; hexane/ethyl acetate) to give the title compound 190 mg (yield 31%).

¹H-NMR (CDCl₃) δ: 1.43 (1H, m), 1.50 (3H, d, J=6.6 Hz), 1.60-1.77 (3H, m), 1.91-1.98 (2H, m), 2.25 (1H, m), 2.61 (2H, t, J=6.5 Hz), 2.81 (1H, m), 3.16 (1H, m), 3.42 (2H, t, J=6.5 Hz), 3.68 (3H, s), 4.75 (1H, q, J=6.6 Hz), 6.55 (2H, d, J=8.6 Hz), 7.03 (2H, d, J=8.6 Hz), 7.46-7.53 (3H, m), 7.65 (1H, d, J=7.4 Hz), 7.75 (1H, d, J=8.2 Hz), 7.88 (1H, d, J=7.8 Hz), 8.20 (1H, d, J=8.2 Hz).

(Step 2) N-{4-[(1R,3S)-3-{[(1R)-1-(Naphthalen-1-yl)ethyl]amino}cyclopentyl]phenyl}-β-alanine 0.5 hydrochloride

[Chemical 170]

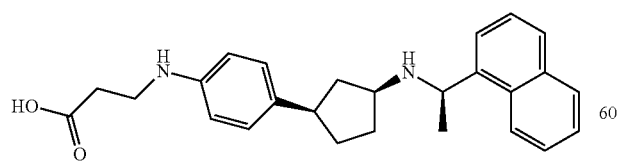

N-{4-[(1R,3S)-3-{[(1R)-1-(Naphthalen-1-yl)ethyl]amino}cyclopentyl]phenyl}-β-alanine methyl ester (185 mg, 0.44 mmol) was used and treated in a similar manner to (Step 4) of (Example 5) to give the title compound (158 mg, 85%).

¹H-NMR (DMSO-D₆) δ: 1.48-1.53 (4H, m), 1.65 (1H, m), 1.81-1.84 (3H, m), 2.18 (1H, m), 2.45 (2H, t, J=6.8 Hz), 2.72 (1H, m), 3.20 (2H, t, J=6.8 Hz), 3.21 (1H, m), 4.98 (1H, br s), 6.48 (2H, d, J=8.3 Hz), 6.93 (2H, d, J=8.3 Hz), 7.54-7.57 (3H, m), 7.85-7.88 (2H, m), 7.97 (1H, d, J=7.8 Hz), 8.29 (1H, d, J=8.3 Hz);

Anal. Calcd. For C₂₆H₃₀N₂O₂.0.5HCl.0.8H₂O Found C, 71.69. H, 7.38. N, 6.29. Cl, 4.37;

IR (KBr) υ max 3382, 2963, 1731, 1615, 1521, 1398, 1247, 804, 780 cm⁻¹;

MS (FAB) m/z: 403 (M+H)⁺.

Example 35

N-{4-[(1R,3S)-3-{[(1R)-1-(4-Fluoronaphthalen-1-yl)ethyl]amino}cyclopentyl]phenyl}glycine 0.3 hydrochloride (Step 1) (1S,3R)-N-[(1R)-1-(4-fluoronaphthalen-1-yl)ethyl]-3-(4-nitrophenyl)cyclopentanamine

[Chemical 171]

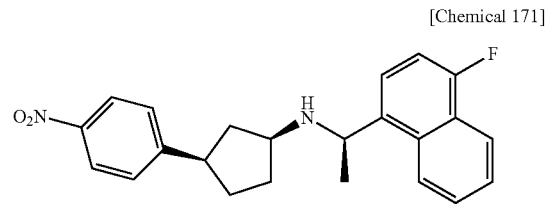 [SMILES: C[C@@H](N[C@H]1CC[C@@H](c2ccc([N+](=O)[O-])cc2)C1)c1ccc(F)c2ccccc12]

(3R)-3-(4-Nitrophenyl)cyclopentanone (448 mg, 2.2 mmol) obtained in (Step 1) of (Example 33) and (1R)-1-(4-fluoronaphthalen-1-yl)ethanamine hydrochloride (360 mg, 1.6 mmol) obtained in (Step 4) of (Example 16) were used and treated in a similar manner to (Step 1) of (Example 17) to give the title compound (140 mg, 23%).

¹H-NMR (CDCl₃) δ: 1.45 (1H, m), 1.49 (3H, d, J=6.3 Hz), 1.69 (1H, m), 1.78 (1H, m), 2.00-2.05 (3H, m), 2.28 (1H, m), 3.03 (1H, m), 3.21 (1H, m), 4.68 (1H, q, J=6.3 Hz), 7.14 (1H, t, J=9.0 Hz), 7.34 (2H, d, J=8.3 Hz), 7.55-7.57 (3H, m), 8.11 (2H, d, J=8.3 Hz), 8.15 (1H, d, J=8.3 Hz), 8.22 (1H, d, J=8.3 Hz).

(Step 2) 4-[(1R,3S)-3-{[(1R)-1-(4-Fluoronaphthalen-1-yl)ethyl]amino}cyclopentyl]aniline

[Chemical 172]

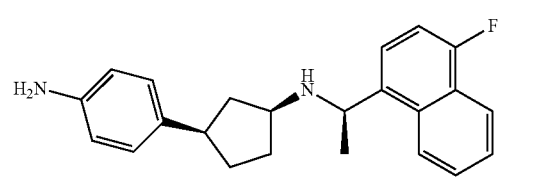

(1S,3R)-N-[(1R)-1-(4-Fluoronaphthalen-1-yl)ethyl]-3-(4-nitrophenyl)cyclopentanamine (138 mg, 0.36 mmol) was (Step 3) N-{4-[(1R,3S)-3-{[(1R)-1-(4-Fluoronaphthalen-1-yl)ethyl]amino}cyclopentyl]phenyl}glycine ethyl ester

[Chemical 173]

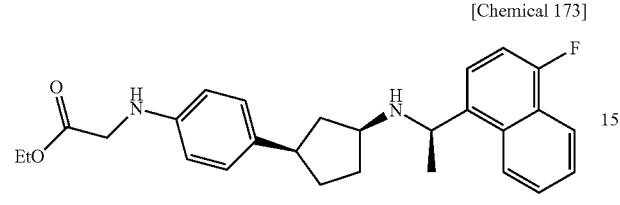

4-[(1R,3S)-3-{[(1R)-1-(4-Fluoronaphthalen-1-yl)ethyl]amino}cyclopentyl]aniline (125 mg, 0.36 mmol) was used and treated in a similar manner to (Step 4) of (Example 10) to give the title compound (106 mg, 68%).

$^1$H-NMR (CDCl$_3$) δ: 1.25 (1H, m), 1.29 (3H, t, J=7.1 Hz), 1.41 (1H, m), 1.48 (3H, d, J=6.3 Hz), 1.65-1.72 (2H, m), 1.93-1.97 (2H, m), 2.23 (1H, m), 2.82 (1H, m), 3.13 (1H, m), 3.87 (2H, s), 4.15 (1H, m), 4.23 (2H, q, J=7.1 Hz), 4.68 (1H, m), 6.54 (2H, d, J=8.3 Hz), 7.04 (2H, d, J=8.3 Hz), 7.14 (1H, m), 7.52-7.60 (3H, m), 8.14 (1H, m), 8.21 (1H, d, J=8.3 Hz).

(Step 4) N-{4-[(1R,3S)-3-{[(1R)-1-(4-Fluoronaphthalen-1-yl)ethyl]amino}cyclopentyl]phenyl}glycine 0.3 hydrochloride

[Chemical 174]

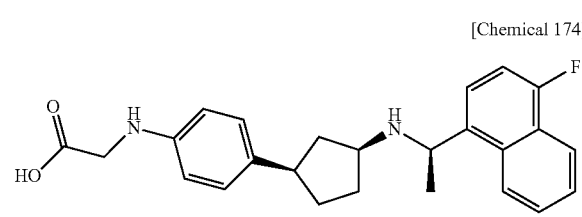 [SMILES: C[C@@H](N[C@H]1CC[C@@H](c2ccc(NCC(=O)O)cc2)C1)c1ccc(F)c2ccccc12]

N-{4-[(1R,3S)-3-{[(1R)-1-(4-Fluoronaphthalen-1-yl)ethyl]amino}cyclopentyl]phenyl}glycine ethyl ester (103 mg, 0.24 mmol) was used and treated in a similar manner to (Step 4) of (Example 5) to give the title compound (85 mg, 85%).

$^1$H-NMR (DMSO-D$_6$) δ: 1.41 (1H, m), 1.47 (3H, d, J=6.3 Hz), 1.62 (1H, m), 1.77-1.81 (3H, m), 2.13 (1H, m), 2.71 (1H, m), 3.14 (1H, m), 3.71 (2H, s), 4.83 (1H, m), 6.46 (2H, d, J=8.3 Hz), 6.92 (2H, d, J=8.3 Hz), 7.37 (1H, m), 7.65-7.67 (2H, m), 7.76 (1H, m), 8.09 (1H, m), 8.37 (1H, d, J=7.8 Hz);
Anal. Calcd. For C25H$_{27}$FN$_2$O$_2$.0.3HCl.0.5H$_2$O Found C, 70.08. H, 6.79. N, 6.68. F, 4.28. Cl, 2.39;
IR (KBr) υ max 3396, 2954, 2869, 1615, 1521, 1390, 1263, 827, 762 cm$^{-1}$;
MS (FAB) m/z: 407 (M+H)$^+$.

Example 36

({4-[(1R,3S)-3-{[(1R)-1-(Naphthalen-1-yl)ethyl]amino}cyclopentyl]phenyl}thio)acetic acid hydrochloride (Step 1) {4-[(2-Ethoxy-2-oxoethyl)thio]phenyl}boric acid

[Chemical 175]

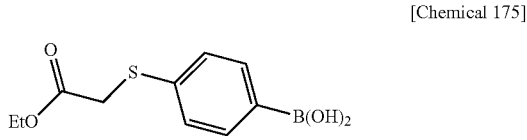 [SMILES: CCOC(=O)CSc1ccc(B(O)O)cc1]

4-Mercaptophenylboric acid 5.55 g (32.5 mmol) was dissolved in 80 mL of acetonitrile, followed by addition of potassium carbonate 6.73 g (48.7 mmol), sodium iodide 0.73 g (4.87 mmol) and ethyl bromoacetate 5.40 mL (8.13 g, 48.7 mmol), and the mixture was stirred for 18 hours at room temperature. The reaction solution was concentrated, followed by addition of water to the residue, and the residue was extracted with ethyl acetate, washed with saturated brine and dried over anhydrous magnesium sulfate. The solvent was concentrated to give the title compound 7.80 g (yield 100%).

$^1$H-NMR (CDCl$_3$) δ: 1.25 (3H, t, J=7.1 Hz), 3.73 (2H, s), 4.19 (2H, q, J=7.1 Hz), 7.41 (2H, br m), 8.07 (2H, br s).

(Step 2) {[4-(3-Oxo-1-cyclopenten-1-yl)phenyl]thio}acetic acid ethyl ester

[Chemical 176]

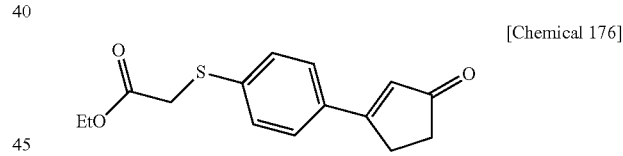

{4-[(2-Ethoxy-2-oxoethyl)thio]phenyl}boric acid 2.80 g (11.7 mmol) and 3-bromo-2-cyclopenten-1-one 1.88 g (11.7 mmol) synthesized according to the method of C. M. Marson et al. were dissolved in 25 mL of 1,2-dimethoxyethane, followed by addition of 12 mL of 3N aqueous sodium carbonate solution and dichloro[1,1'-bis(diphenylphosphino)ferrocene]palladium (II) methylene chloride complex 0.48 g (0.59 mmol), and the mixture was stirred for 4 hours at 90° C. The temperature of the reaction solution was adjusted to room temperature, followed by concentration. Then, water was added to the residue, followed by extraction with methylene chloride and drying over anhydrous magnesium sulfate. The solvent was concentrated, and the crude product obtained was purified by silica gel column chromatography (Biotage, solvent for elution; hexane/ethyl acetate) to give the title compound 2.43 g (yield 75%).

$^1$H-NMR (CDCl$_3$) δ: 1.26 (3H, t, J=7.1 Hz), 2.57-2.59 (2H, m), 3.01-3.02 (2H, m), 3.71 (3H, s), 4.20 (2H, q, J=7.2 Hz), 6.54 (1H, m), 7.42 (2H, d, J=8.5 Hz), 7.58 (2H, d, J=8.5 Hz).

(Step 3) ({4-[(1R)-3-Oxocyclopentyl]phenyl}thio)acetic acid ethyl ester

[Chemical 177]

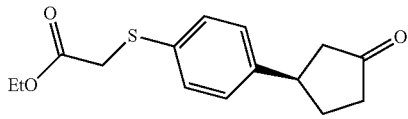

{[4-(3-Oxo-1-cyclopenten-1-yl)phenyl]thio}acetic acid ethyl ester 378 mg (1.37 mmol) and (2S,5S)-5-benzyl-3-methyl-2-(5-methyl-2-furyl)-4-imidazolidinone 54 mg (0.20 mmol) were dissolved in 10 mL of diethylether, followed by stirring at 0° C. Trichloroacetic acid 33 mg (0.20 mmol) and 2,6-dimethyl-1,4-dihydropyridine-3,5-dicarboxylic acid t-butyl diester 340 mg (1.10 mmol) were added thereto, and the mixture was stirred for 12 days at room temperature. The solvent was concentrated, and purified by silica gel column chromatography (Biotage, solvent for elution; hexane/ethyl acetate) to give the title compound 187 mg (yield 67%).

$^1$H-NMR (CDCl$_3$) δ: 1.23 (3H, t, J=7.3 Hz), 1.95 (1H, m), 2.28-2.32 (2H, m), 2.40-2.49 (2H, m), 2.65 (1H, m), 3.39 (1H, m), 3.61 (2H, s), 4.17 (2H, q, J=7.3 Hz), 7.19 (2H, d, J=7.8 Hz), 7.40 (2H, d, J=7.8 Hz).

(Step 4) ({4-[(1R,3S)-3-{[(1R)-1-(Naphthalen-1-yl)ethyl]amino}cyclopentyl]phenyl}thio)acetic acid ethyl ester

[Chemical 178]

({4-[(1R)-3-Oxocyclopentyl]phenyl}thio)acetic acid ethyl ester (184 mg, 0.66 mmol) was used and treated in a similar manner to (Step 2) of (Example 1) to give the title compound (84 mg, 29%).

$^1$H-NMR (CDCl$_3$) δ: 1.21 (3H, t, J=7.1 Hz), 1.44 (1H, m), 1.51 (3H, d, J=6.8 Hz), 1.63-1.81 (2H, m), 1.93-1.98 (2H, m), 2.25 (1H, m), 2.88 (1H, m), 3.18 (1H, m), 3.57-3.59 (2H, m), 4.15 (2H, q, J=7.1 Hz), 4.75 (1H, q, J=6.8 Hz), 7.14 (2H, d, J=8.3 Hz), 7.33 (2H, d, J=8.3 Hz), 7.46-7.53 (3H, m), 7.65 (1H, d, J=6.8 Hz), 7.75 (1H, d, J=8.3 Hz), 7.87 (1H, m), 8.21 (1H, d, J=7.8 Hz).

(Step 5) ({4-[(1R,3S)-3-{[(1R)-1-(Naphthalen-1-yl)ethyl]amino}cyclopentyl]phenyl}thio)acetic acid hydrochloride

[Chemical 179]

({4-[(1R,3S)-3-{[(1R)-1-(Naphthalen-1-yl)ethyl]amino}cyclopentyl]phenyl}thio)acetic acid ethyl ester (81 mg, 0.18 mmol) was used and treated in a similar manner to (Step 4) of (Example 5) to give the title compound (72 mg, 87%).

$^1$H-NMR (DMSO-D$_6$) δ: 1.69 (3H, d, J=6.8 Hz), 1.73-1.76 (2H, m), 1.89-1.94 (2H, m), 2.08 (1H, m), 2.41 (1H, m), 2.94 (1H, m), 3.50 (1H, m), 3.73 (2H, s), 5.28 (1H, m), 7.19 (2H, d, J=8.5 Hz), 7.28 (2H, d, J=8.5 Hz), 7.58-7.65 (3H, m), 7.94-8.03 (3H, m), 8.30 (1H, d, J=8.3 Hz).

Anal. Calcd. For C25H$_{27}$NO$_2$S.HCl.0.7H$_2$O Found C, 65.99. H, 6.47. N, 3.24. Cl, 7.64. S, 7.15;

IR (KBr) υ max 3389, 2956, 2801, 1721, 1585, 1384, 1252, 1174, 1134, 803, 780 cm$^{-1}$;

MS (FAB) m/z: 406 (M+H)$^+$.

Example 37

({4-[(1R,3S)-3-{[(1R)-1-(4-Fluoronaphthalen-1-yl)ethyl]amino}cyclopentyl]phenyl}thio)acetic acid hydrochloride

(Step 1) ({4-[(1R,3S)-3-{[(1R)-1-(4-Fluoronaphthalen-1-yl)ethyl]amino}cyclopentyl]phenyl}thio)acetic acid ethyl ester

[Chemical 180]

({4-[(1R)-3-Oxocyclopentyl]phenyl}thio)acetic acid ethyl ester (486 mg, 1.8 mmol) obtained in (Step 3) of (Example 36) and (1R)-1-(4-fluoronaphthalen-1-yl)ethanamine hydrochloride (433 mg, 1.9 mmol) obtained in (Step 4) of (Example 16) were used and treated in a similar manner to (Step 1) of (Example 17) to give the title compound (184 mg, 23%).

$^1$H-NMR (CDCl$_3$) δ: 1.21 (3H, t, J=7.1 Hz), 1.40-1.42 (1H, m), 1.48 (3H, d, J=6.8 Hz), 1.65-1.74 (2H, m), 1.94-1.98 (2H, m), 2.22-2.27 (1H, m), 2.87-2.91 (1H, m), 3.14-3.20 (1H, m), 3.58 (2H, s), 4.15 (2H, q, J=7.1 Hz), 4.68 (1H, q, J=6.8 Hz), 7.13-7.15 (3H, m), 7.33 (2H, d, J=8.5 Hz), 7.52-7.59 (3H, m), 8.14-8.16 (1H, m), 8.22 (1H, d, J=7.3 Hz).

(Step 2) ({4-[(1R,3S)-3-{[(1R)-1-(4-Fluoronaphthalen-1-yl)ethyl]amino}cyclopentyl]phenyl}thio)acetic acid hydrochloride

[Chemical 181]

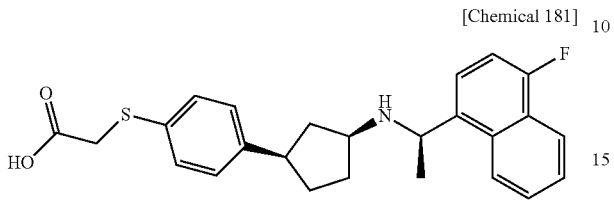

({4-[(1R,3S)-3-{[(1R)-1-(4-Fluoronaphthalen-1-yl)ethyl]amino}cyclopentyl]phenyl}thio)acetic acid ethyl ester (180 mg, 0.40 mmol) was used and treated in a similar manner to (Step 4) of (Example 5) to give the title compound (173 mg, 94%).
$^1$H-NMR (DMSO-D$_6$) δ: 1.70 (3H, d, J=6.8 Hz), 1.74-1.78 (2H, m), 1.87-1.93 (2H, m), 2.10 (1H, m), 2.40 (1H, m), 2.93 (1H, m), 3.44-3.50 (1H, m), 3.74 (2H, s), 5.26 (1H, m), 7.19 (2H, d, J=8.3 Hz), 7.28 (2H, d, J=8.3 Hz), 7.50 (1H, m), 7.70-7.76 (2H, m), 8.00 (1H, m), 8.15 (1H, m), 8.39 (1H, d, J=8.3 Hz);
Anal. Calcd. For C25H26FNO2S.HCl.0.5H2O Found C, 64.06. H, 5.97. N, 3.06. F, 4.04. Cl, 7.36. S, 6.81.
IR (KBr) υ max 3409, 2962, 1718, 1584, 1400, 1224, 838, 764 cm$^{-1}$;
MS (FAB) m/z: 424 (M+H)$^+$.

Example 38

(1S,3R)-N-[(1R)-1-(Naphthalen-1-yl)ethyl]-3-[4-(2H-tetrazol-5-ylmethoxy)phenyl]cyclopentanamine hydrochloride (Step 1) {4-[(1R,3S)-3-{[(1R)-1-(Naphthalen-1-yl)ethyl]amino}cyclopentyl]phenoxy}acetonitrile

[Chemical 182]

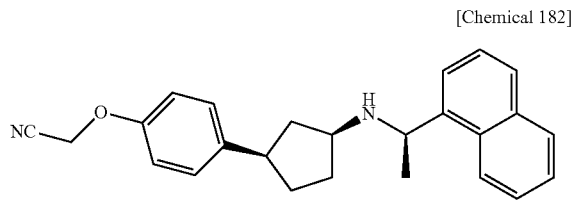 [SMILES: C[C@@H](N[C@H]1CC[C@@H](c2ccc(OCC#N)cc2)C1)c1cccc2ccccc12]

Under a nitrogen stream, N,N-dimethylformamide (3 mL) and chloroacetonitrile (0.11 mL, 1.8 mmol) were added to 4-[(1R,3S)-3-{[(1R)-1-(naphthalen-1-yl)ethyl]amino}cyclopentyl]phenol (500 mg, 1.5 mmol) obtained in Example 10 (Step 3) and potassium carbonate (250 mg, 1.8 mmol), and the mixture was stirred for 5 days at room temperature. Water was added to the reaction solution, and the mixture was extracted with ethyl acetate. The extracted solution was dried over anhydrous magnesium sulfate, and then the solvent was distilled off under reduced pressure. The residue obtained was purified by column chromatography (NH silica; ethyl acetate/hexane:20/80-50/50) to give the title compound (382 mg, 68%).

$^1$H-NMR (CDCl$_3$) δ: 1.40-1.50 (1H, m), 1.51 (3H, d, J=6.6 Hz), 1.64-1.78 (2H, m), 1.92-2.00 (2H, m), 2.23-2.30 (1H, m), 2.84-2.92 (1H, m), 3.14-3.22 (1H, m), 4.73 (2H, s), 4.75 (1H, q, J=6.6 Hz), 6.89 (2H, d, J=8.6 Hz), 7.18 (2H, d, J=8.6 Hz), 7.46-7.54 (3H, m), 7.65 (1H, d, J=7.0 Hz), 7.76 (1H, d, J=8.2 Hz), 7.87-7.90 (1H, m), 8.21 (1H, d, J=8.2 Hz);
IR (ATR) υ max 2948, 2861, 1672, 1509, 1212, 1046, 800, 778 cm$^{-1}$;
MS (FAB) m/z: 371 (M+H)$^+$.

(Step 2) (1S,3R)-N-[(1R)-1-(Naphthalen-1-yl)ethyl]-3-[4-(2H-tetrazol-5-ylmethoxy)phenyl]cyclopentanamine hydrochloride

[Chemical 183]

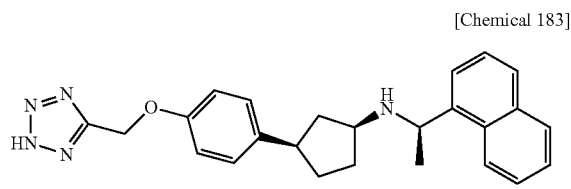 [SMILES: C[C@@H](N[C@H]1CC[C@@H](c2ccc(OCc3nn[nH]n3)cc2)C1)c1cccc2ccccc12]

Under a nitrogen stream, {4-[(1R,3S)-3-{[(1R)-1-(naphthalen-1-yl)ethyl]amino}cyclopentyl]phenoxy}acetonitrile (150 mg, 0.40 mmol), ammonium chloride (325 mg, 6.1 mmol) and sodium azide (263 mg, 4.0 mmol) were suspended in N,N-dimethylformamide (3 mL), followed by stirring for 3 hours at 80° C. The reaction solution was cooled to room temperature, followed by addition of water, and the precipitated powder was collected by filtration and washed with ethyl acetate to give the free form of the title compound (100 mg, 60%). The free form obtained was converted to the hydrochloride using 0.5N hydrochloric acid/dioxane.
$^1$H-NMR (DMSO-D$_6$) δ: 1.72-1.82 (2H, m), 1.72 (3H, d, J=6.3 Hz), 1.85-1.94 (2H, m), 2.09-2.15 (1H, m), 2.38-2.44 (1H, m), 2.88-2.96 (1H, m), 3.50 (1H, br s), 5.32 (1H, br s), 5.44 (2H, s), 6.99 (2H, d, J=8.8 Hz), 7.18 (2H, d, J=8.8 Hz), 7.58-7.66 (3H, m), 7.99-8.04 (3H, m), 8.31 (1H, d, J=8.3 Hz), 9.38 (1H, br s), 10.01 (1H, br s);
IR (KBr) υ max 3415, 2958, 1585, 1513, 1451, 1242, 1120, 1061, 804, 780 cm$^{-1}$;
MS (FAB) m/z: 414 (M+H)$^3$.

Example 39

(1S,3R)-N-[(1R)-1-(4-Fluoronaphthalen-1-yl)ethyl]-3-[4-(2H-tetrazol-5-ylmethoxy)phenyl]cyclopentanamine hydrochloride (Step 1) {4-[(1R,3S)-3-{[(1R)-1-(4-Fluoronaphthalen-1-yl)ethyl]amino}cyclopentyl]phenoxy}acetonitrile

[Chemical 184]

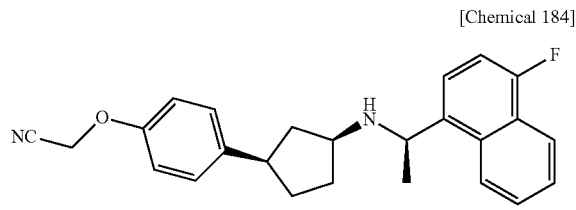 [SMILES: C[C@@H](N[C@H]1CC[C@@H](c2ccc(OCC#N)cc2)C1)c1ccc(F)c2ccccc12]

4-[(1R,3S)-3-{[(1R)-1-(4-Fluoronaphthalen-1-yl)ethyl]amino}cyclopentyl]phenol (103 mg, 0.29 mmol) obtained in (Step 2) of (Example 17) was used and treated in a similar manner to (Step 1) of (Example 38) to give the title compound (80 mg, 70%).

$^1$H-NMR (CDCl$_3$) δ: 1.38-1.48 (1H, m), 1.49 (3H, d, J=6.6 Hz), 1.56-1.78 (2H, m), 1.92-2.04 (2H, m), 2.22-2.29 (1H, m), 2.84-2.92 (1H, m), 3.13-3.21 (1H, m), 4.69 (1H, q, J=6.6 Hz), 4.73 (2H, s), 6.89 (2H, d, J=8.6 Hz), 7.15 (1H, dd, J=10.6, 8.2 Hz), 7.18 (2H, d, J=8.6 Hz), 7.52-7.61 (3H, m), 8.14-8.17 (1H, m), 8.22 (1H, d, J=8.2 Hz);

IR (ATR) υ max 2950, 1673, 1603, 1509, 1387, 1214, 1045, 827, 761 cm$^{-1}$;

MS (FAB) m/z: 389 (M+H)$^+$.

(Step 2) (1S,3R)-N-[(1R)-1-(4-fluoronaphthalen-1-yl)ethyl]-3-[4-(2H-tetrazol-5-ylmethoxy)phenyl]cyclopentanamine hydrochloride

[Chemical 185]

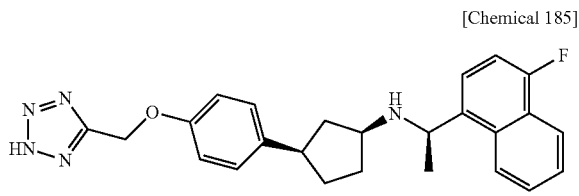 [SMILES: C[C@@H](N[C@H]1CC[C@@H](c2ccc(OCc3nn[nH]n3)cc2)C1)c1ccc(F)c2ccccc12]

{4-[(1R,3S)-3-{[(1R)-1-(4-Fluoronaphthalen-1-yl)ethyl]amino}cyclopentyl]phenoxy}acetonitrile (70 mg, 0.18 mmol) was used and treated in a similar manner to (Step 2) of (Example 38) to give the free form of the title compound (43 mg, 55%). The free form obtained was converted to the hydrochloride using 0.5N hydrochloric acid/dioxane.

$^1$H-NMR (DMSO-D$_6$) δ: 1.68-1.78 (2H, m), 1.71 (3H, d, J=6.5 Hz), 1.88-1.97 (2H, m), 2.02-2.11 (1H, m), 2.38-2.47 (1H, m), 2.88-2.98 (1H, m), 3.52 (1H, br s), 5.31 (1H, q, J=6.5 Hz), 5.44 (2H, s), 6.99 (2H, d, J=8.6 Hz), 7.18 (2H, d, J=8.6 Hz), 7.52 (1H, dd, J=10.6, 8.2 Hz), 7.70-7.78 (2H, m), 7.93-7.98 (1H, m), 8.15-8.18 (1H, m), 8.39 (1H, d, J=7.8 Hz), 9.29 (1H, br s), 9.77 (1H, br s);

IR (KBr) υ max 3412, 2961, 2822, 1605, 1585, 1513, 1453, 1399, 1240, 1050, 832, 764 cm$^{-1}$;

MS (FAB) m/z: 432 (M+H)$^+$.

Test Example 1

Human CaSR Activity Measurement Test

It is reported that human medullary thyroid carcinoma cell lines TT cells are cell lines that express human CaSR, and when CaSR is activated by extracellular calcium ions or the like, intracellular calcium ion concentration increases (Endocrinology 137: 3842-3848, 1996). Accordingly, an activating action of the test compounds with respect to human CaSR was evaluated by using the change in intracellular calcium concentration of TT cells as an indicator.

TT cells were inoculated onto a black well/clear bottom 96 well plate (poly-D-lysine coat: manufactured by BD biosciences), and were cultured for approximately 24 hours in a F-12 Nutrient Mixture (Kaighn's modification) culture media containing 10% calf serum and 0.5% antibiotic antimycotic. Subsequently, culture supernatant was removed by suction, followed by addition of a labeling buffer solution (20 mM HEPES, Hanks' Balanced Salt Solutions (HBSS (Ca, Mg, free) containing 2.5 mM probenecid, 2 mM CaCl$_2$) containing FLIPR calcium 3 assay kit (manufactured by Molecular Device), which labels intracellular calcium ions by fluorescence, by 50 μL per well. Then, the plate was allowed to stand for 1 hour at 37° C. Subsequently, the above-mentioned plate was placed onto FlexStation (manufactured by Molecular Device) or FlexStation 3 (manufactured by Molecular Device), and fluorescence intensity before and after treatment with the test compound dissolved in a buffer for measurement (126 mM NaCl, 4 mM KCl, 1 mM MgCl$_2$, 20 mM HEPES (pH 7.4), 5.6 mM glucose, 2 mM CaCl$_2$) was measured. Here, with respect to the test compound, it was used by dissolving it in a solution mixture of dimethyl sulfoxide and methanol (blend ratio 7:3) in a predetermined concentration, and then it was added as a solution diluted with the buffer for measurement, so that the final concentration became 0.1%.

A concentration-reaction curve was plotted by taking the fluorescence intensity increase in the case of treatment with the buffer for measurement which does not contain the test compound as 0%, and taking the fluorescence intensity increase by 8 mM calcium as 100%, and then calculating the fluorescence intensity increase rate for the cases of treatment with various concentrations of the test compound. Then, human CaSR activation action by each of the test compounds was evaluated by calculating the concentration of the test compound which shows a fluorescence intensity increase rate of 50% (EC$_{50}$ value). Further, EC$_{50}$ was calculated by evaluating Compound A ((R)-1-naphthalen-1-yl-ethyl)-[3-(3-trifluoromethyl-phenyl)-propyl]-amine monohydrochloride, which is described in N. Nagano, Pharmacol. Ther., 2006, March, 109 (3), 339-365 and International Publication No. WO 1996/12697) as a comparative compound, by conducting a similar procedure. From the following equation, the human CaSR activity of each of the test compounds was calculated as the relative activity with respect to Compound A.

Relative activity with respect to Compound A=[EC$_{50}$ of test compound]/[EC$_{50}$ of Compound A]

(Results) Test results are shown in Table 6.

TABLE 6

| Test Compound | Relative activity with respect to Compound A |
|---|---|
| Example 1 | 0.30 |
| Example 3 | 0.18 |
| Example 4 | 0.33 |
| Example 5 | 0.52 |
| Example 7 | 0.26 |
| Example 8 | 0.61 |
| Example 9 | 0.38 |
| Example 10 | 0.28 |
| Example 11 | 0.60 |
| Example 12 | 0.36 |
| Example 15 | 0.38 |
| Example 16 | 0.72 |
| Example 17 | 0.30 |
| Example 21 | 0.38 |
| Example 22 | 0.42 |
| Example 23 | 0.12 |
| Example 24 | 0.30 |
| Example 25 | 0.34 |
| Example 26 | 0.27 |
| Example 27 | 0.59 |
| Example 28 | 0.17 |
| Example 29 | 0.30 |
| Example 30 | 0.31 |
| Example 31 | 0.36 |
| Example 32 | 0.26 |
| Example 33 | 0.23 |
| Example 34 | 0.26 |
| Example 36 | 0.15 |

TABLE 6-continued

| Test Compound | Relative activity with respect to Compound A |
|---|---|
| Example 37 | 0.10 |
| Example 38 | 0.13 |
| Example 39 | 0.07 |

The compound of the present invention shows an excellent CaSR activating (agonist) action, and is useful as a therapeutic agent for hyperparathyroidism, renal osteodystrophy, hypercalcemia or the like.

Test Example 2

Measurement Test for Concentration of Parathyroid Hormone and Calcium Ion in Rat Blood Three male SD rats (manufactured by Japan SLC, Inc.) were orally administered with the test compound, and effects on the concentration of parathyroid hormone (PTH) in the blood and concentration of the calcium ion in the blood were studied.

The test compound was administered by dissolving or suspending it in a 0.5% methyl cellulose 400 (MC) solution or 0.5% MC solution containing 10% of ethanol. (In addition, Compound A used in Test Example 1 was administered as a MC suspension by dosage of 30 mg/kg, and was studied as a comparative example.) Blood was collected from the jugular vein under anesthesia with halothane or isoflurane, before administration of the test compound, and 2, 4, 6 or 8 and 24 hours after administration. Calcium ion concentration in the blood was measured using cartridge EG7+(manufactured by Fuso Chemical Co., Ltd.) and i-STAT 300F (manufactured by Fuso Chemical Co., Ltd.). In addition, plasma intact PTH concentration was measured using Rat intact PTH ELISA kit (manufactured by Immutopics).

In the present test, each of the test compounds reduced the PTH concentration and calcium concentration in the blood.

(Results) Compound A reduced calcium concentration by 15 to 30%, 4 hours after administration with a dosage of 30 mg/kg. On the other hand, compounds of Examples 3, 7, 8, 10, 11, 15, 16, 17, 21, 24, 25, 31, 33, 34, 35 and 36 which are the compounds of the present invention reduced calcium concentration by 30% or more, 4 hours after administration with a dosage of 10 mg/kg.

In addition, compounds of Examples 17, 23, 24, 25, 27, 28, 30 and 31 which are the compounds of the present invention reduced calcium concentration by 20% or more, 4 hours after administration with a dosage of 0.3 mg/kg.

Figure 2:
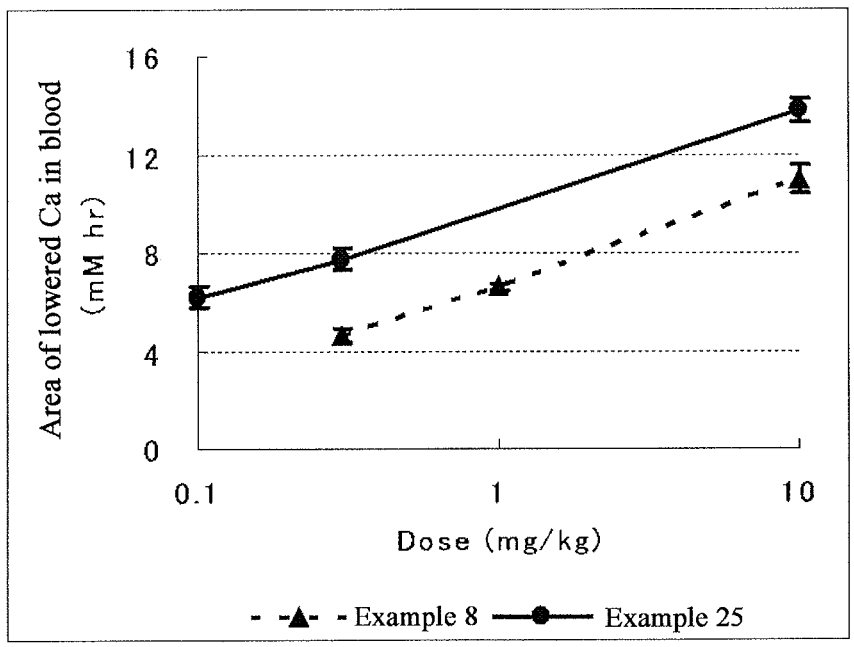
FIG. 2 shows area values of lowered calcium ion concentration in the blood for the compound in Example 8 and the compound in Example 25.
Figure 3:
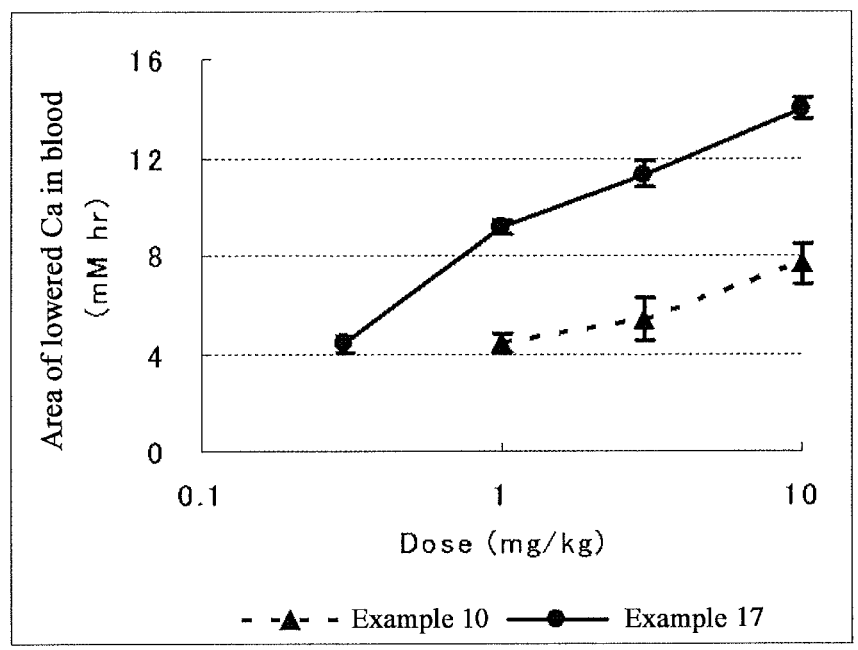
FIG. 3 shows area values of lowered calcium ion concentration in the blood for the compound in Example 10 and the compound in Example 17.
Figure 4:
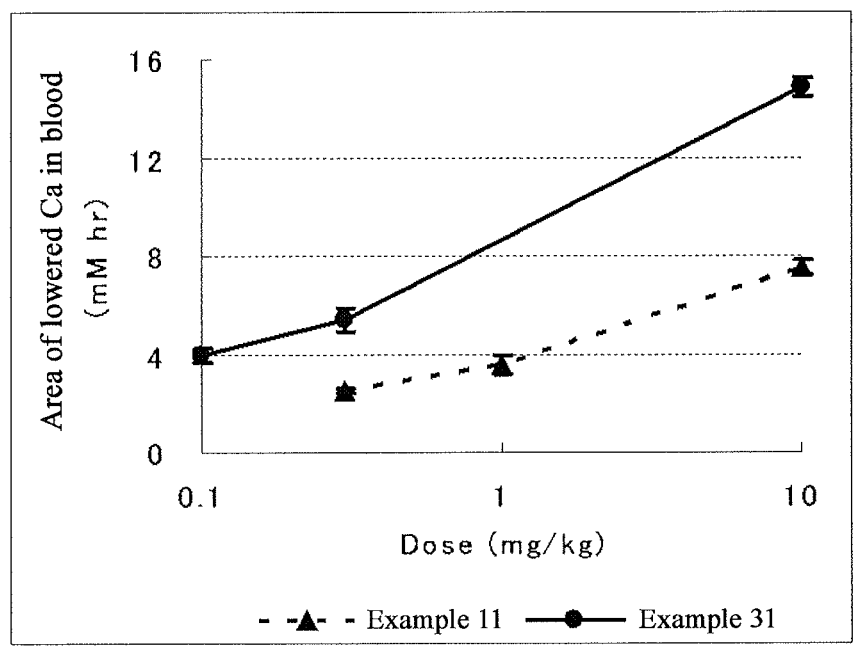
FIG. 4 shows area values of lowered calcium ion concentration in the blood for the compound in Example 11 and the compound in Example 31.

The transition of calcium ion concentration in the blood over time from before administration to 24 hours after administration of each of the test compounds was plotted, and the decrease in calcium ion concentration in the blood from the value before administration was calculated as an area value. The results thereof are shown in FIGS. 1 to 4.

The compound of the present invention shows an excellent lowering effect of parathyroid hormone concentration in the blood and calcium ion concentration, and is useful as a therapeutic agent for hyperparathyroidism, renal osteodystrophy, hypercalcemia or the like.

Preparation Example 1

The compound in Example (1 mg), colloidal silicon dioxide (0.2 mg), magnesium stearate (5 mg), microcrystalline cellulose (180 mg), starch (10 mg) and lactose (103.8 mg) are used in accordance with an ordinary method to produce tablets. Coating can be applied to the tablets obtained if necessary.

INDUSTRIAL APPLICABILITY

The compound of the general formula (1) of the present invention possesses an excellent CaSR activating (agonist) action, and is useful as a therapeutic agent for hyperparathyroidism, renal osteodystrophy, hypercalcemia or the like.

The invention claimed is:
1. A compound of general formula (1):

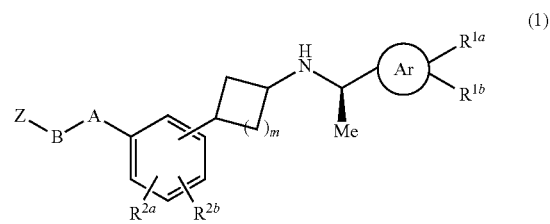

or a pharmacologically acceptable salt thereof, wherein, the partial structure of formula (2):

in the general formula (1) represents a naphthyl group;
$R^{1a}$ and $R^{1b}$ are the same or different from each other, and represent a hydrogen atom, a halogeno group, a C1-C6 alkyl group or a C1-C6 alkoxy group;
$R^{2a}$ and $R^{2b}$ are the same or different from each other, and represent a hydrogen atom, a halogeno group, a C1-C6 alkyl group, a halogeno C1-C6 alkyl group, a hydroxyl group, or a C1-C6 alkoxy group;
A represents a single bond, an oxygen atom, a —NR³— group, a —NR³C(=O)— group, a —NR³—S(O)₂— group or a —S(O)ₙ— group, wherein R³ represents a hydrogen atom, a C1-C4 alkyl group or a C1-C4 acyl group, and n represents 0, 1 or 2;
B represents a C1-C4 alkanediyl group or a C3-C4 cycloalkanediyl group;
Z represents a carboxy group; and
m is 2.
2. The compound or pharmacologically acceptable salt thereof according to claim 1, wherein $R^{1a}$ and $R^{1b}$ are the same or different from each other, and are a hydrogen atom, a halogeno group or a C1-C4 alkyl group.
3. The compound or pharmacologically acceptable salt thereof according to claim 1, wherein $R^{1a}$ and $R^{1b}$ are the same or different from each other, and are a hydrogen atom or a halogeno group.
4. The compound or pharmacologically acceptable salt thereof according to claim 1, wherein $R^{1a}$ is a halogeno group, and $R^{1b}$ is a hydrogen atom or a halogeno group.
5. The compound or pharmacologically acceptable salt thereof according to claim 1, wherein $R^{1a}$ is a halogeno group, and $R^{1b}$ is a hydrogen atom.

6. The compound or pharmacologically acceptable salt thereof according to claim 1, wherein $R^{1a}$ is a fluoro group, and $R^{1b}$ is a hydrogen atom.

7. The compound or pharmacologically acceptable salt thereof according to claim 1, wherein the partial structure:

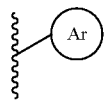

in the general formula (1) is a naphthalen-1-yl group.

8. The compound or pharmacologically acceptable salt thereof according to claim 1, wherein the partial structure:

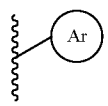

in the general formula (1) is a 4-fluoronaphthalen-1-yl group.

9. The compound or pharmacologically acceptable salt thereof according to claim 1, wherein $R^{2a}$ and $R^{2b}$ are the same or different from each other, and are a hydrogen atom, a halogeno group, a C1-C4 alkyl group, a trifluoromethyl group or a C1-C4 alkoxy group.

10. The compound or pharmacologically acceptable salt thereof according to claim 1, wherein $R^{2a}$ and $R^{2b}$ are the same or different from each other, and are a hydrogen atom, a halogeno group or a C1-C4 alkyl group.

11. The compound or pharmacologically acceptable salt thereof according to claim 1, wherein A is a single bond, an oxygen atom or a —NR³C(=O)— group, and wherein R³ represents a hydrogen atom.

12. The compound or pharmacologically acceptable salt thereof according to claim 1, wherein A is a single bond or an oxygen atom.

13. The compound or pharmacologically acceptable salt thereof according to claim 1 wherein A is a —NR³— group or a —S(O)$_n$— group, wherein R³ represents a hydrogen atom, a C1-C4 alkyl group or a C1-C4 acyl group, and n represents 0, 1 or 2.

14. The compound or pharmacologically acceptable salt thereof according to claim 1, wherein B is a C1-C4 alkanediyl group.

15. The compound or pharmacologically acceptable salt thereof according to claim 1, wherein B is a methylene group or a propane-2,2-diyl group.

16. A compound of general formula (1-a-2a):

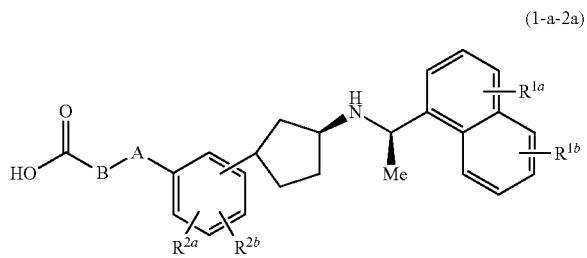

(1-a-2a)

or a pharmacologically acceptable salt thereof, wherein,
$R^{1a}$ and $R^{1b}$ are the same or different from each other, and represent a hydrogen atom, a halogeno group, a C1-C6 alkyl group or a C1-C6 alkoxy group;
$R^{2a}$ and $R^{2b}$ are the same or different from each other, and represent a hydrogen atom, a halogeno group, a C1-C6 alkyl group, a halogeno C1-C6 alkyl group, a hydroxyl group, or a C1-C6 alkoxy group;
A represents a single bond, an oxygen atom, a —NR³— group, a —NR³C(=O)— group, a —NR³—S(O)$_2$— group or a —S(O)$_n$— group, wherein R³ represents a hydrogen atom, a C1-C4 alkyl group or a C1-C4 acyl group, and n represents 0, 1 or 2; and
B represents a C1-C4 alkanediyl group or a C3-C4 cycloalkanediyl group.

17. The compound or pharmacologically acceptable salt thereof according to claim 16, wherein the phenylene group which is a partial structure of the general formula (1-a-2a) is in the m- or p-position.

18. The compound or pharmacologically acceptable salt thereof according to claim 16, wherein $R^{1a}$ and $R^{1b}$ are the same or different from each other, and are a hydrogen atom, a halogeno group or a C1-C4 alkyl group.

19. The compound or pharmacologically acceptable salt thereof according to claim 16, wherein $R^{1a}$ and $R^{1b}$ are the same or different from each other, and are a hydrogen atom or a halogeno group.

20. The compound or pharmacologically acceptable salt thereof according to claim 16, wherein $R^{1a}$ is a halogeno group, and $R^{1b}$ is a hydrogen atom or a halogeno group.

21. The compound or pharmacologically acceptable salt thereof according to claim 16, wherein $R^{1a}$ is a halogeno group, and $R^{1b}$ is a hydrogen atom.

22. The compound or pharmacologically acceptable salt thereof according to claim 16, wherein $R^{1a}$ is a fluoro group, and $R^{1b}$ is a hydrogen atom.

23. The compound or pharmacologically acceptable salt thereof according to claim 16, wherein the partial structure:

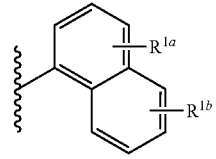

in the general formula (1-a-2) or (1-a-2a) is a 4-fluoronaphthalen-1-yl group.

24. The compound or pharmacologically acceptable salt thereof according to claim 16, wherein $R^{2a}$ and $R^{2b}$ are the same or different from each other, and are a hydrogen atom, a halogeno group, a C1-C4 alkyl group, a trifluoromethyl group or a C1-C4 alkoxy group.

25. The compound or pharmacologically acceptable salt thereof according to claim 16, wherein $R^{2a}$ and $R^{2b}$ are the same or different from each other, and are a hydrogen atom, a halogeno group or a C1-C4 alkyl group.

26. The compound or pharmacologically acceptable salt thereof according to claim 16, wherein A is a single bond, an oxygen atom or a —NR³C(=O)— group, wherein R³ represents a hydrogen atom.

27. The compound or pharmacologically acceptable salt thereof according to claim 16, wherein A is a single bond or an oxygen atom.

28. The compound or pharmacologically acceptable salt thereof according to claim 16, wherein A is a —$NR^3$— group or a —$S(O)_n$— group, wherein $R^3$ represents a hydrogen atom, a C1-C4 alkyl group or a C1-C4 acyl group, and n represents 0, 1 or 2.

29. The compound or pharmacologically acceptable salt thereof according to claim 1 or claim 16, wherein B is a C1-C4 alkanediyl group.

30. The compound or pharmacologically acceptable salt thereof according to claim 16, wherein B is a methylene group or a propane-2,2-diyl group.

31. A compound or a pharmacologically acceptable salt thereof selected from the group consisting of:
N-{4-[3-{[(1R)-1-(naphthalen-1-yl)ethyl]amino}cyclopentyl]benzoyl}glycine,
{3-[3-{[(1R)-1-(naphthalen-1-yl)ethyl]amino}cyclopentyl]phenyl}acetic acid,
{4-[3-{[(1R)-1-(naphthalen-1-yl)ethyl]amino}cyclopentyl]phenyl}acetic acid,
3-{4-[3-{[(1R)-1-(naphthalen-1-yl)ethyl]amino}cyclopentyl]phenyl}propanoic acid,
{4-[3-{[(1R)-1-(naphthalen-1-yl)ethyl]amino}cyclopentyl]phenoxy}acetic acid,
2-methyl-2-{4-[3-{[(1R)-1-(naphthalen-1-yl)ethyl]amino}cyclopentyl]phenoxy}propanoic acid,
{3-[3-{[(1R)-1-(naphthalen-1-yl)ethyl]amino}cyclopentyl]phenoxy}acetic acid,
2-methyl-2-{3-[3-{[(1R)-1-(naphthalen-1-yl)ethyl]amino}cyclopentyl]phenoxy}propanoic acid,
{2-fluoro-4-[3-{[(1R)-1-(naphthalen-1-yl)ethyl]amino}cyclopentyl]phenoxy}acetic acid,
{4-[3-{[(1R)-1-(4-fluoronaphthalen-1-yl)ethyl]amino}cyclopentyl]phenoxy}acetic acid,
{4-[3-{[(1R)-1-(5-fluoronaphthalen-1-yl)ethyl]amino}cyclopentyl]phenoxy}acetic acid,
{4-[3-{[(1R)-1-(6-fluoronaphthalen-1-yl)ethyl]amino}cyclopentyl]phenoxy}acetic acid,
{4-[3-{[(1R)-1-(4,6-difluoronaphthalen-1-yl)ethyl]amino}cyclopentyl]phenoxy}acetic acid,
{3-[3-{[(1R)-1-(4-fluoronaphthalen-1-yl)ethyl]amino}cyclopentyl]phenyl}acetic acid,
{4-[3-{[(1R)-1-(4-fluoronaphthalen-1-yl)ethyl]amino}cyclopentyl]phenyl}acetic acid,
3-{4-[3-{[(1R)-1-(4-fluoronaphthalen-1-yl)ethyl]amino}cyclopentyl]phenyl}propanoic acid,
2-{4-[3-{[(1R)-1-(4-fluoronaphthalen-1-yl)ethyl]amino}cyclopentyl]phenoxy}-2-methylpropanoic acid,
{2-methyl-4-[3-{[(1R)-1-(naphthalen-1-yl)ethyl]amino}cyclopentyl]phenoxy}acetic acid,
N-{4-[3-{[(1R)-1-(naphthalen-1-yl)ethyl]amino}cyclopentyl]phenyl}glycine,
N-{4-[3-{[(1R)-1-(4-fluoronaphthalen-1-yl)ethyl]amino}cyclopentyl]phenyl}glycine,
({4-[3-{[(1R)-1-(naphthalen-1-yl)ethyl]amino}cyclopentyl]phenyl}thio)acetic acid, and
({4-[3-{[(1R)-1-(4-fluoronaphthalen-1-yl)ethyl]amino}cyclopentyl]phenyl}thio)acetic acid.

32. A compound or a pharmacologically acceptable salt thereof selected from the group consisting of:
N-{4-[3-{[(1R)-1-(naphthalen-1-yl)ethyl]amino}cyclopentyl]benzoyl}glycine,
{3-[3-{[(1R)-1-(naphthalen-1-yl)ethyl]amino}cyclopentyl]phenyl}acetic acid,
{4-[3-{[(1R)-1-(naphthalen-1-yl)ethyl]amino}cyclopentyl]phenyl}acetic acid,
3-{4-[3-{[(1R)-1-(naphthalen-1-yl)ethyl]amino}cyclopentyl]phenyl}propanoic acid,
{4-[3-{[(1R)-1-(naphthalen-1-yl)ethyl]amino}cyclopentyl]phenoxy}acetic acid,
2-methyl-2-{4-[3-{[(1R)-1-(naphthalen-1-yl)ethyl]amino}cyclopentyl]phenoxy}propanoic acid,
{3-[3-{[(1R)-1-(naphthalen-1-yl)ethyl]amino}cyclopentyl]phenoxy}acetic acid,
{4-[3-{[(1R)-1-(4-fluoronaphthalen-1-yl)ethyl]amino}cyclopentyl]phenoxy}acetic acid,
{4-[3-{[(1R)-1-(4,6-difluoronaphthalen-1-yl)ethyl]amino}cyclopentyl]phenoxy}acetic acid,
{3-[3-{[(1R)-1-(4-fluoronaphthalen-1-yl)ethyl]amino}cyclopentyl]phenyl}acetic acid,
{4-[3-{[(1R)-1-(4-fluoronaphthalen-1-yl)ethyl]amino}cyclopentyl]phenyl}acetic acid,
3-{4-[3-{[(1R)-1-(4-fluoronaphthalen-1-yl)ethyl]amino}cyclopentyl]phenyl}propanoic acid,
2-{4-[3-{[(1R)-1-(4-fluoronaphthalen-1-yl)ethyl]amino}cyclopentyl]phenoxy}-2-methylpropanoic acid, and
({4-[3-{[(1R)-1-(4-fluoronaphthalen-1-yl)ethyl]amino}cyclopentyl]phenyl}thio)acetic acid.

33. A compound or a pharmacologically acceptable salt thereof selected from the group consisting of:
{4-[3-{[(1R)-1-(4-fluoronaphthalen-1-yl)ethyl]amino}cyclopentyl]phenoxy}acetic acid,
{3-[3-{[(1R)-1-(4-fluoronaphthalen-1-yl)ethyl]amino}cyclopentyl]phenyl}acetic acid,
{4-[3-{[(1R)-1-(4-fluoronaphthalen-1-yl)ethyl]amino}cyclopentyl]phenyl}acetic acid,
3-{4-[3-{[(1R)-1-(4-fluoronaphthalen-1-yl)ethyl]amino}cyclopentyl]phenyl}propanoic acid,
2-{4-[3-{[(1R)-1-(4-fluoronaphthalen-1-yl)ethyl]amino}cyclopentyl]phenoxy}-2-methylpropanoic acid, and
({4-[3-{[(1R)-1-(4-fluoronaphthalen-1-yl)ethyl]amino}cyclopentyl]phenyl}thio)acetic acid.

34. A method for treating hyperparathyroidism comprising administering the compound or pharmacologically acceptable salt thereof to a patient according to any one of claim 1, 16, 31, 32 or 33.

35. A method for treating secondary hyperparathyroidism comprising administering the compound or pharmacologically acceptable salt thereof to a patient according to any one of claim 1, 16, 31, 32 or 33.

36. A method for treating primary hyperparathyroidism comprising administering the compound or pharmacologically acceptable salt thereof to a patient according to any one of claim 1, 16, 31, 32 or 33.

37. A method for treating renal osteodystrophy comprising administering the compound or pharmacologically acceptable salt thereof to a patient according to any one of claim 1, 16, 31, 32 or 33.

38. A method for treating hypercalcemia comprising administering the compound or pharmacologically acceptable salt thereof to a patient according to any one of claim 1, 16, 31, 32 or 33.

39. A pharmaceutical composition comprising the compound or pharmacologically acceptable salt thereof according to any one of claim 1, 16, 31, 32 or 33, and a pharmacologically acceptable carrier.

40. A method for treating hyperparathyroidism, secondary hyperparathyroidism, primary hyperparathyroidism, renal osteodystrophy or hypercalcemia, comprising administering a pharmaceutical composition comprising the compound or pharmacologically acceptable salt thereof to a patient according to any one of claim 1, 16, 31, 32 or 33, and a pharmacologically acceptable carrier.

\* \* \* \* \*

UNITED STATES PATENT AND TRADEMARK OFFICE
CERTIFICATE OF CORRECTION

PATENT NO. : 9,133,140 B2
APPLICATION NO. : 13/059156
DATED : September 15, 2015
INVENTOR(S) : Shinji Marumoto et al.

It is certified that error appears in the above-identified patent and that said Letters Patent is hereby corrected as shown below:

On the Title Page and in the Specification, column 1, In the title, delete "CYCLOALKYLAMNE DERIVATIVES" and insert therefor -- CYCLOALKYLAMINE DERIVATIVES --.

IN THE CLAIMS

In claim 8, in column 127, delete the partial structure:

" 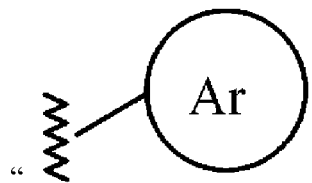 " and insert therefor the partial structure: -- 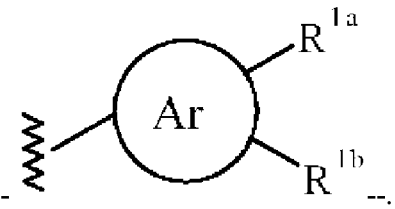 --.

Signed and Sealed this
Fifteenth Day of March, 2016

Michelle K. Lee
*Director of the United States Patent and Trademark Office*